US012486312B2

(12) United States Patent
Swanson et al.

(10) Patent No.: US 12,486,312 B2
(45) Date of Patent: Dec. 2, 2025

(54) IMMUNOMODULATORY PROTEINS WITH TUNABLE AFFINITIES

(71) Applicant: Alpine Immune Sciences, Inc., Seattle, WA (US)

(72) Inventors: Ryan Swanson, Seattle, WA (US); Michael Kornacker, Seattle, WA (US)

(73) Assignee: ALPINE IMMUNE SCIENCES, INC., Seattle, WA (US)

( * ) Notice: Subject to any disclaimer, the term of this patent is extended or adjusted under 35 U.S.C. 154(b) by 254 days.

(21) Appl. No.: 17/707,511

(22) Filed: Mar. 29, 2022

(65) Prior Publication Data

US 2022/0242930 A1 Aug. 4, 2022

Related U.S. Application Data

(62) Division of application No. 15/567,068, filed as application No. PCT/US2016/027995 on Apr. 15, 2016, now Pat. No. 11,319,359.

(60) Provisional application No. 62/218,534, filed on Sep. 14, 2015, provisional application No. 62/149,437, filed on Apr. 17, 2015.

(51) Int. Cl.

*C07K 14/705* (2006.01)
*C07K 14/715* (2006.01)
*G01N 33/564* (2006.01)
*G01N 33/574* (2006.01)

(52) U.S. Cl.

CPC .. *C07K 14/70532* (2013.01); *C07K 14/70521* (2013.01); *C07K 14/70596* (2013.01); *C07K 14/715* (2013.01); *G01N 33/564* (2013.01); *G01N 33/57484* (2013.01); *C07K 2319/30* (2013.01); *C07K 2319/73* (2013.01)

(58) Field of Classification Search

CPC ................................................ C07K 14/70532
See application file for complete search history.

(56) References Cited

U.S. PATENT DOCUMENTS

| | | | |
|---|---|---|---|
| 5,223,409 | A | 6/1993 | Ladner et al. |
| 5,434,131 | A | 7/1995 | Linsley et al. |
| 5,500,362 | A | 3/1996 | Robinson et al. |
| 5,571,698 | A | 11/1996 | Ladner et al. |
| 5,624,821 | A | 4/1997 | Winter et al. |
| 5,648,260 | A | 7/1997 | Winter et al. |
| 5,733,743 | A | 3/1998 | Ladner et al. |
| 5,750,373 | A | 5/1998 | Garrard et al. |
| 5,773,253 | A | 6/1998 | Linsley et al. |
| 5,821,047 | A | 10/1998 | Garrard et al. |
| 5,821,337 | A | 10/1998 | Carter et al. |
| 5,837,500 | A | 11/1998 | Ladner et al. |
| 5,844,095 | A | 12/1998 | Linsley et al. |
| 5,851,795 | A | 12/1998 | Linsley et al. |
| 5,871,907 | A | 2/1999 | Winter et al. |
| 5,885,579 | A | 3/1999 | Linsley et al. |
| 5,885,796 | A | 3/1999 | Linsley et al. |
| 5,891,432 | A | 4/1999 | Hoo |
| 5,942,607 | A | 8/1999 | Freeman et al. |
| 5,969,108 | A | 10/1999 | McCafferty et al. |
| 6,040,136 | A | 3/2000 | Garrard et al. |
| 6,084,067 | A | 7/2000 | Freeman et al. |
| 6,130,316 | A | 10/2000 | Freeman et al. |
| 6,172,197 | B1 | 1/2001 | McCafferty et al. |
| 6,194,551 | B1 | 2/2001 | Idusogie et al. |
| 6,218,510 | B1 | 4/2001 | Sharpe et al. |
| 6,291,159 | B1 | 9/2001 | Winter et al. |
| 6,294,660 | B1 | 9/2001 | Sharpe et al. |
| 6,352,694 | B1 | 3/2002 | June et al. |
| 6,444,792 | B1 | 9/2002 | Gray et al. |
| 6,482,919 | B2 | 11/2002 | Ledbetter et al. |
| 6,534,055 | B1 | 3/2003 | June et al. |
| 6,623,940 | B1 | 9/2003 | Ledbetter et al. |
| 6,630,575 | B2 | 10/2003 | Coyle et al. |
| 6,635,750 | B1 | 10/2003 | Coyle et al. |
| 6,641,809 | B1 | 11/2003 | Linsley et al. |
| 6,685,941 | B1 | 2/2004 | Thompson et al. |
| 6,713,279 | B1 | 3/2004 | Short |
| 6,730,512 | B2 | 5/2004 | Chang |
| 6,737,056 | B1 | 5/2004 | Presta |
| 6,750,334 | B1 | 6/2004 | Gray et al. |
| 6,831,161 | B1 | 12/2004 | Uhlen et al. |
| 6,887,471 | B1 | 5/2005 | Linsley et al. |
| 6,955,877 | B1 | 10/2005 | Nygren et al. |
| 6,979,538 | B2 | 12/2005 | Ladner et al. |
| 7,063,943 | B1 | 6/2006 | McCafferty et al. |
| 7,094,874 | B2 | 8/2006 | Peach et al. |
| 7,094,875 | B2 | 8/2006 | Punnonen et al. |

(Continued)

FOREIGN PATENT DOCUMENTS

| | | |
|---|---|---|
| EP | 0757099 | 2/1997 |
| EP | 1173204 | 1/2002 |

(Continued)

OTHER PUBLICATIONS

Bork. Powers and Pitfalls in Sequence Analysis: The 70% Hurdle. Genome Research, 2000, 10:398-400 (Year: 2000).*
Greenspan et al. 1999. Defining epitopes: It's not as easy as it seems; Nature Biotechnology, 17:936-937 (Year: 1999).*
Bowie et al. Deciphering the Message in Protein Sequences: Tolerance to Amino Acid Substitutions. Science, 1990, 247:1306-1310 (Year: 1990).*
Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine ResidueJ. Cell Biol. 111:2129-2138, 1990 (Year: 1990).*
Lazar et al. Transforming Growth Factor alpha: Mutation of Aspartic Acid 47 and Leucine 48 Results in Different Biological Activities . Mol. Cell. Biol., 8:1247-1252, 1988 (Year: 1988).*

(Continued)

*Primary Examiner* — Prema M Mertz
(74) *Attorney, Agent, or Firm* — McNeill PLLC

(57) ABSTRACT

Provided are immunomodulatory proteins and nucleic acids encoding such proteins. The immunomodulatory proteins provide therapeutic utility for a variety of immunological and oncological conditions. Compositions and methods for making and using such proteins are provided.

25 Claims, 2 Drawing Sheets

Specification includes a Sequence Listing.

(56) References Cited

U.S. PATENT DOCUMENTS 7,105,166 B1 9/2006 Linsley et al.
7,118,879 B2 10/2006 Ladner et al.
7,208,293 B2 4/2007 Ladner et al.
7,304,033 B2 12/2007 Larsen et al.
7,307,064 B2 12/2007 Rusnak
7,332,303 B2 2/2008 Schilling et al.
7,332,571 B2 2/2008 Miao et al.
7,332,581 B2 2/2008 Presta
7,385,028 B2 6/2008 Miao et al.
7,439,230 B2 10/2008 Peach et al.
7,446,189 B1 11/2008 Weiner et al.
7,455,835 B2 11/2008 Cohen et al.
7,482,327 B2 1/2009 Hagerty et al.
7,521,532 B2 4/2009 Dunussi-Joannopoulos et al.
7,560,540 B2 7/2009 Pardoll et al.
7,563,869 B2 7/2009 Honjo et al.
7,569,663 B2 8/2009 Tykocinski et al.
7,612,170 B2 11/2009 Punnonen et al.
7,619,078 B2 11/2009 Sharpe et al.
7,638,299 B2 12/2009 Cho et al.
7,642,044 B2 1/2010 Thogersen et al.
7,670,602 B2 3/2010 Chung et al.
7,671,022 B2 3/2010 Rusnak
7,696,312 B2 4/2010 Miao et al.
7,700,556 B2 4/2010 Peach et al.
7,709,214 B2 5/2010 Freeman et al.
7,722,868 B2 5/2010 Cohen et al.
7,794,718 B2 9/2010 Karrer et al.
7,829,534 B2 11/2010 Larsen et al.
7,888,533 B2 2/2011 Tian et al.
7,915,222 B2 3/2011 Vratsanos et al.
7,915,395 B2 3/2011 Ledbetter et al.
8,053,414 B2 11/2011 Pardoll et al.
8,053,558 B2 11/2011 Pardoll et al.
8,071,095 B2 12/2011 Karrer et al.
8,088,736 B2 1/2012 Franks et al.
8,148,332 B2 4/2012 Cohen et al.
8,202,847 B2 6/2012 Weiner et al.
8,227,420 B2 7/2012 Cohen et al.
8,268,587 B2 9/2012 Karrer et al.
8,283,447 B2 10/2012 Karrer et al.
8,318,176 B2 11/2012 Karrer et al.
8,329,867 B2 12/2012 Lazar et al.
8,435,952 B2 5/2013 Vratsanos et al.
8,445,230 B2 5/2013 Karrer et al.
8,445,447 B2 5/2013 Chen
8,491,899 B2 7/2013 Karrer et al.
8,496,935 B2 7/2013 Karrer et al.
8,497,247 B2 7/2013 Cohen et al.
8,609,625 B2 12/2013 Lan et al.
8,624,010 B1 1/2014 Yoshinaga
8,629,119 B2 1/2014 Olson et al.
8,642,557 B2 2/2014 Akamatsu et al.
8,703,718 B2 4/2014 Cohen et al.
8,709,417 B2 4/2014 Allison et al.
8,722,632 B2 5/2014 Cohen et al.
8,785,398 B2 7/2014 Peach et al.
8,883,971 B2 11/2014 Akamatsu et al.
8,956,619 B2 2/2015 Ostrand-Rosenberg
9,012,408 B2 4/2015 Vratsanos et al.
9,029,315 B2 5/2015 Chen et al.
9,289,480 B2 3/2016 Lan et al.
9,296,808 B2 3/2016 Cohen et al.
9,327,014 B2 5/2016 Gurney et al.
9,375,475 B2 6/2016 Allison et al.
9,540,426 B2 1/2017 Jing et al.
9,587,007 B2 3/2017 Akamatsu et al.
9,650,429 B2 5/2017 Ostrand-Rosenberg
9,709,568 B2 7/2017 Pierce et al.
9,758,565 B2 9/2017 Peach et al.
9,834,604 B2 12/2017 Zhu et al.
9,884,902 B2 2/2018 Minter et al.
10,487,147 B2 11/2019 Nastri et al.
11,078,282 B2 8/2021 Swanson et al.
11,096,988 B2 8/2021 Swanson et al.
11,117,948 B2 9/2021 Swanson et al.
11,117,949 B2 9/2021 Swanson et al.
11,117,950 B2 9/2021 Swanson et al.
11,230,588 B2 1/2022 Swanson et al.
11,319,359 B2 5/2022 Swanson et al.
11,359,022 B2 6/2022 Swanson et al.
11,471,488 B2 10/2022 Swanson et al.
11,479,609 B2 10/2022 Swanson et al.
11,498,967 B2 11/2022 Swanson et al.
11,639,375 B2 5/2023 Swanson et al.
11,732,022 B2 8/2023 Swanson et al.
11,753,458 B2 9/2023 Evans et al.
11,834,490 B2 12/2023 Swanson et al.
2002/0009454 A1 1/2002 Boone et al.
2003/0083246 A1 5/2003 Cohen et al.
2003/0138881 A1 7/2003 Punnonen et al.
2003/0158102 A1 8/2003 Chen et al.
2003/0171551 A1 9/2003 Rosenblatt et al.
2003/0232323 A1 12/2003 Freeman et al.
2004/0072283 A1 4/2004 Seed et al.
2005/0014934 A1 1/2005 Hinton et al.
2008/0113412 A1 5/2008 Sheffer et al.
2008/0300163 A1 12/2008 Cho et al.
2009/0155843 A1 6/2009 Ottow et al.
2009/0208454 A1 8/2009 Kraynov et al.
2009/0252749 A1 10/2009 Leister et al.
2009/0258031 A1 10/2009 Karrer et al.
2010/0035812 A1 2/2010 Hays Putnam et al.
2010/0093608 A1 4/2010 Tian et al.
2010/0178276 A1 7/2010 Sadelain et al.
2010/0261660 A1 10/2010 Punnonen et al.
2010/0303811 A1 12/2010 Ochi
2011/0002956 A1 1/2011 Weiner et al.
2011/0015345 A1 1/2011 Pinkstaff et al.
2011/0159023 A1 6/2011 Langermann
2011/0195068 A1 8/2011 Langermann et al.
2011/0305712 A1 12/2011 Akamatsu et al.
2013/0017199 A1 1/2013 Langermann
2013/0149305 A1 6/2013 Ostrand-Rosenberg
2014/0011370 A1 1/2014 Camphausen
2014/0056890 A1 2/2014 Gurney et al.
2014/0186380 A1 7/2014 Gurney
2014/0308299 A1 10/2014 Allison et al.
2014/0348832 A1 11/2014 Zhu et al.
2015/0104451 A1 4/2015 Orban
2015/0216970 A1 8/2015 Grogan et al.
2015/0232532 A1 8/2015 Ostrand-Rosenberg
2015/0266958 A1 9/2015 Hermans et al.
2016/0017018 A1 1/2016 Wang et al.
2016/0145344 A1 5/2016 Akbari
2016/0158318 A1 6/2016 Cohen et al.
2016/0244524 A1 8/2016 Allison et al.
2016/0264643 A1 9/2016 Lazar et al.
2016/0271218 A1 9/2016 Biro
2016/0340422 A1 11/2016 Chen et al.
2016/0346368 A1 12/2016 Gurney et al.
2016/0347849 A1 12/2016 Cai et al.
2016/0376346 A1 12/2016 Camphausen
2017/0028040 A1 2/2017 Lan et al.
2017/0042972 A1 2/2017 Karyekar
2017/0145071 A1 5/2017 Brennan et al.
2017/0226181 A1 8/2017 Ostrand-Rosenberg
2017/0320959 A1 11/2017 Swanson et al.
2017/0369549 A1 12/2017 Peach et al.
2018/0118805 A1 5/2018 Bernett et al.
2018/0256644 A1 9/2018 Swanson et al.
2018/0319861 A1 11/2018 Lan et al.
2019/0135922 A1 5/2019 Swanson et al.
2019/0175654 A1 6/2019 Swanson et al.
2020/0040059 A1 2/2020 Swanson et al.
2020/0283500 A1 9/2020 Lawrence et al.
2020/0308249 A1 10/2020 Lawrence et al.
2021/0130436 A1 5/2021 Swanson et al.
2021/0130437 A1 5/2021 Swanson et al.
2021/0155668 A1 5/2021 Swanson et al.
2021/0155669 A1 5/2021 Swanson et al.
2021/0163571 A1 6/2021 Swanson et al.
2021/0171603 A1 6/2021 Swanson et al.
2021/0188942 A1 6/2021 Swanson et al.

(56) References Cited

U.S. PATENT DOCUMENTS

| | | | |
|---|---|---|---|
| 2021/0253668 A1 | 8/2021 | Swanson et al. |
| 2021/0347897 A1 | 11/2021 | Swanson et al. |
| 2021/0363219 A1 | 11/2021 | Swanson et al. |
| 2022/0177587 A1 | 6/2022 | Swanson et al. |
| 2023/0101432 A1 | 3/2023 | Swanson |
| 2023/0136723 A1 | 5/2023 | Swanson et al. |
| 2023/0220039 A1 | 7/2023 | Swanson et al. |
| 2023/0250152 A1 | 8/2023 | Evans et al. |
| 2023/0381229 A1 | 11/2023 | Swanson et al. |
| 2024/0002466 A1 | 1/2024 | Swanson et al. |
| 2024/0158463 A1 | 5/2024 | Evans et al. |
| 2024/0360197 A1 | 10/2024 | Swanson et al. |

FOREIGN PATENT DOCUMENTS

| | | |
|---|---|---|
| EP | 1248802 | 10/2002 |
| JP | 2011524743 A | 9/2011 |
| WO | WO-1994/029351 | 12/1994 |
| WO | WO-1999/002711 | 1/1999 |
| WO | WO-1999/051642 | 10/1999 |
| WO | WO-2000/042072 | 7/2000 |
| WO | WO-2002/000717 | 1/2002 |
| WO | WO 2003/002722 | 1/2003 |
| WO | WO-2004/029197 | 4/2004 |
| WO | WO-2004/030636 | 4/2004 |
| WO | WO-2004/056312 | 7/2004 |
| WO | WO-2005/100402 | 10/2005 |
| WO | WO-2006/019447 | 2/2006 |
| WO | WO-2006/029879 | 3/2006 |
| WO | WO-2008/047150 | 4/2008 |
| WO | WO-2009/029342 | 3/2009 |
| WO | WO-2009/105671 | 8/2009 |
| WO | WO-2009/126688 | 10/2009 |
| WO | WO-2010/027423 | 3/2010 |
| WO | WO-2010/027827 | 3/2010 |
| WO | WO-2010/027828 | 3/2010 |
| WO | WO-2011/020024 | 2/2011 |
| WO | WO-2011/066342 | 6/2011 |
| WO | WO-2011/097477 | 8/2011 |
| WO | WO-2011/103584 | 8/2011 |
| WO | WO-2011/109789 | 9/2011 |
| WO | WO-2011/113019 | 9/2011 |
| WO | WO-2012/079000 | 6/2012 |
| WO | WO-2012/140627 | 10/2012 |
| WO | WO-2013/003761 | 1/2013 |
| WO | WO-2013/079174 | 6/2013 |
| WO | WO-2013/130683 | 9/2013 |
| WO | WO-2013/148049 | 10/2013 |
| WO | WO-2013/169338 | 11/2013 |
| WO | WO-2013/184912 | 12/2013 |
| WO | WO-2014/089169 | 6/2014 |
| WO | WO-2014/207063 | 12/2014 |
| WO | WO-2015/009856 | 1/2015 |
| WO | WO-2015/113494 | 8/2015 |
| WO | WO-2015/120363 | 8/2015 |
| WO | WO-2016/008976 | 1/2016 |
| WO | WO-2016/011264 | 1/2016 |
| WO | WO-2016/191643 | 1/2016 |
| WO | WO-2016/022994 | 2/2016 |
| WO | WO-2016/034678 | 3/2016 |
| WO | WO-2016/073704 | 5/2016 |
| WO | WO-2016/118577 | 7/2016 |
| WO | WO-2016/154684 | 10/2016 |
| WO | WO-2016/164428 | 10/2016 |
| WO | WO-2017/019846 | 2/2017 |
| WO | WO-2017/023749 | 2/2017 |
| WO | WO-2017/023779 | 2/2017 |
| WO | WO-2017/029389 | 2/2017 |
| WO | WO-2017/048878 | 3/2017 |
| WO | WO-2017/055547 | 4/2017 |
| WO | WO-2017/079117 | 5/2017 |
| WO | WO-2017/106061 | 6/2017 |
| WO | WO-2017/151818 | 9/2017 |
| WO | WO-2017/181148 | 10/2017 |
| WO | WO-2017/181152 | 10/2017 |
| WO | WO-2018/022945 | 2/2018 |
| WO | WO-2018/022946 | 2/2018 |
| WO | WO-2018/075978 | 4/2018 |
| WO | WO-2018/170021 | 9/2018 |
| WO | WO-2018/170023 | 9/2018 |
| WO | WO-2018/170026 | 9/2018 |
| WO | WO-2019/079520 | 4/2019 |
| WO | WO-2019/136179 | 7/2019 |
| WO | WO 2019/241758 | 12/2019 |
| WO | WO-2020/061376 | 3/2020 |
| WO | WO-2021/181233 | 9/2021 |
| WO | WO-2023/172883 | 9/2023 |

OTHER PUBLICATIONS

U.S. Appl. No. 18/346,092, filed Jun. 30, 2023, by Swanson et al. (Copy not submitted herewith pursuant to the waiver of 37 C.F. R. § 1.98(a)(2)(iii) issued by the Office on Oct. 19, 2004).

U.S. Appl. No. 18/494,677, filed Oct. 25, 2023, by Swanson et al. (Copy not submitted herewith pursuant to the waiver of 37 C.F. R. § 1.98(a)(2)(iii) issued by the Office on Oct. 19, 2004).

"Database accession No. A0A2K5E9H6," Retrieved from UNIPROT, https://www.uniprot.org/uniprot/A0A2K5E9H6. Retrieved Sep. 13, 2019.

"Database accession No. AER57743 Human B7Rp1 extracellular domain (ECD)" Dated Apr. 19, 2007.

"Database accession No. BDH56778", Retrieved from GENESEQ, Retrieved on Sep. 13, 2019.

"Database accession No. BDV07959," Retrieved from GENESEQ, Retrieved on Sep. 12, 2019.

"Database accession No. A0A2J8M811," Retrieved from UNIPROT, https://www.uniprot.org /uniprot/A0A2J8M811. Retrieved on Mar. 5, 2020.

"Database accession No. A9UFX3," version 38. Retrieved from UNIPROT, http://www.uniprot.org/uniprot/A9UFX3.txt?. Retrieved on Jan. 18, 2018.

"Database accession No. ADM18706." Retrieved from IBIS, http://ibis/exam/dbfetch.jsp?id=GSP:ADM18706. Retrieved on Oct. 10, 2017.

"Database accession No. ADM18913." Retrieved from IBIS, http://ibis/exam/dbfetch.jsp?id=GSP:ADM18913. Retrieved on Oct. 10, 2017.

"Database accession No. B3TFD9," version 63. Retrieved from UNIPROT, http://www.uniprot.org/uniprot/B3TFD9.txt?version=63. Retrieved on Dec. 10, 2017.

"Database accession No. BCD07227." Retrieved from IBIS, http://ibis/exam/dbfetch.jsp?id=GSP:BCD07227. Retrieved on Oct. 10, 2017.

"Database accession No. BCD07228." Retrieved from IBIS, http://ibis/exam/dbfetch.jsp?id=GSP:BCD07228. Retrieved on Oct. 10, 2017.

"Database accession No. BD020821," Retrieved from GENESEQ, https://www.ebi.ac.uk/ena/data/view/BD020821. Retrieved on May 16, 2018.

"Database accession No. BD020825," Retrieved from GENESEQ, https://www.ebi.ac.uk/ena/data/view/BD020825. Retrieved on May 16, 2018.

"Database accession No. F1PWL4," version 43. Retrieved from UNIPROT, http://www.uniprot.org/uniprot/F1PWL4.txt?version=43. Retrieved on Dec. 10, 2017.

"Database accession No. F7DZ76," version 32. Retrieved from UNIPROT, http://www.uniprot.org/uniprot/F7DZ76. Retrieved on Jun. 6, 2018.

"Database accession No. G1SUI3," version 36. Retrieved from UNIPROT, http://www.uniprot.org/uniprot/G1SUI3.txt. Retrieved on Jun. 6, 2018.

"Database accession No. H9Z6Y0," version 15. Retrieved from UNISAVE, http://www.ebi.ac.uk/uniprot/unisave/app/#/content/H9Z6Y0/15. Retrieved on Jun. 20, 2017.

"Database accession No. L8Y5K4," version 13. Retrieved from UNISAVE, http://www.ebi.ac.uk/uniprot/unisave/app/#/content/L8Y5K4/13. Retrieved on Sep. 28, 2017.

(56) References Cited

OTHER PUBLICATIONS

"Database accession No. NP_56074.1," version 1. Retrieved from NCBI, https://www.ncbi.nlm.nih.gov/protein/NP_056074.1, Retrieved on Mar. 3, 2020.
"Database accession No. P32506," version 99. Retrieved from UNIPROT, http://www.uniprot.org/uniprot/P32506.txt ?. Retrieved on Jan. 18, 2018.
Adom et al., "ICOSL+ plasmacytoid dendritic cells as inducer of graft-versus-host disease, responsive to a dual ICOS/CD28 antagonist" Sci Transl Med. (2020) 12(564): eaay4799.
Amatore et al., "Inducible Co-Stimulator (ICOS) as a Potential Therapeutic Target for Anti-Cancer Therapy," Expert Opin Ther Targets. (2018) 22(4): 343-351.
Auffermann-Gretzinger et al., "Rapid establishment of dendritic cell chimerism in allogeneic hematopoietic cell transplant recipients," Blood. (2002) 99(4): 1442-1448.
Banovic et al., "Graft-versus-host disease prevents the maturation of plasmacytoid dendritic cells," J Immunol. (2009) 182(2): 912-920.
Behr et al., "Trastuzumab and breast cancer," N Engl J Med. (2001) 345:995-996.
Biasini et al., "Swiss-Model: modelling protein tertiary and quaternary structure using evolutionary information," Nucleic Acids Res (2014) 42:W252-258.
Bittner et al., "Subcutaneous Administration of Biotherapeutics: An Overview of Current Challenges and Opportunities," BioDrugs (2018) 32:425-440.
Boder et al.. "Optimal screening of surface-displayed polypeptide libraries," Biotechnol Prog. (1998) 14:55-62.
Brandt et al., The B7 family member B7-H6 is a tumor cell ligand for the activating natural killer cell receptor NKp30 in humans. J Exp Med. (2009) 206:1495-1503.
Bruggemann et al., "Comparison of the effector functions of human immunoglobulins using a matched set of chimeric antibodies," J Exp Med. (1987) 166(5):1351-1361.
Burmeister et al., ICOS controls the pool size of effector-memory and regulatory T cells. J Immunol.(2008) 180:774-82.
Butte et al., "Programmed death-1 ligand 1 interacts specifically with the B7-1 costimulatory molecule to inhibit T cell responses," Immunity (2007) 27(1):111-122.
Butte et al., "Interaction of human PD-L1 and B7-1," Molecular Immunology (2008) 45:3567-3572.
Carter et al., "Cytotoxic T-lymphocyte antigen-4 and programmed death-1 function as negative regulators of lymphocyte activation," Immunol Res (2003) 28:49-59.
Carter et al., "Humanization of an anti-p185HER2 antibody for human cancer therapy," Proc Natl Acad Sci USA (1992) 89:4285-4289.
Chakrabarti et al., "A mutant B7-1/lg fusion protein that selectively binds to CTLA-4 ameliorates anti-tumor DNA vaccination and counters regulatory T cell activity", Vaccine, Elsevier, Amsterdam, NL, vol. 23, No. 37, Aug. 31, 2005 pp. 4553-4564.
Chao et al., "Isolating and engineering human antibodies using yeast surface display," Nat Protoc. (2006) 1:755-768.
Chattopadhyay et al., "Structural basis of inducible costimulator ligand costimulatory function: determination of the cell surface oligomeric state and functional mapping of the receptor binding site of the protein," J Immunol. Sep. 15, 2006;177(6):3920-9.
Chaudhri et al., "PD-L1 Binds to B7-1 Only In Cis on the Same Cell Surface," Cancer Immunol Res (2018) 6(8):921-929.
Chen et al., "MolProbity: all-atom structure validation for macromolecular crystallography," Acra Crystallogr D Biol Crystallogr (2010) 66(Pt 1):12-21.
Clynes et al., "Fc receptors are required in passive and active immunity to melanoma," Proc Natl Acad Sci U S A. (1998) 95(2):652-656.
Colby et al., "Engineering antibody affinity by yeast surface display," Methods Enzymol. 2004;388:348-58.
Condomines et al., "Tumor-Targeted Human T Cells Expressing CD28-Based Chimeric Antigen Receptors Circumvent CTLA-4 Inhibition," PLoS One (2015) 10(6):e0130518.
Covassin et al., "Human peripheral blood CD4 T cell-engrafted non-obese diabetic-scid IL2rγ(null) H2-Ab1 (tm1Gru) Tg (human leucocyte antigen D-related 4) mice: a mouse model of human allogeneic graft-versus-host disease," Clin Exp Immunol. 2011 166(2): 269-280.
Cragg et al., "Antibody specificity controls in vivo effector mechanisms of anti-CD20 reagents," Blood. (2004) 103(7):2738-2743.
Cragg et al., "Complement-mediated lysis by anti-CD20 mAb correlates with segregation into lipid rafts," Blood. (2003) 101(3):1045-1052.
Cutler et al., in *Thomas' Hematopoietic Cell Transplantation*, F. Appelbaum, S. J. Forman, R. S. Negrin, K. G. Blume, Eds. (Blackwell Publishing Ltd, 2009), chap. 86, pp. 1287-1303.
Davis et al., "Macrophage M1/M2 polarization dynamically adapts to changes in cytokine microenvironments in Cryptococcus neoformans infection," M Bio (2013) 4(3):e00264.
De Filipe et al., "Use of the 2A sequence from foot-and-mouth disease virus in the generation of retroviral vectors for gene therapy," Gene Therapy (1999) 6:198-208.
Deeg et al., "The clinical spectrum of acute graft-versus-host disease," Semin Hematol. (2006) 43(1): 24-31.
Derer et al., Complement in antibody-based tumor therapy. Crit Rev Immunol. (2014) 34:199-214.
Despoix et al., "Mouse CD146/MCAM is a marker of natural killer cell maturation", Eur J Immunol. (2008) 38(10): 2855-2864.
Doty et al., "Two regions in the CD80 cytoplasmic tail regulate CD80 redistribution and T cell costimulation," J Immunol. (1998) 161(6): 2700-2707.
Dull et al., "A Third-Generation Lentivirus Vector with a Conditional Packaging System," J Virology (1998) 72(11): 8463-8471.
Duncan et al., "The binding site for C1q on IgG," Nature. Apr. 21, 1988;332(6166):738-40.
Ehx et al., "Xenogeneic Graft-Versus-Host Disease in Humanized NSG and NSG-HLA-A2/HHD Mice", Front Immunol. (2018) 9:1943.
Ellis et al., "Interactions of CD80 and CD86 with CD28 and CTLA4," J Immunol (1996) 156:2700-2709.
Emsley et al., "Features and development of Coot," Acta Crystallogr D Biol Crystallogr (2010) 66(Pt 4):486-501.
Evans et al., "Crystal structure of a soluble CD28-Fab complex," Nat Immunol (2005) 6(3):271-279.
Fargeas et al., "Identification of residues in the V domain of CD80 (B7-1) implicated in functional interaction with CD28 and CTLA4", Journal of Experimental Medicine, vol. 182, No. 3. Sep. 1, 1995 pp. 667-675.
Ferrara et al., "Regenerating islet-derived 3-alpha is a biomarker of gastrointestinal graft-versus-host disease," Blood. (2011) 118(25): 6702-6708.
Forcade et al., "An activated Th17-prone T cell subset involved in chronic graft-versus-host disease sensitive to pharmacological inhibition," JCI Insight. (2017) 2(12): e92111.
Ford et al., "Targeting co-stimulatory pathways: transplantation and autoimmunity," Nat Rev Nephrol. (2014) 10(1):14-24.
Fowler et al., "R707, a fully human antibody directed against CC-chemokine receptor 7, attenuates xenogeneic acute graft-versus-host disease", Am J Transplant. (2019) 19(7): 1941-1954.
Freeman et al., "Engagement of the PD-1 immunoinhibitory receptor by a novel B7 family member leads to negative regulation of lymphocyte activation," J Exp Med (2000) 192(7):1027-1034.
Gazzano-Santoro et al., "A non-radioactive complement-dependent cytotoxicity assay for anti-CD20 monoclonal antibody," J Immunol Methods. Mar. 28, 1997;202(2):163-71.
Ghiotto, M., et al "PD-L 1 and PD-L2 differ in their molecular mechanisms of interaction with PD-1", International Immunology, 2010, vol. 22, No. 8, pp. 651-660.
Gregoire-Gauthier et al., "Use of immunoglobulins in the prevention of GvHD in a xenogeneic NOD/SCID/gammac-mouse model," Bone Marrow Transplant (2012) 47:439-450.
Haile et al., "A Soluble Form of CD80 Enhances Antitumor Immunity by Neutralizing Programmed Death Ligand-1and Simultaneously Providing Costimulation," Cancer Immunol Res (2014) 2(7): 610-615.

(56) References Cited

OTHER PUBLICATIONS

Haile et al., "Tumor Cell Programmed Death Ligand 1-Mediated T Cell Suppression ins overcome by coexpression of CD80," J Immunol (2011) 186(12):6822-6829.
Haile et al., "Soluble CD80 restores T cell activation and overcomes tumor cell programmed death ligand 1-mediated immune suppression," J Immunol. (2013) 191(5):2829-36.
Halaby et al., "The immunoglobulin superfamily: an insight on its tissular, species, and functional diversity," J Mol Evol (1998) 46:389-400.
Harris et al., "CD80 costimulation is essential for the induction of airway eosinophilia," J Exp Med. Jan. 6, 1997;185(1):177-82.
Hartwell et al., "An early-biomarker algorithm predicts lethal graft-versus-host disease and survival," JCI Insight. (2017) 2(3): e89798.
Hellstrom et al., "Antitumor effects of L6, an IgG2a antibody that reacts with most human carcinomas," Proc Natl Acad Sci U S A. (1986) 83(18):7059-7063.
Hellstrom et al., "Strong antitumor activities of IgG3 antibodies to a human melanoma-associated ganglioside," Proc Natl Acad Sci U S A. (1985) 82(5):1499-1502.
Hezareh et al., "Effector function activities of a panel of mutants of a broadly neutralizing antibody against human immunodeficiency virus type 1," J Virol (2001) 75(24):12161-12168.
Horn et al., "Soluble CD80 Protein Delays Tumor Growth and Promotes Tumor-Infiltrating Lymphocytes," Cancer Immunol Res. (2018) 6(1): 59-68.
Hoseini et al., "A potent tetravalent T-cell-engaging bispecific antibody against CD33 in acute myeloid leukemia", Blood Adv. Jun. 12, 2018;2(11):1250-1258.
Idusogie et al., "Mapping of the C1q binding site on rituxan, a chimeric antibody with a human IgG1 Fc," J Immunol. (2000) 164(8):4178-4184.
Ikemizu et al., "Structure and Dimerization of a Soluble Form of B7-1," Immunity (2000) 12:51-60.
Infante et al., "Overview Clinical and Pharmacodynamic (PD) Results of a Phase 1 Trial with AMP-224 (B7-DC Fc) that Binds to the PD-1 Receptor," Journal of Clinical Oncology (2013) 31(15_ suppl):3044-3044.
Intlekofer et al., "At the bench: preclinical rationale for CTLA-4 and PD-1 blockade as cancer immunotherapy," J Leukoc biol (2013) 94(1):25-39.
Jenkins et al., "CD28 delivers a costimulatory signal involved in antigen-specific IL-2 production by human T cells," J Immunol. (1991) 147:2461-6.
Jones, "Critically assessing the state-of-the-art in protein structure prediction," Pharmacogenomics J. (2001); 1(2): 126-34.
Juneja et al., "PD-L1 on tumor cell is sufficient for immune evasion in immunogenic tumors and inhibits CD8 T cell cytotoxicity." J Exp Med. (2017) 214(4):895-904.
Kabat et al., "Sequences of Proteins of Immunological Interest," Fifth Edition, U.S. Department of Health and Human Services, NIH Publication No. 91-3242 (1991), 83 pages.
Kabsch et al., "XDS" Acta Crystallogr D Biol Crystallogr, 2010. 66(Pt 2): p. 125-32.
Khalil et al., "The future of cancer treatment: immunomodulation, CARs and combination immunotherapy," Nat Rev Clin Oncol. (2016) 13(5):273-90.
Khan et al., "Characterization of the New World monkey homologues of human poliovirus receptor CD155," J Virol. Jul. 2008;82(14):7167-79.
Koike et al., "A second gene for the African green monkey poliovirus receptor that has no putative N-glycosylation site in the functional N-terminal immunoglobulin-like domain," J Virol. Dec. 1992;66(12):7059-66.
Kojima et al., "Fusion Protein of Mutant B7-DC and Fc Enhances the Antitumor Immune Effect of GM-CSF-secreting Whole-cell Vaccine," J Immunother. (2014) 37(3):147-54.
Koura et al., "In vivo T cell costimulation blockade with abatacept for acute graft-versus-host disease prevention: a first-in-disease trial", Biol Blood Marrow Transplant. (2013) 19(11): 1638-1649.
Koyama et al., "Plasmacytoid dendritic cells prime alloreactive T cells to mediate graft-versus-host disease as antigen-presenting cells," Blood. (2009) 113(9): 2088-2095.
Kremer et al., "Treatment of rheumatoid arthritis by selective inhibition of T-cell activation with fusion protein CTLA4lg," N Engl J Med (2003) 349(20):1907-1915.
Laouar et al., "STAT3 is required for Flt3L-dependent dendritic cell differentiation," Immunity. (2003) 19(6): 903-912.
Larsen et al., "Rational development of LEA29Y (belatacept), a high-affinity variant of CTLA4-Ig with potent immunosuppressive properties," Am J Transplant. Mar. 2005;5(3):443-53.
Lazetic et al., "Chimeric co-stimulatory molecules that selectively act through CD28 or CTLA-4 on human T cells," J Biol Chem (2002)11;277(41):38660-38668.
Leabman et al., "Effects of altered FcγR binding on antibody pharmacokinetics in cynomolgus monkeys," MAbs. (2013) 5(6):896-903.
Leitner et al., "T cell stimulator cells, an efficient and versatile cellular system to assess the role of costimulatory ligands in the activation of human T cells," J Immunol Methods (2010) 362(1-2):131-141.
Li et al., "Comparison of anti-CD3 and anti-CD28-coated beads with soluble anti-CD3 for expanding human T cells: differing impact on CD8 T cell phenotype and responsiveness to restimulation," J Transl Med. (2010) 8:104.
Li et al., "Proteomics analysis reveals a Th17-prone cell population in presymptomatic graft-versus-host disease," JCI Insight. (2016) 1(6): e86660.
Li et al., "Structure of the human activating natural cytotoxicity receptor NKp30 bound to its tumor cell ligand B7-H6," J Exp Med (2011) 208(4): 703-714.
Lin et al., "The PD-1/PD-L1 complex resembles the antigen-binding Fv domains of antibodies and T cell receptors," Proc Natl Acad Sci U S A. (2008) 105(8):3011-3016.
Lindblad-Toh et al., "A high-resolution map of human evolutionary constraint using 29 mammals," Nature (2011) 478(7370):476-482.
Lindblad-Toh et al., "Genome sequence, comparative analysis and haplotype structure of the domestic dog," Nature. Dec. 8, 2005;438(7069):803-19.
Linderholm et al., "Immunoglobulin Fc-Fusion Proteins," Bio Process International. (2014) 12(10): 20-27.
Linsley et al., "Human B7-1 (CD80) and B7-2 (CD86) bind with similar avidities but distinct kinetics to CD28 and CTLA-4 receptors," Immunity. (1994) 1(9): 793-801.
Liu et al., "Crystal structure of cell adhesion molecule nectin-2/CD112 and its binding to immune receptor DNAM-1/CD226," J Immunol. Jun. 1, 2012;188(11):5511-20.
Lobner et al., "Engineered IgG1-Fc—one fragment to bind them all," Immunol Rev (2016) 270(1):113-31.
Liu et al., "Combination B7-Fc Fusion Protein Treatment and Treg Cell Depletion Therapy," Clin Cancer Res (2005) 11(23):8492-8502.
Marabelle et al., "Intratumoral immunotherapy: using the tumor as the remedy," Annals of Oncology (2017) 28:xii33-xii43.
Markey et al., "Conventional dendritic cells are the critical donor APC presenting alloantigen after experimental bone marrow transplantation", Blood. 2009 113(22): 5644-5649.
Markey et al., "Flt-3L Expansion of Recipient CD8α + Dendritic Cells Deletes Alloreactive Donor T Cells and Represents an Alternative to Posttransplant Cyclophosphamide for the Prevention of GVHD", Clin Cancer Res. (2018) 24(7): 1604-1616.
Markey et al., "Recipient plasmacytoid DCs are not required to prime allogeneic T-cell responses after BMT," Blood. (2009) 113(23): 6038-6039.
Martin et al., "Increasingly frequent diagnosis of acute gastrointestinal graft-versus-host disease after allogeneic hematopoietic cell transplantation," Biol Blood Marrow Transplant. (2004) 10(5): 320-327.
Matte et al., "Donor APCs are required for maximal GVHD but not for GVL", Nat Med. (2004) 10(9): 987-992.

(56) References Cited

OTHER PUBLICATIONS

Maurer et al., "ALPN-202 combines checkpoint inhibition with conditional T cell costimulation to overcome T cell suppression by M2c macrophages and improve the durability of engineered T cell anti-tumor responses," AACR Annual Meeting 2020; Cancer Res (2020) 80(16suppl):Abstract nr LB-085.
Maute et al., "Engineering high-affinity PD-1 variants for optimized immunotherapy and immuno-PET imaging," Proc Natl Acad Sci U S A. (2015) 112(47): E6506-14.
Mcdonald et al., "Plasma biomarkers of acute GVHD and nonrelapse mortality: predictive value of measurements before GVHD onset and treatment," Blood. (2015) 126(1): 113-120.
Metzler et al., "Solution structure of human CTLA-4 and delineation of a CD80/CD86 binding site conserved in CD28," Nat Struct Biol (1997) 4(7):527-31.
Miller et al., "Construction and screening of antigen targeted immune yeast surface display antibody libraries," Curr Protoc Cytom. Jul. 2008; Chapter 4:Unit4.7, 30 pages.
Mochizuki et al., "Delta-like ligand 4 identifies a previously uncharacterized population of inflammatory dendritic cells that plays important roles in eliciting allogeneic T cell responses in mice," J Immunol. (2013) 190(7): 3772-82.
Mollweide et al., "Only therapeutic ICOS:ICOSL blockade alleviates acute graft versus host disease", Klin Padiatr. (2009) 221(6):344-50.
Morton et al., "Differential effects of CTLA-4 substitutions on the binding of human CD80 (B7-1) and CD86 (B7-2)," J Immunol. (1996) 156(3):1047-1054.
Murshudov et al., "REFMAC5 for the refinement of macromolecular crystal structures," Acta Crystallogr D Biol Crystallogr, 2011. 67(Pt 4): p. 355-67.
Nishimori et al., "Identification and characterization of bovine programmed death-ligand 2," Microbiol Immunol. (2014) 58(7):388-97.
Paczesny et al., "A biomarker panel for acute graft-versus-host disease," Blood. (2009) 113(2): 273-278.
Paczesny et al., "Elafin is a biomarker of graft-versus-host disease of the skin," Sci Transl Med. (2010) 2(13): 13ra2.
Paczesny, "Biomarkers for posttransplantation outcomes," Blood. (2018) 131(20): 2193-2204.
Patton et al., "Evaluation of the efficiency of human immune system reconstitution in NSG mice and NSG mice containing a human HLA.A2 transgene using hematopoietic stem cells purified from different sources", J Immunol Methods. (2015) 422: 13-21.
Paulos et al., "The inducible costimulator (ICOS) is critical for the development of human T(H)17 cells", Sci Transl Med. (2010) 2(55): 55ra78.
Peach et al., "Both extracellular immunoglobin-like domains of CD80 contain residues critical for binding T cell surface receptors CTLA-4 and CD28," J Biol Chem. (1995) 270(36):21181-7.
Peach et al., "Complementarity determining region 1 (CDR1)- and CDR3-analogous regions in CTLA-4 and CD28 determine the binding to B7-1," J Exp Med (1994) 180(6):2049-2058.
Pérez De La Lastra et al., "Epitope mapping of 10 monoclonal antibodies against the pig analogue of human membrane cofactor protein (MCP)," Immunology. (1999) 96(4):663-70.
Petkova et al., "Enhanced half-life of genetically engineered human IgG1 antibodies in a humanized FcRn mouse model: potential application in humorally mediated autoimmune disease," Int Immunol. (2006) 18(12):1759-1769.
Ramadan et al., "From proteomics to discovery of first-in-class ST2 inhibitors active in vivo," JCI Insight. (2018) 3(14): e99208.
Ravetch et al., "Fc receptors," Annu Rev Immunol. (1991) 9:457-492.
Reizis et al., "Plasmacytoid Dendritic Cells: Development, Regulation, and Function," Immunity. (2019) 50(1): 37-50.
Ren et al., "The search for drug-targetable diagnostic, prognostic and predictive biomarkers in chronic graft-versus-host disease," Expert Rev Clin Immunol. (2018) 14(5): 389-404.
Rennert et al., "The IgV domain of human B7-2 (CD86) is sufficient to co-stimulate T lymphocytes and induce cytokine secretion," International Immunology (1997) 9(6):805-813.
Rentero et al., "Screening of Large Molecule Diversities by Phage Display," Chimia (Aarau) (2011) 65(11): 843-845.
Ruperto et al., Abatacept in children with juvenile idiopathic arthritis: a randomised, double-blind, placebo-controlled withdrawal trial. Lancet. (2008) 372:383-391.
Sadelain, M. et al., "The basic principles of chimeric antigen receptor design." Cancer Discov., Apr. 2013, vol. 3, No. 4, pp. 388-398.
Sarmay, Gabriella, et al. "Mapping and comparison of the interaction sites on the Fc region of IgG responsible for triggering antibody dependent cellular cytotoxicity (ADCC) through different types of human Fcγ receptor." Molecular immunology 29.5 (1992): 633-639.
Schildberg et al., "Coinhibitory Pathways in the B7-CD28 Ligand-Receptor Family," Immunity. (2016) 44(5): 955-72.
Scholten et al., "Promiscuous behavior of HPV16E6 specific T cell receptor beta chains hampers functional expression in TCR transgenic T cells, which can be restored in part by genetic modification," Cell Oncol. (2010) 32:43-56.
Schwartz et al., "Structural mechanisms of costimulation," Nat Immunol (2002) 3(5):427-434.
Shields et al., "High resolution mapping of the binding site on human IgG1 for Fc gamma RI, Fc gamma RII, Fc gamma RIII, and FcRn and design of IgG1 variants with improved binding to the Fc gamma R," J Biol Chem. (2001) 276(9):6591-6604.
Shlomchik et al., "Prevention of graft versus host disease by inactivation of host antigen-presenting cells," Science. (1999) 285(5426): 412-415.
Srinivasan et al., "Immunomodulatory peptides from IgSF proteins: a review," Curr Protein Pept Sci. (2005) 6(2):185-96.
Srivastava et al., "Engineering CAR-T cells: Design Concepts," Trends in Immunology (2015) 36(8):494-502.
Stamper et al., "Crystal structure of the B7-1/CTLA-4 complex that inhibits human immune responses," Nature. (2001) 410(6828):608-611.
Stebbings et al., "After TGN1412: recent developments in cytokine release assays," J Immunotoxicol (2013) 10(1):75-82.
Sturmhoefel et al., "Potent Activity of Soluble B7-IgG Fusion Proteins in Therapy of Established Tumors and as Vaccine Adjuvant," Cancer Res. (1999) 59(19): 4964-4972.
Sul et al., "FDA Approval Summary: Pembrolizumab for the Treatment of Patients With Metastatic Non-Small Cell Lung Cancer Whose Tumors Express Programmed Death-Ligand 1," Oncologist (2016) 21(5):643-50.
Sutharalingam et al., "Cytokine storm in a phase 1 trial of the anti-CD28 monoclonal antibody TGN1412," N Engl J Med (2006) 355(10):1018-1028.
Taylor et al., "Targeting of inducible costimulator (ICOS) expressed on alloreactive T cells down-regulates graft-versus-host disease (GVHD) and facilitates engraftment of allogeneic bone marrow (BM)", Blood. (2005) 105(8): 3372-3380.
Terawaki et al., "Specific and high-affinity binding of tetramerized PD-L1 extracellular domain to PD-1-expressing cells: possible application to enhance T cell function," Int Immunol (2007) 19(7):881-890.
Teshima et al., "Response: Recipient plasmacytoid dendritic cells and graft-versus-host disease", Blood. (2009) 114(6): 1280.
Tirapu et al., " Low surface expression of B7-1 (CD80) is an immunoescape mechanism of colon carcinoma," Cancer Res. (2006) 66(4):2442-50.
Topalian et al., "Safety, activity, and immune correlates of anti-PD-1 antibody in cancer," N engl J Med (2012) 366:2443-2454.
Tosatto et al., "Large-scale prediction of protein structure and function from sequence," Curr Pharm Des. (2006); 12(17): 2067-86.
Uniprot H9Z6Y0 ICOS ligand Retrieved from https://www.uniprot.org/uniprot/H9Z6Y0. Retrieve on Jul. 10, 2020.
Uniprot L8Y5K4 ICOS Ligand Retrieved from https://www.uniprot.org/uniprot/L8Y5K4. Retrieved on Jul. 10, 2020.
Uzzaman et al., "Classification of hypersensitivity reactions," Allergy Asthma Proc. (2012) 33: S96-S99.

(56) References Cited

OTHER PUBLICATIONS

Vafa et al., "An engineered Fc variant of an IgG eliminates all immune effector functions via structural perturbations," Methods. (2014) 65(1):114-26.
Van Der Lugt et al., "ST2 as a marker for risk of therapy-resistant graft-versus-host disease and death," N Engl J Med. (2013) 369(6): 529-539.
Van Der Merwe et al., "CD80 (B7-1) binds both CD28 and CTLA-4 with a low affinity and very fast kinetics," J exp Med (1997) 185:393-403.
Vessillier et al., "Cytokine release assays for the prediction of therapeutic mAb safety in first-in man trials—Whole blood cytokine release assays are poorly predictive for TGN1412 cytokine storm," J Immunol Methods (2015) 424:43-52.
Vincenti et al., "Costimulation blockade with belatacept in renal transplantation," N Engl J Med. (2005) 353:770-81.
Wade et al., "Genome sequence, comparative analysis, and population genetics of the domestic horse," Science. Nov. 6, 2009;326(5954):865-867.
Wang et al., "In vitro characterization of the anti-PD-1 antibody nivolumab, BMS-936558, and in vivo toxicology in non-human primates," Cancer Immunol Res. (2014) 2(9):846-856.
Wang et al., "Molecular cloning, characterization and three-dimensional modeling of porcine nectin-2/CD112," Vet Immunol Immunopathol. 2009 132(2-4):257-63.
Wang et al., "Molecular modeling and functional mapping of B7-H1 and B7-DC uncouple costimulatory function from PD-1 interaction," J Exp Med. 2003 197(9):1083-91.
Watkins et al., "CD28 blockade controls T cell activation to prevent graft-versus-host disease in primates", J Clin Invest. (2018) 128(9): 3991-4007.
Weber et al., "ICOS maintains the T follicular helper cell phenotype by down-regulating Kruppel-like factor 2," J Exp Med. (2015) 212:217-33.
Wekerle et al., "Belatacept: from rational design to clinical application," Transplant International (2012) 25:139-150.
Wikenheiser et al., "ICOS Co-Stimulation: Friend or Foe?," Front Immunol (2016) (7):304, 16 pgs.
Winn et al., "Overview of the CCP4 suite and current developments," Acta Crystallogr D Biol Crystallogr (2011) 67(Pt 4):235-242.
Wolchok et al., "Development of ipilimumab: a novel immunotherapeutic approach for the treatment of advanced melanoma," Ann N Y Acad Sci. (2013) 1291:1-13.
Wu et al., "CTLA-4-B7 Interaction Is Sufficient to Costimulate T Cell Clonal Expansion," J. Exp. Med. (1997) 185(7):1327-1335.
Xu et al., "Affinity and cross-reactivity engineering of CTLA4-Ig to modulate T cell costimulation," J Immunol (2012) 189(9):4470-4477.
Yang et al., "First-in-human study of the safety, tolerability, pharmacokinetics, and pharmacodynamics of ALPN-101, a dual CD28/ICOS antagonist, in healthy adult subjects," Clin Transl Sci (2021) 14(4):1314-1326. DOI: 10.1111/cts.12983.
Yao et al., "B7-h2 is a costimulatory ligand for CD28 in human," Immunity. (2011) 34(5):729-40.
Yoshinaga et al., cell co-stimulation through B7RP-1 and ICOS. Nature. (1999) 402:827-832.
Yu et al., "The role of B7-CD28 co-stimulation in tumor rejection," Int Imm (1998) 10(6):791-797.
Zak et al., "Structure of the Complex of Human Programmed Death 1, PD-1, and Its Ligand PD-L1," Structure (2015) 23(12):2341-2348.
Zeiser et al., "Acute Graft-versus-Host Disease—Biologic Process, Prevention, and Therapy", N Engl J Med. Nov. 30, 2017;377(22):2167-2179.
Zhang et al., "An NKp30-Based Chimeric Anitgen Receptor Promotes T Cell Effector Functions and Antitumor Efficacy In Vivo," J Immunol (2012) 189:2290-2299.
Zhang et al., "Identification of another primordial CD8O/86 molecule in rainbow trout: insights into the origin and evolution of CD8O and CD86 in vertebrates," Developmental & Comparative Immunology (2018) 89:73-82.
Zhang et al., "Preterminal host dendritic cells in irradiated mice prime CD8+ T cell-mediated acute graft-versus-host disease," J Clin Invest. (2002) 109(10): 1335-1344.
Zhang et al., "ST2 blockade reduces sST2-producing T cells while maintaining protective mST2-expressing T cells during graft-versus-host disease", Sci Transl Med. (2015) 7(308): 308ra160.
Zhao et al., "A Bispecific Protein Capable of Engaging CTLA-4 and MHCII Protects Non-Obese Diabetic Mice from Autoimmune Diabetes," PLoS One (2013) 8(5):e63530-e63530.
Zhao et al., "Structural Design of Engineered Costimulation Determines Tumor Rejection Kinetics and Persistence of CAR T Cells," Cancer Cell (2015) 28(4):415-428.
Zhao et al., "TIGIT overexpression diminishes the function of CD4 T cells and ameliorates the severity of rheumatoid arthritis in mouse models," Exp Cell Res. Jan. 1, 2016;340(1):132-8.
Zimin et al., "A new rhesus macaque assembly and annotation for next-generation sequencing analyses," Biol Direct. Oct. 14, 2014;9(1):20.
U.S. Appl. No. 18/844,376, filed Sep. 5, 2024, by Maurer et al. (Copy not provided). (Copy not submitted herewith pursuant to the waiver of 37 C.F. R. § 1.98(a)(2)(iii) issued by the Office on Sep. 21, 2004).
"Database accession No. ADM18864." Retrieved from GENESEQ, Dated Jul. 1, 2004; XP002780658.
"Database accession No. ADM18719." Retrieved from GENESEQ, Dated Jul. 1, 2004; XP002780659.
"Database accession No. ADM18706." Retrieved from GENESEQ, Dated Jul. 1, 2004; XP002774557.
"Database accession No. ADM18913." Retrieved from GENESEQ, Dated Jul. 1, 2004; XP002774558.
"Database accession No. ABP68480." Retrieved from GENESEQ, Dated Jan. 8, 2003; XP002780660.
"Database accession No. ABP68546." Retrieved from GENESEQ, Dated Jan. 8, 2003; XP002780661.
"Database accession No. BCD07228." Retrieved from GENESEQ, Dated Sep. 24, 2015; XP002774560.
"Database accession No. BCD07227." Retrieved from GENESEQ, Dated Sep. 24, 2015; XP002774559.

* cited by examiner

SEQUENCE LISTING

```
<160> NUMBER OF SEQ ID NOS: 240

<210> SEQ ID NO 1
<211> LENGTH: 288
<212> TYPE: PRT
<213> ORGANISM: Homo sapiens
<220> FEATURE:
<223> OTHER INFORMATION: CD80(B7-1)

<400> SEQUENCE: 1

Met Gly His Thr Arg Arg Gln Gly Thr Ser Pro Ser Lys Cys Pro Tyr
1               5                   10                  15

Leu Asn Phe Phe Gln Leu Leu Val Leu Ala Gly Leu Ser His Phe Cys
            20                  25                  30

Ser Gly Val Ile His Val Thr Lys Glu Val Lys Glu Val Ala Thr Leu
        35                  40                  45

Ser Cys Gly His Asn Val Ser Val Glu Glu Leu Ala Gln Thr Arg Ile
    50                  55                  60

Tyr Trp Gln Lys Glu Lys Lys Met Val Leu Thr Met Met Ser Gly Asp
65                  70                  75                  80

Met Asn Ile Trp Pro Glu Tyr Lys Asn Arg Thr Ile Phe Asp Ile Thr
                85                  90                  95

Asn Asn Leu Ser Ile Val Ile Leu Ala Leu Arg Pro Ser Asp Glu Gly
            100                 105                 110

Thr Tyr Glu Cys Val Val Leu Lys Tyr Glu Lys Asp Ala Phe Lys Arg
        115                 120                 125

Glu His Leu Ala Glu Val Thr Leu Ser Val Lys Ala Asp Phe Pro Thr
    130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ser Gln Asp
            180                 185                 190

Pro Glu Thr Glu Leu Tyr Ala Val Ser Ser Lys Leu Asp Phe Asn Met
        195                 200                 205

Thr Thr Asn His Ser Phe Met Cys Leu Ile Lys Tyr Gly His Leu Arg
    210                 215                 220

Val Asn Gln Thr Phe Asn Trp Asn Thr Thr Lys Gln Glu His Phe Pro
225                 230                 235                 240

Asp Asn Leu Leu Pro Ser Trp Ala Ile Thr Leu Ile Ser Val Asn Gly
                245                 250                 255

Ile Phe Val Ile Cys Cys Leu Thr Tyr Cys Phe Ala Pro Arg Cys Arg
            260                 265                 270

Glu Arg Arg Arg Asn Glu Arg Leu Arg Arg Glu Ser Val Arg Pro Val
        275                 280                 285


<210> SEQ ID NO 2
<211> LENGTH: 329
<212> TYPE: PRT
<213> ORGANISM: Homo sapiens
```

<220> FEATURE:
<223> OTHER INFORMATION: CD86(B7-2)

<400> SEQUENCE: 2

```
Met Asp Pro Gln Cys Thr Met Gly Leu Ser Asn Ile Leu Phe Val Met
1               5                   10                  15

Ala Phe Leu Leu Ser Gly Ala Ala Pro Leu Lys Ile Gln Ala Tyr Phe
            20                  25                  30

Asn Glu Thr Ala Asp Leu Pro Cys Gln Phe Ala Asn Ser Gln Asn Gln
        35                  40                  45

Ser Leu Ser Glu Leu Val Val Phe Trp Gln Asp Gln Glu Asn Leu Val
    50                  55                  60

Leu Asn Glu Val Tyr Leu Gly Lys Glu Lys Phe Asp Ser Val His Ser
65                  70                  75                  80

Lys Tyr Met Gly Arg Thr Ser Phe Asp Ser Asp Ser Trp Thr Leu Arg
                85                  90                  95

Leu His Asn Leu Gln Ile Lys Asp Lys Gly Leu Tyr Gln Cys Ile Ile
            100                 105                 110

His His Lys Lys Pro Thr Gly Met Ile Arg Ile His Gln Met Asn Ser
        115                 120                 125

Glu Leu Ser Val Leu Ala Asn Phe Ser Gln Pro Glu Ile Val Pro Ile
    130                 135                 140

Ser Asn Ile Thr Glu Asn Val Tyr Ile Asn Leu Thr Cys Ser Ser Ile
145                 150                 155                 160

His Gly Tyr Pro Glu Pro Lys Lys Met Ser Val Leu Leu Arg Thr Lys
                165                 170                 175

Asn Ser Thr Ile Glu Tyr Asp Gly Val Met Gln Lys Ser Gln Asp Asn
            180                 185                 190

Val Thr Glu Leu Tyr Asp Val Ser Ile Ser Leu Ser Val Ser Phe Pro
        195                 200                 205

Asp Val Thr Ser Asn Met Thr Ile Phe Cys Ile Leu Glu Thr Asp Lys
    210                 215                 220

Thr Arg Leu Leu Ser Ser Pro Phe Ser Ile Glu Leu Glu Asp Pro Gln
225                 230                 235                 240

Pro Pro Pro Asp His Ile Pro Trp Ile Thr Ala Val Leu Pro Thr Val
                245                 250                 255

Ile Ile Cys Val Met Val Phe Cys Leu Ile Leu Trp Lys Trp Lys Lys
            260                 265                 270

Lys Lys Arg Pro Arg Asn Ser Tyr Lys Cys Gly Thr Asn Thr Met Glu
        275                 280                 285

Arg Glu Glu Ser Glu Gln Thr Lys Lys Arg Glu Lys Ile His Ile Pro
    290                 295                 300

Glu Arg Ser Asp Glu Ala Gln Arg Val Phe Lys Ser Ser Lys Thr Ser
305                 310                 315                 320

Ser Cys Asp Lys Ser Asp Thr Cys Phe
                325
```

<210> SEQ ID NO 3
<211> LENGTH: 290
<212> TYPE: PRT
<213> ORGANISM: Homo sapiens
<220> FEATURE:
<223> OTHER INFORMATION: CD274 (PD-L1, B7-H1)

<400> SEQUENCE: 3

```
Met Arg Ile Phe Ala Val Phe Ile Phe Met Thr Tyr Trp His Leu Leu
```

```
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290


<210> SEQ ID NO 4
<211> LENGTH: 273
<212> TYPE: PRT
<213> ORGANISM: Homo sapiens
<220> FEATURE:
<223> OTHER INFORMATION: PDCD1LG2(PD-L2, CD273)

<400> SEQUENCE: 4

Met Ile Phe Leu Leu Leu Met Leu Ser Leu Glu Leu Gln Leu His Gln
1               5                   10                  15

Ile Ala Ala Leu Phe Thr Val Thr Val Pro Lys Glu Leu Tyr Ile Ile
            20                  25                  30

Glu His Gly Ser Asn Val Thr Leu Glu Cys Asn Phe Asp Thr Gly Ser
        35                  40                  45

His Val Asn Leu Gly Ala Ile Thr Ala Ser Leu Gln Lys Val Glu Asn
    50                  55                  60

Asp Thr Ser Pro His Arg Glu Arg Ala Thr Leu Leu Glu Glu Gln Leu
```

```
65                  70                  75                  80

Pro Leu Gly Lys Ala Ser Phe His Ile Pro Gln Val Gln Val Arg Asp
                85                  90                  95

Glu Gly Gln Tyr Gln Cys Ile Ile Ile Tyr Gly Val Ala Trp Asp Tyr
            100                 105                 110

Lys Tyr Leu Thr Leu Lys Val Lys Ala Ser Tyr Arg Lys Ile Asn Thr
        115                 120                 125

His Ile Leu Lys Val Pro Glu Thr Asp Glu Val Glu Leu Thr Cys Gln
    130                 135                 140

Ala Thr Gly Tyr Pro Leu Ala Glu Val Ser Trp Pro Asn Val Ser Val
145                 150                 155                 160

Pro Ala Asn Thr Ser His Ser Arg Thr Pro Glu Gly Leu Tyr Gln Val
                165                 170                 175

Thr Ser Val Leu Arg Leu Lys Pro Pro Pro Gly Arg Asn Phe Ser Cys
            180                 185                 190

Val Phe Trp Asn Thr His Val Arg Glu Leu Thr Leu Ala Ser Ile Asp
        195                 200                 205

Leu Gln Ser Gln Met Glu Pro Arg Thr His Pro Thr Trp Leu Leu His
    210                 215                 220

Ile Phe Ile Pro Phe Cys Ile Ile Ala Phe Ile Phe Ile Ala Thr Val
225                 230                 235                 240

Ile Ala Leu Arg Lys Gln Leu Cys Gln Lys Leu Tyr Ser Ser Lys Asp
                245                 250                 255

Thr Thr Lys Arg Pro Val Thr Thr Thr Lys Arg Glu Val Asn Ser Ala
            260                 265                 270

Ile


<210> SEQ ID NO 5
<211> LENGTH: 302
<212> TYPE: PRT
<213> ORGANISM: Homo sapiens
<220> FEATURE:
<223> OTHER INFORMATION: ICOSLG(B7RP1, CD275, ICOSL, B7-H2)

<400> SEQUENCE: 5

Met Arg Leu Gly Ser Pro Gly Leu Leu Phe Leu Leu Phe Ser Ser Leu
1               5                   10                  15

Arg Ala Asp Thr Gln Glu Lys Glu Val Arg Ala Met Val Gly Ser Asp
            20                  25                  30

Val Glu Leu Ser Cys Ala Cys Pro Glu Gly Ser Arg Phe Asp Leu Asn
        35                  40                  45

Asp Val Tyr Val Tyr Trp Gln Thr Ser Glu Ser Lys Thr Val Val Thr
    50                  55                  60

Tyr His Ile Pro Gln Asn Ser Ser Leu Glu Asn Val Asp Ser Arg Tyr
65                  70                  75                  80

Arg Asn Arg Ala Leu Met Ser Pro Ala Gly Met Leu Arg Gly Asp Phe
                85                  90                  95

Ser Leu Arg Leu Phe Asn Val Thr Pro Gln Asp Glu Gln Lys Phe His
            100                 105                 110

Cys Leu Val Leu Ser Gln Ser Leu Gly Phe Gln Glu Val Leu Ser Val
        115                 120                 125

Glu Val Thr Leu His Val Ala Ala Asn Phe Ser Val Pro Val Val Ser
    130                 135                 140

Ala Pro His Ser Pro Ser Gln Asp Glu Leu Thr Phe Thr Cys Thr Ser
145                 150                 155                 160
```

```
Ile Asn Gly Tyr Pro Arg Pro Asn Val Tyr Trp Ile Asn Lys Thr Asp
                165                 170                 175

Asn Ser Leu Leu Asp Gln Ala Leu Gln Asn Asp Thr Val Phe Leu Asn
            180                 185                 190

Met Arg Gly Leu Tyr Asp Val Val Ser Val Leu Arg Ile Ala Arg Thr
        195                 200                 205

Pro Ser Val Asn Ile Gly Cys Cys Ile Glu Asn Val Leu Leu Gln Gln
    210                 215                 220

Asn Leu Thr Val Gly Ser Gln Thr Gly Asn Asp Ile Gly Glu Arg Asp
225                 230                 235                 240

Lys Ile Thr Glu Asn Pro Val Ser Thr Gly Glu Lys Asn Ala Ala Thr
                245                 250                 255

Trp Ser Ile Leu Ala Val Leu Cys Leu Leu Val Val Val Ala Val Ala
            260                 265                 270

Ile Gly Trp Val Cys Arg Asp Arg Cys Leu Gln His Ser Tyr Ala Gly
        275                 280                 285

Ala Trp Ala Val Ser Pro Glu Thr Glu Leu Thr Gly His Val
    290                 295                 300


<210> SEQ ID NO 6
<211> LENGTH: 534
<212> TYPE: PRT
<213> ORGANISM: Homo sapiens
<220> FEATURE:
<223> OTHER INFORMATION: CD276(B7-H3)

<400> SEQUENCE: 6

Met Leu Arg Arg Arg Gly Ser Pro Gly Met Gly Val His Val Gly Ala
1               5                   10                  15

Ala Leu Gly Ala Leu Trp Phe Cys Leu Thr Gly Ala Leu Glu Val Gln
            20                  25                  30

Val Pro Glu Asp Pro Val Val Ala Leu Val Gly Thr Asp Ala Thr Leu
        35                  40                  45

Cys Cys Ser Phe Ser Pro Glu Pro Gly Phe Ser Leu Ala Gln Leu Asn
    50                  55                  60

Leu Ile Trp Gln Leu Thr Asp Thr Lys Gln Leu Val His Ser Phe Ala
65                  70                  75                  80

Glu Gly Gln Asp Gln Gly Ser Ala Tyr Ala Asn Arg Thr Ala Leu Phe
                85                  90                  95

Pro Asp Leu Leu Ala Gln Gly Asn Ala Ser Leu Arg Leu Gln Arg Val
            100                 105                 110

Arg Val Ala Asp Glu Gly Ser Phe Thr Cys Phe Val Ser Ile Arg Asp
        115                 120                 125

Phe Gly Ser Ala Ala Val Ser Leu Gln Val Ala Ala Pro Tyr Ser Lys
    130                 135                 140

Pro Ser Met Thr Leu Glu Pro Asn Lys Asp Leu Arg Pro Gly Asp Thr
145                 150                 155                 160

Val Thr Ile Thr Cys Ser Ser Tyr Gln Gly Tyr Pro Glu Ala Glu Val
                165                 170                 175

Phe Trp Gln Asp Gly Gln Gly Val Pro Leu Thr Gly Asn Val Thr Thr
            180                 185                 190

Ser Gln Met Ala Asn Glu Gln Gly Leu Phe Asp Val His Ser Ile Leu
        195                 200                 205

Arg Val Val Leu Gly Ala Asn Gly Thr Tyr Ser Cys Leu Val Arg Asn
    210                 215                 220
```

```
Pro Val Leu Gln Gln Asp Ala His Ser Ser Val Thr Ile Thr Pro Gln
225                 230                 235                 240

Arg Ser Pro Thr Gly Ala Val Glu Val Gln Val Pro Glu Asp Pro Val
                245                 250                 255

Val Ala Leu Val Gly Thr Asp Ala Thr Leu Arg Cys Ser Phe Ser Pro
            260                 265                 270

Glu Pro Gly Phe Ser Leu Ala Gln Leu Asn Leu Ile Trp Gln Leu Thr
        275                 280                 285

Asp Thr Lys Gln Leu Val His Ser Phe Thr Glu Gly Arg Asp Gln Gly
    290                 295                 300

Ser Ala Tyr Ala Asn Arg Thr Ala Leu Phe Pro Asp Leu Leu Ala Gln
305                 310                 315                 320

Gly Asn Ala Ser Leu Arg Leu Gln Arg Val Arg Val Ala Asp Glu Gly
                325                 330                 335

Ser Phe Thr Cys Phe Val Ser Ile Arg Asp Phe Gly Ser Ala Ala Val
            340                 345                 350

Ser Leu Gln Val Ala Ala Pro Tyr Ser Lys Pro Ser Met Thr Leu Glu
        355                 360                 365

Pro Asn Lys Asp Leu Arg Pro Gly Asp Thr Val Thr Ile Thr Cys Ser
    370                 375                 380

Ser Tyr Arg Gly Tyr Pro Glu Ala Glu Val Phe Trp Gln Asp Gly Gln
385                 390                 395                 400

Gly Val Pro Leu Thr Gly Asn Val Thr Thr Ser Gln Met Ala Asn Glu
                405                 410                 415

Gln Gly Leu Phe Asp Val His Ser Val Leu Arg Val Val Leu Gly Ala
            420                 425                 430

Asn Gly Thr Tyr Ser Cys Leu Val Arg Asn Pro Val Leu Gln Gln Asp
        435                 440                 445

Ala His Gly Ser Val Thr Ile Thr Gly Gln Pro Met Thr Phe Pro Pro
    450                 455                 460

Glu Ala Leu Trp Val Thr Val Gly Leu Ser Val Cys Leu Ile Ala Leu
465                 470                 475                 480

Leu Val Ala Leu Ala Phe Val Cys Trp Arg Lys Ile Lys Gln Ser Cys
                485                 490                 495

Glu Glu Glu Asn Ala Gly Ala Glu Asp Gln Asp Gly Glu Gly Glu Gly
            500                 505                 510

Ser Lys Thr Ala Leu Gln Pro Leu Lys His Ser Asp Ser Lys Glu Asp
        515                 520                 525

Asp Gly Gln Glu Ile Ala
    530


<210> SEQ ID NO 7
<211> LENGTH: 282
<212> TYPE: PRT
<213> ORGANISM: Homo sapiens
<220> FEATURE:
<223> OTHER INFORMATION: VTCN1(B7-H4)

<400> SEQUENCE: 7

Met Ala Ser Leu Gly Gln Ile Leu Phe Trp Ser Ile Ile Ser Ile Ile
1               5                   10                  15

Ile Ile Leu Ala Gly Ala Ile Ala Leu Ile Ile Gly Phe Gly Ile Ser
            20                  25                  30

Gly Arg His Ser Ile Thr Val Thr Thr Val Ala Ser Ala Gly Asn Ile
        35                  40                  45
```

Gly Glu Asp Gly Ile Leu Ser Cys Thr Phe Glu Pro Asp Ile Lys Leu
    50                  55                  60

Ser Asp Ile Val Ile Gln Trp Leu Lys Glu Gly Val Leu Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
    130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser His Leu Gln Leu Leu Asn Ser
                245                 250                 255

Lys Ala Ser Leu Cys Val Ser Ser Phe Phe Ala Ile Ser Trp Ala Leu
            260                 265                 270

Leu Pro Leu Ser Pro Tyr Leu Met Leu Lys
        275                 280

<210> SEQ ID NO 8
<211> LENGTH: 220
<212> TYPE: PRT
<213> ORGANISM: Homo sapiens
<220> FEATURE:
<223> OTHER INFORMATION: CD28

<400> SEQUENCE: 8

Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
        35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
        115                 120                 125

```
Asn Gly Thr Ile Ile His Val Lys Gly Lys His Leu Cys Pro Ser Pro
    130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
        195                 200                 205

Tyr Ala Pro Pro Arg Asp Phe Ala Ala Tyr Arg Ser
    210                 215                 220


<210> SEQ ID NO 9
<211> LENGTH: 223
<212> TYPE: PRT
<213> ORGANISM: Homo sapiens
<220> FEATURE:
<223> OTHER INFORMATION: CTLA4

<400> SEQUENCE: 9

Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
            20                  25                  30

Val Phe Cys Lys Ala Met His Val Ala Gln Pro Ala Val Val Leu Ala
        35                  40                  45

Ser Ser Arg Gly Ile Ala Ser Phe Val Cys Glu Tyr Ala Ser Pro Gly
    50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Pro Tyr Tyr Leu Gly Ile Gly
    130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
            180                 185                 190

Arg Ser Pro Leu Thr Thr Gly Val Tyr Val Lys Met Pro Pro Thr Glu
        195                 200                 205

Pro Glu Cys Glu Lys Gln Phe Gln Pro Tyr Phe Ile Pro Ile Asn
    210                 215                 220


<210> SEQ ID NO 10
<211> LENGTH: 288
<212> TYPE: PRT
<213> ORGANISM: Homo sapiens
<220> FEATURE:
<223> OTHER INFORMATION: PDCD1(PD-1)
```

<400> SEQUENCE: 10

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285

<210> SEQ ID NO 11
<211> LENGTH: 199
<212> TYPE: PRT
<213> ORGANISM: Homo sapiens
<220> FEATURE:
<223> OTHER INFORMATION: ICOS

<400> SEQUENCE: 11

Met Lys Ser Gly Leu Trp Tyr Phe Phe Leu Phe Cys Leu Arg Ile Lys
1               5                   10                  15

Val Leu Thr Gly Glu Ile Asn Gly Ser Ala Asn Tyr Glu Met Phe Ile
            20                  25                  30

Phe His Asn Gly Gly Val Gln Ile Leu Cys Lys Tyr Pro Asp Ile Val
        35                  40                  45

Gln Gln Phe Lys Met Gln Leu Leu Lys Gly Gly Gln Ile Leu Cys Asp
    50                  55                  60

Leu Thr Lys Thr Lys Gly Ser Gly Asn Thr Val Ser Ile Lys Ser Leu

```
65                  70                  75                  80

Lys Phe Cys His Ser Gln Leu Ser Asn Asn Ser Val Ser Phe Phe Leu
                85                  90                  95

Tyr Asn Leu Asp His Ser His Ala Asn Tyr Tyr Phe Cys Asn Leu Ser
            100                 105                 110

Ile Phe Asp Pro Pro Pro Phe Lys Val Thr Leu Thr Gly Gly Tyr Leu
        115                 120                 125

His Ile Tyr Glu Ser Gln Leu Cys Cys Gln Leu Lys Phe Trp Leu Pro
    130                 135                 140

Ile Gly Cys Ala Ala Phe Val Val Val Cys Ile Leu Gly Cys Ile Leu
145                 150                 155                 160

Ile Cys Trp Leu Thr Lys Lys Lys Tyr Ser Ser Ser Val His Asp Pro
                165                 170                 175

Asn Gly Glu Tyr Met Phe Met Arg Ala Val Asn Thr Ala Lys Lys Ser
            180                 185                 190

Arg Leu Thr Asp Val Thr Leu
        195


<210> SEQ ID NO 12
<211> LENGTH: 289
<212> TYPE: PRT
<213> ORGANISM: Homo sapiens
<220> FEATURE:
<223> OTHER INFORMATION: BTLA(CD272)

<400> SEQUENCE: 12

Met Lys Thr Leu Pro Ala Met Leu Gly Thr Gly Lys Leu Phe Trp Val
1               5                   10                  15

Phe Phe Leu Ile Pro Tyr Leu Asp Ile Trp Asn Ile His Gly Lys Glu
            20                  25                  30

Ser Cys Asp Val Gln Leu Tyr Ile Lys Arg Gln Ser Glu His Ser Ile
        35                  40                  45

Leu Ala Gly Asp Pro Phe Glu Leu Glu Cys Pro Val Lys Tyr Cys Ala
    50                  55                  60

Asn Arg Pro His Val Thr Trp Cys Lys Leu Asn Gly Thr Thr Cys Val
65                  70                  75                  80

Lys Leu Glu Asp Arg Gln Thr Ser Trp Lys Glu Glu Lys Asn Ile Ser
                85                  90                  95

Phe Phe Ile Leu His Phe Glu Pro Val Leu Pro Asn Asp Asn Gly Ser
            100                 105                 110

Tyr Arg Cys Ser Ala Asn Phe Gln Ser Asn Leu Ile Glu Ser His Ser
        115                 120                 125

Thr Thr Leu Tyr Val Thr Asp Val Lys Ser Ala Ser Glu Arg Pro Ser
    130                 135                 140

Lys Asp Glu Met Ala Ser Arg Pro Trp Leu Leu Tyr Arg Leu Leu Pro
145                 150                 155                 160

Leu Gly Gly Leu Pro Leu Leu Ile Thr Thr Cys Phe Cys Leu Phe Cys
                165                 170                 175

Cys Leu Arg Arg His Gln Gly Lys Gln Asn Glu Leu Ser Asp Thr Ala
            180                 185                 190

Gly Arg Glu Ile Asn Leu Val Asp Ala His Leu Lys Ser Glu Gln Thr
        195                 200                 205

Glu Ala Ser Thr Arg Gln Asn Ser Gln Val Leu Leu Ser Glu Thr Gly
    210                 215                 220

Ile Tyr Asp Asn Asp Pro Asp Leu Cys Phe Arg Met Gln Glu Gly Ser
```

```
225                 230                 235                 240

Glu Val Tyr Ser Asn Pro Cys Leu Glu Glu Asn Lys Pro Gly Ile Val
                245                 250                 255

Tyr Ala Ser Leu Asn His Ser Val Ile Gly Pro Asn Ser Arg Leu Ala
            260                 265                 270

Arg Asn Val Lys Glu Ala Pro Thr Glu Tyr Ala Ser Ile Cys Val Arg
        275                 280                 285

Ser


<210> SEQ ID NO 13
<211> LENGTH: 458
<212> TYPE: PRT
<213> ORGANISM: Homo sapiens
<220> FEATURE:
<223> OTHER INFORMATION: CD4

<400> SEQUENCE: 13

Met Asn Arg Gly Val Pro Phe Arg His Leu Leu Leu Val Leu Gln Leu
1               5                   10                  15

Ala Leu Leu Pro Ala Ala Thr Gln Gly Lys Lys Val Val Leu Gly Lys
            20                  25                  30

Lys Gly Asp Thr Val Glu Leu Thr Cys Thr Ala Ser Gln Lys Lys Ser
        35                  40                  45

Ile Gln Phe His Trp Lys Asn Ser Asn Gln Ile Lys Ile Leu Gly Asn
    50                  55                  60

Gln Gly Ser Phe Leu Thr Lys Gly Pro Ser Lys Leu Asn Asp Arg Ala
65                  70                  75                  80

Asp Ser Arg Arg Ser Leu Trp Asp Gln Gly Asn Phe Pro Leu Ile Ile
                85                  90                  95

Lys Asn Leu Lys Ile Glu Asp Ser Asp Thr Tyr Ile Cys Glu Val Glu
            100                 105                 110

Asp Gln Lys Glu Glu Val Gln Leu Leu Val Phe Gly Leu Thr Ala Asn
        115                 120                 125

Ser Asp Thr His Leu Leu Gln Gly Gln Ser Leu Thr Leu Thr Leu Glu
    130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
            180                 185                 190

Val Glu Phe Lys Ile Asp Ile Val Val Leu Ala Phe Gln Lys Ala Ser
        195                 200                 205

Ser Ile Val Tyr Lys Lys Glu Gly Glu Gln Val Glu Phe Ser Phe Pro
    210                 215                 220

Leu Ala Phe Thr Val Glu Lys Leu Thr Gly Ser Gly Glu Leu Trp Trp
225                 230                 235                 240

Gln Ala Glu Arg Ala Ser Ser Ser Lys Ser Trp Ile Thr Phe Asp Leu
                245                 250                 255

Lys Asn Lys Glu Val Ser Val Lys Arg Val Thr Gln Asp Pro Lys Leu
            260                 265                 270

Gln Met Gly Lys Lys Leu Pro Leu His Leu Thr Leu Pro Gln Ala Leu
        275                 280                 285

Pro Gln Tyr Ala Gly Ser Gly Asn Leu Thr Leu Ala Leu Glu Ala Lys
    290                 295                 300
```

Thr Gly Lys Leu His Gln Glu Val Asn Leu Val Val Met Arg Ala Thr
305 310 315 320

Gln Leu Gln Lys Asn Leu Thr Cys Glu Val Trp Gly Pro Thr Ser Pro
325 330 335

Lys Leu Met Leu Ser Leu Lys Leu Glu Asn Lys Glu Ala Lys Val Ser
340 345 350

Lys Arg Glu Lys Ala Val Trp Val Leu Asn Pro Glu Ala Gly Met Trp
355 360 365

Gln Cys Leu Leu Ser Asp Ser Gly Gln Val Leu Leu Glu Ser Asn Ile
370 375 380

Lys Val Leu Pro Thr Trp Ser Thr Pro Val Gln Pro Met Ala Leu Ile
385 390 395 400

Val Leu Gly Gly Val Ala Gly Leu Leu Leu Phe Ile Gly Leu Gly Ile
405 410 415

Phe Phe Cys Val Arg Cys Arg His Arg Arg Arg Gln Ala Glu Arg Met
420 425 430

Ser Gln Ile Lys Arg Leu Leu Ser Glu Lys Lys Thr Cys Gln Cys Pro
435 440 445

His Arg Phe Gln Lys Thr Cys Ser Pro Ile
450 455

<210> SEQ ID NO 14
<211> LENGTH: 235
<212> TYPE: PRT
<213> ORGANISM: Homo sapiens
<220> FEATURE:
<223> OTHER INFORMATION: CD8A(CD8-alpha)

<400> SEQUENCE: 14

Met Ala Leu Pro Val Thr Ala Leu Leu Leu Pro Leu Ala Leu Leu Leu
1 5 10 15

His Ala Ala Arg Pro Ser Gln Phe Arg Val Ser Pro Leu Asp Arg Thr
20 25 30

Trp Asn Leu Gly Glu Thr Val Glu Leu Lys Cys Gln Val Leu Leu Ser
35 40 45

Asn Pro Thr Ser Gly Cys Ser Trp Leu Phe Gln Pro Arg Gly Ala Ala
50 55 60

Ala Ser Pro Thr Phe Leu Leu Tyr Leu Ser Gln Asn Lys Pro Lys Ala
65 70 75 80

Ala Glu Gly Leu Asp Thr Gln Arg Phe Ser Gly Lys Arg Leu Gly Asp
85 90 95

Thr Phe Val Leu Thr Leu Ser Asp Phe Arg Arg Glu Asn Glu Gly Tyr
100 105 110

Tyr Phe Cys Ser Ala Leu Ser Asn Ser Ile Met Tyr Phe Ser His Phe
115 120 125

Val Pro Val Phe Leu Pro Ala Lys Pro Thr Thr Thr Pro Ala Pro Arg
130 135 140

Pro Pro Thr Pro Ala Pro Thr Ile Ala Ser Gln Pro Leu Ser Leu Arg
145 150 155 160

Pro Glu Ala Cys Arg Pro Ala Ala Gly Gly Ala Val His Thr Arg Gly
165 170 175

Leu Asp Phe Ala Cys Asp Ile Tyr Ile Trp Ala Pro Leu Ala Gly Thr
180 185 190

Cys Gly Val Leu Leu Leu Ser Leu Val Ile Thr Leu Tyr Cys Asn His
195 200 205

```
Arg Asn Arg Arg Arg Val Cys Lys Cys Pro Arg Pro Val Val Lys Ser
    210                 215                 220

Gly Asp Lys Pro Ser Leu Ser Ala Arg Tyr Val
225                 230                 235


<210> SEQ ID NO 15
<211> LENGTH: 210
<212> TYPE: PRT
<213> ORGANISM: Homo sapiens
<220> FEATURE:
<223> OTHER INFORMATION: CD8B(CD8-beta)

<400> SEQUENCE: 15

Met Arg Pro Arg Leu Trp Leu Leu Leu Ala Ala Gln Leu Thr Val Leu
1               5                   10                  15

His Gly Asn Ser Val Leu Gln Gln Thr Pro Ala Tyr Ile Lys Val Gln
            20                  25                  30

Thr Asn Lys Met Val Met Leu Ser Cys Glu Ala Lys Ile Ser Leu Ser
        35                  40                  45

Asn Met Arg Ile Tyr Trp Leu Arg Gln Arg Gln Ala Pro Ser Ser Asp
    50                  55                  60

Ser His His Glu Phe Leu Ala Leu Trp Asp Ser Ala Lys Gly Thr Ile
65                  70                  75                  80

His Gly Glu Glu Val Glu Gln Glu Lys Ile Ala Val Phe Arg Asp Ala
                85                  90                  95

Ser Arg Phe Ile Leu Asn Leu Thr Ser Val Lys Pro Glu Asp Ser Gly
            100                 105                 110

Ile Tyr Phe Cys Met Ile Val Gly Ser Pro Glu Leu Thr Phe Gly Lys
        115                 120                 125

Gly Thr Gln Leu Ser Val Val Asp Phe Leu Pro Thr Thr Ala Gln Pro
    130                 135                 140

Thr Lys Lys Ser Thr Leu Lys Lys Arg Val Cys Arg Leu Pro Arg Pro
145                 150                 155                 160

Glu Thr Gln Lys Gly Pro Leu Cys Ser Pro Ile Thr Leu Gly Leu Leu
                165                 170                 175

Val Ala Gly Val Leu Val Leu Leu Val Ser Leu Gly Val Ala Ile His
            180                 185                 190

Leu Cys Cys Arg Arg Arg Arg Ala Arg Leu Arg Phe Met Lys Gln Phe
        195                 200                 205

Tyr Lys
    210


<210> SEQ ID NO 16
<211> LENGTH: 525
<212> TYPE: PRT
<213> ORGANISM: Homo sapiens
<220> FEATURE:
<223> OTHER INFORMATION: LAG3

<400> SEQUENCE: 16

Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
            20                  25                  30

Trp Ala Gln Glu Gly Ala Pro Ala Gln Leu Pro Cys Ser Pro Thr Ile
        35                  40                  45

Pro Leu Gln Asp Leu Ser Leu Leu Arg Arg Ala Gly Val Thr Trp Gln
```

```
    50                  55                  60

His Gln Pro Asp Ser Gly Pro Pro Ala Ala Ala Pro Gly His Pro Leu
65                  70                  75                  80

Ala Pro Gly Pro His Pro Ala Ala Pro Ser Ser Trp Gly Pro Arg Pro
                85                  90                  95

Arg Arg Tyr Thr Val Leu Ser Val Gly Pro Gly Gly Leu Arg Ser Gly
            100                 105                 110

Arg Leu Pro Leu Gln Pro Arg Val Gln Leu Asp Glu Arg Gly Arg Gln
        115                 120                 125

Arg Gly Asp Phe Ser Leu Trp Leu Arg Pro Ala Arg Arg Ala Asp Ala
    130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
            180                 185                 190

Arg Pro Asp Arg Pro Ala Ser Val His Trp Phe Arg Asn Arg Gly Gln
        195                 200                 205

Gly Arg Val Pro Val Arg Glu Ser Pro His His His Leu Ala Glu Ser
    210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Pro Thr Pro Leu Thr Val Tyr Ala
            260                 265                 270

Gly Ala Gly Ser Arg Val Gly Leu Pro Cys Arg Leu Pro Ala Gly Val
        275                 280                 285

Gly Thr Arg Ser Phe Leu Thr Ala Lys Trp Thr Pro Pro Gly Gly Gly
    290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
                325                 330                 335

Leu Gln Glu Gln Gln Leu Asn Ala Thr Val Thr Leu Ala Ile Ile Thr
            340                 345                 350

Val Thr Pro Lys Ser Phe Gly Ser Pro Gly Ser Leu Gly Lys Leu Leu
        355                 360                 365

Cys Glu Val Thr Pro Val Ser Gly Gln Glu Arg Phe Val Trp Ser Ser
    370                 375                 380

Leu Asp Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu Tyr Gln
                405                 410                 415

Gly Glu Arg Leu Leu Gly Ala Ala Val Tyr Phe Thr Glu Leu Ser Ser
            420                 425                 430

Pro Gly Ala Gln Arg Ser Gly Arg Ala Pro Gly Ala Leu Pro Ala Gly
        435                 440                 445

His Leu Leu Leu Phe Leu Ile Leu Gly Val Leu Ser Leu Leu Leu Leu
    450                 455                 460

Val Thr Gly Ala Phe Gly Phe His Leu Trp Arg Arg Gln Trp Arg Pro
465                 470                 475                 480
```

```
Arg Arg Phe Ser Ala Leu Glu Gln Gly Ile His Pro Pro Gln Ala Gln
                485                 490                 495

Ser Lys Ile Glu Glu Leu Glu Gln Glu Pro Glu Pro Glu Pro Glu Pro
            500                 505                 510

Glu Pro Glu Pro Glu Pro Glu Pro Glu Pro Glu Gln Leu
        515                 520                 525


<210> SEQ ID NO 17
<211> LENGTH: 301
<212> TYPE: PRT
<213> ORGANISM: Homo sapiens
<220> FEATURE:
<223> OTHER INFORMATION: HAVCR2(TIM-3)

<400> SEQUENCE: 17

Met Phe Ser His Leu Pro Phe Asp Cys Val Leu Leu Leu Leu Leu Leu
1               5                   10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
        35                  40                  45

Val Pro Val Cys Trp Gly Lys Gly Ala Cys Pro Val Phe Glu Cys Gly
    50                  55                  60

Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
        115                 120                 125

Ile Lys Pro Ala Lys Val Thr Pro Ala Pro Thr Arg Gln Arg Asp Phe
    130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
            180                 185                 190

Arg Asp Ser Gly Ala Thr Ile Arg Ile Gly Ile Tyr Ile Gly Ala Gly
        195                 200                 205

Ile Cys Ala Gly Leu Ala Leu Ala Leu Ile Phe Gly Ala Leu Ile Phe
    210                 215                 220

Lys Trp Tyr Ser His Ser Lys Glu Lys Ile Gln Asn Leu Ser Leu Ile
225                 230                 235                 240

Ser Leu Ala Asn Leu Pro Pro Ser Gly Leu Ala Asn Ala Val Ala Glu
                245                 250                 255

Gly Ile Arg Ser Glu Glu Asn Ile Tyr Thr Ile Glu Glu Asn Val Tyr
            260                 265                 270

Glu Val Glu Glu Pro Asn Glu Tyr Tyr Cys Tyr Val Ser Ser Arg Gln
        275                 280                 285

Gln Pro Ser Gln Pro Leu Gly Cys Arg Phe Ala Met Pro
    290                 295                 300


<210> SEQ ID NO 18
```

<211> LENGTH: 526
<212> TYPE: PRT
<213> ORGANISM: Homo sapiens
<220> FEATURE:
<223> OTHER INFORMATION: CEACAM1

<400> SEQUENCE: 18

```
Met Gly His Leu Ser Ala Pro Leu His Arg Val Arg Val Pro Trp Gln
1               5                   10                  15

Gly Leu Leu Leu Thr Ala Ser Leu Leu Thr Phe Trp Asn Pro Pro Thr
            20                  25                  30

Thr Ala Gln Leu Thr Thr Glu Ser Met Pro Phe Asn Val Ala Glu Gly
        35                  40                  45

Lys Glu Val Leu Leu Leu Val His Asn Leu Pro Gln Gln Leu Phe Gly
    50                  55                  60

Tyr Ser Trp Tyr Lys Gly Glu Arg Val Asp Gly Asn Arg Gln Ile Val
65                  70                  75                  80

Gly Tyr Ala Ile Gly Thr Gln Gln Ala Thr Pro Gly Pro Ala Asn Ser
                85                  90                  95

Gly Arg Glu Thr Ile Tyr Pro Asn Ala Ser Leu Leu Ile Gln Asn Val
            100                 105                 110

Thr Gln Asn Asp Thr Gly Phe Tyr Thr Leu Gln Val Ile Lys Ser Asp
        115                 120                 125

Leu Val Asn Glu Glu Ala Thr Gly Gln Phe His Val Tyr Pro Glu Leu
    130                 135                 140

Pro Lys Pro Ser Ile Ser Ser Asn Asn Ser Asn Pro Val Glu Asp Lys
145                 150                 155                 160

Asp Ala Val Ala Phe Thr Cys Glu Pro Glu Thr Gln Asp Thr Thr Tyr
                165                 170                 175

Leu Trp Trp Ile Asn Asn Gln Ser Leu Pro Val Ser Pro Arg Leu Gln
            180                 185                 190

Leu Ser Asn Gly Asn Arg Thr Leu Thr Leu Leu Ser Val Thr Arg Asn
        195                 200                 205

Asp Thr Gly Pro Tyr Glu Cys Glu Ile Gln Asn Pro Val Ser Ala Asn
    210                 215                 220

Arg Ser Asp Pro Val Thr Leu Asn Val Thr Tyr Gly Pro Asp Thr Pro
225                 230                 235                 240

Thr Ile Ser Pro Ser Asp Thr Tyr Tyr Arg Pro Gly Ala Asn Leu Ser
                245                 250                 255

Leu Ser Cys Tyr Ala Ala Ser Asn Pro Pro Ala Gln Tyr Ser Trp Leu
            260                 265                 270

Ile Asn Gly Thr Phe Gln Gln Ser Thr Gln Glu Leu Phe Ile Pro Asn
        275                 280                 285

Ile Thr Val Asn Asn Ser Gly Ser Tyr Thr Cys His Ala Asn Asn Ser
    290                 295                 300

Val Thr Gly Cys Asn Arg Thr Thr Val Lys Thr Ile Ile Val Thr Glu
305                 310                 315                 320

Leu Ser Pro Val Val Ala Lys Pro Gln Ile Lys Ala Ser Lys Thr Thr
                325                 330                 335

Val Thr Gly Asp Lys Asp Ser Val Asn Leu Thr Cys Ser Thr Asn Asp
            340                 345                 350

Thr Gly Ile Ser Ile Arg Trp Phe Phe Lys Asn Gln Ser Leu Pro Ser
        355                 360                 365

Ser Glu Arg Met Lys Leu Ser Gln Gly Asn Thr Thr Leu Ser Ile Asn
    370                 375                 380
```

Pro Val Lys Arg Glu Asp Ala Gly Thr Tyr Trp Cys Glu Val Phe Asn
385 390 395 400

Pro Ile Ser Lys Asn Gln Ser Asp Pro Ile Met Leu Asn Val Asn Tyr
405 410 415

Asn Ala Leu Pro Gln Glu Asn Gly Leu Ser Pro Gly Ala Ile Ala Gly
420 425 430

Ile Val Ile Gly Val Val Ala Leu Val Ala Leu Ile Ala Val Ala Leu
435 440 445

Ala Cys Phe Leu His Phe Gly Lys Thr Gly Arg Ala Ser Asp Gln Arg
450 455 460

Asp Leu Thr Glu His Lys Pro Ser Val Ser Asn His Thr Gln Asp His
465 470 475 480

Ser Asn Asp Pro Pro Asn Lys Met Asn Glu Val Thr Tyr Ser Thr Leu
485 490 495

Asn Phe Glu Ala Gln Gln Pro Thr Gln Pro Thr Ser Ala Ser Pro Ser
500 505 510

Leu Thr Ala Thr Glu Ile Ile Tyr Ser Glu Val Lys Lys Gln
515 520 525

<210> SEQ ID NO 19
<211> LENGTH: 244
<212> TYPE: PRT
<213> ORGANISM: Homo sapiens
<220> FEATURE:
<223> OTHER INFORMATION: TIGIT

<400> SEQUENCE: 19

Met Arg Trp Cys Leu Leu Leu Ile Trp Ala Gln Gly Leu Arg Gln Ala
1 5 10 15

Pro Leu Ala Ser Gly Met Met Thr Gly Thr Ile Glu Thr Thr Gly Asn
20 25 30

Ile Ser Ala Glu Lys Gly Gly Ser Ile Ile Leu Gln Cys His Leu Ser
35 40 45

Ser Thr Thr Ala Gln Val Thr Gln Val Asn Trp Glu Gln Gln Asp Gln
50 55 60

Leu Leu Ala Ile Cys Asn Ala Asp Leu Gly Trp His Ile Ser Pro Ser
65 70 75 80

Phe Lys Asp Arg Val Ala Pro Gly Pro Gly Leu Gly Leu Thr Leu Gln
85 90 95

Ser Leu Thr Val Asn Asp Thr Gly Glu Tyr Phe Cys Ile Tyr His Thr
100 105 110

Tyr Pro Asp Gly Thr Tyr Thr Gly Arg Ile Phe Leu Glu Val Leu Glu
115 120 125

Ser Ser Val Ala Glu His Gly Ala Arg Phe Gln Ile Pro Leu Leu Gly
130 135 140

Ala Met Ala Ala Thr Leu Val Val Ile Cys Thr Ala Val Ile Val Val
145 150 155 160

Val Ala Leu Thr Arg Lys Lys Lys Ala Leu Arg Ile His Ser Val Glu
165 170 175

Gly Asp Leu Arg Arg Lys Ser Ala Gly Gln Glu Glu Trp Ser Pro Ser
180 185 190

Ala Pro Ser Pro Pro Gly Ser Cys Val Gln Ala Glu Ala Ala Pro Ala
195 200 205

Gly Leu Cys Gly Glu Gln Arg Gly Glu Asp Cys Ala Glu Leu His Asp
210 215 220

```
Tyr Phe Asn Val Leu Ser Tyr Arg Ser Leu Gly Asn Cys Ser Phe Phe
225                 230                 235                 240

Thr Glu Thr Gly


<210> SEQ ID NO 20
<211> LENGTH: 417
<212> TYPE: PRT
<213> ORGANISM: Homo sapiens
<220> FEATURE:
<223> OTHER INFORMATION: PVR(CD155)

<400> SEQUENCE: 20

Met Ala Arg Ala Met Ala Ala Ala Trp Pro Leu Leu Leu Val Ala Leu
1               5                   10                  15

Leu Val Leu Ser Trp Pro Pro Pro Gly Thr Gly Asp Val Val Val Gln
            20                  25                  30

Ala Pro Thr Gln Val Pro Gly Phe Leu Gly Asp Ser Val Thr Leu Pro
        35                  40                  45

Cys Tyr Leu Gln Val Pro Asn Met Glu Val Thr His Val Ser Gln Leu
    50                  55                  60

Thr Trp Ala Arg His Gly Glu Ser Gly Ser Met Ala Val Phe His Gln
65                  70                  75                  80

Thr Gln Gly Pro Ser Tyr Ser Glu Ser Lys Arg Leu Glu Phe Val Ala
                85                  90                  95

Ala Arg Leu Gly Ala Glu Leu Arg Asn Ala Ser Leu Arg Met Phe Gly
            100                 105                 110

Leu Arg Val Glu Asp Glu Gly Asn Tyr Thr Cys Leu Phe Val Thr Phe
        115                 120                 125

Pro Gln Gly Ser Arg Ser Val Asp Ile Trp Leu Arg Val Leu Ala Lys
    130                 135                 140

Pro Gln Asn Thr Ala Glu Val Gln Lys Val Gln Leu Thr Gly Glu Pro
145                 150                 155                 160

Val Pro Met Ala Arg Cys Val Ser Thr Gly Gly Arg Pro Pro Ala Gln
                165                 170                 175

Ile Thr Trp His Ser Asp Leu Gly Gly Met Pro Asn Thr Ser Gln Val
            180                 185                 190

Pro Gly Phe Leu Ser Gly Thr Val Thr Val Thr Ser Leu Trp Ile Leu
        195                 200                 205

Val Pro Ser Ser Gln Val Asp Gly Lys Asn Val Thr Cys Lys Val Glu
    210                 215                 220

His Glu Ser Phe Glu Lys Pro Gln Leu Leu Thr Val Asn Leu Thr Val
225                 230                 235                 240

Tyr Tyr Pro Pro Glu Val Ser Ile Ser Gly Tyr Asp Asn Asn Trp Tyr
                245                 250                 255

Leu Gly Gln Asn Glu Ala Thr Leu Thr Cys Asp Ala Arg Ser Asn Pro
            260                 265                 270

Glu Pro Thr Gly Tyr Asn Trp Ser Thr Thr Met Gly Pro Leu Pro Pro
        275                 280                 285

Phe Ala Val Ala Gln Gly Ala Gln Leu Leu Ile Arg Pro Val Asp Lys
    290                 295                 300

Pro Ile Asn Thr Thr Leu Ile Cys Asn Val Thr Asn Ala Leu Gly Ala
305                 310                 315                 320

Arg Gln Ala Glu Leu Thr Val Gln Val Lys Glu Gly Pro Pro Ser Glu
                325                 330                 335
```

His Ser Gly Ile Ser Arg Asn Ala Ile Ile Phe Leu Val Leu Gly Ile
340 345 350

Leu Val Phe Leu Ile Leu Leu Gly Ile Gly Ile Tyr Phe Tyr Trp Ser
355 360 365

Lys Cys Ser Arg Glu Val Leu Trp His Cys His Leu Cys Pro Ser Ser
370 375 380

Thr Glu His Ala Ser Ala Ser Ala Asn Gly His Val Ser Tyr Ser Ala
385 390 395 400

Val Ser Arg Glu Asn Ser Ser Ser Gln Asp Pro Gln Thr Glu Gly Thr
405 410 415

Arg

<210> SEQ ID NO 21
<211> LENGTH: 538
<212> TYPE: PRT
<213> ORGANISM: Homo sapiens
<220> FEATURE:
<223> OTHER INFORMATION: PVRL2(CD112)

<400> SEQUENCE: 21

Met Ala Arg Ala Ala Ala Leu Leu Pro Ser Arg Ser Pro Pro Thr Pro
1 5 10 15

Leu Leu Trp Pro Leu Leu Leu Leu Leu Leu Leu Glu Thr Gly Ala Gln
20 25 30

Asp Val Arg Val Gln Val Leu Pro Glu Val Arg Gly Gln Leu Gly Gly
35 40 45

Thr Val Glu Leu Pro Cys His Leu Leu Pro Pro Val Pro Gly Leu Tyr
50 55 60

Ile Ser Leu Val Thr Trp Gln Arg Pro Asp Ala Pro Ala Asn His Gln
65 70 75 80

Asn Val Ala Ala Phe His Pro Lys Met Gly Pro Ser Phe Pro Ser Pro
85 90 95

Lys Pro Gly Ser Glu Arg Leu Ser Phe Val Ser Ala Lys Gln Ser Thr
100 105 110

Gly Gln Asp Thr Glu Ala Glu Leu Gln Asp Ala Thr Leu Ala Leu His
115 120 125

Gly Leu Thr Val Glu Asp Glu Gly Asn Tyr Thr Cys Glu Phe Ala Thr
130 135 140

Phe Pro Lys Gly Ser Val Arg Gly Met Thr Trp Leu Arg Val Ile Ala
145 150 155 160

Lys Pro Lys Asn Gln Ala Glu Ala Gln Lys Val Thr Phe Ser Gln Asp
165 170 175

Pro Thr Thr Val Ala Leu Cys Ile Ser Lys Glu Gly Arg Pro Pro Ala
180 185 190

Arg Ile Ser Trp Leu Ser Ser Leu Asp Trp Glu Ala Lys Glu Thr Gln
195 200 205

Val Ser Gly Thr Leu Ala Gly Thr Val Thr Val Thr Ser Arg Phe Thr
210 215 220

Leu Val Pro Ser Gly Arg Ala Asp Gly Val Thr Val Thr Cys Lys Val
225 230 235 240

Glu His Glu Ser Phe Glu Glu Pro Ala Leu Ile Pro Val Thr Leu Ser
245 250 255

Val Arg Tyr Pro Pro Glu Val Ser Ile Ser Gly Tyr Asp Asp Asn Trp
260 265 270

Tyr Leu Gly Arg Thr Asp Ala Thr Leu Ser Cys Asp Val Arg Ser Asn

```
        275                 280                 285

Pro Glu Pro Thr Gly Tyr Asp Trp Ser Thr Thr Ser Gly Thr Phe Pro
    290                 295                 300

Thr Ser Ala Val Ala Gln Gly Ser Gln Leu Val Ile His Ala Val Asp
305                 310                 315                 320

Ser Leu Phe Asn Thr Thr Phe Val Cys Thr Val Thr Asn Ala Val Gly
                325                 330                 335

Met Gly Arg Ala Glu Gln Val Ile Phe Val Arg Glu Thr Pro Asn Thr
            340                 345                 350

Ala Gly Ala Gly Ala Thr Gly Gly Ile Ile Gly Gly Ile Ile Ala Ala
        355                 360                 365

Ile Ile Ala Thr Ala Val Ala Ala Thr Gly Ile Leu Ile Cys Arg Gln
    370                 375                 380

Gln Arg Lys Glu Gln Thr Leu Gln Gly Ala Glu Glu Asp Glu Asp Leu
385                 390                 395                 400

Glu Gly Pro Pro Ser Tyr Lys Pro Pro Thr Pro Lys Ala Lys Leu Glu
                405                 410                 415

Ala Gln Glu Met Pro Ser Gln Leu Phe Thr Leu Gly Ala Ser Glu His
            420                 425                 430

Ser Pro Leu Lys Thr Pro Tyr Phe Asp Ala Gly Ala Ser Cys Thr Glu
        435                 440                 445

Gln Glu Met Pro Arg Tyr His Glu Leu Pro Thr Leu Glu Glu Arg Ser
    450                 455                 460

Gly Pro Leu His Pro Gly Ala Thr Ser Leu Gly Ser Pro Ile Pro Val
465                 470                 475                 480

Pro Pro Gly Pro Pro Ala Val Glu Asp Val Ser Leu Asp Leu Glu Asp
                485                 490                 495

Glu Glu Gly Glu Glu Glu Glu Glu Tyr Leu Asp Lys Ile Asn Pro Ile
            500                 505                 510

Tyr Asp Ala Leu Ser Tyr Ser Ser Pro Ser Asp Ser Tyr Gln Gly Lys
        515                 520                 525

Gly Phe Val Met Ser Arg Ala Met Tyr Val
    530                 535
```

<210> SEQ ID NO 22
<211> LENGTH: 336
<212> TYPE: PRT
<213> ORGANISM: Homo sapiens
<220> FEATURE:
<223> OTHER INFORMATION: CD226

<400> SEQUENCE: 22

```
Met Asp Tyr Pro Thr Leu Leu Leu Ala Leu Leu His Val Tyr Arg Ala
1               5                   10                  15

Leu Cys Glu Glu Val Leu Trp His Thr Ser Val Pro Phe Ala Glu Asn
            20                  25                  30

Met Ser Leu Glu Cys Val Tyr Pro Ser Met Gly Ile Leu Thr Gln Val
        35                  40                  45

Glu Trp Phe Lys Ile Gly Thr Gln Gln Asp Ser Ile Ala Ile Phe Ser
    50                  55                  60

Pro Thr His Gly Met Val Ile Arg Lys Pro Tyr Ala Glu Arg Val Tyr
65                  70                  75                  80

Phe Leu Asn Ser Thr Met Ala Ser Asn Asn Met Thr Leu Phe Phe Arg
                85                  90                  95

Asn Ala Ser Glu Asp Asp Val Gly Tyr Tyr Ser Cys Ser Leu Tyr Thr
```

```
            100                 105                 110

Tyr Pro Gln Gly Thr Trp Gln Lys Val Ile Gln Val Val Gln Ser Asp
        115                 120                 125

Ser Phe Glu Ala Ala Val Pro Ser Asn Ser His Ile Val Ser Glu Pro
    130                 135                 140

Gly Lys Asn Val Thr Leu Thr Cys Gln Pro Gln Met Thr Trp Pro Val
145                 150                 155                 160

Gln Ala Val Arg Trp Glu Lys Ile Gln Pro Arg Gln Ile Asp Leu Leu
                165                 170                 175

Thr Tyr Cys Asn Leu Val His Gly Arg Asn Phe Thr Ser Lys Phe Pro
            180                 185                 190

Arg Gln Ile Val Ser Asn Cys Ser His Gly Arg Trp Ser Val Ile Val
        195                 200                 205

Ile Pro Asp Val Thr Val Ser Asp Ser Gly Leu Tyr Arg Cys Tyr Leu
    210                 215                 220

Gln Ala Ser Ala Gly Glu Asn Glu Thr Phe Val Met Arg Leu Thr Val
225                 230                 235                 240

Ala Glu Gly Lys Thr Asp Asn Gln Tyr Thr Leu Phe Val Ala Gly Gly
                245                 250                 255

Thr Val Leu Leu Leu Leu Phe Val Ile Ser Ile Thr Thr Ile Ile Val
            260                 265                 270

Ile Phe Leu Asn Arg Arg Arg Arg Arg Glu Arg Arg Asp Leu Phe Thr
        275                 280                 285

Glu Ser Trp Asp Thr Gln Lys Ala Pro Asn Asn Tyr Arg Ser Pro Ile
    290                 295                 300

Ser Thr Ser Gln Pro Thr Asn Gln Ser Met Asp Asp Thr Arg Glu Asp
305                 310                 315                 320

Ile Tyr Val Asn Tyr Pro Thr Phe Ser Arg Arg Pro Lys Thr Arg Val
                325                 330                 335


<210> SEQ ID NO 23
<211> LENGTH: 351
<212> TYPE: PRT
<213> ORGANISM: Homo sapiens
<220> FEATURE:
<223> OTHER INFORMATION: CD2

<400> SEQUENCE: 23

Met Ser Phe Pro Cys Lys Phe Val Ala Ser Phe Leu Leu Ile Phe Asn
1               5                   10                  15

Val Ser Ser Lys Gly Ala Val Ser Lys Glu Ile Thr Asn Ala Leu Glu
            20                  25                  30

Thr Trp Gly Ala Leu Gly Gln Asp Ile Asn Leu Asp Ile Pro Ser Phe
        35                  40                  45

Gln Met Ser Asp Asp Ile Asp Asp Ile Lys Trp Glu Lys Thr Ser Asp
    50                  55                  60

Lys Lys Lys Ile Ala Gln Phe Arg Lys Glu Lys Glu Thr Phe Lys Glu
65                  70                  75                  80

Lys Asp Thr Tyr Lys Leu Phe Lys Asn Gly Thr Leu Lys Ile Lys His
                85                  90                  95

Leu Lys Thr Asp Asp Gln Asp Ile Tyr Lys Val Ser Ile Tyr Asp Thr
            100                 105                 110

Lys Gly Lys Asn Val Leu Glu Lys Ile Phe Asp Leu Lys Ile Gln Glu
        115                 120                 125

Arg Val Ser Lys Pro Lys Ile Ser Trp Thr Cys Ile Asn Thr Thr Leu
```

130 135 140

Thr Cys Glu Val Met Asn Gly Thr Asp Pro Glu Leu Asn Leu Tyr Gln
145 150 155 160

Asp Gly Lys His Leu Lys Leu Ser Gln Arg Val Ile Thr His Lys Trp
165 170 175

Thr Thr Ser Leu Ser Ala Lys Phe Lys Cys Thr Ala Gly Asn Lys Val
180 185 190

Ser Lys Glu Ser Ser Val Glu Pro Val Ser Cys Pro Glu Lys Gly Leu
195 200 205

Asp Ile Tyr Leu Ile Ile Gly Ile Cys Gly Gly Gly Ser Leu Leu Met
210 215 220

Val Phe Val Ala Leu Leu Val Phe Tyr Ile Thr Lys Arg Lys Lys Gln
225 230 235 240

Arg Ser Arg Arg Asn Asp Glu Glu Leu Glu Thr Arg Ala His Arg Val
245 250 255

Ala Thr Glu Glu Arg Gly Arg Lys Pro His Gln Ile Pro Ala Ser Thr
260 265 270

Pro Gln Asn Pro Ala Thr Ser Gln His Pro Pro Pro Pro Pro Gly His
275 280 285

Arg Ser Gln Ala Pro Ser His Arg Pro Pro Pro Pro Gly His Arg Val
290 295 300

Gln His Gln Pro Gln Lys Arg Pro Pro Ala Pro Ser Gly Thr Gln Val
305 310 315 320

His Gln Gln Lys Gly Pro Pro Leu Pro Arg Pro Arg Val Gln Pro Lys
325 330 335

Pro Pro His Gly Ala Ala Glu Asn Ser Leu Ser Pro Ser Ser Asn
340 345 350

<210> SEQ ID NO 24
<211> LENGTH: 180
<212> TYPE: PRT
<213> ORGANISM: Homo sapiens
<220> FEATURE:
<223> OTHER INFORMATION: CD160

<400> SEQUENCE: 24

Met Leu Leu Glu Pro Gly Arg Gly Cys Cys Ala Leu Ala Ile Leu Leu
1 5 10 15

Ala Ile Val Asp Ile Gln Ser Gly Gly Cys Ile Asn Ile Thr Ser Ser
20 25 30

Ala Ser Gln Glu Gly Thr Arg Leu Asn Leu Ile Cys Thr Val Trp His
35 40 45

Lys Lys Glu Glu Ala Glu Gly Phe Val Val Phe Leu Cys Lys Asp Arg
50 55 60

Ser Gly Asp Cys Ser Pro Glu Thr Ser Leu Lys Gln Leu Arg Leu Lys
65 70 75 80

Arg Asp Pro Gly Ile Asp Gly Val Gly Glu Ile Ser Ser Gln Leu Met
85 90 95

Phe Thr Ile Ser Gln Val Thr Pro Leu His Ser Gly Thr Tyr Gln Cys
100 105 110

Cys Ala Arg Ser Gln Lys Ser Gly Ile Arg Leu Gln Gly His Phe Phe
115 120 125

Ser Ile Leu Phe Thr Glu Thr Gly Asn Tyr Thr Val Thr Gly Leu Lys
130 135 140

Gln Arg Gln His Leu Glu Phe Ser His Asn Glu Gly Thr Leu Ser Ser 145 150 155 160

Gly Phe Leu Gln Glu Lys Val Trp Val Met Leu Val Thr Ser Leu Val
165 170 175

Ala Leu Gln Ala
180

<210> SEQ ID NO 25
<211> LENGTH: 278
<212> TYPE: PRT
<213> ORGANISM: Homo sapiens
<220> FEATURE:
<223> OTHER INFORMATION: CD200

<400> SEQUENCE: 25

Met Glu Arg Leu Val Ile Arg Met Pro Phe Ser His Leu Ser Thr Tyr
1 5 10 15

Ser Leu Val Trp Val Met Ala Ala Val Val Leu Cys Thr Ala Gln Val
20 25 30

Gln Val Val Thr Gln Asp Glu Arg Glu Gln Leu Tyr Thr Pro Ala Ser
35 40 45

Leu Lys Cys Ser Leu Gln Asn Ala Gln Glu Ala Leu Ile Val Thr Trp
50 55 60

Gln Lys Lys Lys Ala Val Ser Pro Glu Asn Met Val Thr Phe Ser Glu
65 70 75 80

Asn His Gly Val Val Ile Gln Pro Ala Tyr Lys Asp Lys Ile Asn Ile
85 90 95

Thr Gln Leu Gly Leu Gln Asn Ser Thr Ile Thr Phe Trp Asn Ile Thr
100 105 110

Leu Glu Asp Glu Gly Cys Tyr Met Cys Leu Phe Asn Thr Phe Gly Phe
115 120 125

Gly Lys Ile Ser Gly Thr Ala Cys Leu Thr Val Tyr Val Gln Pro Ile
130 135 140

Val Ser Leu His Tyr Lys Phe Ser Glu Asp His Leu Asn Ile Thr Cys
145 150 155 160

Ser Ala Thr Ala Arg Pro Ala Pro Met Val Phe Trp Lys Val Pro Arg
165 170 175

Ser Gly Ile Glu Asn Ser Thr Val Thr Leu Ser His Pro Asn Gly Thr
180 185 190

Thr Ser Val Thr Ser Ile Leu His Ile Lys Asp Pro Lys Asn Gln Val
195 200 205

Gly Lys Glu Val Ile Cys Gln Val Leu His Leu Gly Thr Val Thr Asp
210 215 220

Phe Lys Gln Thr Val Asn Lys Gly Tyr Trp Phe Ser Val Pro Leu Leu
225 230 235 240

Leu Ser Ile Val Ser Leu Val Ile Leu Leu Val Leu Ile Ser Ile Leu
245 250 255

Leu Tyr Trp Lys Arg His Arg Asn Gln Asp Arg Gly Glu Leu Ser Gln
260 265 270

Gly Val Gln Lys Met Thr
275

<210> SEQ ID NO 26
<211> LENGTH: 325
<212> TYPE: PRT
<213> ORGANISM: Homo sapiens
<220> FEATURE:
<223> OTHER INFORMATION: CD200R1(CD200R)

```
<400> SEQUENCE: 26

Met Leu Cys Pro Trp Arg Thr Ala Asn Leu Gly Leu Leu Leu Ile Leu
1               5                   10                  15

Thr Ile Phe Leu Val Ala Ala Ser Ser Ser Leu Cys Met Asp Glu Lys
            20                  25                  30

Gln Ile Thr Gln Asn Tyr Ser Lys Val Leu Ala Glu Val Asn Thr Ser
        35                  40                  45

Trp Pro Val Lys Met Ala Thr Asn Ala Val Leu Cys Cys Pro Pro Ile
    50                  55                  60

Ala Leu Arg Asn Leu Ile Ile Ile Thr Trp Glu Ile Ile Leu Arg Gly
65                  70                  75                  80

Gln Pro Ser Cys Thr Lys Ala Tyr Arg Lys Glu Thr Asn Glu Thr Lys
                85                  90                  95

Glu Thr Asn Cys Thr Asp Glu Arg Ile Thr Trp Val Ser Arg Pro Asp
            100                 105                 110

Gln Asn Ser Asp Leu Gln Ile Arg Pro Val Ala Ile Thr His Asp Gly
        115                 120                 125

Tyr Tyr Arg Cys Ile Met Val Thr Pro Asp Gly Asn Phe His Arg Gly
    130                 135                 140

Tyr His Leu Gln Val Leu Val Thr Pro Glu Val Thr Leu Phe Gln Asn
145                 150                 155                 160

Arg Asn Arg Thr Ala Val Cys Lys Ala Val Ala Gly Lys Pro Ala Ala
                165                 170                 175

Gln Ile Ser Trp Ile Pro Glu Gly Asp Cys Ala Thr Lys Gln Glu Tyr
            180                 185                 190

Trp Ser Asn Gly Thr Val Thr Val Lys Ser Thr Cys His Trp Glu Val
        195                 200                 205

His Asn Val Ser Thr Val Thr Cys His Val Ser His Leu Thr Gly Asn
    210                 215                 220

Lys Ser Leu Tyr Ile Glu Leu Leu Pro Val Pro Gly Ala Lys Lys Ser
225                 230                 235                 240

Ala Lys Leu Tyr Ile Pro Tyr Ile Ile Leu Thr Ile Ile Ile Leu Thr
                245                 250                 255

Ile Val Gly Phe Ile Trp Leu Leu Lys Val Asn Gly Cys Arg Lys Tyr
            260                 265                 270

Lys Leu Asn Lys Thr Glu Ser Thr Pro Val Val Glu Glu Asp Glu Met
        275                 280                 285

Gln Pro Tyr Ala Ser Tyr Thr Glu Lys Asn Asn Pro Leu Tyr Asp Thr
    290                 295                 300

Thr Asn Lys Val Lys Ala Ser Glu Ala Leu Gln Ser Glu Val Asp Thr
305                 310                 315                 320

Asp Leu His Thr Leu
                325


<210> SEQ ID NO 27
<211> LENGTH: 201
<212> TYPE: PRT
<213> ORGANISM: Homo sapiens
<220> FEATURE:
<223> OTHER INFORMATION: NC R3 (NKp30)

<400> SEQUENCE: 27

Met Ala Trp Met Leu Leu Leu Ile Leu Ile Met Val His Pro Gly Ser
1               5                   10                  15
```

Cys Ala Leu Trp Val Ser Gln Pro Pro Glu Ile Arg Thr Leu Glu Gly
20 25 30

Ser Ser Ala Phe Leu Pro Cys Ser Phe Asn Ala Ser Gln Gly Arg Leu
35 40 45

Ala Ile Gly Ser Val Thr Trp Phe Arg Asp Glu Val Val Pro Gly Lys
50 55 60

Glu Val Arg Asn Gly Thr Pro Glu Phe Arg Gly Arg Leu Ala Pro Leu
65 70 75 80

Ala Ser Ser Arg Phe Leu His Asp His Gln Ala Glu Leu His Ile Arg
85 90 95

Asp Val Arg Gly His Asp Ala Ser Ile Tyr Val Cys Arg Val Glu Val
100 105 110

Leu Gly Leu Gly Val Gly Thr Gly Asn Gly Thr Arg Leu Val Val Glu
115 120 125

Lys Glu His Pro Gln Leu Gly Ala Gly Thr Val Leu Leu Leu Arg Ala
130 135 140

Gly Phe Tyr Ala Val Ser Phe Leu Ser Val Ala Val Gly Ser Thr Val
145 150 155 160

Tyr Tyr Gln Gly Lys Cys Leu Thr Trp Lys Gly Pro Arg Arg Gln Leu
165 170 175

Pro Ala Val Val Pro Ala Pro Leu Pro Pro Pro Cys Gly Ser Ser Ala
180 185 190

His Leu Leu Pro Pro Val Pro Gly Gly
195 200

<210> SEQ ID NO 28
<211> LENGTH: 208
<212> TYPE: PRT
<213> ORGANISM: Homo sapiens
<220> FEATURE:
<223> OTHER INFORMATION: CD80(B7-1) ECD

<400> SEQUENCE: 28

Val Ile His Val Thr Lys Glu Val Lys Glu Val Ala Thr Leu Ser Cys
1 5 10 15

Gly His Asn Val Ser Val Glu Glu Leu Ala Gln Thr Arg Ile Tyr Trp
20 25 30

Gln Lys Glu Lys Lys Met Val Leu Thr Met Met Ser Gly Asp Met Asn
35 40 45

Ile Trp Pro Glu Tyr Lys Asn Arg Thr Ile Phe Asp Ile Thr Asn Asn
50 55 60

Leu Ser Ile Val Ile Leu Ala Leu Arg Pro Ser Asp Glu Gly Thr Tyr
65 70 75 80

Glu Cys Val Val Leu Lys Tyr Glu Lys Asp Ala Phe Lys Arg Glu His
85 90 95

Leu Ala Glu Val Thr Leu Ser Val Lys Ala Asp Phe Pro Thr Pro Ser
100 105 110

Ile Ser Asp Phe Glu Ile Pro Thr Ser Asn Ile Arg Arg Ile Ile Cys
115 120 125

Ser Thr Ser Gly Gly Phe Pro Glu Pro His Leu Ser Trp Leu Glu Asn
130 135 140

Gly Glu Glu Leu Asn Ala Ile Asn Thr Thr Val Ser Gln Asp Pro Glu
145 150 155 160

Thr Glu Leu Tyr Ala Val Ser Ser Lys Leu Asp Phe Asn Met Thr Thr
165 170 175

Asn His Ser Phe Met Cys Leu Ile Lys Tyr Gly His Leu Arg Val Asn
180 185 190

Gln Thr Phe Asn Trp Asn Thr Thr Lys Gln Glu His Phe Pro Asp Asn
195 200 205

<210> SEQ ID NO 29
<211> LENGTH: 224
<212> TYPE: PRT
<213> ORGANISM: Homo sapiens
<220> FEATURE:
<223> OTHER INFORMATION: CD86(B7-2) ECD

<400> SEQUENCE: 29

Ala Pro Leu Lys Ile Gln Ala Tyr Phe Asn Glu Thr Ala Asp Leu Pro
1 5 10 15

Cys Gln Phe Ala Asn Ser Gln Asn Gln Ser Leu Ser Glu Leu Val Val
20 25 30

Phe Trp Gln Asp Gln Glu Asn Leu Val Leu Asn Glu Val Tyr Leu Gly
35 40 45

Lys Glu Lys Phe Asp Ser Val His Ser Lys Tyr Met Gly Arg Thr Ser
50 55 60

Phe Asp Ser Asp Ser Trp Thr Leu Arg Leu His Asn Leu Gln Ile Lys
65 70 75 80

Asp Lys Gly Leu Tyr Gln Cys Ile Ile His His Lys Lys Pro Thr Gly
85 90 95

Met Ile Arg Ile His Gln Met Asn Ser Glu Leu Ser Val Leu Ala Asn
100 105 110

Phe Ser Gln Pro Glu Ile Val Pro Ile Ser Asn Ile Thr Glu Asn Val
115 120 125

Tyr Ile Asn Leu Thr Cys Ser Ser Ile His Gly Tyr Pro Glu Pro Lys
130 135 140

Lys Met Ser Val Leu Leu Arg Thr Lys Asn Ser Thr Ile Glu Tyr Asp
145 150 155 160

Gly Val Met Gln Lys Ser Gln Asp Asn Val Thr Glu Leu Tyr Asp Val
165 170 175

Ser Ile Ser Leu Ser Val Ser Phe Pro Asp Val Thr Ser Asn Met Thr
180 185 190

Ile Phe Cys Ile Leu Glu Thr Asp Lys Thr Arg Leu Leu Ser Ser Pro
195 200 205

Phe Ser Ile Glu Leu Glu Asp Pro Gln Pro Pro Pro Asp His Ile Pro
210 215 220

<210> SEQ ID NO 30
<211> LENGTH: 220
<212> TYPE: PRT
<213> ORGANISM: Homo sapiens
<220> FEATURE:
<223> OTHER INFORMATION: CD274 (PD-L1, B7-H1) ECD

<400> SEQUENCE: 30

Phe Thr Val Thr Val Pro Lys Asp Leu Tyr Val Val Glu Tyr Gly Ser
1 5 10 15

Asn Met Thr Ile Glu Cys Lys Phe Pro Val Glu Lys Gln Leu Asp Leu
20 25 30

Ala Ala Leu Ile Val Tyr Trp Glu Met Glu Asp Lys Asn Ile Ile Gln
35 40 45

Phe Val His Gly Glu Glu Asp Leu Lys Val Gln His Ser Ser Tyr Arg
50 55 60

```
Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
            180                 185                 190

Phe Arg Arg Leu Asp Pro Glu Glu Asn His Thr Ala Glu Leu Val Ile
        195                 200                 205

Pro Glu Leu Pro Leu Ala His Pro Pro Asn Glu Arg
    210                 215                 220


<210> SEQ ID NO 31
<211> LENGTH: 201
<212> TYPE: PRT
<213> ORGANISM: Homo sapiens
<220> FEATURE:
<223> OTHER INFORMATION: PDCD1LG2(PD-L2, CD273) ECD

<400> SEQUENCE: 31

Leu Phe Thr Val Thr Val Pro Lys Glu Leu Tyr Ile Ile Glu His Gly
1               5                   10                  15

Ser Asn Val Thr Leu Glu Cys Asn Phe Asp Thr Gly Ser His Val Asn
            20                  25                  30

Leu Gly Ala Ile Thr Ala Ser Leu Gln Lys Val Glu Asn Asp Thr Ser
        35                  40                  45

Pro His Arg Glu Arg Ala Thr Leu Leu Glu Glu Gln Leu Pro Leu Gly
    50                  55                  60

Lys Ala Ser Phe His Ile Pro Gln Val Gln Val Arg Asp Glu Gly Gln
65                  70                  75                  80

Tyr Gln Cys Ile Ile Ile Tyr Gly Val Ala Trp Asp Tyr Lys Tyr Leu
                85                  90                  95

Thr Leu Lys Val Lys Ala Ser Tyr Arg Lys Ile Asn Thr His Ile Leu
            100                 105                 110

Lys Val Pro Glu Thr Asp Glu Val Glu Leu Thr Cys Gln Ala Thr Gly
        115                 120                 125

Tyr Pro Leu Ala Glu Val Ser Trp Pro Asn Val Ser Val Pro Ala Asn
    130                 135                 140

Thr Ser His Ser Arg Thr Pro Glu Gly Leu Tyr Gln Val Thr Ser Val
145                 150                 155                 160

Leu Arg Leu Lys Pro Pro Pro Gly Arg Asn Phe Ser Cys Val Phe Trp
                165                 170                 175

Asn Thr His Val Arg Glu Leu Thr Leu Ala Ser Ile Asp Leu Gln Ser
            180                 185                 190

Gln Met Glu Pro Arg Thr His Pro Thr
        195                 200
```

<210> SEQ ID NO 32
<211> LENGTH: 238
<212> TYPE: PRT
<213> ORGANISM: Homo sapiens
<220> FEATURE:
<223> OTHER INFORMATION: ICOSLG(B7RP1, CD275, ICOSL, B7-H2) ECD

<400> SEQUENCE: 32

```
Asp Thr Gln Glu Lys Glu Val Arg Ala Met Val Gly Ser Asp Val Glu
1               5                   10                  15

Leu Ser Cys Ala Cys Pro Glu Gly Ser Arg Phe Asp Leu Asn Asp Val
            20                  25                  30

Tyr Val Tyr Trp Gln Thr Ser Glu Ser Lys Thr Val Val Thr Tyr His
        35                  40                  45

Ile Pro Gln Asn Ser Ser Leu Glu Asn Val Asp Ser Arg Tyr Arg Asn
    50                  55                  60

Arg Ala Leu Met Ser Pro Ala Gly Met Leu Arg Gly Asp Phe Ser Leu
65                  70                  75                  80

Arg Leu Phe Asn Val Thr Pro Gln Asp Glu Gln Lys Phe His Cys Leu
                85                  90                  95

Val Leu Ser Gln Ser Leu Gly Phe Gln Glu Val Leu Ser Val Glu Val
            100                 105                 110

Thr Leu His Val Ala Ala Asn Phe Ser Val Pro Val Val Ser Ala Pro
        115                 120                 125

His Ser Pro Ser Gln Asp Glu Leu Thr Phe Thr Cys Thr Ser Ile Asn
    130                 135                 140

Gly Tyr Pro Arg Pro Asn Val Tyr Trp Ile Asn Lys Thr Asp Asn Ser
145                 150                 155                 160

Leu Leu Asp Gln Ala Leu Gln Asn Asp Thr Val Phe Leu Asn Met Arg
                165                 170                 175

Gly Leu Tyr Asp Val Val Ser Val Leu Arg Ile Ala Arg Thr Pro Ser
            180                 185                 190

Val Asn Ile Gly Cys Cys Ile Glu Asn Val Leu Leu Gln Gln Asn Leu
        195                 200                 205

Thr Val Gly Ser Gln Thr Gly Asn Asp Ile Gly Glu Arg Asp Lys Ile
    210                 215                 220

Thr Glu Asn Pro Val Ser Thr Gly Glu Lys Asn Ala Ala Thr
225                 230                 235
```

<210> SEQ ID NO 33
<211> LENGTH: 438
<212> TYPE: PRT
<213> ORGANISM: Homo sapiens
<220> FEATURE:
<223> OTHER INFORMATION: CD276(B7-H3) ECD

<400> SEQUENCE: 33

```
Leu Glu Val Gln Val Pro Glu Asp Pro Val Val Ala Leu Val Gly Thr
1               5                   10                  15

Asp Ala Thr Leu Cys Cys Ser Phe Ser Pro Glu Pro Gly Phe Ser Leu
            20                  25                  30

Ala Gln Leu Asn Leu Ile Trp Gln Leu Thr Asp Thr Lys Gln Leu Val
        35                  40                  45

His Ser Phe Ala Glu Gly Gln Asp Gln Gly Ser Ala Tyr Ala Asn Arg
    50                  55                  60

Thr Ala Leu Phe Pro Asp Leu Leu Ala Gln Gly Asn Ala Ser Leu Arg
```

```
65                  70                  75                  80

Leu Gln Arg Val Arg Val Ala Asp Glu Gly Ser Phe Thr Cys Phe Val
                85                  90                  95

Ser Ile Arg Asp Phe Gly Ser Ala Ala Val Ser Leu Gln Val Ala Ala
            100                 105                 110

Pro Tyr Ser Lys Pro Ser Met Thr Leu Glu Pro Asn Lys Asp Leu Arg
        115                 120                 125

Pro Gly Asp Thr Val Thr Ile Thr Cys Ser Ser Tyr Gln Gly Tyr Pro
    130                 135                 140

Glu Ala Glu Val Phe Trp Gln Asp Gly Gln Gly Val Pro Leu Thr Gly
145                 150                 155                 160

Asn Val Thr Thr Ser Gln Met Ala Asn Glu Gln Gly Leu Phe Asp Val
                165                 170                 175

His Ser Ile Leu Arg Val Val Leu Gly Ala Asn Gly Thr Tyr Ser Cys
            180                 185                 190

Leu Val Arg Asn Pro Val Leu Gln Gln Asp Ala His Ser Ser Val Thr
        195                 200                 205

Ile Thr Pro Gln Arg Ser Pro Thr Gly Ala Val Glu Val Gln Val Pro
    210                 215                 220

Glu Asp Pro Val Val Ala Leu Val Gly Thr Asp Ala Thr Leu Arg Cys
225                 230                 235                 240

Ser Phe Ser Pro Glu Pro Gly Phe Ser Leu Ala Gln Leu Asn Leu Ile
                245                 250                 255

Trp Gln Leu Thr Asp Thr Lys Gln Leu Val His Ser Phe Thr Glu Gly
            260                 265                 270

Arg Asp Gln Gly Ser Ala Tyr Ala Asn Arg Thr Ala Leu Phe Pro Asp
        275                 280                 285

Leu Leu Ala Gln Gly Asn Ala Ser Leu Arg Leu Gln Arg Val Arg Val
    290                 295                 300

Ala Asp Glu Gly Ser Phe Thr Cys Phe Val Ser Ile Arg Asp Phe Gly
305                 310                 315                 320

Ser Ala Ala Val Ser Leu Gln Val Ala Ala Pro Tyr Ser Lys Pro Ser
                325                 330                 335

Met Thr Leu Glu Pro Asn Lys Asp Leu Arg Pro Gly Asp Thr Val Thr
            340                 345                 350

Ile Thr Cys Ser Ser Tyr Arg Gly Tyr Pro Glu Ala Glu Val Phe Trp
        355                 360                 365

Gln Asp Gly Gln Gly Val Pro Leu Thr Gly Asn Val Thr Thr Ser Gln
    370                 375                 380

Met Ala Asn Glu Gln Gly Leu Phe Asp Val His Ser Val Leu Arg Val
385                 390                 395                 400

Val Leu Gly Ala Asn Gly Thr Tyr Ser Cys Leu Val Arg Asn Pro Val
                405                 410                 415

Leu Gln Gln Asp Ala His Gly Ser Val Thr Ile Thr Gly Gln Pro Met
            420                 425                 430

Thr Phe Pro Pro Glu Ala
        435
```

```
<210> SEQ ID NO 34
<211> LENGTH: 235
<212> TYPE: PRT
<213> ORGANISM: Homo sapiens
<220> FEATURE:
<223> OTHER INFORMATION: VTCN1(B7-H4) ECD
```

<400> SEQUENCE: 34

Leu Ile Ile Gly Phe Gly Ile Ser Gly Arg His Ser Ile Thr Val Thr
1 5 10 15

Thr Val Ala Ser Ala Gly Asn Ile Gly Glu Asp Gly Ile Leu Ser Cys
20 25 30

Thr Phe Glu Pro Asp Ile Lys Leu Ser Asp Ile Val Ile Gln Trp Leu
35 40 45

Lys Glu Gly Val Leu Gly Leu Val His Glu Phe Lys Glu Gly Lys Asp
50 55 60

Glu Leu Ser Glu Gln Asp Glu Met Phe Arg Gly Arg Thr Ala Val Phe
65 70 75 80

Ala Asp Gln Val Ile Val Gly Asn Ala Ser Leu Arg Leu Lys Asn Val
85 90 95

Gln Leu Thr Asp Ala Gly Thr Tyr Lys Cys Tyr Ile Ile Thr Ser Lys
100 105 110

Gly Lys Gly Asn Ala Asn Leu Glu Tyr Lys Thr Gly Ala Phe Ser Met
115 120 125

Pro Glu Val Asn Val Asp Tyr Asn Ala Ser Ser Glu Thr Leu Arg Cys
130 135 140

Glu Ala Pro Arg Trp Phe Pro Gln Pro Thr Val Val Trp Ala Ser Gln
145 150 155 160

Val Asp Gln Gly Ala Asn Phe Ser Glu Val Ser Asn Thr Ser Phe Glu
165 170 175

Leu Asn Ser Glu Asn Val Thr Met Lys Val Val Ser Val Leu Tyr Asn
180 185 190

Val Thr Ile Asn Asn Thr Tyr Ser Cys Met Ile Glu Asn Asp Ile Ala
195 200 205

Lys Ala Thr Gly Asp Ile Lys Val Thr Glu Ser Glu Ile Lys Arg Arg
210 215 220

Ser His Leu Gln Leu Leu Asn Ser Lys Ala Ser
225 230 235

<210> SEQ ID NO 35
<211> LENGTH: 134
<212> TYPE: PRT
<213> ORGANISM: Homo sapiens
<220> FEATURE:
<223> OTHER INFORMATION: CD28 ECD

<400> SEQUENCE: 35

Asn Lys Ile Leu Val Lys Gln Ser Pro Met Leu Val Ala Tyr Asp Asn
1 5 10 15

Ala Val Asn Leu Ser Cys Lys Tyr Ser Tyr Asn Leu Phe Ser Arg Glu
20 25 30

Phe Arg Ala Ser Leu His Lys Gly Leu Asp Ser Ala Val Glu Val Cys
35 40 45

Val Val Tyr Gly Asn Tyr Ser Gln Gln Leu Gln Val Tyr Ser Lys Thr
50 55 60

Gly Phe Asn Cys Asp Gly Lys Leu Gly Asn Glu Ser Val Thr Phe Tyr
65 70 75 80

Leu Gln Asn Leu Tyr Val Asn Gln Thr Asp Ile Tyr Phe Cys Lys Ile
85 90 95

Glu Val Met Tyr Pro Pro Pro Tyr Leu Asp Asn Glu Lys Ser Asn Gly
100 105 110

Thr Ile Ile His Val Lys Gly Lys His Leu Cys Pro Ser Pro Leu Phe

```
        115                 120                 125

Pro Gly Pro Ser Lys Pro
    130


<210> SEQ ID NO 36
<211> LENGTH: 126
<212> TYPE: PRT
<213> ORGANISM: Homo sapiens
<220> FEATURE:
<223> OTHER INFORMATION: CTLA4 ECD

<400> SEQUENCE: 36

Lys Ala Met His Val Ala Gln Pro Ala Val Val Leu Ala Ser Ser Arg
1               5                   10                  15

Gly Ile Ala Ser Phe Val Cys Glu Tyr Ala Ser Pro Gly Lys Ala Thr
            20                  25                  30

Glu Val Arg Val Thr Val Leu Arg Gln Ala Asp Ser Gln Val Thr Glu
        35                  40                  45

Val Cys Ala Ala Thr Tyr Met Met Gly Asn Glu Leu Thr Phe Leu Asp
    50                  55                  60

Asp Ser Ile Cys Thr Gly Thr Ser Ser Gly Asn Gln Val Asn Leu Thr
65                  70                  75                  80

Ile Gln Gly Leu Arg Ala Met Asp Thr Gly Leu Tyr Ile Cys Lys Val
                85                  90                  95

Glu Leu Met Tyr Pro Pro Pro Tyr Tyr Leu Gly Ile Gly Asn Gly Thr
            100                 105                 110

Gln Ile Tyr Val Ile Asp Pro Glu Pro Cys Pro Asp Ser Asp
        115                 120                 125


<210> SEQ ID NO 37
<211> LENGTH: 150
<212> TYPE: PRT
<213> ORGANISM: Homo sapiens
<220> FEATURE:
<223> OTHER INFORMATION: PDCD1(PD-1) ECD

<400> SEQUENCE: 37

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150
```

<210> SEQ ID NO 38
<211> LENGTH: 120
<212> TYPE: PRT
<213> ORGANISM: Homo sapiens
<220> FEATURE:
<223> OTHER INFORMATION: ICOS ECD

<400> SEQUENCE: 38

```
Glu Ile Asn Gly Ser Ala Asn Tyr Glu Met Phe Ile Phe His Asn Gly
1               5                   10                  15

Gly Val Gln Ile Leu Cys Lys Tyr Pro Asp Ile Val Gln Gln Phe Lys
            20                  25                  30

Met Gln Leu Leu Lys Gly Gly Gln Ile Leu Cys Asp Leu Thr Lys Thr
        35                  40                  45

Lys Gly Ser Gly Asn Thr Val Ser Ile Lys Ser Leu Lys Phe Cys His
    50                  55                  60

Ser Gln Leu Ser Asn Asn Ser Val Ser Phe Phe Leu Tyr Asn Leu Asp
65                  70                  75                  80

His Ser His Ala Asn Tyr Tyr Phe Cys Asn Leu Ser Ile Phe Asp Pro
                85                  90                  95

Pro Pro Phe Lys Val Thr Leu Thr Gly Gly Tyr Leu His Ile Tyr Glu
            100                 105                 110

Ser Gln Leu Cys Cys Gln Leu Lys
        115                 120
```

<210> SEQ ID NO 39
<211> LENGTH: 127
<212> TYPE: PRT
<213> ORGANISM: Homo sapiens
<220> FEATURE:
<223> OTHER INFORMATION: BTLA(CD272) ECD

<400> SEQUENCE: 39

```
Lys Glu Ser Cys Asp Val Gln Leu Tyr Ile Lys Arg Gln Ser Glu His
1               5                   10                  15

Ser Ile Leu Ala Gly Asp Pro Phe Glu Leu Glu Cys Pro Val Lys Tyr
            20                  25                  30

Cys Ala Asn Arg Pro His Val Thr Trp Cys Lys Leu Asn Gly Thr Thr
        35                  40                  45

Cys Val Lys Leu Glu Asp Arg Gln Thr Ser Trp Lys Glu Glu Lys Asn
    50                  55                  60

Ile Ser Phe Phe Ile Leu His Phe Glu Pro Val Leu Pro Asn Asp Asn
65                  70                  75                  80

Gly Ser Tyr Arg Cys Ser Ala Asn Phe Gln Ser Asn Leu Ile Glu Ser
                85                  90                  95

His Ser Thr Thr Leu Tyr Val Thr Asp Val Lys Ser Ala Ser Glu Arg
            100                 105                 110

Pro Ser Lys Asp Glu Met Ala Ser Arg Pro Trp Leu Leu Tyr Arg
        115                 120                 125
```

<210> SEQ ID NO 40
<211> LENGTH: 371
<212> TYPE: PRT
<213> ORGANISM: Homo sapiens
<220> FEATURE:
<223> OTHER INFORMATION: CD4 ECD

<400> SEQUENCE: 40

```
Lys Lys Val Val Leu Gly Lys Lys Gly Asp Thr Val Glu Leu Thr Cys
```

-continued

```
1               5                   10                  15

Thr Ala Ser Gln Lys Lys Ser Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Ala Asp Ser Arg Arg Ser Leu Trp Asp Gln
    50                  55                  60

Gly Asn Phe Pro Leu Ile Ile Lys Asn Leu Lys Ile Glu Asp Ser Asp
65                  70                  75                  80

Thr Tyr Ile Cys Glu Val Glu Asp Gln Lys Glu Glu Val Gln Leu Leu
                85                  90                  95

Val Phe Gly Leu Thr Ala Asn Ser Asp Thr His Leu Leu Gln Gly Gln
            100                 105                 110

Ser Leu Thr Leu Thr Leu Glu Ser Pro Pro Gly Ser Ser Pro Ser Val
        115                 120                 125

Gln Cys Arg Ser Pro Arg Gly Lys Asn Ile Gln Gly Gly Lys Thr Leu
    130                 135                 140

Ser Val Ser Gln Leu Glu Leu Gln Asp Ser Gly Thr Trp Thr Cys Thr
145                 150                 155                 160

Val Leu Gln Asn Gln Lys Lys Val Glu Phe Lys Ile Asp Ile Val Val
                165                 170                 175

Leu Ala Phe Gln Lys Ala Ser Ser Ile Val Tyr Lys Lys Glu Gly Glu
            180                 185                 190

Gln Val Glu Phe Ser Phe Pro Leu Ala Phe Thr Val Glu Lys Leu Thr
        195                 200                 205

Gly Ser Gly Glu Leu Trp Trp Gln Ala Glu Arg Ala Ser Ser Ser Lys
    210                 215                 220

Ser Trp Ile Thr Phe Asp Leu Lys Asn Lys Glu Val Ser Val Lys Arg
225                 230                 235                 240

Val Thr Gln Asp Pro Lys Leu Gln Met Gly Lys Lys Leu Pro Leu His
                245                 250                 255

Leu Thr Leu Pro Gln Ala Leu Pro Gln Tyr Ala Gly Ser Gly Asn Leu
            260                 265                 270

Thr Leu Ala Leu Glu Ala Lys Thr Gly Lys Leu His Gln Glu Val Asn
        275                 280                 285

Leu Val Val Met Arg Ala Thr Gln Leu Gln Lys Asn Leu Thr Cys Glu
    290                 295                 300

Val Trp Gly Pro Thr Ser Pro Lys Leu Met Leu Ser Leu Lys Leu Glu
305                 310                 315                 320

Asn Lys Glu Ala Lys Val Ser Lys Arg Glu Lys Ala Val Trp Val Leu
                325                 330                 335

Asn Pro Glu Ala Gly Met Trp Gln Cys Leu Leu Ser Asp Ser Gly Gln
            340                 345                 350

Val Leu Leu Glu Ser Asn Ile Lys Val Leu Pro Thr Trp Ser Thr Pro
        355                 360                 365

Val Gln Pro
    370
```

<210> SEQ ID NO 41
<211> LENGTH: 161
<212> TYPE: PRT
<213> ORGANISM: Homo sapiens
<220> FEATURE:
<223> OTHER INFORMATION: CD8A(CD8-alpha) ECD

<400> SEQUENCE: 41

Ser Gln Phe Arg Val Ser Pro Leu Asp Arg Thr Trp Asn Leu Gly Glu
1 5 10 15

Thr Val Glu Leu Lys Cys Gln Val Leu Leu Ser Asn Pro Thr Ser Gly
20 25 30

Cys Ser Trp Leu Phe Gln Pro Arg Gly Ala Ala Ala Ser Pro Thr Phe
35 40 45

Leu Leu Tyr Leu Ser Gln Asn Lys Pro Lys Ala Ala Glu Gly Leu Asp
50 55 60

Thr Gln Arg Phe Ser Gly Lys Arg Leu Gly Asp Thr Phe Val Leu Thr
65 70 75 80

Leu Ser Asp Phe Arg Arg Glu Asn Glu Gly Tyr Tyr Phe Cys Ser Ala
85 90 95

Leu Ser Asn Ser Ile Met Tyr Phe Ser His Phe Val Pro Val Phe Leu
100 105 110

Pro Ala Lys Pro Thr Thr Thr Pro Ala Pro Arg Pro Pro Thr Pro Ala
115 120 125

Pro Thr Ile Ala Ser Gln Pro Leu Ser Leu Arg Pro Glu Ala Cys Arg
130 135 140

Pro Ala Ala Gly Gly Ala Val His Thr Arg Gly Leu Asp Phe Ala Cys
145 150 155 160

Asp

<210> SEQ ID NO 42
<211> LENGTH: 149
<212> TYPE: PRT
<213> ORGANISM: Homo sapiens
<220> FEATURE:
<223> OTHER INFORMATION: CD8B(CD8-beta) ECD

<400> SEQUENCE: 42

Leu Gln Gln Thr Pro Ala Tyr Ile Lys Val Gln Thr Asn Lys Met Val
1 5 10 15

Met Leu Ser Cys Glu Ala Lys Ile Ser Leu Ser Asn Met Arg Ile Tyr
20 25 30

Trp Leu Arg Gln Arg Gln Ala Pro Ser Ser Asp Ser His His Glu Phe
35 40 45

Leu Ala Leu Trp Asp Ser Ala Lys Gly Thr Ile His Gly Glu Glu Val
50 55 60

Glu Gln Glu Lys Ile Ala Val Phe Arg Asp Ala Ser Arg Phe Ile Leu
65 70 75 80

Asn Leu Thr Ser Val Lys Pro Glu Asp Ser Gly Ile Tyr Phe Cys Met
85 90 95

Ile Val Gly Ser Pro Glu Leu Thr Phe Gly Lys Gly Thr Gln Leu Ser
100 105 110

Val Val Asp Phe Leu Pro Thr Thr Ala Gln Pro Thr Lys Lys Ser Thr
115 120 125

Leu Lys Lys Arg Val Cys Arg Leu Pro Arg Pro Glu Thr Gln Lys Gly
130 135 140

Pro Leu Cys Ser Pro
145

<210> SEQ ID NO 43
<211> LENGTH: 422
<212> TYPE: PRT
<213> ORGANISM: Homo sapiens

<220> FEATURE:
<223> OTHER INFORMATION: LAG3 ECD

<400> SEQUENCE: 43

```
Val Pro Val Val Trp Ala Gln Glu Gly Ala Pro Ala Gln Leu Pro Cys
1               5                   10                  15

Ser Pro Thr Ile Pro Leu Gln Asp Leu Ser Leu Leu Arg Arg Ala Gly
            20                  25                  30

Val Thr Trp Gln His Gln Pro Asp Ser Gly Pro Pro Ala Ala Ala Pro
        35                  40                  45

Gly His Pro Leu Ala Pro Gly Pro His Pro Ala Ala Pro Ser Ser Trp
    50                  55                  60

Gly Pro Arg Pro Arg Arg Tyr Thr Val Leu Ser Val Gly Pro Gly Gly
65                  70                  75                  80

Leu Arg Ser Gly Arg Leu Pro Leu Gln Pro Arg Val Gln Leu Asp Glu
                85                  90                  95

Arg Gly Arg Gln Arg Gly Asp Phe Ser Leu Trp Leu Arg Pro Ala Arg
            100                 105                 110

Arg Ala Asp Ala Gly Glu Tyr Arg Ala Ala Val His Leu Arg Asp Arg
        115                 120                 125

Ala Leu Ser Cys Arg Leu Arg Leu Arg Leu Gly Gln Ala Ser Met Thr
    130                 135                 140

Ala Ser Pro Pro Gly Ser Leu Arg Ala Ser Asp Trp Val Ile Leu Asn
145                 150                 155                 160

Cys Ser Phe Ser Arg Pro Asp Arg Pro Ala Ser Val His Trp Phe Arg
                165                 170                 175

Asn Arg Gly Gln Gly Arg Val Pro Val Arg Glu Ser Pro His His His
            180                 185                 190

Leu Ala Glu Ser Phe Leu Phe Leu Pro Gln Val Ser Pro Met Asp Ser
        195                 200                 205

Gly Pro Trp Gly Cys Ile Leu Thr Tyr Arg Asp Gly Phe Asn Val Ser
    210                 215                 220

Ile Met Tyr Asn Leu Thr Val Leu Gly Leu Glu Pro Pro Thr Pro Leu
225                 230                 235                 240

Thr Val Tyr Ala Gly Ala Gly Ser Arg Val Gly Leu Pro Cys Arg Leu
                245                 250                 255

Pro Ala Gly Val Gly Thr Arg Ser Phe Leu Thr Ala Lys Trp Thr Pro
            260                 265                 270

Pro Gly Gly Gly Pro Asp Leu Leu Val Thr Gly Asp Asn Gly Asp Phe
        275                 280                 285

Thr Leu Arg Leu Glu Asp Val Ser Gln Ala Gln Ala Gly Thr Tyr Thr
    290                 295                 300

Cys His Ile His Leu Gln Glu Gln Gln Leu Asn Ala Thr Val Thr Leu
305                 310                 315                 320

Ala Ile Ile Thr Val Thr Pro Lys Ser Phe Gly Ser Pro Gly Ser Leu
                325                 330                 335

Gly Lys Leu Leu Cys Glu Val Thr Pro Val Ser Gly Gln Glu Arg Phe
            340                 345                 350

Val Trp Ser Ser Leu Asp Thr Pro Ser Gln Arg Ser Phe Ser Gly Pro
        355                 360                 365

Trp Leu Glu Ala Gln Glu Ala Gln Leu Leu Ser Gln Pro Trp Gln Cys
    370                 375                 380

Gln Leu Tyr Gln Gly Glu Arg Leu Leu Gly Ala Ala Val Tyr Phe Thr
385                 390                 395                 400
```

Glu Leu Ser Ser Pro Gly Ala Gln Arg Ser Gly Arg Ala Pro Gly Ala
405 410 415

Leu Pro Ala Gly His Leu
420

<210> SEQ ID NO 44
<211> LENGTH: 181
<212> TYPE: PRT
<213> ORGANISM: Homo sapiens
<220> FEATURE:
<223> OTHER INFORMATION: HAVCR2(TIM-3) ECD

<400> SEQUENCE: 44

Ser Glu Val Glu Tyr Arg Ala Glu Val Gly Gln Asn Ala Tyr Leu Pro
1 5 10 15

Cys Phe Tyr Thr Pro Ala Ala Pro Gly Asn Leu Val Pro Val Cys Trp
20 25 30

Gly Lys Gly Ala Cys Pro Val Phe Glu Cys Gly Asn Val Val Leu Arg
35 40 45

Thr Asp Glu Arg Asp Val Asn Tyr Trp Thr Ser Arg Tyr Trp Leu Asn
50 55 60

Gly Asp Phe Arg Lys Gly Asp Val Ser Leu Thr Ile Glu Asn Val Thr
65 70 75 80

Leu Ala Asp Ser Gly Ile Tyr Cys Cys Arg Ile Gln Ile Pro Gly Ile
85 90 95

Met Asn Asp Glu Lys Phe Asn Leu Lys Leu Val Ile Lys Pro Ala Lys
100 105 110

Val Thr Pro Ala Pro Thr Arg Gln Arg Asp Phe Thr Ala Ala Phe Pro
115 120 125

Arg Met Leu Thr Thr Arg Gly His Gly Pro Ala Glu Thr Gln Thr Leu
130 135 140

Gly Ser Leu Pro Asp Ile Asn Leu Thr Gln Ile Ser Thr Leu Ala Asn
145 150 155 160

Glu Leu Arg Asp Ser Arg Leu Ala Asn Asp Leu Arg Asp Ser Gly Ala
165 170 175

Thr Ile Arg Ile Gly
180

<210> SEQ ID NO 45
<211> LENGTH: 394
<212> TYPE: PRT
<213> ORGANISM: Homo sapiens
<220> FEATURE:
<223> OTHER INFORMATION: CEACAM1 ECD

<400> SEQUENCE: 45

Gln Leu Thr Thr Glu Ser Met Pro Phe Asn Val Ala Glu Gly Lys Glu
1 5 10 15

Val Leu Leu Leu Val His Asn Leu Pro Gln Gln Leu Phe Gly Tyr Ser
20 25 30

Trp Tyr Lys Gly Glu Arg Val Asp Gly Asn Arg Gln Ile Val Gly Tyr
35 40 45

Ala Ile Gly Thr Gln Gln Ala Thr Pro Gly Pro Ala Asn Ser Gly Arg
50 55 60

Glu Thr Ile Tyr Pro Asn Ala Ser Leu Leu Ile Gln Asn Val Thr Gln
65 70 75 80

Asn Asp Thr Gly Phe Tyr Thr Leu Gln Val Ile Lys Ser Asp Leu Val

```
                85                  90                  95

Asn Glu Glu Ala Thr Gly Gln Phe His Val Tyr Pro Glu Leu Pro Lys
            100                 105                 110

Pro Ser Ile Ser Ser Asn Asn Ser Asn Pro Val Glu Asp Lys Asp Ala
        115                 120                 125

Val Ala Phe Thr Cys Glu Pro Glu Thr Gln Asp Thr Thr Tyr Leu Trp
    130                 135                 140

Trp Ile Asn Asn Gln Ser Leu Pro Val Ser Pro Arg Leu Gln Leu Ser
145                 150                 155                 160

Asn Gly Asn Arg Thr Leu Thr Leu Leu Ser Val Thr Arg Asn Asp Thr
                165                 170                 175

Gly Pro Tyr Glu Cys Glu Ile Gln Asn Pro Val Ser Ala Asn Arg Ser
            180                 185                 190

Asp Pro Val Thr Leu Asn Val Thr Tyr Gly Pro Asp Thr Pro Thr Ile
        195                 200                 205

Ser Pro Ser Asp Thr Tyr Tyr Arg Pro Gly Ala Asn Leu Ser Leu Ser
    210                 215                 220

Cys Tyr Ala Ala Ser Asn Pro Pro Ala Gln Tyr Ser Trp Leu Ile Asn
225                 230                 235                 240

Gly Thr Phe Gln Gln Ser Thr Gln Glu Leu Phe Ile Pro Asn Ile Thr
                245                 250                 255

Val Asn Asn Ser Gly Ser Tyr Thr Cys His Ala Asn Asn Ser Val Thr
            260                 265                 270

Gly Cys Asn Arg Thr Thr Val Lys Thr Ile Ile Val Thr Glu Leu Ser
        275                 280                 285

Pro Val Val Ala Lys Pro Gln Ile Lys Ala Ser Lys Thr Thr Val Thr
    290                 295                 300

Gly Asp Lys Asp Ser Val Asn Leu Thr Cys Ser Thr Asn Asp Thr Gly
305                 310                 315                 320

Ile Ser Ile Arg Trp Phe Phe Lys Asn Gln Ser Leu Pro Ser Ser Glu
                325                 330                 335

Arg Met Lys Leu Ser Gln Gly Asn Thr Thr Leu Ser Ile Asn Pro Val
            340                 345                 350

Lys Arg Glu Asp Ala Gly Thr Tyr Trp Cys Glu Val Phe Asn Pro Ile
        355                 360                 365

Ser Lys Asn Gln Ser Asp Pro Ile Met Leu Asn Val Asn Tyr Asn Ala
    370                 375                 380

Leu Pro Gln Glu Asn Gly Leu Ser Pro Gly
385                 390


<210> SEQ ID NO 46
<211> LENGTH: 120
<212> TYPE: PRT
<213> ORGANISM: Homo sapiens
<220> FEATURE:
<223> OTHER INFORMATION: TIGIT ECD

<400> SEQUENCE: 46

Met Met Thr Gly Thr Ile Glu Thr Thr Gly Asn Ile Ser Ala Glu Lys
1               5                   10                  15

Gly Gly Ser Ile Ile Leu Gln Cys His Leu Ser Ser Thr Thr Ala Gln
            20                  25                  30

Val Thr Gln Val Asn Trp Glu Gln Gln Asp Gln Leu Leu Ala Ile Cys
        35                  40                  45

Asn Ala Asp Leu Gly Trp His Ile Ser Pro Ser Phe Lys Asp Arg Val
```

```
    50                  55                  60

Ala Pro Gly Pro Gly Leu Gly Leu Thr Leu Gln Ser Leu Thr Val Asn
65                  70                  75                  80

Asp Thr Gly Glu Tyr Phe Cys Ile Tyr His Thr Tyr Pro Asp Gly Thr
                85                  90                  95

Tyr Thr Gly Arg Ile Phe Leu Glu Val Leu Glu Ser Ser Val Ala Glu
            100                 105                 110

His Gly Ala Arg Phe Gln Ile Pro
        115                 120


<210> SEQ ID NO 47
<211> LENGTH: 323
<212> TYPE: PRT
<213> ORGANISM: Homo sapiens
<220> FEATURE:
<223> OTHER INFORMATION: PVR(CD155) ECD

<400> SEQUENCE: 47

Trp Pro Pro Pro Gly Thr Gly Asp Val Val Val Gln Ala Pro Thr Gln
1               5                   10                  15

Val Pro Gly Phe Leu Gly Asp Ser Val Thr Leu Pro Cys Tyr Leu Gln
            20                  25                  30

Val Pro Asn Met Glu Val Thr His Val Ser Gln Leu Thr Trp Ala Arg
        35                  40                  45

His Gly Glu Ser Gly Ser Met Ala Val Phe His Gln Thr Gln Gly Pro
    50                  55                  60

Ser Tyr Ser Glu Ser Lys Arg Leu Glu Phe Val Ala Ala Arg Leu Gly
65                  70                  75                  80

Ala Glu Leu Arg Asn Ala Ser Leu Arg Met Phe Gly Leu Arg Val Glu
                85                  90                  95

Asp Glu Gly Asn Tyr Thr Cys Leu Phe Val Thr Phe Pro Gln Gly Ser
            100                 105                 110

Arg Ser Val Asp Ile Trp Leu Arg Val Leu Ala Lys Pro Gln Asn Thr
        115                 120                 125

Ala Glu Val Gln Lys Val Gln Leu Thr Gly Glu Pro Val Pro Met Ala
    130                 135                 140

Arg Cys Val Ser Thr Gly Gly Arg Pro Pro Ala Gln Ile Thr Trp His
145                 150                 155                 160

Ser Asp Leu Gly Gly Met Pro Asn Thr Ser Gln Val Pro Gly Phe Leu
                165                 170                 175

Ser Gly Thr Val Thr Val Thr Ser Leu Trp Ile Leu Val Pro Ser Ser
            180                 185                 190

Gln Val Asp Gly Lys Asn Val Thr Cys Lys Val Glu His Glu Ser Phe
        195                 200                 205

Glu Lys Pro Gln Leu Leu Thr Val Asn Leu Thr Val Tyr Tyr Pro Pro
    210                 215                 220

Glu Val Ser Ile Ser Gly Tyr Asp Asn Asn Trp Tyr Leu Gly Gln Asn
225                 230                 235                 240

Glu Ala Thr Leu Thr Cys Asp Ala Arg Ser Asn Pro Glu Pro Thr Gly
                245                 250                 255

Tyr Asn Trp Ser Thr Thr Met Gly Pro Leu Pro Pro Phe Ala Val Ala
            260                 265                 270

Gln Gly Ala Gln Leu Leu Ile Arg Pro Val Asp Lys Pro Ile Asn Thr
        275                 280                 285

Thr Leu Ile Cys Asn Val Thr Asn Ala Leu Gly Ala Arg Gln Ala Glu
```

```
    290                 295                 300

Leu Thr Val Gln Val Lys Glu Gly Pro Pro Ser Glu His Ser Gly Ile
305                 310                 315                 320

Ser Arg Asn


<210> SEQ ID NO 48
<211> LENGTH: 329
<212> TYPE: PRT
<213> ORGANISM: Homo sapiens
<220> FEATURE:
<223> OTHER INFORMATION: PVRL2(CD112) ECD

<400> SEQUENCE: 48

Gln Asp Val Arg Val Gln Val Leu Pro Glu Val Arg Gly Gln Leu Gly
1               5                   10                  15

Gly Thr Val Glu Leu Pro Cys His Leu Leu Pro Pro Val Pro Gly Leu
            20                  25                  30

Tyr Ile Ser Leu Val Thr Trp Gln Arg Pro Asp Ala Pro Ala Asn His
        35                  40                  45

Gln Asn Val Ala Ala Phe His Pro Lys Met Gly Pro Ser Phe Pro Ser
    50                  55                  60

Pro Lys Pro Gly Ser Glu Arg Leu Ser Phe Val Ser Ala Lys Gln Ser
65                  70                  75                  80

Thr Gly Gln Asp Thr Glu Ala Glu Leu Gln Asp Ala Thr Leu Ala Leu
                85                  90                  95

His Gly Leu Thr Val Glu Asp Glu Gly Asn Tyr Thr Cys Glu Phe Ala
            100                 105                 110

Thr Phe Pro Lys Gly Ser Val Arg Gly Met Thr Trp Leu Arg Val Ile
        115                 120                 125

Ala Lys Pro Lys Asn Gln Ala Glu Ala Gln Lys Val Thr Phe Ser Gln
    130                 135                 140

Asp Pro Thr Thr Val Ala Leu Cys Ile Ser Lys Glu Gly Arg Pro Pro
145                 150                 155                 160

Ala Arg Ile Ser Trp Leu Ser Ser Leu Asp Trp Glu Ala Lys Glu Thr
                165                 170                 175

Gln Val Ser Gly Thr Leu Ala Gly Thr Val Thr Val Thr Ser Arg Phe
            180                 185                 190

Thr Leu Val Pro Ser Gly Arg Ala Asp Gly Val Thr Val Thr Cys Lys
        195                 200                 205

Val Glu His Glu Ser Phe Glu Glu Pro Ala Leu Ile Pro Val Thr Leu
    210                 215                 220

Ser Val Arg Tyr Pro Pro Glu Val Ser Ile Ser Gly Tyr Asp Asp Asn
225                 230                 235                 240

Trp Tyr Leu Gly Arg Thr Asp Ala Thr Leu Ser Cys Asp Val Arg Ser
                245                 250                 255

Asn Pro Glu Pro Thr Gly Tyr Asp Trp Ser Thr Thr Ser Gly Thr Phe
            260                 265                 270

Pro Thr Ser Ala Val Ala Gln Gly Ser Gln Leu Val Ile His Ala Val
        275                 280                 285

Asp Ser Leu Phe Asn Thr Thr Phe Val Cys Thr Val Thr Asn Ala Val
    290                 295                 300

Gly Met Gly Arg Ala Glu Gln Val Ile Phe Val Arg Glu Thr Pro Asn
305                 310                 315                 320

Thr Ala Gly Ala Gly Ala Thr Gly Gly
                325
```

<210> SEQ ID NO 49
<211> LENGTH: 236
<212> TYPE: PRT
<213> ORGANISM: Homo sapiens
<220> FEATURE:
<223> OTHER INFORMATION: CD226 ECD

<400> SEQUENCE: 49

Glu Glu Val Leu Trp His Thr Ser Val Pro Phe Ala Glu Asn Met Ser
1 5 10 15

Leu Glu Cys Val Tyr Pro Ser Met Gly Ile Leu Thr Gln Val Glu Trp
20 25 30

Phe Lys Ile Gly Thr Gln Gln Asp Ser Ile Ala Ile Phe Ser Pro Thr
35 40 45

His Gly Met Val Ile Arg Lys Pro Tyr Ala Glu Arg Val Tyr Phe Leu
50 55 60

Asn Ser Thr Met Ala Ser Asn Asn Met Thr Leu Phe Phe Arg Asn Ala
65 70 75 80

Ser Glu Asp Asp Val Gly Tyr Tyr Ser Cys Ser Leu Tyr Thr Tyr Pro
85 90 95

Gln Gly Thr Trp Gln Lys Val Ile Gln Val Val Gln Ser Asp Ser Phe
100 105 110

Glu Ala Ala Val Pro Ser Asn Ser His Ile Val Ser Glu Pro Gly Lys
115 120 125

Asn Val Thr Leu Thr Cys Gln Pro Gln Met Thr Trp Pro Val Gln Ala
130 135 140

Val Arg Trp Glu Lys Ile Gln Pro Arg Gln Ile Asp Leu Leu Thr Tyr
145 150 155 160

Cys Asn Leu Val His Gly Arg Asn Phe Thr Ser Lys Phe Pro Arg Gln
165 170 175

Ile Val Ser Asn Cys Ser His Gly Arg Trp Ser Val Ile Val Ile Pro
180 185 190

Asp Val Thr Val Ser Asp Ser Gly Leu Tyr Arg Cys Tyr Leu Gln Ala
195 200 205

Ser Ala Gly Glu Asn Glu Thr Phe Val Met Arg Leu Thr Val Ala Glu
210 215 220

Gly Lys Thr Asp Asn Gln Tyr Thr Leu Phe Val Ala
225 230 235

<210> SEQ ID NO 50
<211> LENGTH: 185
<212> TYPE: PRT
<213> ORGANISM: Homo sapiens
<220> FEATURE:
<223> OTHER INFORMATION: CD2 ECD

<400> SEQUENCE: 50

Lys Glu Ile Thr Asn Ala Leu Glu Thr Trp Gly Ala Leu Gly Gln Asp
1 5 10 15

Ile Asn Leu Asp Ile Pro Ser Phe Gln Met Ser Asp Asp Ile Asp Asp
20 25 30

Ile Lys Trp Glu Lys Thr Ser Asp Lys Lys Lys Ile Ala Gln Phe Arg
35 40 45

Lys Glu Lys Glu Thr Phe Lys Glu Lys Asp Thr Tyr Lys Leu Phe Lys
50 55 60

Asn Gly Thr Leu Lys Ile Lys His Leu Lys Thr Asp Asp Gln Asp Ile

```
65                  70                  75                  80

Tyr Lys Val Ser Ile Tyr Asp Thr Lys Gly Lys Asn Val Leu Glu Lys
                85                  90                  95

Ile Phe Asp Leu Lys Ile Gln Glu Arg Val Ser Lys Pro Lys Ile Ser
            100                 105                 110

Trp Thr Cys Ile Asn Thr Thr Leu Thr Cys Glu Val Met Asn Gly Thr
        115                 120                 125

Asp Pro Glu Leu Asn Leu Tyr Gln Asp Gly Lys His Leu Lys Leu Ser
    130                 135                 140

Gln Arg Val Ile Thr His Lys Trp Thr Thr Ser Leu Ser Ala Lys Phe
145                 150                 155                 160

Lys Cys Thr Ala Gly Asn Lys Val Ser Lys Glu Ser Ser Val Glu Pro
                165                 170                 175

Val Ser Cys Pro Glu Lys Gly Leu Asp
            180                 185


<210> SEQ ID NO 51
<211> LENGTH: 133
<212> TYPE: PRT
<213> ORGANISM: Homo sapiens
<220> FEATURE:
<223> OTHER INFORMATION: CD160 ECD

<400> SEQUENCE: 51

Ile Asn Ile Thr Ser Ser Ala Ser Gln Glu Gly Thr Arg Leu Asn Leu
1               5                   10                  15

Ile Cys Thr Val Trp His Lys Lys Glu Glu Ala Glu Gly Phe Val Val
            20                  25                  30

Phe Leu Cys Lys Asp Arg Ser Gly Asp Cys Ser Pro Glu Thr Ser Leu
        35                  40                  45

Lys Gln Leu Arg Leu Lys Arg Asp Pro Gly Ile Asp Gly Val Gly Glu
    50                  55                  60

Ile Ser Ser Gln Leu Met Phe Thr Ile Ser Gln Val Thr Pro Leu His
65                  70                  75                  80

Ser Gly Thr Tyr Gln Cys Cys Ala Arg Ser Gln Lys Ser Gly Ile Arg
                85                  90                  95

Leu Gln Gly His Phe Phe Ser Ile Leu Phe Thr Glu Thr Gly Asn Tyr
            100                 105                 110

Thr Val Thr Gly Leu Lys Gln Arg Gln His Leu Glu Phe Ser His Asn
        115                 120                 125

Glu Gly Thr Leu Ser
    130


<210> SEQ ID NO 52
<211> LENGTH: 202
<212> TYPE: PRT
<213> ORGANISM: Homo sapiens
<220> FEATURE:
<223> OTHER INFORMATION: CD200 ECD

<400> SEQUENCE: 52

Gln Val Gln Val Val Thr Gln Asp Glu Arg Glu Gln Leu Tyr Thr Pro
1               5                   10                  15

Ala Ser Leu Lys Cys Ser Leu Gln Asn Ala Gln Glu Ala Leu Ile Val
            20                  25                  30

Thr Trp Gln Lys Lys Lys Ala Val Ser Pro Glu Asn Met Val Thr Phe
        35                  40                  45
```

```
Ser Glu Asn His Gly Val Val Ile Gln Pro Ala Tyr Lys Asp Lys Ile
    50                  55                  60

Asn Ile Thr Gln Leu Gly Leu Gln Asn Ser Thr Ile Thr Phe Trp Asn
65                  70                  75                  80

Ile Thr Leu Glu Asp Glu Gly Cys Tyr Met Cys Leu Phe Asn Thr Phe
                85                  90                  95

Gly Phe Gly Lys Ile Ser Gly Thr Ala Cys Leu Thr Val Tyr Val Gln
            100                 105                 110

Pro Ile Val Ser Leu His Tyr Lys Phe Ser Glu Asp His Leu Asn Ile
        115                 120                 125

Thr Cys Ser Ala Thr Ala Arg Pro Ala Pro Met Val Phe Trp Lys Val
    130                 135                 140

Pro Arg Ser Gly Ile Glu Asn Ser Thr Val Thr Leu Ser His Pro Asn
145                 150                 155                 160

Gly Thr Thr Ser Val Thr Ser Ile Leu His Ile Lys Asp Pro Lys Asn
                165                 170                 175

Gln Val Gly Lys Glu Val Ile Cys Gln Val Leu His Leu Gly Thr Val
            180                 185                 190

Thr Asp Phe Lys Gln Thr Val Asn Lys Gly
        195                 200


<210> SEQ ID NO 53
<211> LENGTH: 215
<212> TYPE: PRT
<213> ORGANISM: Homo sapiens
<220> FEATURE:
<223> OTHER INFORMATION: CD200R1(CD200R) ECD

<400> SEQUENCE: 53

Met Asp Glu Lys Gln Ile Thr Gln Asn Tyr Ser Lys Val Leu Ala Glu
1               5                   10                  15

Val Asn Thr Ser Trp Pro Val Lys Met Ala Thr Asn Ala Val Leu Cys
            20                  25                  30

Cys Pro Pro Ile Ala Leu Arg Asn Leu Ile Ile Ile Thr Trp Glu Ile
        35                  40                  45

Ile Leu Arg Gly Gln Pro Ser Cys Thr Lys Ala Tyr Arg Lys Glu Thr
    50                  55                  60

Asn Glu Thr Lys Glu Thr Asn Cys Thr Asp Glu Arg Ile Thr Trp Val
65                  70                  75                  80

Ser Arg Pro Asp Gln Asn Ser Asp Leu Gln Ile Arg Pro Val Ala Ile
                85                  90                  95

Thr His Asp Gly Tyr Tyr Arg Cys Ile Met Val Thr Pro Asp Gly Asn
            100                 105                 110

Phe His Arg Gly Tyr His Leu Gln Val Leu Val Thr Pro Glu Val Thr
        115                 120                 125

Leu Phe Gln Asn Arg Asn Arg Thr Ala Val Cys Lys Ala Val Ala Gly
    130                 135                 140

Lys Pro Ala Ala Gln Ile Ser Trp Ile Pro Glu Gly Asp Cys Ala Thr
145                 150                 155                 160

Lys Gln Glu Tyr Trp Ser Asn Gly Thr Val Thr Val Lys Ser Thr Cys
                165                 170                 175

His Trp Glu Val His Asn Val Ser Thr Val Thr Cys His Val Ser His
            180                 185                 190

Leu Thr Gly Asn Lys Ser Leu Tyr Ile Glu Leu Leu Pro Val Pro Gly
        195                 200                 205
```

```
Ala Lys Lys Ser Ala Lys Leu
    210                 215


<210> SEQ ID NO 54
<211> LENGTH: 117
<212> TYPE: PRT
<213> ORGANISM: Homo sapiens
<220> FEATURE:
<223> OTHER INFORMATION: NC R3 (NKp30) ECD

<400> SEQUENCE: 54

Leu Trp Val Ser Gln Pro Pro Glu Ile Arg Thr Leu Glu Gly Ser Ser
1               5                   10                  15

Ala Phe Leu Pro Cys Ser Phe Asn Ala Ser Gln Gly Arg Leu Ala Ile
            20                  25                  30

Gly Ser Val Thr Trp Phe Arg Asp Glu Val Val Pro Gly Lys Glu Val
        35                  40                  45

Arg Asn Gly Thr Pro Glu Phe Arg Gly Arg Leu Ala Pro Leu Ala Ser
    50                  55                  60

Ser Arg Phe Leu His Asp His Gln Ala Glu Leu His Ile Arg Asp Val
65                  70                  75                  80

Arg Gly His Asp Ala Ser Ile Tyr Val Cys Arg Val Glu Val Leu Gly
                85                  90                  95

Leu Gly Val Gly Thr Gly Asn Gly Thr Arg Leu Val Val Glu Lys Glu
            100                 105                 110

His Pro Gln Leu Gly
        115


<210> SEQ ID NO 55
<211> LENGTH: 208
<212> TYPE: PRT
<213> ORGANISM: Artificial Sequence
<220> FEATURE:
<223> OTHER INFORMATION: CD80 v1 ECD

<400> SEQUENCE: 55

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Gln Ala Leu Arg Pro Ser Asp Glu Gly Thr Tyr
65                  70                  75                  80

Glu Cys Val Val Leu Lys Tyr Glu Lys Asp Gly Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175
```

```
Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205


<210> SEQ ID NO 56
<211> LENGTH: 208
<212> TYPE: PRT
<213> ORGANISM: Artificial Sequence
<220> FEATURE:
<223> OTHER INFORMATION: CD80 v2 ECD

<400> SEQUENCE: 56

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Gln Ala Leu Arg Pro Ser Asp Glu Gly Thr Tyr
65                  70                  75                  80

Glu Cys Val Val Leu Lys Tyr Glu Lys Asp Gly Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Ala Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205


<210> SEQ ID NO 57
<211> LENGTH: 208
<212> TYPE: PRT
<213> ORGANISM: Artificial Sequence
<220> FEATURE:
<223> OTHER INFORMATION: CD80 v3 ECD

<400> SEQUENCE: 57

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Gln Ala Leu Arg Pro Ser Asp Glu Gly Thr Tyr
```

```
65                  70                  75                  80

Glu Cys Val Val Leu Lys Tyr Glu Lys Asp Gly Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ala Pro Ser Ser Asn Ile Arg Arg Ile Ile Cys
        115                 120                 125

Ser Ala Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205


<210> SEQ ID NO 58
<211> LENGTH: 208
<212> TYPE: PRT
<213> ORGANISM: Artificial Sequence
<220> FEATURE:
<223> OTHER INFORMATION: CD80 v4 ECD

<400> SEQUENCE: 58

Val Ile His Met Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Gln Ala Leu Arg Pro Ser Asp Glu Gly Thr Tyr
65                  70                  75                  80

Glu Cys Val Val Leu Lys Tyr Glu Lys Asp Gly Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Ser Ser Asn Ile Arg Arg Ile Ile Cys
        115                 120                 125

Ser Ala Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205


<210> SEQ ID NO 59
<211> LENGTH: 208
<212> TYPE: PRT
```

<213> ORGANISM: Artificial Sequence
<220> FEATURE:
<223> OTHER INFORMATION: CD80 v5 ECD

<400> SEQUENCE: 59

```
Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Gln Ala Leu Arg Pro Ser Asp Glu Gly Thr Tyr
65                  70                  75                  80

Glu Cys Val Val Leu Lys Tyr Glu Lys Asp Gly Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Ser Ser Asn Ile Arg Arg Ile Ile Cys
        115                 120                 125

Ser Ala Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205
```

<210> SEQ ID NO 60
<211> LENGTH: 208
<212> TYPE: PRT
<213> ORGANISM: Artificial Sequence
<220> FEATURE:
<223> OTHER INFORMATION: CD80 v6 ECD

<400> SEQUENCE: 60

```
Val Ile His Val Thr Lys Glu Val Lys Glu Val Ala Thr Leu Ser Cys
1               5                   10                  15

Gly His Asn Leu Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Gln Ala Leu Arg Pro Ser Asp Glu Gly Thr Tyr
65                  70                  75                  80

Glu Cys Val Val Leu Lys Tyr Glu Lys Asp Ser Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Ser Ser Asn Ile Arg Arg Ile Ile Cys
        115                 120                 125
```

```
Ser Ala Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205


<210> SEQ ID NO 61
<211> LENGTH: 208
<212> TYPE: PRT
<213> ORGANISM: Artificial Sequence
<220> FEATURE:
<223> OTHER INFORMATION: CD80 v7 ECD

<400> SEQUENCE: 61

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Pro Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Gln Ala Leu Arg Pro Ser Asp Glu Gly Thr Tyr
65                  70                  75                  80

Glu Cys Val Val Leu Lys Tyr Glu Lys Asp Gly Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Ala Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205


<210> SEQ ID NO 62
<211> LENGTH: 208
<212> TYPE: PRT
<213> ORGANISM: Artificial Sequence
<220> FEATURE:
<223> OTHER INFORMATION: CD80 v8 ECD

<400> SEQUENCE: 62

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30
```

Gln Lys Glu Lys Lys Met Val Leu Thr Met Met Ser Gly Asp Met Asn
35 40 45

Ile Trp Pro Glu Tyr Lys Asn Arg Thr Ile Phe Asp Ile Thr Asn Asn
50 55 60

Leu Ser Ile Val Ile Gln Ala Leu Arg Pro Ser Asp Glu Gly Thr Tyr
65 70 75 80

Glu Cys Val Val Leu Lys Tyr Glu Lys Asp Gly Phe Lys Arg Glu His
85 90 95

Leu Ala Glu Val Thr Leu Ser Val Lys Ala Asp Phe Pro Thr Pro Ser
100 105 110

Ile Ser Asp Phe Gly Ile Pro Ser Ser Asn Ile Arg Arg Ile Ile Cys
115 120 125

Ser Ala Ser Gly Gly Phe Pro Glu Pro His Leu Ser Trp Leu Glu Asn
130 135 140

Gly Glu Glu Leu Asn Ala Ile Asn Thr Thr Val Ser Gln Asp Pro Glu
145 150 155 160

Thr Glu Leu Tyr Ala Val Ser Ser Lys Leu Asp Phe Asn Met Thr Thr
165 170 175

Asn His Ser Phe Met Cys Leu Ile Lys Tyr Gly His Leu Arg Val Asn
180 185 190

Gln Thr Phe Asn Trp Asn Thr Thr Lys Gln Glu His Phe Pro Asp Asn
195 200 205

<210> SEQ ID NO 63
<211> LENGTH: 208
<212> TYPE: PRT
<213> ORGANISM: Artificial Sequence
<220> FEATURE:
<223> OTHER INFORMATION: CD80 v9 ECD

<400> SEQUENCE: 63

Val Ile His Val Thr Lys Glu Val Lys Glu Val Ala Thr Leu Ser Cys
1 5 10 15

Gly His Asn Val Ser Val Glu Glu Leu Ala Gln Thr Arg Ile Tyr Trp
20 25 30

Gln Lys Glu Lys Lys Met Val Leu Thr Met Met Ser Gly Asp Met Asn
35 40 45

Ile Trp Pro Glu Tyr Lys Asn Arg Thr Ile Phe Asp Ile Thr Asn Asn
50 55 60

Leu Ser Ile Val Ile Leu Ala Leu Arg Pro Ser Asp Glu Gly Thr Tyr
65 70 75 80

Glu Cys Val Val Leu Lys Tyr Glu Lys Asp Gly Phe Lys Arg Glu His
85 90 95

Leu Ala Glu Val Thr Leu Ser Val Lys Ala Asp Phe Pro Thr Pro Ser
100 105 110

Ile Ser Asp Phe Glu Ile Pro Ser Ser Asn Ile Arg Arg Ile Ile Cys
115 120 125

Ser Ala Ser Gly Gly Phe Pro Glu Pro His Leu Ser Trp Leu Glu Asn
130 135 140

Gly Glu Glu Leu Asn Ala Ile Asn Thr Thr Val Ser Gln Asp Pro Glu
145 150 155 160

Thr Glu Leu Tyr Ala Val Ser Ser Lys Leu Asp Phe Asn Met Thr Thr
165 170 175

Asn His Ser Phe Met Cys Leu Ile Lys Tyr Gly His Leu Arg Val Asn
180 185 190

```
Gln Thr Phe Asn Trp Asn Thr Thr Lys Gln Glu His Phe Pro Asp Asn
        195                 200                 205
```

<210> SEQ ID NO 64
<211> LENGTH: 208
<212> TYPE: PRT
<213> ORGANISM: Artificial Sequence
<220> FEATURE:
<223> OTHER INFORMATION: CD80 v10 ECD

<400> SEQUENCE: 64

```
Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Arg Ala Leu Arg Pro Ser Asp Glu Gly Thr Tyr
65                  70                  75                  80

Glu Cys Val Val Leu Lys Tyr Glu Lys Asp Gly Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Ser Ser Asn Ile Arg Arg Ile Ile Cys
        115                 120                 125

Ser Ala Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205
```

<210> SEQ ID NO 65
<211> LENGTH: 208
<212> TYPE: PRT
<213> ORGANISM: Artificial Sequence
<220> FEATURE:
<223> OTHER INFORMATION: CD80 v11 ECD

<400> SEQUENCE: 65

```
Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Gln Ala Leu Arg Pro Ser Asp Glu Gly Thr Tyr
65                  70                  75                  80

Ala Cys Val Val Leu Lys Tyr Glu Lys Asp Gly Phe Lys Arg Glu His
```

```
                85                  90                  95

Leu Ala Glu Val Thr Leu Ser Val Lys Ala Asp Phe Pro Thr Pro Ser
            100                 105                 110

Ile Ser Asp Phe Glu Ile Pro Ser Ser Asn Ile Arg Arg Ile Thr Cys
        115                 120                 125

Ser Ala Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205


<210> SEQ ID NO 66
<211> LENGTH: 208
<212> TYPE: PRT
<213> ORGANISM: Artificial Sequence
<220> FEATURE:
<223> OTHER INFORMATION: CD80 v12 ECD

<400> SEQUENCE: 66

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Gln Ala Leu Arg Pro Ser Asp Glu Gly Thr Tyr
65                  70                  75                  80

Glu Cys Val Val Leu Lys Asn Glu Lys Asp Gly Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Ala Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205


<210> SEQ ID NO 67
<211> LENGTH: 208
<212> TYPE: PRT
<213> ORGANISM: Artificial Sequence
<220> FEATURE:
<223> OTHER INFORMATION: CD80 v13 ECD
```

<400> SEQUENCE: 67

Val Ile His Val Thr Lys Glu Val Lys Glu Val Ala Thr Leu Ser Cys
1               5                   10                  15

Gly His Asn Val Ser Val Glu Glu Leu Ala Gln Ser Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Gln Ala Leu Arg Pro Ser Asp Glu Gly Thr Tyr
65                  70                  75                  80

Glu Cys Val Val Leu Lys Tyr Glu Lys Asp Gly Phe Lys Arg Lys His
                85                  90                  95

Leu Ala Glu Val Thr Leu Ser Val Lys Ala Asp Phe Pro Thr Pro Ser
            100                 105                 110

Ile Ser Asp Phe Glu Ile Pro Ser Ser Asn Ile Arg Arg Ile Ile Cys
        115                 120                 125

Ser Ala Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205

<210> SEQ ID NO 68
<211> LENGTH: 208
<212> TYPE: PRT
<213> ORGANISM: Artificial Sequence
<220> FEATURE:
<223> OTHER INFORMATION: CD80 v14 ECD

<400> SEQUENCE: 68

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Ser Asn
    50                  55                  60

Leu Ser Ile Val Ile Gln Ala Leu Arg Pro Ser Asp Glu Gly Thr Tyr
65                  70                  75                  80

Glu Cys Val Val Leu Lys Tyr Glu Lys Asp Gly Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Ser Ser Asn Ile Arg Arg Ile Ile Cys
        115                 120                 125

Ser Ala Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145 150 155 160

Thr Glu Leu Tyr Ala Val Ser Ser Lys Leu Asp Phe Asn Met Thr Thr
165 170 175

Asn His Ser Phe Met Cys Leu Ile Lys Tyr Gly His Leu Arg Val Asn
180 185 190

Gln Thr Phe Asn Trp Asn Thr Thr Lys Gln Glu His Phe Pro Asp Asn
195 200 205

<210> SEQ ID NO 69
<211> LENGTH: 208
<212> TYPE: PRT
<213> ORGANISM: Artificial Sequence
<220> FEATURE:
<223> OTHER INFORMATION: CD80 v15 ECD

<400> SEQUENCE: 69

Val Ile His Val Thr Lys Glu Val Lys Glu Val Ala Thr Leu Ser Cys
1 5 10 15

Gly His Asn Val Ser Val Glu Glu Leu Ala Gln Thr Arg Ile Tyr Trp
20 25 30

Gln Lys Glu Glu Lys Met Val Leu Thr Met Met Ser Gly Asp Met Asn
35 40 45

Ile Trp Pro Glu Tyr Lys Asn Arg Thr Ile Phe Asp Ile Thr Asn Asn
50 55 60

Leu Ser Thr Val Ile Gln Ala Leu Arg Pro Ser Asp Glu Gly Thr Tyr
65 70 75 80

Glu Cys Val Val Leu Lys Tyr Glu Lys Asp Gly Phe Lys Arg Glu His
85 90 95

Leu Ala Glu Val Thr Leu Ser Val Lys Ala Asp Phe Pro Thr Pro Ser
100 105 110

Ile Ser Asp Phe Glu Ile Pro Ser Ser Asn Ile Arg Arg Ile Ile Cys
115 120 125

Ser Ala Ser Gly Gly Phe Pro Glu Pro His Leu Ser Trp Leu Glu Asn
130 135 140

Gly Glu Glu Leu Asn Ala Ile Thr Thr Thr Val Ser Gln Asp Pro Glu
145 150 155 160

Thr Glu Leu Tyr Ala Val Ser Ser Lys Leu Asp Phe Asn Met Thr Thr
165 170 175

Asn His Ser Phe Met Cys Leu Ile Lys Tyr Gly His Leu Arg Val Asn
180 185 190

Gln Thr Phe Asn Trp Asn Thr Thr Lys Gln Glu His Phe Pro Asp Asn
195 200 205

<210> SEQ ID NO 70
<211> LENGTH: 208
<212> TYPE: PRT
<213> ORGANISM: Artificial Sequence
<220> FEATURE:
<223> OTHER INFORMATION: CD80 v16 ECD

<400> SEQUENCE: 70

Val Ile His Val Thr Lys Glu Val Lys Glu Val Ala Thr Leu Ser Cys
1 5 10 15

Gly His Asn Val Ser Val Glu Glu Leu Ala Gln Thr Arg Ile Tyr Trp
20 25 30

Gln Lys Glu Lys Lys Met Val Leu Thr Met Met Ser Gly Asp Met Asn
35 40 45

Ile Trp Pro Gly Tyr Lys Asn Arg Thr Ile Phe Asp Ile Thr Asn Asn
50 55 60

Leu Ser Ile Val Ile Gln Ala Leu Arg Pro Ser Asp Glu Gly Thr Tyr
65 70 75 80

Glu Cys Val Val Leu Lys Tyr Glu Lys Asp Gly Phe Lys Arg Glu His
85 90 95

Leu Ala Glu Val Thr Leu Ser Val Lys Ala Asp Phe Pro Thr Pro Ser
100 105 110

Ile Ser Asp Phe Glu Ile Pro Ser Ser Asn Ile Arg Arg Ile Ile Cys
115 120 125

Ser Ala Ser Gly Gly Phe Pro Glu Pro His Leu Ser Trp Leu Glu Asn
130 135 140

Gly Glu Glu Leu Asn Ala Ile Asn Thr Thr Val Ser Gln Asp Pro Glu
145 150 155 160

Thr Glu Leu Tyr Ala Val Ser Ser Lys Leu Asp Phe Asn Met Thr Thr
165 170 175

Asn His Ser Phe Met Cys Leu Ile Lys Tyr Gly His Leu Arg Val Asn
180 185 190

Gln Thr Phe Asn Trp Asn Thr Thr Lys Gln Glu His Phe Pro Asp Asn
195 200 205

<210> SEQ ID NO 71
<211> LENGTH: 208
<212> TYPE: PRT
<213> ORGANISM: Artificial Sequence
<220> FEATURE:
<223> OTHER INFORMATION: CD80 v17 ECD

<400> SEQUENCE: 71

Val Ile His Val Thr Lys Glu Val Lys Glu Val Ala Thr Leu Ser Cys
1 5 10 15

Gly His Asn Val Ser Val Glu Glu Leu Ala Gln Thr Arg Ile Tyr Trp
20 25 30

Gln Lys Glu Lys Glu Met Val Leu Thr Met Met Ser Gly Asp Met Asn
35 40 45

Ile Trp Pro Glu Tyr Lys Asn Arg Thr Ile Ser Asp Ile Thr Asn Asn
50 55 60

Leu Ser Ile Val Ile Gln Ala Leu Arg Pro Ser Asp Glu Gly Thr Tyr
65 70 75 80

Glu Cys Val Val Leu Lys Tyr Glu Lys Asp Gly Phe Lys Arg Glu His
85 90 95

Leu Ala Glu Val Thr Leu Ser Val Lys Ala Asp Phe Pro Thr Pro Ser
100 105 110

Ile Ser Asp Phe Glu Ile Pro Ser Ser Asn Ile Arg Arg Ile Ile Cys
115 120 125

Ser Ala Ser Gly Gly Phe Pro Glu Pro His Leu Ser Trp Leu Glu Asn
130 135 140

Gly Glu Glu Leu Asn Ala Ile Asn Thr Thr Val Ser Gln Asp Pro Glu
145 150 155 160

Thr Glu Leu Tyr Ala Val Ser Ser Lys Leu Asp Phe Asn Met Thr Thr
165 170 175

Asn His Ser Phe Met Cys Leu Ile Lys Tyr Gly His Leu Arg Val Asn
180 185 190

Gln Thr Phe Asn Trp Asn Thr Thr Lys Gln Glu His Phe Pro Asp Asn
195 200 205

<210> SEQ ID NO 72
<211> LENGTH: 208
<212> TYPE: PRT
<213> ORGANISM: Artificial Sequence
<220> FEATURE:
<223> OTHER INFORMATION: CD80 v18 ECD

<400> SEQUENCE: 72

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Gly Phe Lys Arg Glu His
                85                  90                  95

Leu Ala Glu Val Thr Leu Pro Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205

<210> SEQ ID NO 73
<211> LENGTH: 208
<212> TYPE: PRT
<213> ORGANISM: Artificial Sequence
<220> FEATURE:
<223> OTHER INFORMATION: CD80 v19 ECD

<400> SEQUENCE: 73

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Glu Asp Ala Phe Lys Arg Glu His
                85                  90                  95

Leu Ala Glu Val Thr Leu Ser Val Lys Ala Asp Phe Pro Thr Pro Ser

```
            100                 105                 110

Ile Ser Asp Phe Glu Ile Pro Thr Ser Asn Ile Arg Arg Ile Ile Cys
        115                 120                 125

Ser Ala Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205


<210> SEQ ID NO 74
<211> LENGTH: 208
<212> TYPE: PRT
<213> ORGANISM: Artificial Sequence
<220> FEATURE:
<223> OTHER INFORMATION: CD80 v20 ECD

<400> SEQUENCE: 74

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Gly Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205


<210> SEQ ID NO 75
<211> LENGTH: 208
<212> TYPE: PRT
<213> ORGANISM: Artificial Sequence
<220> FEATURE:
<223> OTHER INFORMATION: CD80 v21 ECD

<400> SEQUENCE: 75
```

Val Ile His Val Thr Lys Glu Val Lys Glu Val Ala Thr Leu Ser Cys
1 5 10 15

Gly His Asn Val Ser Val Glu Glu Leu Ala Gln Thr Arg Ile Tyr Trp
20 25 30

Gln Lys Glu Lys Lys Met Val Leu Thr Met Met Ser Gly Asp Met Asn
35 40 45

Ile Trp Pro Glu Tyr Lys Asn Arg Thr Ile Phe Val Ile Thr Asn Asn
50 55 60

Leu Ser Ile Val Ile Leu Ala Leu Arg Pro Ser Asp Glu Gly Thr Tyr
65 70 75 80

Glu Cys Val Val Leu Lys Tyr Glu Lys Asp Gly Phe Lys Arg Glu His
85 90 95

Leu Ala Glu Val Thr Leu Ser Val Lys Ala Asp Phe Pro Thr Pro Ser
100 105 110

Ile Ser Asp Phe Glu Ile Pro Ser Ser Asn Ile Arg Arg Ile Ile Cys
115 120 125

Ser Ala Ser Gly Gly Phe Pro Glu Pro His Leu Ser Trp Leu Glu Asn
130 135 140

Gly Glu Glu Leu Asn Ala Ile Asn Thr Thr Val Ser Gln Asp Pro Glu
145 150 155 160

Thr Glu Leu Tyr Ala Val Ser Ser Lys Leu Asp Phe Asn Met Thr Thr
165 170 175

Asn His Ser Phe Met Cys Leu Ile Lys Tyr Gly His Leu Arg Val Asn
180 185 190

Gln Thr Phe Asn Trp Asn Thr Thr Lys Gln Glu His Phe Pro Asp Asn
195 200 205

<210> SEQ ID NO 76
<211> LENGTH: 208
<212> TYPE: PRT
<213> ORGANISM: Artificial Sequence
<220> FEATURE:
<223> OTHER INFORMATION: CD80 v22 ECD

<400> SEQUENCE: 76

Val Ile His Val Thr Lys Glu Val Lys Glu Val Ala Thr Leu Ser Cys
1 5 10 15

Gly His Asn Val Ser Val Glu Glu Leu Ala Gln Thr Arg Ile Tyr Trp
20 25 30

Gln Lys Glu Lys Lys Met Val Leu Thr Met Met Ser Gly Asp Met Asn
35 40 45

Ile Trp Pro Glu Tyr Met Asn Arg Thr Ile Phe Asp Ile Thr Asn Asn
50 55 60

Leu Ser Ile Val Ile Leu Ala Leu Arg Pro Ser Asp Glu Gly Thr Tyr
65 70 75 80

Glu Cys Val Val Leu Lys Tyr Glu Lys Asp Gly Phe Lys Arg Glu His
85 90 95

Leu Ala Glu Val Thr Leu Ser Val Lys Ala Asp Phe Pro Thr Pro Ser
100 105 110

Ile Ser Asp Phe Glu Ile Pro Ser Ser Asn Ile Arg Arg Ile Ile Cys
115 120 125

Ser Thr Ser Gly Gly Phe Pro Glu Pro His Leu Ser Trp Leu Glu Asn
130 135 140

Gly Glu Glu Leu Asn Ala Ile Asn Thr Thr Val Ser Gln Asp Pro Glu
145 150 155 160

Thr Glu Leu Tyr Ala Val Ser Ser Lys Leu Asp Phe Asn Met Thr Thr
165 170 175

Asn His Ser Phe Met Cys Leu Ile Lys Tyr Gly His Leu Arg Val Asn
180 185 190

Gln Thr Phe Asn Trp Asn Thr Thr Lys Gln Glu His Phe Pro Asp Asn
195 200 205

<210> SEQ ID NO 77
<211> LENGTH: 208
<212> TYPE: PRT
<213> ORGANISM: Artificial Sequence
<220> FEATURE:
<223> OTHER INFORMATION: CD80 v23 ECD

<400> SEQUENCE: 77

Val Ile His Val Thr Lys Glu Val Lys Glu Val Ala Thr Leu Ser Cys
1 5 10 15

Gly His Asn Val Ser Val Glu Glu Leu Ala Gln Thr Arg Ile Tyr Trp
20 25 30

Gln Lys Glu Lys Lys Thr Val Leu Thr Met Met Ser Gly Asp Met Asn
35 40 45

Ile Trp Pro Glu Tyr Lys Asn Arg Thr Ile Phe Asp Ile Thr Asn Asn
50 55 60

Leu Ser Ile Val Ile Gln Ala Leu Arg Pro Ser Asp Gly Gly Thr Tyr
65 70 75 80

Glu Cys Val Val Leu Lys Tyr Glu Lys Asp Gly Phe Lys Arg Glu His
85 90 95

Leu Ala Glu Val Thr Leu Ser Val Lys Ala Asp Phe Pro Thr Pro Ser
100 105 110

Ile Ser Asp Phe Glu Ile Pro Ser Ser Asn Ile Arg Arg Ile Ile Cys
115 120 125

Ser Ala Ser Gly Gly Phe Pro Glu Pro His Leu Ser Trp Leu Glu Asn
130 135 140

Gly Glu Glu Leu Asn Ala Ile Thr Thr Thr Val Ser Gln Asp Pro Glu
145 150 155 160

Thr Glu Leu Tyr Ala Val Ser Ser Lys Leu Asp Phe Asn Met Thr Thr
165 170 175

Asn His Ser Phe Met Cys Leu Ile Lys Tyr Gly His Leu Arg Val Asn
180 185 190

Gln Thr Phe Asn Trp Asn Thr Thr Lys Gln Glu His Phe Pro Asp Asn
195 200 205

<210> SEQ ID NO 78
<211> LENGTH: 208
<212> TYPE: PRT
<213> ORGANISM: Artificial Sequence
<220> FEATURE:
<223> OTHER INFORMATION: CD80 v24 ECD

<400> SEQUENCE: 78

Val Ile His Val Thr Lys Glu Val Lys Glu Val Ala Thr Leu Ser Cys
1 5 10 15

Gly His Asn Val Ser Val Glu Glu Leu Ala Gln Thr His Ile Tyr Trp
20 25 30

Gln Lys Glu Lys Lys Met Val Leu Thr Met Met Ser Gly Asp Met Asn
35 40 45

Ile Trp Pro Gly Tyr Lys Asn Arg Thr Ile Phe Asp Ile Thr Asn Asn
50 55 60

```
Leu Ser Ile Val Ile Arg Ala Leu Arg Pro Ser Asp Glu Gly Thr Tyr
65                  70                  75                  80

Glu Cys Val Val Leu Lys Tyr Gly Lys Asp Gly Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Ala Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205


<210> SEQ ID NO 79
<211> LENGTH: 208
<212> TYPE: PRT
<213> ORGANISM: Artificial Sequence
<220> FEATURE:
<223> OTHER INFORMATION: CD80 v25 ECD

<400> SEQUENCE: 79

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile His Trp
            20                  25                  30

Gln Lys Glu Lys Lys Met Val Leu Gly Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Gln Ala Leu Arg Pro Ser Asp Glu Gly Thr Tyr
65                  70                  75                  80

Glu Cys Val Val Leu Lys Tyr Glu Lys Asp Gly Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Ser Ser Asn Ile Arg Arg Ile Ile Cys
        115                 120                 125

Ser Ala Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205


<210> SEQ ID NO 80
```

<211> LENGTH: 208
<212> TYPE: PRT
<213> ORGANISM: Artificial Sequence
<220> FEATURE:
<223> OTHER INFORMATION: CD80 v26 ECD

<400> SEQUENCE: 80

Val Ile His Val Thr Lys Glu Val Lys Glu Val Ala Thr Leu Ser Cys
1 5 10 15

Gly His Asn Val Ser Val Glu Glu Leu Ala Gln Thr Arg Ile Tyr Trp
20 25 30

Gln Lys Glu Lys Lys Met Val Leu Thr Met Met Ser Gly Asp Met Asn
35 40 45

Ile Trp Pro Glu Tyr Lys Asn Arg Thr Ile Phe Asp Ile Thr Asn Asn
50 55 60

Leu Ser Ile Ala Ile Leu Ala Leu Arg Pro Ser Asp Glu Gly Thr Tyr
65 70 75 80

Glu Cys Val Val Leu Lys Tyr Glu Lys Asp Ala Phe Lys Arg Glu His
85 90 95

Leu Ala Glu Val Thr Leu Ser Val Lys Ala Asp Phe Pro Ala Pro Ser
100 105 110

Ile Ser Asp Phe Glu Ile Pro Thr Ser Asn Ile Arg Arg Ile Ile Cys
115 120 125

Ser Thr Ser Gly Gly Phe Pro Glu Pro His Leu Ser Trp Leu Glu Asn
130 135 140

Gly Glu Glu Leu Asn Ala Ile Asn Thr Thr Val Ser Gln Asp Pro Glu
145 150 155 160

Thr Glu Leu Tyr Ala Val Ser Ser Lys Leu Asp Phe Asn Met Thr Thr
165 170 175

Asn His Ser Phe Met Cys Leu Ile Lys Tyr Gly His Leu Arg Val Asn
180 185 190

Gln Thr Phe Asn Trp Asn Thr Thr Lys Gln Glu His Phe Pro Asp Asn
195 200 205

<210> SEQ ID NO 81
<211> LENGTH: 208
<212> TYPE: PRT
<213> ORGANISM: Artificial Sequence
<220> FEATURE:
<223> OTHER INFORMATION: CD80 v27 ECD

<400> SEQUENCE: 81

Val Ile His Val Thr Lys Glu Val Lys Glu Val Ala Thr Leu Ser Cys
1 5 10 15

Gly His Asn Val Ser Val Glu Glu Leu Ala Gln Thr Arg Ile Tyr Trp
20 25 30

Gln Lys Glu Lys Lys Met Val Leu Thr Met Met Ser Gly Asp Met Asn
35 40 45

Ile Trp Pro Glu Tyr Lys Asn Arg Thr Ile Phe Asp Ile Thr Asn Asn
50 55 60

Leu His Ile Val Ile Leu Ala Leu Arg Pro Ser Asp Glu Gly Thr Tyr
65 70 75 80

Glu Cys Val Val Leu Lys Tyr Glu Lys Gly Ala Phe Lys Arg Glu His
85 90 95

Leu Ala Glu Val Thr Leu Ser Val Lys Ala Asp Phe Pro Ala Pro Ser
100 105 110

Ile Ser Asp Leu Glu Ile Pro Thr Ser Asn Ile Arg Arg Ile Ile Cys

```
        115                 120                 125

Ser Thr Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205


<210> SEQ ID NO 82
<211> LENGTH: 208
<212> TYPE: PRT
<213> ORGANISM: Artificial Sequence
<220> FEATURE:
<223> OTHER INFORMATION: CD80 v28 ECD

<400> SEQUENCE: 82

Val Ile His Val Thr Lys Glu Val Lys Glu Val Ala Thr Leu Ser Cys
1               5                   10                  15

Gly His Asn Val Ser Val Glu Glu Leu Ala Gln Thr His Ile Tyr Trp
            20                  25                  30

Gln Lys Glu Lys Lys Met Val Leu Thr Met Met Ser Gly Asp Met Asn
        35                  40                  45

Ile Trp Pro Gly Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Ser Ser Asn Ile Arg Arg Ile Ile Cys
        115                 120                 125

Ser Ala Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205


<210> SEQ ID NO 83
<211> LENGTH: 208
<212> TYPE: PRT
<213> ORGANISM: Artificial Sequence
<220> FEATURE:
<223> OTHER INFORMATION: CD80 v29 ECD

<400> SEQUENCE: 83

Val Ile His Val Thr Lys Glu Val Lys Glu Val Ala Thr Leu Ser Cys
1               5                   10                  15
```

```
Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Gly Phe Lys Arg Glu His
                85                  90                  95

Leu Ala Glu Val Thr Ser Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205


<210> SEQ ID NO 84
<211> LENGTH: 208
<212> TYPE: PRT
<213> ORGANISM: Artificial Sequence
<220> FEATURE:
<223> OTHER INFORMATION: CD80 v30 ECD

<400> SEQUENCE: 84

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Thr Val Ile Gln Ala Leu Arg Pro Ser Asp Glu Gly Thr Tyr
65                  70                  75                  80

Glu Cys Val Val Leu Lys Tyr Glu Lys Asp Gly Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Ser Ser Asn Ile Arg Arg Ile Ile Cys
        115                 120                 125

Ser Thr Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175
```

Asn His Ser Phe Met Cys Leu Ile Lys Tyr Gly His Leu Arg Val Asn
180 185 190

Gln Thr Phe Asn Trp Asn Thr Thr Lys Gln Glu His Phe Pro Asp Asn
195 200 205

<210> SEQ ID NO 85
<211> LENGTH: 208
<212> TYPE: PRT
<213> ORGANISM: Artificial Sequence
<220> FEATURE:
<223> OTHER INFORMATION: CD80 v31 ECD

<400> SEQUENCE: 85

Val Ile His Val Thr Lys Glu Val Lys Glu Val Ala Thr Leu Ser Cys
1 5 10 15

Gly His Asn Val Ser Val Glu Glu Leu Ala Gln Thr Arg Ile Tyr Trp
20 25 30

Gln Lys Glu Lys Lys Met Val Leu Thr Met Met Ser Gly Asp Met Asn
35 40 45

Ile Trp Pro Glu Tyr Lys Asn Arg Thr Ile Phe Asp Ile Thr Asn Asn
50 55 60

Leu Ser Ile Val Ile Gln Ala Leu Arg Pro Ser Asp Glu Gly Thr Tyr
65 70 75 80

Glu Cys Val Val Leu Lys Tyr Glu Lys Asp Gly Phe Lys Arg Glu His
85 90 95

Leu Ala Glu Val Thr Leu Ser Val Lys Ala Asp Phe Pro Ala Pro Ser
100 105 110

Ile Ser Asp Phe Glu Ile Pro Ser Ser Asn Ile Arg Arg Ile Ile Cys
115 120 125

Ser Ala Ser Gly Gly Phe Pro Glu Pro His Leu Ser Trp Leu Glu Asn
130 135 140

Gly Glu Glu Leu Asn Ala Ile Asn Thr Thr Val Ser Gln Asp Pro Glu
145 150 155 160

Thr Glu Leu Tyr Ala Val Ser Ser Lys Leu Asp Phe Asn Met Thr Thr
165 170 175

Asn His Ser Phe Met Cys Leu Ile Lys Tyr Gly His Leu Arg Val Asn
180 185 190

Gln Thr Phe Asn Trp Asn Thr Thr Lys Gln Glu His Phe Pro Asp Asn
195 200 205

<210> SEQ ID NO 86
<211> LENGTH: 208
<212> TYPE: PRT
<213> ORGANISM: Artificial Sequence
<220> FEATURE:
<223> OTHER INFORMATION: CD80 v32 ECD

<400> SEQUENCE: 86

Val Ile His Val Thr Lys Glu Val Lys Glu Val Ala Thr Leu Ser Cys
1 5 10 15

Gly His Asn Val Ser Val Glu Glu Leu Ala Gln Thr Arg Ile Tyr Trp
20 25 30

Gln Lys Glu Lys Lys Val Val Leu Asp Met Ile Ser Gly Asp Met Asn
35 40 45

Ile Gly Pro Glu Tyr Lys Asn Arg Thr Ile Phe Asp Ile Thr Asn Asn
50 55 60

Leu Ser Ile Val Ile Leu Ala Leu Arg Pro Ser Gly Glu Gly Thr Tyr
65 70 75 80

Glu Cys Ala Val Leu Lys Tyr Glu Glu Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Ser Ser Asn Ile Arg Arg Ile Ile Cys
        115                 120                 125

Ser Ala Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205

<210> SEQ ID NO 87
<211> LENGTH: 208
<212> TYPE: PRT
<213> ORGANISM: Artificial Sequence
<220> FEATURE:
<223> OTHER INFORMATION: CD80 v33 ECD

<400> SEQUENCE: 87

Val Ile His Val Thr Lys Glu Val Lys Glu Val Ala Thr Leu Ser Cys
1               5                   10                  15

Gly His Asn Val Ser Ala Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Gln Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Pro Asn Ile Arg Arg Ile Ile Cys
        115                 120                 125

Ser Thr Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205

<210> SEQ ID NO 88
<211> LENGTH: 208
<212> TYPE: PRT
<213> ORGANISM: Artificial Sequence
<220> FEATURE:
<223> OTHER INFORMATION: CD80 v34 ECD

<400> SEQUENCE: 88

Val Ile His Val Thr Lys Glu Val Lys Glu Val Val Thr Leu Phe Cys
1 5 10 15

Gly His Asn Val Ser Val Glu Glu Leu Ala Gln Thr Arg Ile His Trp
20 25 30

Gln Lys Glu Lys Lys Met Val Leu Gly Met Met Ser Gly Asp Met Asn
35 40 45

Ile Trp Pro Glu Tyr Lys Asn Arg Thr Ile Phe Asp Ile Thr Asn Asn
50 55 60

Leu Ser Ile Val Ile Leu Ala Leu Arg Pro Ser Asp Glu Gly Thr Tyr
65 70 75 80

Glu Cys Val Val Leu Lys Tyr Glu Lys Asp Ala Phe Lys Arg Glu His
85 90 95

Leu Ala Glu Val Thr Leu Ser Val Lys Ala Asp Phe Pro Thr Pro Ser
100 105 110

Ile Ser Asp Phe Glu Ile Pro Thr Ser Asn Ile Arg Arg Ile Ile Cys
115 120 125

Ser Ala Ser Gly Gly Phe Pro Glu Leu His Leu Ser Trp Leu Glu Asn
130 135 140

Gly Glu Glu Leu Asn Ala Ile Thr Thr Thr Val Ser Gln Asp Pro Glu
145 150 155 160

Thr Glu Leu Tyr Ala Val Ser Ser Lys Leu Asp Phe Asn Met Thr Thr
165 170 175

Asn His Ser Phe Met Cys Leu Ile Lys Tyr Gly His Leu Arg Val Asn
180 185 190

Gln Thr Phe Asn Trp Asn Thr Thr Lys Gln Glu His Phe Pro Asp Asn
195 200 205

<210> SEQ ID NO 89
<211> LENGTH: 208
<212> TYPE: PRT
<213> ORGANISM: Artificial Sequence
<220> FEATURE:
<223> OTHER INFORMATION: CD80 v35 ECD

<400> SEQUENCE: 89

Val Ile His Val Thr Lys Glu Val Lys Glu Val Ala Thr Leu Ser Cys
1 5 10 15

Gly His Asn Val Ser Val Glu Glu Leu Ala Gln Thr Arg Ile Tyr Trp
20 25 30

Gln Lys Glu Lys Lys Met Val Leu Thr Met Met Ser Gly Asp Met Asn
35 40 45

Ile Trp Pro Glu Tyr Lys Asn Arg Thr Ile Phe Asp Ile Thr Asn Asn
50 55 60

Leu Ser Phe Val Ile Arg Ala Leu Arg Pro Ser Asp Glu Gly Thr Tyr
65 70 75 80

Glu Cys Val Val Leu Lys Tyr Gly Lys Asp Gly Phe Lys Arg Glu His
85 90 95

Leu Ala Glu Val Thr Leu Ser Val Lys Ala Asp Phe Pro Thr Pro Ser
100 105 110

Ile Ser Asp Phe Glu Ile Pro Ser Ser Asn Ile Arg Arg Ile Ile Cys
115 120 125

Ser Ala Ser Gly Gly Phe Pro Glu Pro His Leu Ser Trp Leu Glu Asn

```
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205


<210> SEQ ID NO 90
<211> LENGTH: 208
<212> TYPE: PRT
<213> ORGANISM: Artificial Sequence
<220> FEATURE:
<223> OTHER INFORMATION: CD80 v36 ECD

<400> SEQUENCE: 90

Val Ile His Val Thr Lys Glu Val Lys Glu Val Ala Thr Leu Ser Cys
1               5                   10                  15

Gly His Asn Val Ser Val Glu Gly Pro Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Gln Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Ser Ser Asn Ile Arg Arg Ile Ile Cys
        115                 120                 125

Ser Thr Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205


<210> SEQ ID NO 91
<211> LENGTH: 208
<212> TYPE: PRT
<213> ORGANISM: Artificial Sequence
<220> FEATURE:
<223> OTHER INFORMATION: CD80 v37 ECD

<400> SEQUENCE: 91

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30
```

```
Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Gly Leu Lys Arg Glu His
                85                  90                  95

Leu Ala Glu Val Thr Leu Ser Val Lys Ala Asp Leu Pro Thr Pro Ser
            100                 105                 110

Ile Ser Asp Phe Glu Ile Pro Ser Ser Asn Ile Arg Arg Ile Ile Cys
        115                 120                 125

Ser Thr Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205


<210> SEQ ID NO 92
<211> LENGTH: 208
<212> TYPE: PRT
<213> ORGANISM: Artificial Sequence
<220> FEATURE:
<223> OTHER INFORMATION: CD80 v38 ECD

<400> SEQUENCE: 92

Val Ile His Val Thr Lys Glu Val Lys Glu Val Ala Thr Leu Ser Cys
1               5                   10                  15

Gly His Asn Val Ser Val Glu Glu Leu Ala Gln Thr Asp Ile Leu Trp
            20                  25                  30

His Lys Glu Gly Lys Ile Val Leu Ala Met Arg Ser Gly Asp Thr Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Val Cys Val Val Arg Lys Tyr Glu Asn Asp Thr Pro Val Leu Glu His
                85                  90                  95

Leu Ala Glu Val Thr Leu Ser Val Lys Ala Asp Phe Pro Thr Pro Ser
            100                 105                 110

Ile Ser Asp Phe Glu Thr Pro Thr Ser Asn Ile Arg Arg Ile Ile Cys
        115                 120                 125

Ser Thr Ser Gly Gly Phe Pro Glu Pro His Leu Ser Trp Leu Glu Asn
    130                 135                 140

Gly Glu Glu Leu Ser Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190
```

Gln Thr Phe Asn Trp Asn Thr Thr Lys Gln Glu His Phe Pro Asp Asn
195 200 205

<210> SEQ ID NO 93
<211> LENGTH: 208
<212> TYPE: PRT
<213> ORGANISM: Artificial Sequence
<220> FEATURE:
<223> OTHER INFORMATION: CD80 v39 ECD

<400> SEQUENCE: 93

Val Ile His Val Thr Lys Glu Val Lys Glu Val Ala Thr Leu Ser Cys
1 5 10 15

Gly His Asn Val Ser Val Glu Glu Leu Ala Gln Thr Asp Ile Leu Trp
20 25 30

His Lys Glu Gly Lys Ile Val Leu Ala Met Arg Ser Gly Asp Thr Asn
35 40 45

Ile Trp Pro Glu Tyr Lys Asn Arg Thr Ile Phe Asp Ile Thr Asn Asn
50 55 60

Leu Ser Ile Val Ile Leu Ala Leu Arg Pro Ser Asp Glu Gly Thr Tyr
65 70 75 80

Val Cys Val Val Arg Lys Tyr Glu Asn Asp Thr Pro Val Leu Glu His
85 90 95

Leu Ala Glu Val Thr Leu Ser Val Lys Ala Asp Phe Pro Thr Pro Ser
100 105 110

Ile Ser Asp Phe Glu Ile Pro Thr Ser Asn Ile Arg Arg Ile Ile Cys
115 120 125

Ser Thr Ser Gly Gly Phe Pro Glu Pro His Leu Ser Trp Leu Glu Ser
130 135 140

Gly Glu Glu Leu Ser Ala Ile Asn Thr Thr Val Ser Gln Asp Pro Glu
145 150 155 160

Thr Glu Leu Tyr Ala Val Ser Ser Lys Leu Asp Phe Asn Met Thr Thr
165 170 175

Asn His Ser Phe Met Cys Leu Ile Lys Tyr Gly His Leu Arg Val Asn
180 185 190

Gln Thr Phe Asn Trp Asn Thr Thr Lys Gln Glu His Phe Pro Asp Asn
195 200 205

<210> SEQ ID NO 94
<211> LENGTH: 208
<212> TYPE: PRT
<213> ORGANISM: Artificial Sequence
<220> FEATURE:
<223> OTHER INFORMATION: CD80 v40 ECD

<400> SEQUENCE: 94

Val Ile His Val Thr Lys Glu Val Lys Glu Val Ala Thr Leu Ser Cys
1 5 10 15

Gly His Asn Val Ser Val Glu Glu Leu Ala Gln Thr Asp Ile Leu Trp
20 25 30

His Lys Glu Gly Lys Ile Val Leu Ala Thr Arg Ser Gly Asp Thr Asn
35 40 45

Ile Trp Pro Glu Tyr Lys Asn Arg Thr Ile Phe Asp Ile Thr Asn Asn
50 55 60

Leu Ser Ile Val Ile Leu Ala Leu Arg Pro Ser Asp Glu Gly Thr Tyr
65 70 75 80

Val Cys Val Val Arg Lys Tyr Glu Asn Asp Thr Pro Val Leu Glu His
85 90 95

```
Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
    130                 135                 140

Gly Glu Glu Ser Ser Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205


<210> SEQ ID NO 95
<211> LENGTH: 208
<212> TYPE: PRT
<213> ORGANISM: Artificial Sequence
<220> FEATURE:
<223> OTHER INFORMATION: CD80 v41 ECD

<400> SEQUENCE: 95

Val Ile His Val Thr Lys Glu Val Lys Glu Val Ala Thr Leu Ser Cys
1               5                   10                  15

Gly His Asn Val Ser Val Glu Gly Leu Ala Gln Thr Asp Ile Leu Trp
            20                  25                  30

His Lys Glu Gly Lys Ile Val Leu Ala Met Arg Ser Gly Asp Thr Asn
        35                  40                  45

Ile Trp Pro Glu Tyr Lys Asn Arg Thr Ile Leu Asp Ile Thr Asn Asn
    50                  55                  60

Leu Ser Ile Val Ile Leu Ala Leu Arg Pro Ser Asp Glu Gly Thr Tyr
65                  70                  75                  80

Val Cys Val Val Arg Lys Tyr Glu Asn Asp Thr Pro Val Leu Glu Arg
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
    130                 135                 140

Gly Glu Glu Leu Ser Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Ser Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205


<210> SEQ ID NO 96
<211> LENGTH: 208
<212> TYPE: PRT
<213> ORGANISM: Artificial Sequence
<220> FEATURE:
<223> OTHER INFORMATION: CD80 v42 ECD
```

<400> SEQUENCE: 96

Val Ile His Val Thr Lys Glu Val Lys Glu Val Ala Thr Leu Ser Cys
1               5                   10                  15

Gly His Asn Val Ser Val Glu Glu Leu Ala Gln Thr Asp Ile Leu Trp
            20                  25                  30

His Lys Glu Gly Lys Ile Val Leu Ala Met Arg Ser Gly Asp Thr Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Val Cys Val Val Arg Lys Tyr Glu Asn Asp Thr Pro Val Leu Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
    130                 135                 140

Gly Glu Glu Leu Ser Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205

<210> SEQ ID NO 97
<211> LENGTH: 208
<212> TYPE: PRT
<213> ORGANISM: Artificial Sequence
<220> FEATURE:
<223> OTHER INFORMATION: CD80 v43 ECD

<400> SEQUENCE: 97

Val Ile His Val Thr Lys Glu Val Lys Glu Val Ala Thr Leu Ser Cys
1               5                   10                  15

Gly His Asn Val Ser Val Glu Glu Leu Ala Gln Thr Val Ile Tyr Trp
            20                  25                  30

Gln Lys Glu Lys Lys Met Val Leu Thr Met Gln Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Arg Cys Val Val Ile Lys Tyr Glu Arg Leu Glu Asn Gln Gly Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu 145 150 155 160

Thr Glu Leu Tyr Ala Val Ser Ser Lys Leu Asp Phe Asn Met Thr Thr
165 170 175

Asn His Ser Phe Met Cys Leu Ile Lys Tyr Gly His Leu Arg Val Asn
180 185 190

Gln Thr Phe Asn Trp Asn Thr Thr Lys Gln Glu His Phe Pro Asp Asn
195 200 205

<210> SEQ ID NO 98
<211> LENGTH: 208
<212> TYPE: PRT
<213> ORGANISM: Artificial Sequence
<220> FEATURE:
<223> OTHER INFORMATION: CD80 v44 ECD

<400> SEQUENCE: 98

Val Ile His Val Thr Lys Glu Val Lys Glu Val Ala Thr Leu Ser Cys
1 5 10 15

Gly His Asn Val Ser Val Glu Glu Leu Ala Gln Thr Arg Ile Tyr Trp
20 25 30

Gln Lys Glu Lys Lys Met Val Leu Ile Met Met Ser Gly Asp Met Asn
35 40 45

Ile Trp Pro Glu Tyr Lys Asn Arg Thr Ile Phe Asp Ile Thr Asn Asn
50 55 60

Leu Ser Ile Val Ile Leu Ala Leu Arg Pro Ser Asp Glu Gly Thr Tyr
65 70 75 80

Glu Cys Val Val Leu Lys Tyr Glu Lys Asp Gly Phe Lys Arg Glu His
85 90 95

Leu Ala Glu Val Thr Leu Ser Val Lys Ala Asp Phe Pro Thr Pro Ser
100 105 110

Ile Ser Asp Phe Glu Ile Pro Thr Ser Asn Ile Arg Arg Ile Ile Cys
115 120 125

Ser Thr Ser Gly Gly Phe Pro Glu Pro His Leu Ser Trp Leu Glu Asn
130 135 140

Gly Glu Glu Leu Asn Ala Ile Asn Thr Thr Val Ser Gln Asp Pro Glu
145 150 155 160

Thr Glu Leu Tyr Ala Val Ser Ser Lys Leu Asp Phe Asn Met Thr Thr
165 170 175

Asn His Ser Phe Met Cys Leu Ile Lys Tyr Gly His Leu Arg Val Asn
180 185 190

Gln Thr Phe Asn Trp Asn Thr Thr Lys Gln Glu His Phe Pro Asp Asn
195 200 205

<210> SEQ ID NO 99
<211> LENGTH: 208
<212> TYPE: PRT
<213> ORGANISM: Artificial Sequence
<220> FEATURE:
<223> OTHER INFORMATION: CD80 v45 ECD

<400> SEQUENCE: 99

Val Ile His Val Thr Lys Glu Val Lys Glu Val Ala Thr Leu Ser Cys
1 5 10 15

Gly His Asn Val Ser Val Glu Glu Leu Ala Gln Thr Arg Ile Tyr Trp
20 25 30

Gln Lys Glu Lys Lys Met Val Leu Thr Met Met Ser Gly Asp Met Asn
35 40 45

```
Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Arg Lys Gly Tyr Arg Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Ser Ile Arg Arg Ile Ile Cys
        115                 120                 125

Ser Thr Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Ser His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205
```

<210> SEQ ID NO 100
<211> LENGTH: 208
<212> TYPE: PRT
<213> ORGANISM: Artificial Sequence
<220> FEATURE:
<223> OTHER INFORMATION: CD80 v46 ECD

<400> SEQUENCE: 100

```
Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Arg Lys Gly Tyr Arg Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205
```

<210> SEQ ID NO 101
<211> LENGTH: 208
<212> TYPE: PRT
<213> ORGANISM: Artificial Sequence
<220> FEATURE:
<223> OTHER INFORMATION: CD80 v47 ECD

<400> SEQUENCE: 101

Val Ile His Val Thr Lys Glu Val Lys Glu Val Ala Thr Leu Ser Cys
1 5 10 15

Gly His Asn Val Ser Val Glu Glu Leu Ala Gln Thr Arg Ile Tyr Trp
20 25 30

Gln Lys Glu Gly Gln Ile Val Leu Thr Met Met Ser Gly Asp Met Asn
35 40 45

Ile Trp Pro Glu Tyr Lys Asn Arg Thr Ile Leu Asp Ile Thr Asn Asn
50 55 60

Leu Ser Ile Val Ile Leu Ala Leu Arg Pro Ser Asp Glu Gly Thr Tyr
65 70 75 80

Val Cys Val Val Arg Lys Tyr Glu Asn Asp Thr Pro Val Leu Glu His
85 90 95

Leu Ala Gly Val Thr Leu Ser Val Lys Ala Asp Phe Pro Thr Pro Ser
100 105 110

Ile Ser Asp Phe Glu Ile Pro Thr Ser Asn Ile Arg Arg Ile Ile Cys
115 120 125

Ser Ala Ser Gly Gly Phe Pro Glu Pro His Leu Ser Trp Leu Glu Asn
130 135 140

Gly Glu Glu Leu Ser Ala Ile Asn Thr Thr Val Ser Gln Asp Pro Glu
145 150 155 160

Thr Glu Leu Tyr Ala Val Ser Ser Lys Leu Asp Phe Asn Met Thr Thr
165 170 175

Asn His Ser Phe Met Cys Leu Ile Lys Tyr Gly His Leu Arg Val Asn
180 185 190

Gln Thr Phe Asn Trp Asn Thr Thr Lys Gln Glu His Phe Pro Asp Asn
195 200 205

<210> SEQ ID NO 102
<211> LENGTH: 208
<212> TYPE: PRT
<213> ORGANISM: Artificial Sequence
<220> FEATURE:
<223> OTHER INFORMATION: CD80 v48 ECD

<400> SEQUENCE: 102

Val Ile His Val Thr Lys Glu Val Lys Glu Val Ala Thr Leu Ser Cys
1 5 10 15

Gly His Asn Val Ser Val Glu Glu Leu Ala Gln Thr Arg Ile Tyr Trp
20 25 30

Gln Lys Glu Lys Lys Met Val Leu Thr Met Met Ser Gly Asp Met Asn
35 40 45

Ile Trp Pro Glu Tyr Lys Asn Arg Thr Ile Phe Asp Ile Thr Asn Asn
50 55 60

Leu Ser Ile Val Ile Leu Ala Leu Arg Pro Ser Asp Glu Gly Thr Tyr
65 70 75 80

Glu Cys Val Val Leu Lys Tyr Asp Arg Lys Gly Tyr Arg Arg Glu His
85 90 95

Leu Ala Glu Val Thr Leu Ser Val Lys Ala Asp Phe Pro Thr Pro Ser
100 105 110

Ile Ser Asp Phe Glu Ile Pro Thr Ser Asn Ile Arg Arg Ile Ile Cys
115 120 125

Ser Thr Ser Gly Gly Phe Pro Glu Pro His Leu Ser Trp Leu Glu Asn
130 135 140

Gly Glu Glu Leu Asn Ala Ile Asn Thr Thr Val Ser Gln Asp Pro Glu
145 150 155 160

Thr Glu Leu Tyr Ala Val Ser Ser Lys Leu Asp Phe Asn Met Thr Thr
165 170 175

Asn His Ser Phe Met Cys Leu Ile Lys Tyr Gly His Leu Arg Val Asn
180 185 190

Gln Thr Phe Asn Trp Asn Thr Thr Lys Gln Glu His Phe Pro Asp Asn
195 200 205

<210> SEQ ID NO 103
<211> LENGTH: 208
<212> TYPE: PRT
<213> ORGANISM: Artificial Sequence
<220> FEATURE:
<223> OTHER INFORMATION: CD80 v49 ECD

<400> SEQUENCE: 103

Val Ile His Val Thr Lys Glu Val Lys Glu Val Ala Thr Leu Ser Cys
1 5 10 15

Gly His Asn Val Ser Val Glu Glu Leu Ala Gln Thr Arg Ile Tyr Trp
20 25 30

Gln Lys Glu Gly Gln Ile Val Met Thr Met Met Ser Gly Asp Met Asn
35 40 45

Ile Trp Pro Glu Tyr Lys Asn Arg Thr Ile Phe Asp Ile Thr Asn Asn
50 55 60

Leu Ser Ile Val Ile Leu Ala Leu Arg Pro Ser Asp Glu Gly Thr Tyr
65 70 75 80

Glu Cys Val Val Leu Lys Tyr Glu Lys Asp Ala Phe Lys Arg Glu His
85 90 95

Leu Ala Glu Val Thr Leu Ser Val Lys Ala Asp Phe Pro Thr Pro Ser
100 105 110

Ile Ser Asp Phe Glu Ile Pro Thr Ser Asn Ile Arg Arg Ile Ile Cys
115 120 125

Ser Thr Ser Gly Gly Phe Pro Glu Pro His Leu Ser Trp Leu Glu Asn
130 135 140

Gly Glu Glu Leu Asn Ala Ile Asn Thr Thr Val Ser Gln Asp Pro Glu
145 150 155 160

Thr Glu Leu Tyr Ala Val Ser Ser Lys Leu Asp Phe Asn Met Thr Thr
165 170 175

Asn His Ser Phe Met Cys Leu Ile Lys Tyr Gly His Leu Arg Val Asn
180 185 190

Gln Thr Phe Asn Trp Asn Thr Thr Lys Gln Glu His Phe Pro Asp Asn
195 200 205

<210> SEQ ID NO 104
<211> LENGTH: 208
<212> TYPE: PRT
<213> ORGANISM: Artificial Sequence
<220> FEATURE:
<223> OTHER INFORMATION: CD80 v50 ECD

<400> SEQUENCE: 104

Val Ile His Val Thr Lys Glu Val Lys Glu Val Ala Thr Leu Ser Cys

```
1               5                   10                  15

Gly His Asn Val Ser Val Glu Glu Leu Ala Gln Thr Arg Ile Tyr Trp
            20                  25                  30

Gln Lys Glu Gly Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205


<210> SEQ ID NO 105
<211> LENGTH: 208
<212> TYPE: PRT
<213> ORGANISM: Artificial Sequence
<220> FEATURE:
<223> OTHER INFORMATION: CD80 v51 ECD

<400> SEQUENCE: 105

Val Ile His Val Thr Lys Glu Val Lys Glu Val Ala Thr Leu Ser Cys
1               5                   10                  15

Gly His Asn Val Ser Val Glu Glu Leu Ala Gln Thr His Ile His Trp
            20                  25                  30

Gln Lys Glu Lys Lys Met Val Leu Gly Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Asn Gly Glu Asn Gly Phe Lys Arg Glu His
                85                  90                  95

Leu Ala Glu Val Thr Leu Ser Val Lys Ala Asp Phe Ser Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
```

```
            165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205


<210> SEQ ID NO 106
<211> LENGTH: 208
<212> TYPE: PRT
<213> ORGANISM: Artificial Sequence
<220> FEATURE:
<223> OTHER INFORMATION: CD80 v52 ECD

<400> SEQUENCE: 106

Val Ile His Val Thr Lys Glu Val Lys Glu Val Thr Thr Leu Ser Cys
1               5                   10                  15

Gly Leu Asn Val Ser Val Glu Glu Leu Ala Gln Thr Arg Ile Tyr Trp
            20                  25                  30

Gln Lys Glu Lys Lys Met Val Leu Thr Met Val Ser Gly Asp Met Asn
        35                  40                  45

Ile Trp Pro Glu Tyr Lys Asn Arg Thr Ile Leu Asp Ile Thr Asn Asn
    50                  55                  60

Leu Ser Ile Val Ile Leu Ala Leu Arg Pro Ser Asp Lys Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Ser Thr Pro Ser
            100                 105                 110

Ile Ser Asp Phe Glu Thr Pro Thr Ser Asn Ile Arg Arg Ile Ile Cys
        115                 120                 125

Ser Thr Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205


<210> SEQ ID NO 107
<211> LENGTH: 208
<212> TYPE: PRT
<213> ORGANISM: Artificial Sequence
<220> FEATURE:
<223> OTHER INFORMATION: CD80 v53 ECD

<400> SEQUENCE: 107

Val Ile His Val Thr Lys Glu Val Lys Glu Val Ala Thr Leu Ser Cys
1               5                   10                  15

Gly His Asn Val Ser Val Glu Glu Leu Ala Gln Thr Val Ile Phe Trp
            20                  25                  30

Gln Lys Glu Gly Lys Leu Val Leu Thr Met Gln Ser Gly Asp Met Asn
        35                  40                  45

Ile Trp Pro Glu Tyr Lys Asn Arg Thr Ile Phe Asp Ile Thr Asn Asn
    50                  55                  60
```

Leu Ser Ile Val Ile Leu Ala Leu Arg Pro Ser Asp Glu Gly Thr Tyr
65 70 75 80

Arg Cys Ile Val Ile Lys Tyr Glu Arg Leu Glu Asn Gln Gly Glu His
85 90 95

Leu Ala Glu Val Thr Leu Ser Val Lys Ala Asp Phe Pro Thr Pro Ser
100 105 110

Ile Ser Asp Phe Glu Ile Pro Thr Ser Asn Ile Arg Arg Ile Ile Cys
115 120 125

Ser Thr Ser Gly Gly Phe Pro Glu Pro His Leu Ser Trp Leu Glu Asn
130 135 140

Gly Glu Glu Leu Asn Ala Ile Asn Thr Thr Val Ser Gln Asp Pro Glu
145 150 155 160

Thr Glu Leu Tyr Ala Val Ser Ser Lys Leu Asp Phe Asn Met Thr Thr
165 170 175

Asn His Ser Phe Met Cys Leu Ile Lys Tyr Gly His Leu Arg Val Asn
180 185 190

Gln Thr Phe Asn Trp Asn Thr Thr Lys Gln Glu His Phe Pro Asp Asn
195 200 205

<210> SEQ ID NO 108
<211> LENGTH: 208
<212> TYPE: PRT
<213> ORGANISM: Artificial Sequence
<220> FEATURE:
<223> OTHER INFORMATION: CD80 v54 ECD

<400> SEQUENCE: 108

Val Ile His Val Thr Lys Glu Val Lys Glu Val Ala Thr Leu Ser Cys
1 5 10 15

Gly His Asn Val Ser Val Glu Glu Leu Ala Gln Thr Arg Ile Tyr Trp
20 25 30

Gln Lys Glu Lys Lys Met Val Leu Thr Met Met Ser Gly Asp Met Asn
35 40 45

Ile Trp Pro Glu Tyr Lys Asn Arg Thr Ile Phe Asp Ile Thr Asn Asn
50 55 60

Leu Ser Ile Met Ile Pro Ala Pro Arg Pro Ser Asp Glu Gly Thr Tyr
65 70 75 80

Glu Cys Val Val Leu Glu Tyr Glu Lys Asp Ala Phe Lys Arg Glu His
85 90 95

Leu Ala Glu Val Thr Leu Ser Val Lys Ala Asp Phe Pro Thr Pro Ser
100 105 110

Ile Ser Asp Phe Glu Ile Pro Thr Ser Asn Ile Arg Arg Ile Ile Cys
115 120 125

Ser Thr Ser Gly Gly Phe Pro Glu Pro His Leu Ser Trp Leu Glu Asn
130 135 140

Gly Glu Glu Leu Asn Ala Ile Asn Thr Thr Val Ser Gln Asp Pro Glu
145 150 155 160

Thr Glu Leu Tyr Ala Val Ser Ser Lys Leu Asp Phe Asn Met Thr Thr
165 170 175

Asn His Ser Phe Met Cys Leu Ile Lys Tyr Gly His Leu Arg Val Asn
180 185 190

Gln Thr Phe Asn Trp Asn Thr Thr Lys Gln Glu His Phe Pro Asp Asn
195 200 205

<210> SEQ ID NO 109
<211> LENGTH: 238

```
<212> TYPE: PRT
<213> ORGANISM: Artificial Sequence
<220> FEATURE:
<223> OTHER INFORMATION: ICOSL v1 ECD

<400> SEQUENCE: 109

Asp Thr Gln Glu Lys Glu Val Arg Ala Met Val Gly Ser Asp Val Glu
1               5                   10                  15

Leu Ser Cys Ala Cys Pro Glu Gly Ser Arg Phe Asp Leu Asn Asp Val
            20                  25                  30

Tyr Val Tyr Trp Gln Thr Ser Glu Ser Lys Thr Val Val Thr Tyr His
        35                  40                  45

Ile Pro Gln Ser Ser Ser Leu Glu Asn Val Asp Ser Arg Tyr Arg Asn
    50                  55                  60

Arg Ala Leu Met Ser Pro Ala Gly Met Leu Arg Gly Asp Phe Ser Leu
65                  70                  75                  80

Arg Leu Phe Asn Val Thr Pro Gln Asp Glu Gln Lys Phe His Cys Leu
                85                  90                  95

Val Leu Ser Gln Ser Leu Gly Phe Gln Glu Val Leu Ser Val Glu Val
            100                 105                 110

Thr Leu His Val Ala Ala Asn Phe Ser Val Pro Val Val Ser Ala Pro
        115                 120                 125

His Ser Pro Ser Gln Asp Glu Leu Thr Phe Thr Cys Thr Ser Ile Asn
    130                 135                 140

Gly Tyr Pro Arg Pro Asn Val Tyr Trp Ile Asn Lys Thr Asp Asn Ser
145                 150                 155                 160

Leu Leu Asp Gln Ala Leu Gln Asn Asp Thr Val Phe Leu Asn Met Arg
                165                 170                 175

Gly Leu Tyr Asp Val Val Ser Val Leu Arg Ile Ala Arg Thr Pro Ser
            180                 185                 190

Val Asn Ile Gly Cys Cys Ile Glu Asn Val Leu Leu Gln Gln Asn Leu
        195                 200                 205

Thr Val Gly Ser Gln Thr Gly Asn Asp Ile Gly Glu Arg Asp Lys Ile
    210                 215                 220

Thr Glu Asn Pro Val Ser Thr Gly Glu Lys Asn Ala Ala Thr
225                 230                 235


<210> SEQ ID NO 110
<211> LENGTH: 238
<212> TYPE: PRT
<213> ORGANISM: Artificial Sequence
<220> FEATURE:
<223> OTHER INFORMATION: ICOSL v2 ECD

<400> SEQUENCE: 110

Asp Thr Gln Glu Lys Glu Val Arg Ala Met Val Gly Ser Asp Val Glu
1               5                   10                  15

Leu Ser Cys Ala Cys Pro Glu Gly Ser Arg Phe Asp Leu Asn Asp Val
            20                  25                  30

Tyr Val Tyr Trp Gln Thr Ser Glu Ser Lys Thr Val Val Thr Tyr His
        35                  40                  45

Ile Pro Gln His Ser Ser Leu Glu Asn Val Asp Ser Arg Tyr Arg Asn
    50                  55                  60

Arg Ala Leu Met Ser Pro Ala Gly Met Leu Arg Gly Asp Phe Ser Leu
65                  70                  75                  80

Arg Leu Phe Asn Val Thr Pro Gln Asp Glu Gln Lys Phe His Cys Leu
                85                  90                  95
```

```
Val Leu Ser Gln Ser Leu Gly Phe Gln Glu Val Leu Ser Val Glu Val
            100                 105                 110

Thr Leu His Val Ala Ala Asn Phe Ser Val Pro Val Val Ser Ala Pro
        115                 120                 125

His Ser Pro Ser Gln Asp Glu Leu Thr Phe Thr Cys Thr Ser Ile Asn
    130                 135                 140

Gly Tyr Pro Arg Pro Asn Val Tyr Trp Ile Asn Lys Thr Asp Asn Ser
145                 150                 155                 160

Leu Leu Asp Gln Ala Leu Gln Asn Asp Thr Val Phe Leu Asn Met Arg
                165                 170                 175

Gly Leu Tyr Asp Val Val Ser Val Leu Arg Ile Ala Arg Thr Pro Ser
            180                 185                 190

Val Asn Ile Gly Cys Cys Ile Glu Asn Val Leu Leu Gln Gln Asn Leu
        195                 200                 205

Thr Val Gly Ser Gln Thr Gly Asn Asp Ile Gly Glu Arg Asp Lys Ile
    210                 215                 220

Thr Glu Asn Pro Val Ser Thr Gly Glu Lys Asn Ala Ala Thr
225                 230                 235


<210> SEQ ID NO 111
<211> LENGTH: 238
<212> TYPE: PRT
<213> ORGANISM: Artificial Sequence
<220> FEATURE:
<223> OTHER INFORMATION: ICOSL v3 ECD

<400> SEQUENCE: 111

Asp Thr Gln Glu Lys Glu Val Arg Ala Met Val Gly Ser Asp Val Glu
1               5                   10                  15

Leu Ser Cys Ala Cys Pro Glu Gly Ser Arg Phe Asp Leu Asn Asp Val
            20                  25                  30

Tyr Val Tyr Trp Gln Thr Ser Glu Ser Lys Thr Val Val Thr Tyr His
        35                  40                  45

Ile Pro Gln Asp Ser Ser Leu Glu Asn Val Asp Ser Arg Tyr Arg Asn
    50                  55                  60

Arg Ala Leu Met Ser Pro Ala Gly Met Leu Arg Gly Asp Phe Ser Leu
65                  70                  75                  80

Arg Leu Phe Asn Val Thr Pro Gln Asp Glu Gln Lys Phe His Cys Leu
                85                  90                  95

Val Leu Ser Gln Ser Leu Gly Phe Gln Glu Val Leu Ser Val Glu Val
            100                 105                 110

Thr Leu His Val Ala Ala Asn Phe Ser Val Pro Val Val Ser Ala Pro
        115                 120                 125

His Ser Pro Ser Gln Asp Glu Leu Thr Phe Thr Cys Thr Ser Ile Asn
    130                 135                 140

Gly Tyr Pro Arg Pro Asn Val Tyr Trp Ile Asn Lys Thr Asp Asn Ser
145                 150                 155                 160

Leu Leu Asp Gln Ala Leu Gln Asn Asp Thr Val Phe Leu Asn Met Arg
                165                 170                 175

Gly Leu Tyr Asp Val Val Ser Val Leu Arg Ile Ala Arg Thr Pro Ser
            180                 185                 190

Val Asn Ile Gly Cys Cys Ile Glu Asn Val Leu Leu Gln Gln Asn Leu
        195                 200                 205

Thr Val Gly Ser Gln Thr Gly Asn Asp Ile Gly Glu Arg Asp Lys Ile
    210                 215                 220
```

Thr Glu Asn Pro Val Ser Thr Gly Glu Lys Asn Ala Ala Thr
225 230 235

<210> SEQ ID NO 112
<211> LENGTH: 238
<212> TYPE: PRT
<213> ORGANISM: Artificial Sequence
<220> FEATURE:
<223> OTHER INFORMATION: ICOSL v4 ECD

<400> SEQUENCE: 112

Asp Thr Gln Glu Lys Glu Val Arg Ala Met Val Gly Ser Asp Val Glu
1 5 10 15

Leu Ser Cys Ala Cys Pro Glu Gly Ser Arg Phe Asp Leu Asn Asp Val
20 25 30

Tyr Val Tyr Trp Gln Thr Ser Glu Ser Lys Thr Val Val Thr Tyr His
35 40 45

Ile Pro Gln Tyr Ser Ser Leu Glu Tyr Val Asp Ser Arg Tyr Arg Asn
50 55 60

Arg Ala Leu Met Ser Pro Ala Gly Met Leu Arg Gly Asp Phe Ser Leu
65 70 75 80

Arg Leu Phe Asn Val Thr Pro Gln Asp Glu Gln Lys Phe His Cys Leu
85 90 95

Val Leu Ser Gln Ser Leu Gly Phe Gln Glu Val Leu Ser Val Glu Val
100 105 110

Thr Leu His Val Ala Ala Asn Phe Ser Val Pro Val Val Ser Ala Pro
115 120 125

His Ser Pro Ser Gln Asp Glu Leu Thr Leu Thr Cys Thr Ser Ile Asn
130 135 140

Gly Tyr Pro Arg Pro Asn Val Tyr Trp Ile Asn Lys Thr Asp Asn Ser
145 150 155 160

Leu Leu Asp Gln Ala Leu Gln Asn Asp Thr Val Phe Leu Asn Met Arg
165 170 175

Gly Leu Tyr Asp Val Val Ser Val Leu Arg Ile Ala Arg Thr Pro Ser
180 185 190

Val Asn Ile Gly Cys Cys Ile Glu Asn Val Pro Leu Gln Gln Asn Leu
195 200 205

Thr Val Gly Ser Gln Thr Gly Asn Asp Ile Gly Glu Arg Asp Lys Ile
210 215 220

Thr Glu Asn Pro Val Ser Thr Gly Glu Lys Asn Ala Ala Thr
225 230 235

<210> SEQ ID NO 113
<211> LENGTH: 238
<212> TYPE: PRT
<213> ORGANISM: Artificial Sequence
<220> FEATURE:
<223> OTHER INFORMATION: ICOSL v5 ECD

<400> SEQUENCE: 113

Asp Thr Gln Glu Lys Glu Val Arg Ala Met Val Gly Ser Asp Val Glu
1 5 10 15

Leu Ser Cys Ala Cys Pro Glu Gly Ser Arg Phe Asp Leu Asn Asp Val
20 25 30

Tyr Val Tyr Trp Gln Thr Ser Glu Ser Lys Thr Val Val Thr Tyr His
35 40 45

Ile Pro Gln His Ser Ser Leu Glu Tyr Val Asp Ser Arg Tyr Arg Asn

```
    50                  55                  60

Arg Ala Leu Met Ser Pro Ala Gly Met Leu Arg Gly Asp Phe Ser Leu
65                  70                  75                  80

Arg Leu Phe Asn Val Thr Pro Gln Asp Glu Gln Lys Phe His Cys Leu
                85                  90                  95

Val Leu Ser Pro Ser Leu Gly Phe Gln Glu Val Leu Ser Val Glu Val
            100                 105                 110

Thr Leu His Val Ala Ala Asn Phe Ser Val Pro Val Val Ser Ala Pro
        115                 120                 125

His Ser Pro Ser Gln Asp Glu Leu Thr Phe Thr Cys Thr Ser Ile Asn
    130                 135                 140

Gly Tyr Pro Arg Pro Asn Val Tyr Trp Ile Asn Lys Thr Asp Asn Ser
145                 150                 155                 160

Leu Leu Asp Gln Ala Leu Gln Asn Asp Thr Val Phe Leu Asn Met Arg
                165                 170                 175

Gly Leu Tyr Asp Val Val Ser Val Leu Arg Ile Ala Arg Thr Pro Ser
            180                 185                 190

Val Asn Ile Gly Cys Cys Ile Glu Asn Val Leu Leu Gln Gln Asn Leu
        195                 200                 205

Thr Val Gly Ser Gln Thr Gly Asn Asp Ile Gly Glu Arg Asp Lys Ile
    210                 215                 220

Thr Glu Asn Pro Val Ser Thr Gly Glu Lys Asn Ala Ala Thr
225                 230                 235


<210> SEQ ID NO 114
<211> LENGTH: 238
<212> TYPE: PRT
<213> ORGANISM: Artificial Sequence
<220> FEATURE:
<223> OTHER INFORMATION: ICOSL v6 ECD

<400> SEQUENCE: 114

Asp Thr Gln Glu Lys Glu Val Arg Ala Met Val Gly Ser Asp Val Glu
1               5                   10                  15

Leu Ser Cys Ala Cys Pro Glu Gly Ser Arg Phe Asp Leu Asn Asp Val
            20                  25                  30

Tyr Val Tyr Trp Gln Thr Ser Glu Ser Lys Thr Val Val Thr Tyr His
        35                  40                  45

Ile Pro Gln Ser Ser Ser Leu Glu Asn Val Asp Ser Arg Tyr Arg Asn
    50                  55                  60

Arg Ala Leu Met Ser Pro Ala Gly Met Leu Arg Gly Asp Phe Ser Leu
65                  70                  75                  80

Arg Leu Phe Asn Val Thr Pro Gln Asp Glu Gln Lys Phe His Cys Leu
                85                  90                  95

Val Leu Ser Gln Ser Leu Gly Phe Gln Glu Val Leu Ser Val Glu Val
            100                 105                 110

Thr Leu His Val Ala Ala Asn Phe Ser Val Pro Val Val Ser Ala Pro
        115                 120                 125

His Ser Pro Ser Gln Asp Glu Leu Thr Phe Thr Cys Thr Ser Ile Asn
    130                 135                 140

Gly Cys Pro Arg Pro Asn Val Cys Trp Ile Asn Lys Thr Asp Asn Ser
145                 150                 155                 160

Leu Leu Asp Gln Ala Leu Gln Asn Asp Thr Val Phe Leu Asn Met Arg
                165                 170                 175

Gly Leu Tyr Asp Val Val Ser Val Leu Arg Ile Ala Arg Thr Pro Ser
```

```
            180                 185                 190

Val Asn Ile Gly Cys Cys Ile Glu Asn Val Leu Leu Gln Gln Asn Leu
        195                 200                 205

Thr Val Gly Ser Gln Thr Gly Asn Asp Ile Gly Glu Arg Asp Lys Ile
    210                 215                 220

Thr Glu Asn Pro Val Ser Thr Gly Glu Lys Asn Ala Ala Thr
225                 230                 235


<210> SEQ ID NO 115
<211> LENGTH: 238
<212> TYPE: PRT
<213> ORGANISM: Artificial Sequence
<220> FEATURE:
<223> OTHER INFORMATION: ICOSL v7 ECD

<400> SEQUENCE: 115

Asp Thr Gln Glu Lys Glu Val Arg Ala Met Val Gly Ser Asp Val Glu
1               5                   10                  15

Leu Ser Cys Ala Cys Pro Glu Gly Ser Arg Phe Asp Leu Asn Asp Val
            20                  25                  30

Tyr Val Tyr Trp Gln Thr Ser Glu Ser Lys Thr Val Val Thr Tyr His
        35                  40                  45

Ile Pro Gln His Ser Ser Leu Glu Asn Val Asp Ser Arg Tyr Arg Asn
    50                  55                  60

Arg Ala Leu Met Ser Pro Ala Gly Met Leu Arg Gly Asp Phe Ser Leu
65                  70                  75                  80

Arg Leu Phe Asn Val Thr Pro Gln Asp Glu Gln Lys Phe His Cys Leu
                85                  90                  95

Val Leu Ser Gln Ser Leu Gly Phe Gln Glu Val Leu Ser Val Glu Val
            100                 105                 110

Thr Leu His Val Ala Ala Asn Phe Ser Val Pro Val Val Ser Ala Pro
        115                 120                 125

His Ser Pro Ser Gln Asp Glu Leu Thr Phe Thr Cys Thr Ser Ile Asn
    130                 135                 140

Gly Tyr Pro Arg Pro Asn Val Tyr Trp Ile Asn Lys Thr Asp Asn Ser
145                 150                 155                 160

Leu Leu Asp Gln Ala Leu Gln Asn Asp Thr Val Phe Leu Asn Met Arg
                165                 170                 175

Gly Leu Tyr Asp Val Val Ser Val Leu Arg Ile Ala Arg Thr Pro Ser
            180                 185                 190

Val Asn Ile Gly Cys Arg Ile Glu Asn Val Leu Leu Gln Gln Asn Leu
        195                 200                 205

Thr Val Gly Ser Gln Thr Gly Asn Asp Ile Gly Glu Arg Asp Lys Ile
    210                 215                 220

Thr Glu Asn Pro Val Ser Thr Gly Glu Lys Asn Ala Ala Thr
225                 230                 235


<210> SEQ ID NO 116
<211> LENGTH: 238
<212> TYPE: PRT
<213> ORGANISM: Artificial Sequence
<220> FEATURE:
<223> OTHER INFORMATION: ICOSL v8 ECD

<400> SEQUENCE: 116

Asp Thr Gln Glu Lys Glu Val Arg Ala Met Val Gly Ser Asp Val Glu
1               5                   10                  15
```

```
Leu Ser Cys Ala Cys Pro Glu Gly Ser Arg Phe Asp Leu Asn Asp Val
            20                  25                  30

Tyr Val Tyr Trp Gln Thr Ser Glu Ser Lys Thr Val Val Thr Tyr His
        35                  40                  45

Ile Pro Gln His Ser Ser Leu Glu Asn Val Asp Ser Arg Tyr Arg Asn
    50                  55                  60

Arg Ala Leu Met Ser Pro Ala Gly Met Leu Arg Gly Asp Phe Ser Leu
65                  70                  75                  80

Arg Leu Phe Asn Val Thr Pro Gln Asp Glu Gln Lys Phe His Cys Leu
                85                  90                  95

Val Leu Ser Gln Ser Leu Gly Phe Gln Glu Val Leu Ser Val Glu Val
            100                 105                 110

Thr Leu His Val Ala Ala Asn Phe Ser Val Pro Val Val Ser Ala Pro
        115                 120                 125

His Ser Pro Ser Gln Asp Glu Leu Thr Phe Thr Asp Thr Ser Ile Asn
    130                 135                 140

Gly Tyr Pro Arg Pro Asn Val Tyr Trp Ile Asn Lys Thr Asp Asn Ser
145                 150                 155                 160

Leu Leu Asp Gln Ala Leu Gln Asn Asp Thr Val Phe Leu Asn Met Arg
                165                 170                 175

Gly Leu Tyr Asp Val Val Ser Val Leu Arg Ile Ala Arg Thr Pro Ser
            180                 185                 190

Val Asn Ile Gly Cys Cys Ile Glu Asn Val Leu Leu Gln Gln Asn Leu
        195                 200                 205

Thr Val Gly Ser Gln Thr Gly Asn Asp Ile Gly Glu Arg Asp Lys Ile
    210                 215                 220

Ala Glu Asn Pro Val Ser Thr Gly Glu Lys Asn Ala Ala Thr
225                 230                 235
```

<210> SEQ ID NO 117
<211> LENGTH: 238
<212> TYPE: PRT
<213> ORGANISM: Artificial Sequence
<220> FEATURE:
<223> OTHER INFORMATION: ICOSL v9 ECD

<400> SEQUENCE: 117

```
Asp Thr Gln Glu Lys Glu Val Arg Ala Met Val Gly Ser Asp Val Glu
1               5                   10                  15

Leu Ser Cys Ala Cys Pro Glu Gly Ser Arg Phe Asp Leu Asn Asp Val
            20                  25                  30

Tyr Val Tyr Trp Gln Thr Ser Glu Ser Lys Thr Val Val Thr Tyr His
        35                  40                  45

Ile Pro Gln His Ser Ser Leu Glu Asn Val Asp Ser Arg Tyr Arg Asn
    50                  55                  60

Arg Ala Leu Met Ser Pro Ala Gly Met Leu Arg Gly Asp Phe Ser Leu
65                  70                  75                  80

Arg Leu Phe Asn Val Thr Pro Gln Asp Glu Gln Lys Phe His Cys Leu
                85                  90                  95

Val Leu Ser Gln Ser Leu Gly Phe Gln Glu Val Leu Ser Val Glu Val
            100                 105                 110

Thr Leu His Val Ala Ala Asn Phe Ser Val Pro Val Val Ser Ala Pro
        115                 120                 125

His Ser Pro Ser Gln Asp Glu Leu Thr Phe Thr Cys Thr Ser Ile Asn
    130                 135                 140
```

```
Gly Tyr Pro Arg Pro Asn Val Tyr Trp Ile Asn Lys Thr Asp Asn Ser
145                 150                 155                 160

Leu Leu Asp Gln Ala Leu Gln Asn Asp Thr Val Phe Leu Asn Met Arg
                165                 170                 175

Gly Leu Tyr Asp Val Val Ser Val Leu Arg Ile Ala Arg Thr Pro Ser
            180                 185                 190

Val Asn Ile Gly Cys Arg Ile Glu Asn Val Leu Leu Gln Gln Asn Leu
        195                 200                 205

Thr Val Gly Ser Gln Thr Gly Asn Asp Ile Gly Glu Arg Asp Lys Ile
    210                 215                 220

Ala Glu Asn Pro Val Ser Thr Gly Glu Lys Asn Ala Ala Thr
225                 230                 235


<210> SEQ ID NO 118
<211> LENGTH: 238
<212> TYPE: PRT
<213> ORGANISM: Artificial Sequence
<220> FEATURE:
<223> OTHER INFORMATION: ICOSL v10 ECD

<400> SEQUENCE: 118

Asp Thr Gln Glu Lys Glu Val Arg Ala Met Val Gly Ser Asp Val Glu
1               5                   10                  15

Leu Ser Cys Ala Cys Pro Glu Gly Ser Arg Phe Asp Leu Asn Asp Val
            20                  25                  30

Tyr Val Tyr Trp Gln Thr Ser Glu Ser Lys Thr Val Val Thr Tyr His
        35                  40                  45

Ile Pro Gln His Ser Ser Leu Glu Asn Val Asp Ser Arg Tyr Arg Asn
    50                  55                  60

Arg Ala Leu Met Ser Pro Ala Gly Met Leu Arg Gly Asp Phe Ser Leu
65                  70                  75                  80

Arg Leu Phe Asn Val Thr Pro Gln Asp Glu Gln Arg Phe His Cys Leu
                85                  90                  95

Val Leu Ser Gln Ser Leu Gly Phe Gln Glu Val Leu Ser Val Glu Val
            100                 105                 110

Thr Leu His Val Ala Ala Asn Phe Ser Val Pro Val Val Ser Ala Pro
        115                 120                 125

His Ser Pro Ser Gln Asp Glu Leu Thr Phe Thr Cys Thr Ser Ile Asn
    130                 135                 140

Gly Tyr Pro Arg Pro Asn Val Tyr Trp Ile Asn Lys Thr Asp Asn Ser
145                 150                 155                 160

Leu Leu Asp Gln Ala Leu Gln Asn Asp Thr Val Phe Leu Asn Met Arg
                165                 170                 175

Gly Leu Tyr Asp Val Val Ser Val Leu Arg Ile Ala Arg Thr Pro Ser
            180                 185                 190

Val Asn Ile Gly Cys Cys Ile Glu Asn Val Leu Leu Gln Gln Asn Leu
        195                 200                 205

Thr Val Gly Ser Gln Thr Gly Asn Asp Ile Gly Glu Arg Asp Lys Ile
    210                 215                 220

Thr Glu Asn Pro Val Ser Thr Gly Glu Lys Asn Ala Ala Thr
225                 230                 235


<210> SEQ ID NO 119
<211> LENGTH: 238
<212> TYPE: PRT
<213> ORGANISM: Artificial Sequence
<220> FEATURE:
```

<223> OTHER INFORMATION: ICOSL v11 ECD

<400> SEQUENCE: 119

Asp Thr Gln Glu Lys Glu Val Arg Ala Met Val Gly Ser Asp Val Glu
1 5 10 15

Leu Ser Cys Ala Cys Pro Glu Gly Ser Arg Phe Asp Leu Asn Asp Val
20 25 30

Tyr Val Tyr Trp Gln Thr Ser Glu Ser Lys Thr Val Val Thr Tyr His
35 40 45

Ile Pro Gln His Ser Ser Leu Glu Asn Val Asp Ser Arg Tyr Arg Asn
50 55 60

Arg Ala Leu Met Ser Pro Ala Gly Met Leu Arg Gly Asp Phe Ser Leu
65 70 75 80

Arg Leu Phe Asn Val Thr Pro Gln Asp Glu Gln Lys Phe His Cys Leu
85 90 95

Val Leu Gly Gln Ser Leu Gly Phe Gln Glu Val Leu Ser Val Glu Val
100 105 110

Thr Leu His Val Ala Ala Asn Phe Ser Val Pro Val Val Ser Ala Pro
115 120 125

His Ser Pro Ser Gln Asp Glu Leu Thr Phe Thr Cys Thr Ser Ile Asn
130 135 140

Gly Tyr Pro Arg Pro Asn Val Tyr Trp Ile Asn Lys Thr Asp Asn Ser
145 150 155 160

Leu Leu Asp Gln Ala Leu Gln Asn Asp Thr Val Phe Leu Asn Met Arg
165 170 175

Gly Leu Tyr Asp Val Val Ser Val Leu Arg Ile Ala Arg Thr Pro Ser
180 185 190

Val Asn Ile Gly Cys Cys Ile Glu Asn Val Leu Leu Gln Gln Asn Leu
195 200 205

Thr Val Gly Ser Gln Thr Gly Asn Asp Ile Gly Glu Arg Asp Lys Ile
210 215 220

Thr Glu Asn Pro Val Ser Thr Gly Glu Lys Asn Ala Ala Thr
225 230 235

<210> SEQ ID NO 120
<211> LENGTH: 238
<212> TYPE: PRT
<213> ORGANISM: Artificial Sequence
<220> FEATURE:
<223> OTHER INFORMATION: ICOSL v12 ECD

<400> SEQUENCE: 120

Asp Thr Gln Glu Lys Glu Val Arg Ala Met Val Gly Ser Asp Val Glu
1 5 10 15

Leu Ser Cys Ala Cys Pro Glu Gly Ser Arg Phe Asp Leu Asn Asp Val
20 25 30

Tyr Val Tyr Trp Gln Thr Ser Glu Ser Lys Thr Val Val Thr Tyr His
35 40 45

Ile Pro Gln Tyr Ser Ser Leu Glu Asn Val Asp Ser Arg Tyr Arg Asn
50 55 60

Arg Ala Leu Met Ser Pro Ala Gly Met Leu Arg Gly Asp Phe Ser Leu
65 70 75 80

Arg Leu Phe Asn Val Thr Pro Gln Asp Glu Gln Lys Phe His Cys Leu
85 90 95

Val Leu Ser Gln Ser Leu Gly Phe Gln Glu Val Leu Ser Val Glu Val
100 105 110

Thr Leu His Val Ala Ala Asn Phe Ser Val Pro Val Val Ser Ala Pro
115 120 125

His Ser Pro Ser Gln Asp Glu Leu Thr Phe Thr Cys Thr Ser Ile Asn
130 135 140

Gly Tyr Pro Arg Pro Asn Val Tyr Trp Ile Asn Lys Thr Asp Asn Ser
145 150 155 160

Leu Leu Asp Gln Ala Leu Gln Asn Asp Thr Val Phe Leu Asn Met Arg
165 170 175

Gly Leu Tyr Asp Val Val Ser Val Leu Arg Ile Ala Arg Thr Pro Ser
180 185 190

Val Asn Ile Gly Cys Cys Ile Glu Asn Val Leu Leu Gln Gln Asn Leu
195 200 205

Thr Val Gly Ser Gln Thr Gly Asn Asp Ile Gly Glu Arg Asp Lys Ile
210 215 220

Thr Glu Asn Pro Val Ser Thr Gly Glu Lys Asn Ala Ala Thr
225 230 235

<210> SEQ ID NO 121
<211> LENGTH: 238
<212> TYPE: PRT
<213> ORGANISM: Artificial Sequence
<220> FEATURE:
<223> OTHER INFORMATION: ICOSL v13 ECD

<400> SEQUENCE: 121

Asp Thr Gln Glu Lys Glu Val Arg Ala Met Val Gly Ser Asp Val Glu
1 5 10 15

Leu Ser Cys Ala Cys Pro Glu Gly Ser Arg Phe Asp Leu Asn Asp Val
20 25 30

Tyr Val Tyr Trp Gln Thr Ser Glu Ser Lys Thr Val Val Thr Tyr His
35 40 45

Ile Pro Gln Asn Ser Ser Leu Glu Tyr Val Asp Ser Arg Tyr Arg Asn
50 55 60

Arg Ala Leu Met Ser Pro Ala Gly Met Leu Arg Gly Asp Phe Ser Leu
65 70 75 80

Arg Leu Phe Asn Val Thr Pro Gln Asp Glu Gln Lys Phe His Cys Leu
85 90 95

Val Leu Ser Gln Ser Leu Gly Phe Gln Glu Val Leu Ser Val Glu Val
100 105 110

Thr Leu His Val Ala Ala Asn Phe Ser Val Pro Val Val Ser Ala Pro
115 120 125

His Ser Pro Ser Gln Asp Glu Leu Thr Phe Thr Cys Thr Ser Ile Asn
130 135 140

Gly Tyr Pro Arg Pro Asn Val Tyr Trp Ile Asn Lys Thr Asp Asn Ser
145 150 155 160

Leu Leu Asp Gln Ala Leu Gln Asn Asp Thr Val Phe Leu Asn Met Arg
165 170 175

Gly Leu Tyr Asp Val Val Ser Val Leu Arg Ile Ala Arg Thr Pro Ser
180 185 190

Val Asn Ile Gly Cys Cys Ile Glu Asn Val Leu Leu Gln Gln Asn Leu
195 200 205

Thr Val Gly Ser Gln Thr Gly Asn Asp Ile Gly Glu Arg Asp Lys Ile
210 215 220

Thr Glu Asn Pro Val Ser Thr Gly Glu Lys Asn Ala Ala Thr
225 230 235

<210> SEQ ID NO 122
<211> LENGTH: 238
<212> TYPE: PRT
<213> ORGANISM: Artificial Sequence
<220> FEATURE:
<223> OTHER INFORMATION: ICOSL v14 ECD

<400> SEQUENCE: 122

```
Asp Thr Gln Glu Lys Glu Val Arg Ala Met Val Gly Ser Asp Val Glu
1               5                   10                  15

Leu Ser Cys Ala Cys Pro Glu Gly Ser Arg Phe Asp Leu Asn Asp Val
            20                  25                  30

Tyr Val Tyr Trp Gln Thr Ser Glu Ser Lys Thr Val Val Thr Tyr His
        35                  40                  45

Ile Pro Gln Asn Ser Ser Leu Glu Tyr Val Asp Ser Arg Tyr Arg Asn
    50                  55                  60

Arg Ala Leu Met Ser Pro Ala Gly Met Leu Arg Gly Asp Phe Ser Leu
65                  70                  75                  80

Arg Leu Phe Asn Val Thr Pro Gln Asp Glu Gln Lys Phe His Cys Leu
                85                  90                  95

Val Leu Ser Pro Ser Leu Gly Phe Gln Glu Val Leu Ser Val Glu Val
            100                 105                 110

Thr Leu His Val Ala Ala Asn Phe Ser Val Pro Val Val Ser Ala Pro
        115                 120                 125

His Ser Pro Ser Gln Asp Glu Leu Thr Phe Thr Cys Thr Ser Ile Asn
    130                 135                 140

Gly Tyr Pro Arg Pro Asn Val Tyr Trp Ile Asn Lys Thr Asp Asn Ser
145                 150                 155                 160

Leu Leu Asp Gln Ala Leu Gln Asn Asp Thr Val Phe Leu Asn Met Arg
                165                 170                 175

Gly Leu Tyr Asp Val Val Ser Val Leu Arg Ile Ala Arg Thr Pro Ser
            180                 185                 190

Val Asn Ile Gly Cys Cys Ile Glu Asn Val Leu Leu Gln Gln Asn Leu
        195                 200                 205

Thr Val Gly Ser Gln Thr Gly Asn Asp Ile Gly Glu Arg Asp Lys Ile
    210                 215                 220

Thr Glu Asn Pro Val Ser Thr Gly Glu Lys Asn Ala Ala Thr
225                 230                 235
```

<210> SEQ ID NO 123
<211> LENGTH: 238
<212> TYPE: PRT
<213> ORGANISM: Artificial Sequence
<220> FEATURE:
<223> OTHER INFORMATION: ICOSL v15 ECD

<400> SEQUENCE: 123

```
Asp Thr Gln Glu Lys Glu Val Arg Ala Met Val Gly Ser Asp Val Glu
1               5                   10                  15

Leu Ser Cys Ala Cys Pro Glu Gly Ser Arg Phe Asp Leu Asn Asp Val
            20                  25                  30

Tyr Val Tyr Trp Gln Thr Ser Glu Ser Lys Thr Val Val Thr Tyr His
        35                  40                  45

Ile Pro Gln Ser Ser Ser Leu Glu Asn Val Asp Ser Arg Tyr Arg Asn
    50                  55                  60

Arg Ala Leu Met Ser Pro Ala Gly Met Leu Arg Gly Asp Phe Ser Leu
```

```
65                  70                  75                  80

Arg Leu Phe Asn Val Thr Pro Gln Asp Glu Gln Lys Phe His Cys Leu
                85                  90                  95

Val Leu Ser Gln Ser Leu Gly Phe Gln Glu Val Leu Ser Val Glu Val
            100                 105                 110

Thr Leu His Val Ala Ala Asn Phe Ser Val Pro Val Val Ser Ala Pro
        115                 120                 125

His Gly Pro Ser Gln Asp Glu Leu Thr Phe Thr Cys Thr Ser Ile Asn
    130                 135                 140

Gly Tyr Pro Arg Pro Asn Val Cys Trp Ile Asn Lys Thr Asp Asn Ser
145                 150                 155                 160

Leu Leu Asp Gln Ala Leu Gln Asn Asp Thr Val Phe Leu Asn Met Arg
                165                 170                 175

Gly Leu Tyr Asp Val Val Ser Val Leu Arg Ile Ala Arg Thr Pro Ser
            180                 185                 190

Val Asn Ile Gly Cys Cys Ile Glu Asn Val Leu Leu Gln Gln Asn Leu
        195                 200                 205

Thr Val Gly Ser Gln Thr Gly Asn Asp Ile Gly Glu Arg Asp Lys Ile
    210                 215                 220

Thr Glu Asn Pro Val Ser Thr Gly Glu Lys Asn Ala Ala Thr
225                 230                 235


<210> SEQ ID NO 124
<211> LENGTH: 238
<212> TYPE: PRT
<213> ORGANISM: Artificial Sequence
<220> FEATURE:
<223> OTHER INFORMATION: ICOSL v16 ECD

<400> SEQUENCE: 124

Asp Thr Gln Glu Lys Glu Val Arg Ala Met Val Gly Ser Asp Val Glu
1               5                   10                  15

Leu Ser Cys Ala Cys Pro Glu Gly Ser Arg Phe Asp Leu Asn Asp Val
            20                  25                  30

Tyr Val Tyr Trp Gln Thr Ser Glu Ser Lys Thr Val Val Thr Tyr His
        35                  40                  45

Ile Pro Gln Ser Ser Ser Leu Glu Asn Val Asp Ser Arg Tyr Arg Asn
    50                  55                  60

Arg Ala Leu Met Ser Pro Ala Gly Met Leu Arg Gly Asp Phe Ser Leu
65                  70                  75                  80

Arg Leu Phe Asn Val Thr Pro Gln Asp Glu Gln Lys Phe His Cys Leu
                85                  90                  95

Val Leu Ser Gln Ser Leu Gly Phe Gln Glu Val Leu Ser Val Glu Val
            100                 105                 110

Thr Leu His Val Ala Ala Asn Phe Ser Val Pro Val Val Ser Ala Pro
        115                 120                 125

His Ser Pro Ser Gln Asp Glu Leu Thr Phe Thr Cys Thr Ser Ile Asn
    130                 135                 140

Gly Tyr Pro Arg Pro Asn Val Cys Trp Ile Asn Lys Thr Asp Asn Ser
145                 150                 155                 160

Leu Leu Asp Gln Ala Leu Gln Asn Asp Thr Val Phe Leu Asn Met Arg
                165                 170                 175

Gly Leu Tyr Asp Val Val Ser Val Leu Arg Ile Ala Arg Thr Pro Ser
            180                 185                 190

Val Asn Ile Gly Cys Cys Ile Glu Asn Val Leu Leu Gln Gln Asn Leu
```

```
        195                 200                 205

Thr Val Gly Ser Gln Thr Gly Asn Asp Ile Gly Glu Arg Asp Lys Ile
    210                 215                 220

Thr Glu Asn Pro Val Ser Thr Gly Glu Lys Asn Ala Ala Thr
225                 230                 235


<210> SEQ ID NO 125
<211> LENGTH: 238
<212> TYPE: PRT
<213> ORGANISM: Artificial Sequence
<220> FEATURE:
<223> OTHER INFORMATION: ICOSL v17 ECD

<400> SEQUENCE: 125

Asp Thr Gln Glu Lys Glu Val Arg Ala Met Val Gly Ser Asp Val Glu
1               5                   10                  15

Leu Ser Cys Ala Cys Pro Glu Gly Ser Arg Phe Asp Leu Asn Asp Val
            20                  25                  30

Tyr Val Tyr Trp Gln Thr Ser Glu Ser Lys Thr Val Val Thr Tyr His
        35                  40                  45

Ile Pro Gln Ser Ser Ser Leu Glu Asn Val Asp Ser Arg Tyr Arg Asn
    50                  55                  60

Arg Ala Leu Met Ser Pro Ala Gly Met Leu Arg Gly Asp Phe Ser Leu
65                  70                  75                  80

Arg Leu Phe Asn Val Thr Pro Gln Asp Glu Gln Lys Phe His Cys Leu
                85                  90                  95

Val Leu Ser Gln Ser Leu Gly Phe Gln Glu Val Leu Ser Val Glu Val
            100                 105                 110

Thr Leu His Val Ala Ala Asn Phe Ser Val Pro Val Val Ser Ala Pro
        115                 120                 125

His Ser Pro Ser Gln Asp Glu Leu Thr Phe Thr Cys Thr Ser Ile Asn
    130                 135                 140

Gly Tyr Pro Arg Pro Asn Val Tyr Trp Ile Asn Lys Thr Asp Asn Ser
145                 150                 155                 160

Leu Leu Asp Gln Ala Leu Gln Asn Asp Thr Val Phe Leu Asn Met Arg
                165                 170                 175

Gly Leu Tyr Asp Val Val Ser Val Leu Arg Ile Ala Arg Thr Pro Ser
            180                 185                 190

Val Asn Ile Gly Cys Arg Ile Glu Asn Val Leu Leu Gln Gln Asn Leu
        195                 200                 205

Thr Val Gly Ser Gln Thr Gly Asn Asp Ile Gly Glu Arg Asp Lys Ile
    210                 215                 220

Thr Glu Asn Pro Val Ser Thr Gly Glu Lys Asn Ala Ala Thr
225                 230                 235


<210> SEQ ID NO 126
<211> LENGTH: 238
<212> TYPE: PRT
<213> ORGANISM: Artificial Sequence
<220> FEATURE:
<223> OTHER INFORMATION: ICOSL v18 ECD

<400> SEQUENCE: 126

Asp Thr Gln Glu Lys Glu Val Arg Ala Met Val Gly Ser Asp Val Glu
1               5                   10                  15

Leu Ser Cys Ala Cys Pro Glu Gly Ser Arg Phe Asp Leu Asn Asp Val
            20                  25                  30
```

```
Tyr Val Tyr Trp Gln Thr Ser Glu Ser Lys Thr Val Val Thr Tyr His
        35                  40                  45

Ile Pro Gln Tyr Ser Ser Leu Glu Tyr Val Asp Ser Arg Tyr Arg Asn
    50                  55                  60

Arg Ala Leu Met Ser Pro Ala Gly Met Leu Arg Gly Asp Phe Ser Leu
65                  70                  75                  80

Arg Leu Phe Asn Val Thr Pro Gln Asp Glu Gln Lys Phe His Cys Leu
                85                  90                  95

Val Leu Ser Gln Ser Leu Gly Phe Gln Glu Val Leu Ser Val Glu Val
            100                 105                 110

Thr Leu His Val Ala Ala Asn Phe Ser Val Pro Val Val Ser Ala Pro
        115                 120                 125

His Ser Pro Ser Gln Asp Glu Leu Thr Phe Thr Cys Thr Ser Ile Asn
    130                 135                 140

Gly Tyr Pro Arg Pro Asn Val Cys Trp Ile Asn Lys Thr Asp Asn Ser
145                 150                 155                 160

Leu Leu Asp Gln Ala Leu Gln Asn Asp Thr Val Phe Leu Asn Met Arg
                165                 170                 175

Gly Leu Tyr Asp Val Val Ser Val Leu Arg Ile Ala Arg Thr Pro Ser
            180                 185                 190

Val Asn Ile Gly Cys Cys Ile Glu Asn Val Leu Leu Gln Gln Asn Leu
        195                 200                 205

Thr Val Gly Ser Gln Thr Gly Asn Asp Ile Gly Glu Arg Asp Lys Ile
    210                 215                 220

Thr Glu Asn Pro Val Ser Thr Gly Glu Lys Asn Ala Ala Thr
225                 230                 235


<210> SEQ ID NO 127
<211> LENGTH: 238
<212> TYPE: PRT
<213> ORGANISM: Artificial Sequence
<220> FEATURE:
<223> OTHER INFORMATION: ICOSL v19 ECD

<400> SEQUENCE: 127

Asp Thr Gln Glu Lys Glu Val Arg Ala Met Val Gly Ser Asp Val Glu
1               5                   10                  15

Leu Ser Cys Ala Cys Pro Glu Gly Ser Arg Phe Asp Leu Asn Asp Val
            20                  25                  30

Tyr Val Tyr Trp Gln Thr Ser Glu Ser Lys Thr Val Val Thr Tyr His
        35                  40                  45

Ile Pro Gln Tyr Ser Ser Leu Glu Tyr Val Asp Ser Arg Tyr Arg Asn
    50                  55                  60

Arg Ala Leu Met Ser Pro Ala Gly Met Leu Arg Gly Asp Phe Ser Leu
65                  70                  75                  80

Arg Leu Phe Asn Val Thr Pro Gln Asp Glu Gln Lys Phe His Cys Leu
                85                  90                  95

Val Leu Ser Gln Ser Leu Gly Phe Gln Glu Val Leu Ser Val Glu Val
            100                 105                 110

Thr Leu His Val Ala Ala Asn Phe Ser Val Pro Val Val Ser Ala Pro
        115                 120                 125

Pro Ser Pro Ser Gln Asp Glu Leu Thr Phe Thr Cys Thr Ser Ile Asn
    130                 135                 140

Gly Tyr Pro Arg Pro Asn Val Tyr Trp Ile Asn Lys Thr Asp Asn Ser
145                 150                 155                 160
```

```
Leu Leu Asp Gln Ala Leu Gln Asn Asp Thr Val Phe Leu Asn Met Arg
                165                 170                 175

Gly Leu Tyr Asp Val Val Ser Val Leu Arg Ile Ala Arg Thr Pro Ser
            180                 185                 190

Val Asn Ile Gly Cys Arg Ile Glu Asn Val Leu Leu Gln Gln Asn Leu
        195                 200                 205

Thr Val Gly Ser Gln Thr Gly Asn Asp Ile Gly Glu Arg Asp Lys Ile
    210                 215                 220

Thr Glu Asn Pro Val Ser Thr Gly Glu Lys Asn Ala Ala Thr
225                 230                 235


<210> SEQ ID NO 128
<211> LENGTH: 238
<212> TYPE: PRT
<213> ORGANISM: Artificial Sequence
<220> FEATURE:
<223> OTHER INFORMATION: ICOSL v20 ECD

<400> SEQUENCE: 128

Asp Thr Gln Glu Lys Glu Val Arg Ala Met Val Gly Ser Asp Val Glu
1               5                   10                  15

Leu Ser Cys Ala Cys Pro Glu Gly Ser Arg Phe Asp Leu Asn Asp Val
            20                  25                  30

Tyr Val Tyr Trp Gln Thr Ser Glu Ser Lys Thr Val Val Thr Tyr His
        35                  40                  45

Ile Pro Gln His Ser Ser Leu Glu Asn Val Asp Ser Arg Tyr Arg Asn
    50                  55                  60

Arg Ala Leu Met Ser Pro Ala Gly Met Leu Arg Gly Asp Phe Ser Leu
65                  70                  75                  80

Arg Leu Phe Asn Val Thr Pro Gln Asp Glu Gln Lys Phe His Cys Leu
                85                  90                  95

Val Leu Ser Gln Ser Leu Gly Phe Gln Glu Val Leu Ser Val Glu Val
            100                 105                 110

Thr Leu His Val Ala Ala Asn Phe Ser Val Pro Val Val Ser Ala Pro
        115                 120                 125

His Ser Pro Ser Gln Asp Glu Leu Thr Phe Thr Cys Thr Ser Ile Asn
    130                 135                 140

Gly Tyr Pro Arg Pro Asn Val Tyr Trp Ile Asn Lys Thr Asp Asn Ser
145                 150                 155                 160

Pro Leu Asp Gln Ala Leu Gln Asn Asp Thr Val Phe Leu Asn Met Arg
                165                 170                 175

Gly Leu Tyr Asp Val Val Ser Val Leu Arg Ile Ala Arg Thr Pro Ser
            180                 185                 190

Val Asn Ile Gly Cys Arg Ile Glu Asn Val Leu Leu Gln Gln Asn Leu
        195                 200                 205

Thr Val Gly Ser Gln Thr Gly Asn Asp Ile Gly Glu Arg Asp Lys Ile
    210                 215                 220

Thr Glu Asn Pro Val Ser Thr Gly Glu Lys Asn Ala Ala Thr
225                 230                 235


<210> SEQ ID NO 129
<211> LENGTH: 238
<212> TYPE: PRT
<213> ORGANISM: Artificial Sequence
<220> FEATURE:
<223> OTHER INFORMATION: ICOSL v21 ECD

<400> SEQUENCE: 129
```

```
Asp Thr Gln Glu Lys Glu Val Arg Ala Met Val Gly Ser Asp Val Glu
1               5                   10                  15

Leu Ser Cys Ala Cys Pro Glu Gly Ser Arg Phe Asp Leu Asn Asp Val
            20                  25                  30

Tyr Val Tyr Trp Gln Thr Ser Glu Ser Lys Thr Val Val Thr Tyr His
        35                  40                  45

Ile Pro Gln Ser Ser Ser Leu Glu Asn Val Asp Ser Arg Tyr Arg Asn
    50                  55                  60

Arg Ala Leu Met Ser Pro Ala Gly Met Leu Arg Gly Asp Phe Ser Leu
65                  70                  75                  80

Arg Leu Phe Asn Val Thr Pro Gln Asp Glu Gln Lys Phe His Cys Leu
                85                  90                  95

Val Leu Ser Gln Ser Leu Gly Phe Gln Glu Val Leu Ser Val Glu Val
            100                 105                 110

Glu Leu His Val Ala Ala Asn Phe Ser Val Pro Val Val Ser Ala Pro
        115                 120                 125

His Ser Pro Ser Gln Asp Glu Leu Thr Phe Thr Cys Thr Ser Ile Asn
    130                 135                 140

Gly Tyr Pro Arg Pro Asn Val Tyr Trp Ile Asn Lys Thr Asp Asn Ser
145                 150                 155                 160

Leu Leu Asp Gln Ala Leu Gln Asn Asp Thr Val Phe Leu Asn Met Arg
                165                 170                 175

Gly Leu Tyr Asp Val Val Ser Val Leu Arg Ile Ala Arg Thr Pro Ser
            180                 185                 190

Val Asn Ile Gly Cys Cys Ile Glu Asn Val Leu Leu Gln Gln Asn Leu
        195                 200                 205

Thr Val Gly Ser Gln Thr Gly Asn Asp Ile Gly Glu Arg Asp Lys Ile
    210                 215                 220

Thr Glu Asn Pro Val Ser Thr Gly Glu Lys Asn Ala Ala Thr
225                 230                 235
```

```
<210> SEQ ID NO 130
<211> LENGTH: 238
<212> TYPE: PRT
<213> ORGANISM: Artificial Sequence
<220> FEATURE:
<223> OTHER INFORMATION: ICOSL v22 ECD

<400> SEQUENCE: 130

Asp Thr Gln Glu Lys Glu Val Arg Ala Met Val Gly Ser Asp Val Glu
1               5                   10                  15

Leu Ser Cys Ala Cys Pro Glu Gly Ser Arg Phe Asp Leu Asn Asp Val
            20                  25                  30

Tyr Val Tyr Trp Gln Thr Ser Glu Ser Lys Thr Val Val Thr Tyr His
        35                  40                  45

Ile Pro Gln Asn Ser Ala Leu Glu Asn Val Asp Ser Arg Tyr Arg Asn
    50                  55                  60

Arg Ala Leu Met Ser Pro Ala Gly Met Leu Arg Gly Asp Phe Ser Leu
65                  70                  75                  80

Arg Leu Phe Asn Val Thr Pro Gln Asp Glu Gln Lys Phe His Cys Leu
                85                  90                  95

Val Leu Ser Gln Ser Leu Gly Phe Gln Glu Val Leu Ser Val Glu Val
            100                 105                 110

Thr Leu His Val Ala Ala Asn Phe Ser Val Pro Val Val Ser Ala Pro
        115                 120                 125
```

```
His Ser Pro Ser Gln Asp Glu Leu Thr Phe Thr Cys Thr Ser Ile Asn
    130                 135                 140

Gly Tyr Pro Arg Pro Asn Val Tyr Trp Ile Asn Lys Thr Asp Asn Ser
145                 150                 155                 160

Leu Leu Asp Gln Ala Leu Gln Asn Asp Thr Val Phe Leu Asn Met Arg
                165                 170                 175

Gly Leu Tyr Asp Val Val Ser Val Leu Arg Ile Ala Arg Thr Pro Ser
            180                 185                 190

Val Asn Ile Gly Cys Cys Ile Glu Asn Val Leu Leu Gln Gln Asn Leu
        195                 200                 205

Thr Val Gly Ser Gln Thr Gly Asn Asp Ile Gly Glu Arg Asp Lys Ile
    210                 215                 220

Thr Glu Asn Pro Val Ser Thr Gly Glu Lys Asn Ala Ala Thr
225                 230                 235


<210> SEQ ID NO 131
<211> LENGTH: 238
<212> TYPE: PRT
<213> ORGANISM: Artificial Sequence
<220> FEATURE:
<223> OTHER INFORMATION: ICOSL v23 ECD

<400> SEQUENCE: 131

Asp Thr Gln Glu Lys Glu Val Arg Ala Met Val Gly Ser Asp Val Glu
1               5                   10                  15

Leu Ser Cys Ala Cys Pro Glu Gly Ser Arg Phe Asp Leu Asn Asp Val
            20                  25                  30

Tyr Val Tyr Trp Gln Thr Ser Glu Ser Lys Thr Val Val Thr Tyr His
        35                  40                  45

Ile Pro Gln Asp Ser Pro Leu Glu Asn Val Asp Ser Arg Tyr Arg Asn
    50                  55                  60

Arg Ala Leu Met Ser Pro Ala Gly Met Leu Arg Gly Asp Phe Ser Leu
65                  70                  75                  80

Arg Leu Phe Asn Val Thr Pro Gln Asp Glu Gln Lys Phe His Cys Leu
                85                  90                  95

Val Leu Ser Gln Ser Leu Gly Phe Gln Glu Val Leu Ser Val Glu Val
            100                 105                 110

Thr Leu His Val Ala Ala Asn Phe Ser Val Pro Val Val Ser Ala Pro
        115                 120                 125

His Ser Pro Ser Gln Asp Glu Leu Thr Phe Thr Cys Thr Ser Ile Asn
    130                 135                 140

Gly Tyr Pro Arg Pro Asn Val Tyr Trp Ile Asn Lys Thr Asp Asn Ser
145                 150                 155                 160

Leu Leu Asp Gln Ala Leu Gln Asn Asp Thr Val Phe Leu Asn Met Arg
                165                 170                 175

Gly Leu Tyr Asp Val Val Ser Val Leu Arg Ile Ala Arg Thr Pro Ser
            180                 185                 190

Val Asn Ile Gly Cys Cys Ile Glu Asn Val Leu Leu Gln Gln Asn Leu
        195                 200                 205

Thr Val Gly Ser Gln Thr Gly Asn Asp Ile Gly Glu Arg Asp Lys Ile
    210                 215                 220

Thr Glu Asn Pro Val Ser Thr Gly Glu Lys Asn Ala Ala Thr
225                 230                 235


<210> SEQ ID NO 132
```

<211> LENGTH: 238
<212> TYPE: PRT
<213> ORGANISM: Artificial Sequence
<220> FEATURE:
<223> OTHER INFORMATION: ICOSL v24 ECD

<400> SEQUENCE: 132

Asp Thr Gln Glu Lys Glu Val Arg Ala Met Val Gly Ser Asp Val Glu
1               5                   10                  15

Leu Ser Cys Ala Cys Pro Glu Gly Ser Arg Phe Asp Leu Asn Asp Val
            20                  25                  30

Tyr Val Tyr Trp Gln Thr Ser Glu Ser Lys Thr Val Val Thr Tyr His
        35                  40                  45

Ile Pro Gln Lys Ser Ser Leu Glu Asn Val Asp Ser Arg Tyr Arg Asn
    50                  55                  60

Arg Ala Leu Met Ser Pro Ala Gly Met Leu Arg Gly Asp Phe Ser Leu
65                  70                  75                  80

Arg Leu Phe Asn Val Thr Pro Gln Asp Glu Gln Lys Phe His Cys Leu
                85                  90                  95

Val Leu Ser Gln Ser Leu Gly Phe Gln Glu Val Leu Ser Val Glu Val
            100                 105                 110

Thr Leu His Val Ala Ala Asn Phe Ser Val Pro Val Val Ser Ala Pro
        115                 120                 125

His Ser Pro Ser Gln Asp Glu Leu Thr Phe Thr Cys Thr Ser Ile Asn
    130                 135                 140

Gly Tyr Pro Arg Pro Asn Val Tyr Trp Ile Asn Lys Thr Asp Asn Ser
145                 150                 155                 160

Leu Leu Asp Gln Ala Leu Gln Asn Asp Thr Val Phe Leu Asn Met Arg
                165                 170                 175

Gly Leu Tyr Asp Val Val Ser Val Leu Arg Ile Ala Arg Thr Pro Ser
            180                 185                 190

Val Asn Ile Gly Cys Cys Ile Glu Asn Val Leu Leu Gln Gln Asn Pro
        195                 200                 205

Thr Val Gly Ser Gln Thr Gly Asn Asp Ile Gly Glu Arg Asp Lys Ile
    210                 215                 220

Thr Glu Asn Pro Val Ser Thr Gly Glu Lys Asn Ala Ala Thr
225                 230                 235

<210> SEQ ID NO 133
<211> LENGTH: 238
<212> TYPE: PRT
<213> ORGANISM: Artificial Sequence
<220> FEATURE:
<223> OTHER INFORMATION: ICOSL v25 ECD

<400> SEQUENCE: 133

Asp Thr Gln Glu Lys Glu Val Arg Ala Met Val Gly Ser Asp Val Glu
1               5                   10                  15

Leu Ser Cys Ala Cys Pro Glu Gly Ser Arg Phe Asp Leu Asn Asp Val
            20                  25                  30

Tyr Val Tyr Trp Gln Thr Ser Glu Ser Lys Thr Val Val Thr Tyr His
        35                  40                  45

Ile Pro Gln Ser Ser Ser Leu Glu Asn Val Asp Ser Arg Tyr Arg Asn
    50                  55                  60

Arg Ala Leu Met Ser Pro Ala Gly Met Leu Arg Gly Asp Phe Ser Leu
65                  70                  75                  80

Arg Leu Phe Asn Val Thr Pro Gln Asp Glu Gln Lys Phe His Cys Leu

```
                85                  90                  95

Val Leu Ser Gln Ser Leu Gly Phe Gln Glu Val Leu Ser Val Glu Val
            100                 105                 110

Thr Leu His Val Ala Ala Asn Phe Ser Val Pro Val Val Ser Ala Pro
        115                 120                 125

His Ser Pro Ser Gln Asp Glu Leu Thr Phe Thr Cys Thr Ser Ile Asn
    130                 135                 140

Gly Tyr Pro Arg Pro Asn Val His Trp Ile Asn Lys Thr Asp Asn Ser
145                 150                 155                 160

Leu Leu Asp Gln Ala Leu Gln Asn Asp Thr Val Phe Leu Asn Met Arg
                165                 170                 175

Gly Leu Tyr Asp Val Val Ser Val Leu Arg Ile Ala Arg Thr Pro Ser
            180                 185                 190

Val Asn Ile Gly Cys Cys Ile Glu Asn Val Leu Leu Gln Gln Asn Leu
        195                 200                 205

Thr Val Gly Ser Gln Thr Gly Asn Asp Ile Gly Glu Arg Asp Lys Ile
    210                 215                 220

Thr Glu Asn Pro Val Ser Thr Gly Glu Lys Asn Ala Ala Thr
225                 230                 235


<210> SEQ ID NO 134
<211> LENGTH: 238
<212> TYPE: PRT
<213> ORGANISM: Artificial Sequence
<220> FEATURE:
<223> OTHER INFORMATION: ICOSL v26 ECD

<400> SEQUENCE: 134

Asp Thr Gln Glu Lys Glu Val Arg Ala Met Val Gly Ser Asp Val Glu
1               5                   10                  15

Leu Ser Cys Ala Cys Pro Glu Gly Ser Arg Phe Asp Leu Asn Asp Val
            20                  25                  30

Tyr Val Tyr Trp Gln Thr Ser Glu Ser Lys Thr Val Val Thr Tyr His
        35                  40                  45

Ile Pro Gln Asp Ser Ser Leu Glu Asn Val Asp Ser Arg Tyr Arg Asn
    50                  55                  60

Arg Ala Leu Met Ser Pro Ala Gly Met Leu Arg Gly Asp Phe Ser Leu
65                  70                  75                  80

Arg Leu Phe Asn Val Thr Pro Gln Asp Glu Gln Lys Phe His Cys Leu
                85                  90                  95

Val Leu Ser Gln Ser Leu Gly Phe Gln Glu Val Leu Ser Val Glu Val
            100                 105                 110

Thr Leu His Val Ala Ala Asn Phe Ser Val Pro Val Val Ser Ala Pro
        115                 120                 125

His Ser Pro Ser Gln Asp Glu Leu Thr Phe Thr Cys Thr Ser Ile Asn
    130                 135                 140

Gly Tyr Pro Arg Pro Asn Ala Tyr Trp Ile Asn Lys Thr Asp Asn Ser
145                 150                 155                 160

Leu Leu Asp Gln Ala Leu Gln Asn Asp Thr Val Phe Leu Asn Met Arg
                165                 170                 175

Gly Leu Tyr Asp Val Val Ser Val Leu Arg Ile Ala Arg Thr Pro Ser
            180                 185                 190

Val Asn Ile Gly Cys Cys Ile Glu Asn Val Leu Leu Gln Gln Asn Leu
        195                 200                 205

Thr Val Gly Ser Gln Thr Gly Asn Asp Ile Gly Glu Arg Asp Lys Ile
```

```
    210                 215                 220

Thr Glu Asn Pro Val Ser Thr Gly Glu Lys Asn Ala Ala Thr
225                 230                 235


<210> SEQ ID NO 135
<211> LENGTH: 238
<212> TYPE: PRT
<213> ORGANISM: Artificial Sequence
<220> FEATURE:
<223> OTHER INFORMATION: ICOSL v27 ECD

<400> SEQUENCE: 135

Asp Thr Gln Glu Lys Glu Val Arg Ala Met Val Gly Ser Asp Val Glu
1               5                   10                  15

Leu Ser Cys Ala Cys Pro Glu Gly Ser Arg Phe Asp Leu Asn Asp Val
            20                  25                  30

Tyr Val Tyr Trp Gln Thr Ser Glu Ser Lys Thr Val Val Thr Tyr His
        35                  40                  45

Ile Pro Gln His Ser Ser Leu Glu Asn Val Asp Ser Arg Tyr Arg Asn
    50                  55                  60

Arg Ala Leu Met Ser Pro Ala Gly Met Leu Arg Gly Asp Phe Ser Leu
65                  70                  75                  80

Arg Leu Phe Asn Val Thr Pro Gln Asp Glu Gln Lys Phe His Cys Leu
                85                  90                  95

Val Leu Ser Gln Ser Leu Gly Phe Gln Glu Val Leu Ser Val Glu Val
            100                 105                 110

Thr Leu His Val Ala Ala Asn Phe Ser Val Pro Val Val Ser Ala Pro
        115                 120                 125

His Ser Pro Ser Gln Asp Glu Leu Thr Phe Thr Cys Thr Ser Thr Asn
    130                 135                 140

Gly Tyr Pro Arg Pro Asn Val Tyr Trp Ile Asn Lys Thr Asp Asn Ser
145                 150                 155                 160

Leu Leu Asp Gln Ala Leu Gln Asn Asp Thr Val Phe Leu Asn Met Arg
                165                 170                 175

Gly Leu Tyr Asp Val Val Ser Val Leu Arg Ile Ala Arg Thr Pro Ser
            180                 185                 190

Val Asn Ile Gly Cys Cys Ile Glu Asn Val Leu Leu Gln Gln Asn Leu
        195                 200                 205

Thr Val Gly Ser Gln Thr Gly Asn Asp Ile Gly Glu Arg Asp Lys Ile
    210                 215                 220

Thr Glu Asn Pro Val Ser Thr Gly Glu Lys Asn Ala Ala Thr
225                 230                 235


<210> SEQ ID NO 136
<211> LENGTH: 238
<212> TYPE: PRT
<213> ORGANISM: Artificial Sequence
<220> FEATURE:
<223> OTHER INFORMATION: ICOSL v28 ECD

<400> SEQUENCE: 136

Asp Thr Gln Glu Lys Glu Val Arg Ala Met Val Gly Ser Asp Val Glu
1               5                   10                  15

Leu Ser Cys Ala Cys Pro Glu Gly Ser Arg Phe Asp Leu Asn Asp Val
            20                  25                  30

Tyr Val Tyr Trp Gln Thr Ser Glu Ser Lys Thr Val Val Thr Tyr His
        35                  40                  45
```

```
Ile Pro Gln Ser Ser Ser Leu Glu Asn Val Asp Ser Arg Tyr Arg Asn
    50                  55                  60

Arg Ala Leu Met Ser Pro Ala Gly Met Leu Arg Gly Asp Phe Ser Pro
65                  70                  75                  80

Arg Leu Phe Asn Val Thr Pro Gln Asp Glu Gln Lys Phe His Cys Leu
                85                  90                  95

Val Leu Ser Gln Ser Leu Gly Phe Gln Glu Val Leu Ser Val Glu Val
            100                 105                 110

Thr Leu His Val Ala Ala Asn Phe Ser Val Pro Val Val Ser Ala Pro
        115                 120                 125

His Ser Pro Ser Gln Asp Glu Leu Thr Phe Thr Cys Thr Ser Ile Asn
    130                 135                 140

Gly Tyr Pro Arg Pro Asn Val Tyr Trp Ile Asn Lys Thr Asp Asn Ser
145                 150                 155                 160

Leu Leu Asp Gln Ala Leu Gln Asn Asp Thr Val Phe Leu Asn Met Arg
                165                 170                 175

Gly Leu Tyr Asp Val Val Ser Val Leu Arg Ile Ala Arg Thr Pro Ser
            180                 185                 190

Val Asn Ile Gly Cys Cys Ile Glu Asn Val Leu Leu Gln Gln Asn Leu
        195                 200                 205

Thr Val Gly Ser Gln Thr Gly Asn Asp Ile Gly Glu Arg Asp Lys Ile
    210                 215                 220

Thr Glu Asn Pro Val Ser Thr Gly Glu Lys Asn Ala Ala Thr
225                 230                 235


<210> SEQ ID NO 137
<211> LENGTH: 238
<212> TYPE: PRT
<213> ORGANISM: Artificial Sequence
<220> FEATURE:
<223> OTHER INFORMATION: ICOSL v29 ECD

<400> SEQUENCE: 137

Asp Thr Gln Glu Lys Glu Val Arg Ala Met Val Gly Ser Asp Val Glu
1               5                   10                  15

Leu Ser Cys Ala Cys Pro Glu Gly Ser Arg Phe Asp Leu Asn Asp Val
            20                  25                  30

Tyr Val Tyr Trp Gln Thr Ser Glu Ser Lys Thr Val Val Thr Tyr His
        35                  40                  45

Ile Pro Gln Asn Ser Ser Leu Glu Asn Val Asp Ser Arg Tyr Arg Asn
    50                  55                  60

Arg Ala Leu Met Ser Pro Ala Gly Met Leu Arg Gly Asp Phe Ser Leu
65                  70                  75                  80

Arg Leu Phe Asn Val Thr Pro Gln Asp Glu Gln Lys Phe His Cys Leu
                85                  90                  95

Val Leu Ser Gln Ser Leu Gly Phe Gln Glu Val Leu Ser Val Glu Val
            100                 105                 110

Thr Leu His Val Ala Ala Asn Ser Ser Val Pro Val Val Ser Ala Pro
        115                 120                 125

His Ser Pro Ser Gln Asp Glu Leu Thr Phe Thr Cys Thr Ser Ile Asn
    130                 135                 140

Gly Tyr Pro Arg Pro Asn Val His Trp Ile Asn Lys Thr Asp Asn Ser
145                 150                 155                 160

Leu Leu Asp Gln Ala Leu Gln Asn Asp Thr Val Phe Leu Asn Met Arg
                165                 170                 175
```

Gly Leu Tyr Asp Val Val Ser Val Leu Arg Ile Ala Arg Thr Pro Ser
180 185 190

Val Asn Ile Gly Cys Cys Ile Glu Ser Val Leu Leu Gln Gln Asn Leu
195 200 205

Thr Val Gly Ser Gln Thr Gly Asn Asp Ile Gly Glu Arg Asp Lys Ile
210 215 220

Thr Glu Asn Pro Val Ser Thr Gly Glu Lys Asn Ala Ala Thr
225 230 235

<210> SEQ ID NO 138
<211> LENGTH: 238
<212> TYPE: PRT
<213> ORGANISM: Artificial Sequence
<220> FEATURE:
<223> OTHER INFORMATION: ICOSL v30 ECD

<400> SEQUENCE: 138

Asp Thr Gln Glu Lys Glu Val Arg Ala Met Val Gly Ser Asp Val Glu
1 5 10 15

Leu Ser Cys Ala Cys Pro Glu Gly Ser Arg Phe Asp Leu Asn Asp Val
20 25 30

Tyr Val Tyr Trp Gln Thr Ser Glu Ser Lys Thr Val Val Thr Tyr His
35 40 45

Ile Pro Gln Ser Ser Ser Leu Glu Asn Val Asp Ser Arg Tyr Arg Asn
50 55 60

Arg Ala Leu Met Ser Pro Ala Gly Met Leu Gln Gly Asp Phe Ser Leu
65 70 75 80

Arg Leu Phe Asn Val Thr Pro Gln Asp Glu Gln Lys Phe His Cys Leu
85 90 95

Val Leu Ser Gln Ser Leu Gly Phe Gln Glu Val Leu Ser Val Glu Val
100 105 110

Thr Leu His Val Ala Ala Asn Phe Ser Val Pro Val Val Ser Ala Pro
115 120 125

His Ser Pro Ser Gln Asp Glu Leu Thr Phe Thr Cys Thr Ser Ile Asn
130 135 140

Gly Tyr Pro Arg Pro Asn Val Tyr Trp Ile Asn Lys Thr Asp Asn Ser
145 150 155 160

Leu Leu Asp Gln Ala Leu Gln Asn Asp Thr Val Phe Leu Asn Met Arg
165 170 175

Gly Leu Tyr Asp Val Val Ser Val Leu Arg Ile Ala Arg Thr Pro Ser
180 185 190

Val Asn Ile Gly Cys Cys Ile Glu Asn Val Pro Leu Gln Gln Asn Leu
195 200 205

Thr Val Gly Ser Gln Thr Gly Asn Asp Ile Gly Glu Arg Asp Lys Ile
210 215 220

Thr Glu Asn Pro Val Ser Thr Gly Glu Lys Asn Ala Ala Thr
225 230 235

<210> SEQ ID NO 139
<211> LENGTH: 238
<212> TYPE: PRT
<213> ORGANISM: Artificial Sequence
<220> FEATURE:
<223> OTHER INFORMATION: ICOSL v31 ECD

<400> SEQUENCE: 139

Asp Thr Gln Glu Lys Glu Val Arg Ala Met Val Gly Ser Asp Val Glu
1 5 10 15

```
Leu Ser Cys Ala Cys Pro Glu Gly Ser Arg Phe Asp Leu Asn Asp Val
            20                  25                  30

Tyr Val Tyr Trp Gln Thr Ser Glu Ser Lys Thr Val Val Thr Tyr His
        35                  40                  45

Ile Pro Gln Ser Ser Ser Leu Glu Asn Val Asp Ser Arg Tyr Arg Asn
    50                  55                  60

Arg Ala Leu Met Ser Pro Ala Gly Met Leu Arg Gly Asp Phe Ser Leu
65                  70                  75                  80

Arg Leu Phe Asn Val Thr Pro Gln Asp Glu Gln Lys Phe His Cys Leu
                85                  90                  95

Val Leu Ser Gln Ser Leu Gly Phe Gln Glu Val Leu Ser Val Glu Val
            100                 105                 110

Thr Leu His Val Ala Ala Asn Phe Ser Val Pro Val Val Ser Ala Pro
        115                 120                 125

His Ser Pro Ser Gln Asp Glu Leu Thr Phe Thr Cys Thr Ser Ile Asn
    130                 135                 140

Gly Tyr Pro Arg Pro Asn Val Tyr Trp Ile Asn Lys Thr Gly Asn Ser
145                 150                 155                 160

Leu Leu Asp Gln Ala Leu Gln Asn Asp Thr Val Phe Leu Asn Met Arg
                165                 170                 175

Gly Leu Tyr Asp Val Val Ser Val Leu Arg Ile Ala Arg Thr Pro Ser
            180                 185                 190

Val Asn Ile Gly Cys Cys Ile Glu Asn Val Leu Leu Gln Gln Asn Leu
        195                 200                 205

Thr Val Gly Ser Gln Thr Gly Asn Asp Ile Gly Glu Arg Asp Lys Ile
    210                 215                 220

Thr Glu Asn Pro Val Ser Thr Gly Glu Lys Asn Ala Ala Thr
225                 230                 235


<210> SEQ ID NO 140
<211> LENGTH: 238
<212> TYPE: PRT
<213> ORGANISM: Artificial Sequence
<220> FEATURE:
<223> OTHER INFORMATION: ICOSL v32 ECD

<400> SEQUENCE: 140

Asp Thr Gln Glu Lys Glu Val Arg Ala Met Val Gly Ser Asp Val Glu
1               5                   10                  15

Leu Ser Cys Ala Cys Pro Glu Gly Ser Arg Phe Asp Leu Asn Asp Val
            20                  25                  30

Tyr Val Tyr Trp Gln Thr Ser Glu Ser Lys Thr Val Val Thr Tyr His
        35                  40                  45

Ile Pro Gln Asp Ser Ser Leu Glu Asn Val Asp Ser Arg Tyr Arg Asn
    50                  55                  60

Arg Ala Leu Met Ser Pro Ala Gly Met Leu Arg Gly Asp Phe Ser Leu
65                  70                  75                  80

Arg Leu Phe Asn Val Thr Pro Gln Asp Glu Gln Lys Phe His Cys Leu
                85                  90                  95

Val Leu Ser Gln Ser Leu Gly Phe Gln Glu Val Leu Ser Val Glu Val
            100                 105                 110

Thr Leu His Val Ala Ala Asn Phe Ser Val Pro Val Val Ser Ala Pro
        115                 120                 125

His Ser Pro Ser His Asp Glu Leu Thr Phe Thr Cys Thr Ser Ile Asn
    130                 135                 140
```

Gly Tyr Pro Arg Pro Asn Val Tyr Trp Ile Asn Lys Thr Asp Asn Ser
145 150 155 160

Leu Leu Asp Gln Ala Leu Gln Asn Asp Thr Val Phe Leu Asn Met Arg
165 170 175

Gly Leu Tyr Asp Val Val Ser Val Leu Arg Ile Ala Arg Thr Pro Ser
180 185 190

Val Asn Ile Gly Cys Cys Ile Glu Asn Val Leu Leu Gln Gln Asn Leu
195 200 205

Thr Val Gly Ser Gln Thr Gly Asn Asp Ile Gly Glu Arg Asp Lys Ile
210 215 220

Thr Glu Asn Pro Val Ser Thr Gly Glu Lys Asn Ala Ala Thr
225 230 235

<210> SEQ ID NO 141
<211> LENGTH: 238
<212> TYPE: PRT
<213> ORGANISM: Artificial Sequence
<220> FEATURE:
<223> OTHER INFORMATION: ICOSL v33 ECD

<400> SEQUENCE: 141

Asp Thr Gln Glu Lys Glu Val Arg Ala Met Val Gly Ser Asp Val Glu
1 5 10 15

Leu Ser Cys Ala Cys Pro Glu Gly Ser Arg Phe Asp Leu Asn Asp Val
20 25 30

Tyr Val Tyr Trp Gln Thr Ser Glu Ser Lys Thr Val Val Thr Tyr His
35 40 45

Ile Pro Gln Ser Ser Ser Leu Glu Tyr Val Asp Ser Arg Tyr Arg Asn
50 55 60

Arg Ala Leu Met Ser Pro Ala Gly Met Leu Arg Gly Asp Phe Ser Leu
65 70 75 80

Arg Leu Phe Asn Val Thr Pro Gln Asp Glu Gln Lys Phe Asp Cys Phe
85 90 95

Val Phe Ser Arg Ser Leu Gly Phe Gln Glu Val Leu Ser Val Glu Val
100 105 110

Thr Leu His Val Ala Ala Asn Phe Ser Val Pro Val Val Ser Ala Pro
115 120 125

His Ser Pro Ser Gln Asp Glu Leu Thr Phe Thr Cys Thr Ser Ile Asn
130 135 140

Gly Tyr Pro Arg Pro Asn Val Tyr Trp Ile Asn Lys Thr Asp Asn Ser
145 150 155 160

Leu Leu Asp Gln Ala Leu Gln Asn Asp Thr Val Phe Leu Asn Met Arg
165 170 175

Gly Leu Tyr Asp Val Val Ser Val Leu Arg Ile Ala Arg Thr Pro Ser
180 185 190

Val Asn Ile Gly Cys Cys Ile Glu Asn Val Leu Leu Gln Gln Asn Leu
195 200 205

Thr Val Gly Ser Gln Thr Gly Asn Asp Ile Gly Glu Arg Asp Lys Ile
210 215 220

Thr Glu Asn Pro Val Ser Thr Gly Glu Lys Asn Ala Ala Thr
225 230 235

<210> SEQ ID NO 142
<211> LENGTH: 238
<212> TYPE: PRT
<213> ORGANISM: Artificial Sequence
<220> FEATURE:
<223> OTHER INFORMATION: ICOSL v34 ECD

<400> SEQUENCE: 142

Asp Thr Gln Glu Lys Glu Val Arg Ala Met Val Gly Ser Asp Val Glu
1 5 10 15

Leu Ser Cys Ala Cys Pro Glu Gly Ser Arg Phe Asp Leu Asn Asp Val
20 25 30

Tyr Val Tyr Trp Gln Thr Ser Glu Ser Lys Thr Val Val Thr Tyr His
35 40 45

Ile Pro Gln Ser Ser Ser Leu Glu Tyr Val Asp Ser Arg Tyr Arg Asn
50 55 60

Arg Ala Leu Met Ser Pro Ala Gly Met Leu Arg Gly Asp Phe Ser Leu
65 70 75 80

Arg Leu Phe Asn Val Thr Pro Gln Asp Glu Gln Lys Phe Asp Cys Phe
85 90 95

Val Phe Ser Arg Ser Leu Glu Phe Gln Glu Val Leu Ser Val Glu Val
100 105 110

Thr Leu His Val Ala Ala Asn Ser Ser Val Pro Val Val Ser Ala Pro
115 120 125

His Ser Pro Ser Gln Asp Glu Leu Thr Phe Thr Cys Thr Ser Ile Asn
130 135 140

Gly Tyr Pro Arg Pro Asn Val Tyr Trp Ile Asn Lys Thr Asp Asn Ser
145 150 155 160

Leu Leu Asp Gln Ala Leu Gln Asn Asp Thr Val Phe Leu Asn Met Arg
165 170 175

Gly Leu Tyr Asp Val Val Ser Val Leu Arg Ile Ala Arg Thr Pro Ser
180 185 190

Val Asn Ile Gly Cys Cys Ile Glu Asn Val Leu Leu Gln Gln Asn Leu
195 200 205

Thr Val Gly Ser Gln Thr Gly Asn Asp Ile Gly Glu Arg Asp Lys Ile
210 215 220

Thr Glu Asn Pro Val Ser Thr Gly Glu Lys Asn Ala Ala Thr
225 230 235

<210> SEQ ID NO 143
<211> LENGTH: 117
<212> TYPE: PRT
<213> ORGANISM: Artificial Sequence
<220> FEATURE:
<223> OTHER INFORMATION: NKp30 v1 ECD

<400> SEQUENCE: 143

Leu Trp Val Ser Gln Pro Pro Glu Ile Arg Thr Leu Glu Gly Ser Ser
1 5 10 15

Ala Phe Leu Pro Cys Ser Phe Asn Ala Ser Gln Gly Arg Val Ala Ile
20 25 30

Gly Ser Val Thr Trp Phe Arg Asp Glu Val Val Pro Gly Lys Glu Val
35 40 45

Arg Asn Gly Thr Pro Glu Phe Arg Gly Arg Leu Val Pro Leu Ala Pro
50 55 60

Ser Arg Phe Leu His Asp His Gln Ala Glu Leu His Ile Arg Asp Val
65 70 75 80

Arg Gly His Asp Ala Gly Ile Tyr Val Cys Arg Val Glu Val Leu Gly
85 90 95

Leu Gly Val Gly Thr Gly Asn Gly Thr Arg Leu Val Val Glu Lys Glu

```
            100                 105                 110

His Pro Gln Leu Gly
        115


<210> SEQ ID NO 144
<211> LENGTH: 117
<212> TYPE: PRT
<213> ORGANISM: Artificial Sequence
<220> FEATURE:
<223> OTHER INFORMATION: NKp30 v2 ECD

<400> SEQUENCE: 144

Leu Trp Val Ser Gln Pro Pro Glu Ile Arg Thr Leu Glu Gly Ser Ser
1               5                   10                  15

Ala Phe Leu Pro Cys Ser Phe Asn Ala Ser Gln Gly Arg Val Ala Ile
            20                  25                  30

Gly Ser Val Thr Trp Phe Arg Asp Glu Val Val Pro Gly Lys Glu Val
        35                  40                  45

Arg Asn Gly Thr Pro Glu Phe Arg Gly Arg Leu Ala Pro Leu Ala Ser
    50                  55                  60

Ser Arg Phe Leu His Asp His Gln Ala Glu Leu His Ile Arg Asp Val
65                  70                  75                  80

Arg Gly His Asp Ala Ser Ile Tyr Val Cys Arg Val Glu Val Leu Gly
                85                  90                  95

Leu Gly Val Gly Thr Gly Asn Gly Thr Arg Leu Val Val Glu Lys Glu
            100                 105                 110

His Pro Gln Leu Gly
        115


<210> SEQ ID NO 145
<211> LENGTH: 117
<212> TYPE: PRT
<213> ORGANISM: Artificial Sequence
<220> FEATURE:
<223> OTHER INFORMATION: NKp30 v3 ECD

<400> SEQUENCE: 145

Leu Trp Val Ser Gln Pro Pro Glu Ile Arg Thr Leu Glu Gly Ser Ser
1               5                   10                  15

Ala Phe Leu Pro Cys Ser Phe Asn Ala Ser Gln Gly Arg Leu Ala Ile
            20                  25                  30

Gly Ser Val Thr Trp Phe Arg Asp Glu Val Val Pro Gly Lys Glu Val
        35                  40                  45

Arg Asn Gly Thr Pro Glu Phe Arg Gly Arg Leu Val Pro Leu Ala Ser
    50                  55                  60

Ser Arg Phe Leu His Asp His Gln Ala Glu Leu His Ile Arg Asp Val
65                  70                  75                  80

Arg Gly His Asp Ala Ser Ile Tyr Val Cys Arg Val Glu Val Leu Gly
                85                  90                  95

Leu Gly Val Gly Thr Gly Asn Gly Thr Arg Leu Val Val Glu Lys Glu
            100                 105                 110

His Pro Gln Leu Gly
        115


<210> SEQ ID NO 146
<211> LENGTH: 117
<212> TYPE: PRT
<213> ORGANISM: Artificial Sequence
<220> FEATURE:
```

<223> OTHER INFORMATION: NKp30 v4 ECD

<400> SEQUENCE: 146

Leu Trp Val Ser Gln Pro Pro Glu Ile Arg Thr Leu Glu Gly Ser Ser
1 5 10 15

Ala Phe Leu Pro Cys Ser Phe Asn Ala Ser Gln Gly Arg Leu Ala Ile
20 25 30

Gly Ser Val Thr Trp Phe Arg Asp Glu Val Val Pro Gly Lys Glu Val
35 40 45

Arg Asn Gly Thr Pro Glu Phe Arg Gly Arg Leu Ala Pro Leu Ala Pro
50 55 60

Ser Arg Phe Leu His Asp His Gln Ala Glu Leu His Ile Arg Asp Val
65 70 75 80

Arg Gly His Asp Ala Ser Ile Tyr Val Cys Arg Val Glu Val Leu Gly
85 90 95

Leu Gly Val Gly Thr Gly Asn Gly Thr Arg Leu Val Val Glu Lys Glu
100 105 110

His Pro Gln Leu Gly
115

<210> SEQ ID NO 147
<211> LENGTH: 117
<212> TYPE: PRT
<213> ORGANISM: Homo sapiens
<220> FEATURE:
<223> OTHER INFORMATION: NKp30 v5 ECD

<400> SEQUENCE: 147

Leu Trp Val Ser Gln Pro Pro Glu Ile Arg Thr Leu Glu Gly Ser Ser
1 5 10 15

Ala Phe Leu Pro Cys Ser Phe Asn Ala Ser Gln Gly Arg Leu Ala Ile
20 25 30

Gly Ser Val Thr Trp Phe Arg Asp Glu Val Val Pro Gly Lys Glu Val
35 40 45

Arg Asn Gly Thr Pro Glu Phe Arg Gly Arg Leu Ala Pro Leu Ala Ser
50 55 60

Ser Arg Phe Leu His Asp His Gln Ala Glu Leu His Ile Arg Asp Val
65 70 75 80

Arg Gly His Asp Ala Gly Ile Tyr Val Cys Arg Val Glu Val Leu Gly
85 90 95

Leu Gly Val Gly Thr Gly Asn Gly Thr Arg Leu Val Val Glu Lys Glu
100 105 110

His Pro Gln Leu Gly
115

<210> SEQ ID NO 148
<211> LENGTH: 224
<212> TYPE: PRT
<213> ORGANISM: Artificial Sequence
<220> FEATURE:
<223> OTHER INFORMATION: CD86 v1 ECD

<400> SEQUENCE: 148

Ala Pro Leu Lys Ile Gln Ala Tyr Phe Asn Glu Thr Ala Asp Leu Pro
1 5 10 15

Cys Gln Phe Ala Asn Ser Gln Asn Gln Ser Leu Ser Glu Leu Val Val
20 25 30

Phe Trp His Asp Gln Glu Asn Leu Val Leu Asn Glu Val Tyr Leu Gly

```
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile Leu His Lys Lys Pro Thr Gly
                85                  90                  95

Met Ile Arg Ile His His Met Asn Ser Glu Leu Ser Val Leu Ala Asn
            100                 105                 110

Phe Ser Gln Pro Glu Ile Val Pro Ile Ser Asn Ile Thr Glu Asn Val
        115                 120                 125

Tyr Ile Asn Leu Thr Cys Ser Ser Ile His Gly Tyr Pro Glu Pro Lys
    130                 135                 140

Lys Met Ser Val Leu Leu Arg Thr Lys Asn Ser Thr Ile Glu Tyr Asp
145                 150                 155                 160

Gly Val Met Gln Lys Ser Gln Asp Asn Val Thr Glu Leu Tyr Asp Val
                165                 170                 175

Ser Ile Ser Leu Ser Val Ser Phe Pro Asp Val Thr Ser Asn Met Thr
            180                 185                 190

Ile Phe Cys Ile Leu Glu Thr Asp Lys Thr Arg Leu Leu Ser Ser Pro
        195                 200                 205

Phe Ser Ile Glu Leu Glu Asp Pro Gln Pro Pro Pro Asp His Ile Pro
    210                 215                 220


<210> SEQ ID NO 149
<211> LENGTH: 224
<212> TYPE: PRT
<213> ORGANISM: Artificial Sequence
<220> FEATURE:
<223> OTHER INFORMATION: CD86 v2 ECD

<400> SEQUENCE: 149

Ala Pro Leu Lys Ile Gln Ala Tyr Phe Asn Glu Thr Ala Asp Leu Pro
1               5                   10                  15

Cys Gln Phe Ala Asn Ser Gln Asn Gln Ser Leu Ser Glu Leu Val Val
            20                  25                  30

Phe Trp His Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile His His Lys Lys Pro Thr Gly
                85                  90                  95

Met Ile Arg Ile His Gln Met Asn Ser Glu Leu Ser Val Leu Ala Asn
            100                 105                 110

Phe Ser Gln Pro Glu Ile Val Pro Ile Ser Asn Ile Thr Glu Asn Val
        115                 120                 125

Tyr Ile Asn Leu Thr Cys Ser Ser Ile His Gly Tyr Pro Glu Pro Lys
    130                 135                 140

Lys Met Ser Val Leu Leu Arg Thr Lys Asn Ser Thr Ile Glu Tyr Asp
145                 150                 155                 160

Gly Val Met Gln Lys Ser Gln Asp Asn Val Thr Glu Leu Tyr Asp Val
                165                 170                 175

Ser Ile Ser Leu Ser Val Ser Phe Pro Asp Val Thr Ser Asn Met Thr
```

```
            180                 185                 190

Ile Phe Cys Ile Leu Glu Thr Asp Lys Thr Arg Leu Leu Ser Ser Pro
        195                 200                 205

Phe Ser Ile Glu Leu Glu Asp Pro Gln Pro Pro Pro Asp His Ile Pro
    210                 215                 220


<210> SEQ ID NO 150
<211> LENGTH: 224
<212> TYPE: PRT
<213> ORGANISM: Artificial Sequence
<220> FEATURE:
<223> OTHER INFORMATION: CD86 v3 ECD

<400> SEQUENCE: 150

Ala Pro Leu Lys Ile Gln Ala Tyr Phe Asn Glu Thr Ala Asp Leu Pro
1               5                   10                  15

Cys Gln Phe Ala Asn Ser Gln Asn Gln Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile Leu His Lys Lys Pro Thr Gly
                85                  90                  95

Met Ile Arg Ile His Gln Met Asn Ser Glu Leu Ser Val Leu Ala Asn
            100                 105                 110

Phe Ser Gln Pro Glu Ile Val Pro Ile Ser Asn Ile Thr Glu Asn Val
        115                 120                 125

Tyr Ile Asn Leu Thr Cys Ser Ser Ile His Gly Tyr Pro Glu Pro Lys
    130                 135                 140

Lys Met Ser Val Leu Leu Arg Thr Lys Asn Ser Thr Ile Glu Tyr Asp
145                 150                 155                 160

Gly Val Met Gln Lys Ser Gln Asp Asn Val Thr Glu Leu Tyr Asp Val
                165                 170                 175

Ser Ile Ser Leu Ser Val Ser Phe Pro Asp Val Thr Ser Asn Met Thr
            180                 185                 190

Ile Phe Cys Ile Leu Glu Thr Asp Lys Thr Arg Leu Leu Ser Ser Pro
        195                 200                 205

Phe Ser Ile Glu Leu Glu Asp Pro Gln Pro Pro Pro Asp His Ile Pro
    210                 215                 220


<210> SEQ ID NO 151
<211> LENGTH: 224
<212> TYPE: PRT
<213> ORGANISM: Artificial Sequence
<220> FEATURE:
<223> OTHER INFORMATION: CD86 v4 ECD

<400> SEQUENCE: 151

Ala Pro Leu Lys Ile Gln Ala Tyr Phe Asn Glu Thr Ala Asp Leu Pro
1               5                   10                  15

Cys Gln Phe Ala Asn Ser Gln Asn Gln Ser Leu Ser Glu Leu Val Val
            20                  25                  30

Phe Trp Gln Asp Gln Glu Asn Leu Val Leu Asn Glu Val Tyr Leu Gly
        35                  40                  45
```

```
Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile His His Lys Lys Pro Thr Gly
                85                  90                  95

Met Ile Arg Ile His His Met Asn Ser Glu Leu Ser Val Leu Ala Asn
            100                 105                 110

Phe Ser Gln Pro Glu Ile Val Pro Ile Ser Asn Ile Thr Glu Asn Val
        115                 120                 125

Tyr Ile Asn Leu Thr Cys Ser Ser Ile His Gly Tyr Pro Glu Pro Lys
    130                 135                 140

Lys Met Ser Val Leu Leu Arg Thr Lys Asn Ser Thr Ile Glu Tyr Asp
145                 150                 155                 160

Gly Val Met Gln Lys Ser Gln Asp Asn Val Thr Glu Leu Tyr Asp Val
                165                 170                 175

Ser Ile Ser Leu Ser Val Ser Phe Pro Asp Val Thr Ser Asn Met Thr
            180                 185                 190

Ile Phe Cys Ile Leu Glu Thr Asp Lys Thr Arg Leu Leu Ser Ser Pro
        195                 200                 205

Phe Ser Ile Glu Leu Glu Asp Pro Gln Pro Pro Pro Asp His Ile Pro
    210                 215                 220


<210> SEQ ID NO 152
<211> LENGTH: 101
<212> TYPE: PRT
<213> ORGANISM: Artificial Sequence
<220> FEATURE:
<223> OTHER INFORMATION: CD80 WT IgV

<400> SEQUENCE: 152

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr
            100


<210> SEQ ID NO 153
<211> LENGTH: 101
<212> TYPE: PRT
<213> ORGANISM: Artificial Sequence
<220> FEATURE:
<223> OTHER INFORMATION: CD80 v1 IgV

<400> SEQUENCE: 153

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30
```

```
Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Gln Ala Leu Arg Pro Ser Asp Glu Gly Thr Tyr
65                  70                  75                  80

Glu Cys Val Val Leu Lys Tyr Glu Lys Asp Gly Phe Lys Arg Glu His
                85                  90                  95

Leu Ala Glu Val Thr
            100


<210> SEQ ID NO 154
<211> LENGTH: 101
<212> TYPE: PRT
<213> ORGANISM: Artificial Sequence
<220> FEATURE:
<223> OTHER INFORMATION: CD80 v4 IgV

<400> SEQUENCE: 154

Val Ile His Met Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Gln Ala Leu Arg Pro Ser Asp Glu Gly Thr Tyr
65                  70                  75                  80

Glu Cys Val Val Leu Lys Tyr Glu Lys Asp Gly Phe Lys Arg Glu His
                85                  90                  95

Leu Ala Glu Val Thr
            100


<210> SEQ ID NO 155
<211> LENGTH: 101
<212> TYPE: PRT
<213> ORGANISM: Artificial Sequence
<220> FEATURE:
<223> OTHER INFORMATION: CD80 v6 IgV

<400> SEQUENCE: 155

Val Ile His Val Thr Lys Glu Val Lys Glu Val Ala Thr Leu Ser Cys
1               5                   10                  15

Gly His Asn Leu Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Gln Ala Leu Arg Pro Ser Asp Glu Gly Thr Tyr
65                  70                  75                  80

Glu Cys Val Val Leu Lys Tyr Glu Lys Asp Ser Phe Lys Arg Glu His
                85                  90                  95

Leu Ala Glu Val Thr
            100
```

<210> SEQ ID NO 156
<211> LENGTH: 101
<212> TYPE: PRT
<213> ORGANISM: Artificial Sequence
<220> FEATURE:
<223> OTHER INFORMATION: CD80 v7 IgV

<400> SEQUENCE: 156

```
Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Pro Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Gln Ala Leu Arg Pro Ser Asp Glu Gly Thr Tyr
65                  70                  75                  80

Glu Cys Val Val Leu Lys Tyr Glu Lys Asp Gly Phe Lys Arg Glu His
                85                  90                  95

Leu Ala Glu Val Thr
            100
```

<210> SEQ ID NO 157
<211> LENGTH: 101
<212> TYPE: PRT
<213> ORGANISM: Artificial Sequence
<220> FEATURE:
<223> OTHER INFORMATION: CD80 v9 IgV

<400> SEQUENCE: 157

```
Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Gly Phe Lys Arg Glu His
                85                  90                  95

Leu Ala Glu Val Thr
            100
```

<210> SEQ ID NO 158
<211> LENGTH: 101
<212> TYPE: PRT
<213> ORGANISM: Artificial Sequence
<220> FEATURE:
<223> OTHER INFORMATION: CD80 v10 IgV

<400> SEQUENCE: 158

```
Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45
```

Ile Trp Pro Glu Tyr Lys Asn Arg Thr Ile Phe Asp Ile Thr Asn Asn
50 55 60

Leu Ser Ile Val Ile Arg Ala Leu Arg Pro Ser Asp Glu Gly Thr Tyr
65 70 75 80

Glu Cys Val Val Leu Lys Tyr Glu Lys Asp Gly Phe Lys Arg Glu His
85 90 95

Leu Ala Glu Val Thr
100

<210> SEQ ID NO 159
<211> LENGTH: 101
<212> TYPE: PRT
<213> ORGANISM: Artificial Sequence
<220> FEATURE:
<223> OTHER INFORMATION: CD80 v11 IgV

<400> SEQUENCE: 159

Val Ile His Val Thr Lys Glu Val Lys Glu Val Ala Thr Leu Ser Cys
1 5 10 15

Gly His Asn Val Ser Val Glu Glu Leu Ala Gln Thr Arg Ile Tyr Trp
20 25 30

Gln Lys Glu Lys Lys Met Val Leu Thr Met Met Ser Gly Asp Met Asn
35 40 45

Ile Trp Pro Glu Tyr Lys Asn Arg Thr Ile Phe Asp Ile Thr Asn Asn
50 55 60

Leu Ser Ile Val Ile Gln Ala Leu Arg Pro Ser Asp Glu Gly Thr Tyr
65 70 75 80

Ala Cys Val Val Leu Lys Tyr Glu Lys Asp Gly Phe Lys Arg Glu His
85 90 95

Leu Ala Glu Val Thr
100

<210> SEQ ID NO 160
<211> LENGTH: 101
<212> TYPE: PRT
<213> ORGANISM: Artificial Sequence
<220> FEATURE:
<223> OTHER INFORMATION: CD80 v12 IgV

<400> SEQUENCE: 160

Val Ile His Val Thr Lys Glu Val Lys Glu Val Ala Thr Leu Ser Cys
1 5 10 15

Gly His Asn Val Ser Val Glu Glu Leu Ala Gln Thr Arg Ile Tyr Trp
20 25 30

Gln Lys Glu Lys Lys Met Val Leu Thr Met Met Ser Gly Asp Met Asn
35 40 45

Ile Trp Pro Glu Tyr Lys Asn Arg Thr Ile Phe Asp Ile Thr Asn Asn
50 55 60

Leu Ser Ile Val Ile Gln Ala Leu Arg Pro Ser Asp Glu Gly Thr Tyr
65 70 75 80

Glu Cys Val Val Leu Lys Asn Glu Lys Asp Gly Phe Lys Arg Glu His
85 90 95

Leu Ala Glu Val Thr
100

<210> SEQ ID NO 161
<211> LENGTH: 101
<212> TYPE: PRT

<213> ORGANISM: Artificial Sequence
<220> FEATURE:
<223> OTHER INFORMATION: CD80 v13 IgV

<400> SEQUENCE: 161

Val Ile His Val Thr Lys Glu Val Lys Glu Val Ala Thr Leu Ser Cys
1 5 10 15

Gly His Asn Val Ser Val Glu Glu Leu Ala Gln Ser Arg Ile Tyr Trp
20 25 30

Gln Lys Glu Lys Lys Met Val Leu Thr Met Met Ser Gly Asp Met Asn
35 40 45

Ile Trp Pro Glu Tyr Lys Asn Arg Thr Ile Phe Asp Ile Thr Asn Asn
50 55 60

Leu Ser Ile Val Ile Gln Ala Leu Arg Pro Ser Asp Glu Gly Thr Tyr
65 70 75 80

Glu Cys Val Val Leu Lys Tyr Glu Lys Asp Gly Phe Lys Arg Lys His
85 90 95

Leu Ala Glu Val Thr
100

<210> SEQ ID NO 162
<211> LENGTH: 101
<212> TYPE: PRT
<213> ORGANISM: Artificial Sequence
<220> FEATURE:
<223> OTHER INFORMATION: CD80 v14 IgV

<400> SEQUENCE: 162

Val Ile His Val Thr Lys Glu Val Lys Glu Val Ala Thr Leu Ser Cys
1 5 10 15

Gly His Asn Val Ser Val Glu Glu Leu Ala Gln Thr Arg Ile Tyr Trp
20 25 30

Gln Lys Glu Lys Lys Met Val Leu Thr Met Met Ser Gly Asp Met Asn
35 40 45

Ile Trp Pro Glu Tyr Lys Asn Arg Thr Ile Phe Asp Ile Thr Ser Asn
50 55 60

Leu Ser Ile Val Ile Gln Ala Leu Arg Pro Ser Asp Glu Gly Thr Tyr
65 70 75 80

Glu Cys Val Val Leu Lys Tyr Glu Lys Asp Gly Phe Lys Arg Glu His
85 90 95

Leu Ala Glu Val Thr
100

<210> SEQ ID NO 163
<211> LENGTH: 101
<212> TYPE: PRT
<213> ORGANISM: Artificial Sequence
<220> FEATURE:
<223> OTHER INFORMATION: CD80 v15 IgV

<400> SEQUENCE: 163

Val Ile His Val Thr Lys Glu Val Lys Glu Val Ala Thr Leu Ser Cys
1 5 10 15

Gly His Asn Val Ser Val Glu Glu Leu Ala Gln Thr Arg Ile Tyr Trp
20 25 30

Gln Lys Glu Glu Lys Met Val Leu Thr Met Met Ser Gly Asp Met Asn
35 40 45

Ile Trp Pro Glu Tyr Lys Asn Arg Thr Ile Phe Asp Ile Thr Asn Asn
50 55 60

Leu Ser Thr Val Ile Gln Ala Leu Arg Pro Ser Asp Glu Gly Thr Tyr
65 70 75 80

Glu Cys Val Val Leu Lys Tyr Glu Lys Asp Gly Phe Lys Arg Glu His
85 90 95

Leu Ala Glu Val Thr
100

<210> SEQ ID NO 164
<211> LENGTH: 101
<212> TYPE: PRT
<213> ORGANISM: Artificial Sequence
<220> FEATURE:
<223> OTHER INFORMATION: CD80 v16 IgV

<400> SEQUENCE: 164

Val Ile His Val Thr Lys Glu Val Lys Glu Val Ala Thr Leu Ser Cys
1 5 10 15

Gly His Asn Val Ser Val Glu Glu Leu Ala Gln Thr Arg Ile Tyr Trp
20 25 30

Gln Lys Glu Lys Lys Met Val Leu Thr Met Met Ser Gly Asp Met Asn
35 40 45

Ile Trp Pro Gly Tyr Lys Asn Arg Thr Ile Phe Asp Ile Thr Asn Asn
50 55 60

Leu Ser Ile Val Ile Gln Ala Leu Arg Pro Ser Asp Glu Gly Thr Tyr
65 70 75 80

Glu Cys Val Val Leu Lys Tyr Glu Lys Asp Gly Phe Lys Arg Glu His
85 90 95

Leu Ala Glu Val Thr
100

<210> SEQ ID NO 165
<211> LENGTH: 101
<212> TYPE: PRT
<213> ORGANISM: Artificial Sequence
<220> FEATURE:
<223> OTHER INFORMATION: CD80 v17 IgV

<400> SEQUENCE: 165

Val Ile His Val Thr Lys Glu Val Lys Glu Val Ala Thr Leu Ser Cys
1 5 10 15

Gly His Asn Val Ser Val Glu Glu Leu Ala Gln Thr Arg Ile Tyr Trp
20 25 30

Gln Lys Glu Lys Glu Met Val Leu Thr Met Met Ser Gly Asp Met Asn
35 40 45

Ile Trp Pro Glu Tyr Lys Asn Arg Thr Ile Ser Asp Ile Thr Asn Asn
50 55 60

Leu Ser Ile Val Ile Gln Ala Leu Arg Pro Ser Asp Glu Gly Thr Tyr
65 70 75 80

Glu Cys Val Val Leu Lys Tyr Glu Lys Asp Gly Phe Lys Arg Glu His
85 90 95

Leu Ala Glu Val Thr
100

<210> SEQ ID NO 166
<211> LENGTH: 101
<212> TYPE: PRT
<213> ORGANISM: Artificial Sequence
<220> FEATURE:
<223> OTHER INFORMATION: CD80 v19 IgV

<400> SEQUENCE: 166

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Glu Asp Ala Phe Lys Arg Glu His
                85                  90                  95

Leu Ala Glu Val Thr
            100

<210> SEQ ID NO 167
<211> LENGTH: 101
<212> TYPE: PRT
<213> ORGANISM: Artificial Sequence
<220> FEATURE:
<223> OTHER INFORMATION: CD80 v21 IgV

<400> SEQUENCE: 167

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Val Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Gly Phe Lys Arg Glu His
                85                  90                  95

Leu Ala Glu Val Thr
            100

<210> SEQ ID NO 168
<211> LENGTH: 101
<212> TYPE: PRT
<213> ORGANISM: Artificial Sequence
<220> FEATURE:
<223> OTHER INFORMATION: CD80 v22 IgV

<400> SEQUENCE: 168

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Met Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

```
Glu Cys Val Val Leu Lys Tyr Glu Lys Asp Gly Phe Lys Arg Glu His
                85                  90                  95

Leu Ala Glu Val Thr
            100


<210> SEQ ID NO 169
<211> LENGTH: 101
<212> TYPE: PRT
<213> ORGANISM: Artificial Sequence
<220> FEATURE:
<223> OTHER INFORMATION: CD80 v23 IgV

<400> SEQUENCE: 169

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Thr Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Gln Ala Leu Arg Pro Ser Asp Gly Gly Thr Tyr
65                  70                  75                  80

Glu Cys Val Val Leu Lys Tyr Glu Lys Asp Gly Phe Lys Arg Glu His
                85                  90                  95

Leu Ala Glu Val Thr
            100


<210> SEQ ID NO 170
<211> LENGTH: 101
<212> TYPE: PRT
<213> ORGANISM: Artificial Sequence
<220> FEATURE:
<223> OTHER INFORMATION: CD80 v24 IgV

<400> SEQUENCE: 170

Val Ile His Val Thr Lys Glu Val Lys Glu Val Ala Thr Leu Ser Cys
1               5                   10                  15

Gly His Asn Val Ser Val Glu Glu Leu Ala Gln Thr His Ile Tyr Trp
            20                  25                  30

Gln Lys Glu Lys Lys Met Val Leu Thr Met Met Ser Gly Asp Met Asn
        35                  40                  45

Ile Trp Pro Gly Tyr Lys Asn Arg Thr Ile Phe Asp Ile Thr Asn Asn
    50                  55                  60

Leu Ser Ile Val Ile Arg Ala Leu Arg Pro Ser Asp Glu Gly Thr Tyr
65                  70                  75                  80

Glu Cys Val Val Leu Lys Tyr Gly Lys Asp Gly Phe Lys Arg Glu His
                85                  90                  95

Leu Ala Glu Val Thr
            100


<210> SEQ ID NO 171
<211> LENGTH: 101
<212> TYPE: PRT
<213> ORGANISM: Artificial Sequence
<220> FEATURE:
<223> OTHER INFORMATION: CD80 v25 IgV

<400> SEQUENCE: 171
```

Val Ile His Val Thr Lys Glu Val Lys Glu Val Ala Thr Leu Ser Cys
1 5 10 15

Gly His Asn Val Ser Val Glu Glu Leu Ala Gln Thr Arg Ile His Trp
20 25 30

Gln Lys Glu Lys Lys Met Val Leu Gly Met Met Ser Gly Asp Met Asn
35 40 45

Ile Trp Pro Glu Tyr Lys Asn Arg Thr Ile Phe Asp Ile Thr Asn Asn
50 55 60

Leu Ser Ile Val Ile Gln Ala Leu Arg Pro Ser Asp Glu Gly Thr Tyr
65 70 75 80

Glu Cys Val Val Leu Lys Tyr Glu Lys Asp Gly Phe Lys Arg Glu His
85 90 95

Leu Ala Glu Val Thr
100

<210> SEQ ID NO 172
<211> LENGTH: 101
<212> TYPE: PRT
<213> ORGANISM: Artificial Sequence
<220> FEATURE:
<223> OTHER INFORMATION: CD80 v26 IgV

<400> SEQUENCE: 172

Val Ile His Val Thr Lys Glu Val Lys Glu Val Ala Thr Leu Ser Cys
1 5 10 15

Gly His Asn Val Ser Val Glu Glu Leu Ala Gln Thr Arg Ile Tyr Trp
20 25 30

Gln Lys Glu Lys Lys Met Val Leu Thr Met Met Ser Gly Asp Met Asn
35 40 45

Ile Trp Pro Glu Tyr Lys Asn Arg Thr Ile Phe Asp Ile Thr Asn Asn
50 55 60

Leu Ser Ile Ala Ile Leu Ala Leu Arg Pro Ser Asp Glu Gly Thr Tyr
65 70 75 80

Glu Cys Val Val Leu Lys Tyr Glu Lys Asp Ala Phe Lys Arg Glu His
85 90 95

Leu Ala Glu Val Thr
100

<210> SEQ ID NO 173
<211> LENGTH: 101
<212> TYPE: PRT
<213> ORGANISM: Artificial Sequence
<220> FEATURE:
<223> OTHER INFORMATION: CD80 v27 IgV

<400> SEQUENCE: 173

Val Ile His Val Thr Lys Glu Val Lys Glu Val Ala Thr Leu Ser Cys
1 5 10 15

Gly His Asn Val Ser Val Glu Glu Leu Ala Gln Thr Arg Ile Tyr Trp
20 25 30

Gln Lys Glu Lys Lys Met Val Leu Thr Met Met Ser Gly Asp Met Asn
35 40 45

Ile Trp Pro Glu Tyr Lys Asn Arg Thr Ile Phe Asp Ile Thr Asn Asn
50 55 60

Leu His Ile Val Ile Leu Ala Leu Arg Pro Ser Asp Glu Gly Thr Tyr
65 70 75 80

Glu Cys Val Val Leu Lys Tyr Glu Lys Gly Ala Phe Lys Arg Glu His
85 90 95

```
Leu Ala Glu Val Thr
            100


<210> SEQ ID NO 174
<211> LENGTH: 101
<212> TYPE: PRT
<213> ORGANISM: Artificial Sequence
<220> FEATURE:
<223> OTHER INFORMATION: CD80 v28 IgV

<400> SEQUENCE: 174

Val Ile His Val Thr Lys Glu Val Lys Glu Val Ala Thr Leu Ser Cys
1               5                   10                  15

Gly His Asn Val Ser Val Glu Glu Leu Ala Gln Thr His Ile Tyr Trp
            20                  25                  30

Gln Lys Glu Lys Lys Met Val Leu Thr Met Met Ser Gly Asp Met Asn
        35                  40                  45

Ile Trp Pro Gly Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr
            100


<210> SEQ ID NO 175
<211> LENGTH: 101
<212> TYPE: PRT
<213> ORGANISM: Artificial Sequence
<220> FEATURE:
<223> OTHER INFORMATION: CD80 v30 IgV

<400> SEQUENCE: 175

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Thr Val Ile Gln Ala Leu Arg Pro Ser Asp Glu Gly Thr Tyr
65                  70                  75                  80

Glu Cys Val Val Leu Lys Tyr Glu Lys Asp Gly Phe Lys Arg Glu His
                85                  90                  95

Leu Ala Glu Val Thr
            100


<210> SEQ ID NO 176
<211> LENGTH: 101
<212> TYPE: PRT
<213> ORGANISM: Artificial Sequence
<220> FEATURE:
<223> OTHER INFORMATION: CD80 v32 IgV

<400> SEQUENCE: 176

Val Ile His Val Thr Lys Glu Val Lys Glu Val Ala Thr Leu Ser Cys
1               5                   10                  15
```

Gly His Asn Val Ser Val Glu Glu Leu Ala Gln Thr Arg Ile Tyr Trp
20 25 30

Gln Lys Glu Lys Lys Val Val Leu Asp Met Ile Ser Gly Asp Met Asn
35 40 45

Ile Gly Pro Glu Tyr Lys Asn Arg Thr Ile Phe Asp Ile Thr Asn Asn
50 55 60

Leu Ser Ile Val Ile Leu Ala Leu Arg Pro Ser Gly Glu Gly Thr Tyr
65 70 75 80

Glu Cys Ala Val Leu Lys Tyr Glu Glu Asp Ala Phe Lys Arg Glu His
85 90 95

Leu Ala Glu Val Thr
100

<210> SEQ ID NO 177
<211> LENGTH: 101
<212> TYPE: PRT
<213> ORGANISM: Artificial Sequence
<220> FEATURE:
<223> OTHER INFORMATION: CD80 v33 IgV

<400> SEQUENCE: 177

Val Ile His Val Thr Lys Glu Val Lys Glu Val Ala Thr Leu Ser Cys
1 5 10 15

Gly His Asn Val Ser Ala Glu Glu Leu Ala Gln Thr Arg Ile Tyr Trp
20 25 30

Gln Lys Glu Lys Lys Met Val Leu Thr Met Met Ser Gly Asp Met Asn
35 40 45

Ile Trp Pro Glu Tyr Lys Asn Arg Thr Ile Phe Asp Ile Thr Asn Asn
50 55 60

Leu Ser Ile Val Ile Gln Ala Leu Arg Pro Ser Asp Glu Gly Thr Tyr
65 70 75 80

Glu Cys Val Val Leu Lys Tyr Glu Lys Asp Ala Phe Lys Arg Glu His
85 90 95

Leu Ala Glu Val Thr
100

<210> SEQ ID NO 178
<211> LENGTH: 101
<212> TYPE: PRT
<213> ORGANISM: Artificial Sequence
<220> FEATURE:
<223> OTHER INFORMATION: CD80 v34 IgV

<400> SEQUENCE: 178

Val Ile His Val Thr Lys Glu Val Lys Glu Val Val Thr Leu Phe Cys
1 5 10 15

Gly His Asn Val Ser Val Glu Glu Leu Ala Gln Thr Arg Ile His Trp
20 25 30

Gln Lys Glu Lys Lys Met Val Leu Gly Met Met Ser Gly Asp Met Asn
35 40 45

Ile Trp Pro Glu Tyr Lys Asn Arg Thr Ile Phe Asp Ile Thr Asn Asn
50 55 60

Leu Ser Ile Val Ile Leu Ala Leu Arg Pro Ser Asp Glu Gly Thr Tyr
65 70 75 80

Glu Cys Val Val Leu Lys Tyr Glu Lys Asp Ala Phe Lys Arg Glu His
85 90 95

Leu Ala Glu Val Thr
100

<210> SEQ ID NO 179
<211> LENGTH: 101
<212> TYPE: PRT
<213> ORGANISM: Artificial Sequence
<220> FEATURE:
<223> OTHER INFORMATION: CD80 v35 IgV

<400> SEQUENCE: 179

```
Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Phe Val Ile Arg Ala Leu Arg Pro Ser Asp Glu Gly Thr Tyr
65                  70                  75                  80

Glu Cys Val Val Leu Lys Tyr Gly Lys Asp Gly Phe Lys Arg Glu His
                85                  90                  95

Leu Ala Glu Val Thr
            100
```

<210> SEQ ID NO 180
<211> LENGTH: 101
<212> TYPE: PRT
<213> ORGANISM: Artificial Sequence
<220> FEATURE:
<223> OTHER INFORMATION: CD80 v36 IgV

<400> SEQUENCE: 180

```
Val Ile His Val Thr Lys Glu Val Lys Glu Val Ala Thr Leu Ser Cys
1               5                   10                  15

Gly His Asn Val Ser Val Glu Gly Pro Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Gln Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr
            100
```

<210> SEQ ID NO 181
<211> LENGTH: 101
<212> TYPE: PRT
<213> ORGANISM: Artificial Sequence
<220> FEATURE:
<223> OTHER INFORMATION: CD80 v37 IgV

<400> SEQUENCE: 181

```
Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30
```

```
Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Gly Leu Lys Arg Glu His
                85                  90                  95

Leu Ala Glu Val Thr
            100


<210> SEQ ID NO 182
<211> LENGTH: 101
<212> TYPE: PRT
<213> ORGANISM: Artificial Sequence
<220> FEATURE:
<223> OTHER INFORMATION: CD80 v38 IgV

<400> SEQUENCE: 182

Val Ile His Val Thr Lys Glu Val Lys Glu Val Ala Thr Leu Ser Cys
1               5                   10                  15

Gly His Asn Val Ser Val Glu Glu Leu Ala Gln Thr Asp Ile Leu Trp
            20                  25                  30

His Lys Glu Gly Lys Ile Val Leu Ala Met Arg Ser Gly Asp Thr Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Val Cys Val Val Arg Lys Tyr Glu Asn Asp Thr Pro Val Leu Glu His
                85                  90                  95

Leu Ala Glu Val Thr
            100


<210> SEQ ID NO 183
<211> LENGTH: 101
<212> TYPE: PRT
<213> ORGANISM: Artificial Sequence
<220> FEATURE:
<223> OTHER INFORMATION: CD80 v40 IgV

<400> SEQUENCE: 183

Val Ile His Val Thr Lys Glu Val Lys Glu Val Ala Thr Leu Ser Cys
1               5                   10                  15

Gly His Asn Val Ser Val Glu Glu Leu Ala Gln Thr Asp Ile Leu Trp
            20                  25                  30

His Lys Glu Gly Lys Ile Val Leu Ala Thr Arg Ser Gly Asp Thr Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Val Cys Val Val Arg Lys Tyr Glu Asn Asp Thr Pro Val Leu Glu His
                85                  90                  95

Leu Ala Glu Val Thr
            100


<210> SEQ ID NO 184
```

<211> LENGTH: 101
<212> TYPE: PRT
<213> ORGANISM: Artificial Sequence
<220> FEATURE:
<223> OTHER INFORMATION: CD80 v41 IgV

<400> SEQUENCE: 184

```
Val Ile His Val Thr Lys Glu Val Lys Glu Val Ala Thr Leu Ser Cys
1               5                   10                  15

Gly His Asn Val Ser Val Glu Gly Leu Ala Gln Thr Asp Ile Leu Trp
            20                  25                  30

His Lys Glu Gly Lys Ile Val Leu Ala Met Arg Ser Gly Asp Thr Asn
        35                  40                  45

Ile Trp Pro Glu Tyr Lys Asn Arg Thr Ile Leu Asp Ile Thr Asn Asn
    50                  55                  60

Leu Ser Ile Val Ile Leu Ala Leu Arg Pro Ser Asp Glu Gly Thr Tyr
65                  70                  75                  80

Val Cys Val Val Arg Lys Tyr Glu Asn Asp Thr Pro Val Leu Glu Arg
                85                  90                  95

Leu Ala Glu Val Thr
            100
```

<210> SEQ ID NO 185
<211> LENGTH: 101
<212> TYPE: PRT
<213> ORGANISM: Artificial Sequence
<220> FEATURE:
<223> OTHER INFORMATION: CD80 v43 IgV

<400> SEQUENCE: 185

```
Val Ile His Val Thr Lys Glu Val Lys Glu Val Ala Thr Leu Ser Cys
1               5                   10                  15

Gly His Asn Val Ser Val Glu Glu Leu Ala Gln Thr Val Ile Tyr Trp
            20                  25                  30

Gln Lys Glu Lys Lys Met Val Leu Thr Met Gln Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Arg Cys Val Val Ile Lys Tyr Glu Arg Leu Glu Asn Gln Gly Glu His
                85                  90                  95

Leu Ala Glu Val Thr
            100
```

<210> SEQ ID NO 186
<211> LENGTH: 101
<212> TYPE: PRT
<213> ORGANISM: Artificial Sequence
<220> FEATURE:
<223> OTHER INFORMATION: CD80 v44 IgV

<400> SEQUENCE: 186

```
Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Ile Met Met Ser Gly Asp Met Asn
        35                  40                  45
```

```
Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Gly Phe Lys Arg Glu His
                85                  90                  95

Leu Ala Glu Val Thr
            100


<210> SEQ ID NO 187
<211> LENGTH: 101
<212> TYPE: PRT
<213> ORGANISM: Homo sapiens
<220> FEATURE:
<223> OTHER INFORMATION: CD80 v45 IgV

<400> SEQUENCE: 187

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Arg Lys Gly Tyr Arg Arg Glu His
                85                  90                  95

Leu Ala Glu Val Thr
            100


<210> SEQ ID NO 188
<211> LENGTH: 101
<212> TYPE: PRT
<213> ORGANISM: Artificial Sequence
<220> FEATURE:
<223> OTHER INFORMATION: CD80 v47 IgV

<400> SEQUENCE: 188

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Gly Gln Ile Val Leu Thr Met Met Ser Gly Asp Met Asn
        35                  40                  45

Ile Trp Pro Glu Tyr Lys Asn Arg Thr Ile Leu Asp Ile Thr Asn Asn
    50                  55                  60

Leu Ser Ile Val Ile Leu Ala Leu Arg Pro Ser Asp Glu Gly Thr Tyr
65                  70                  75                  80

Val Cys Val Val Arg Lys Tyr Glu Asn Asp Thr Pro Val Leu Glu His
                85                  90                  95

Leu Ala Gly Val Thr
            100


<210> SEQ ID NO 189
<211> LENGTH: 101
<212> TYPE: PRT
<213> ORGANISM: Artificial Sequence
```

```
<220> FEATURE:
<223> OTHER INFORMATION: CD80 v48 IgV

<400> SEQUENCE: 189

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Asp Arg Lys Gly Tyr Arg Arg Glu His
                85                  90                  95

Leu Ala Glu Val Thr
            100


<210> SEQ ID NO 190
<211> LENGTH: 101
<212> TYPE: PRT
<213> ORGANISM: Artificial Sequence
<220> FEATURE:
<223> OTHER INFORMATION: CD80 v49 IgV

<400> SEQUENCE: 190

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Gly Gln Ile Val Met Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr
            100


<210> SEQ ID NO 191
<211> LENGTH: 101
<212> TYPE: PRT
<213> ORGANISM: Artificial Sequence
<220> FEATURE:
<223> OTHER INFORMATION: CD80 v50 IgV

<400> SEQUENCE: 191

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Gly Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60
```

Leu Ser Ile Val Ile Leu Ala Leu Arg Pro Ser Asp Glu Gly Thr Tyr
65 70 75 80

Glu Cys Val Val Leu Lys Tyr Glu Lys Asp Ala Phe Lys Arg Glu His
85 90 95

Leu Ala Glu Val Thr
100

<210> SEQ ID NO 192
<211> LENGTH: 101
<212> TYPE: PRT
<213> ORGANISM: Artificial Sequence
<220> FEATURE:
<223> OTHER INFORMATION: CD80 v51 IgV

<400> SEQUENCE: 192

Val Ile His Val Thr Lys Glu Val Lys Glu Val Ala Thr Leu Ser Cys
1 5 10 15

Gly His Asn Val Ser Val Glu Glu Leu Ala Gln Thr His Ile His Trp
20 25 30

Gln Lys Glu Lys Lys Met Val Leu Gly Met Met Ser Gly Asp Met Asn
35 40 45

Ile Trp Pro Glu Tyr Lys Asn Arg Thr Ile Phe Asp Ile Thr Asn Asn
50 55 60

Leu Ser Ile Val Ile Leu Ala Leu Arg Pro Ser Asp Glu Gly Thr Tyr
65 70 75 80

Glu Cys Val Val Leu Lys Asn Gly Glu Asn Gly Phe Lys Arg Glu His
85 90 95

Leu Ala Glu Val Thr
100

<210> SEQ ID NO 193
<211> LENGTH: 101
<212> TYPE: PRT
<213> ORGANISM: Artificial Sequence
<220> FEATURE:
<223> OTHER INFORMATION: CD80 v52 IgV

<400> SEQUENCE: 193

Val Ile His Val Thr Lys Glu Val Lys Glu Val Thr Thr Leu Ser Cys
1 5 10 15

Gly Leu Asn Val Ser Val Glu Glu Leu Ala Gln Thr Arg Ile Tyr Trp
20 25 30

Gln Lys Glu Lys Lys Met Val Leu Thr Met Val Ser Gly Asp Met Asn
35 40 45

Ile Trp Pro Glu Tyr Lys Asn Arg Thr Ile Leu Asp Ile Thr Asn Asn
50 55 60

Leu Ser Ile Val Ile Leu Ala Leu Arg Pro Ser Asp Lys Gly Thr Tyr
65 70 75 80

Glu Cys Val Val Leu Lys Tyr Glu Lys Asp Ala Phe Lys Arg Glu His
85 90 95

Leu Ala Glu Val Thr
100

<210> SEQ ID NO 194
<211> LENGTH: 101
<212> TYPE: PRT
<213> ORGANISM: Artificial Sequence
<220> FEATURE:
<223> OTHER INFORMATION: CD80 v53 IgV

<400> SEQUENCE: 194

Val Ile His Val Thr Lys Glu Val Lys Glu Val Ala Thr Leu Ser Cys
1               5                   10                  15

Gly His Asn Val Ser Val Glu Glu Leu Ala Gln Thr Val Ile Phe Trp
            20                  25                  30

Gln Lys Glu Gly Lys Leu Val Leu Thr Met Gln Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Arg Cys Ile Val Ile Lys Tyr Glu Arg Leu Glu Asn Gln Gly Glu His
                85                  90                  95

Leu Ala Glu Val Thr
            100

<210> SEQ ID NO 195
<211> LENGTH: 101
<212> TYPE: PRT
<213> ORGANISM: Artificial Sequence
<220> FEATURE:
<223> OTHER INFORMATION: CD80 v54 IgV

<400> SEQUENCE: 195

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Met Ile Pro Ala Pro Arg Pro Ser Asp Glu Gly Thr Tyr
65                  70                  75                  80

Glu Cys Val Val Leu Glu Tyr Glu Lys Asp Ala Phe Lys Arg Glu His
                85                  90                  95

Leu Ala Glu Val Thr
            100

<210> SEQ ID NO 196
<211> LENGTH: 111
<212> TYPE: PRT
<213> ORGANISM: Artificial Sequence
<220> FEATURE:
<223> OTHER INFORMATION: ICOSL WT IgV

<400> SEQUENCE: 196

Asp Thr Gln Glu Lys Glu Val Arg Ala Met Val Gly Ser Asp Val Glu
1               5                   10                  15

Leu Ser Cys Ala Cys Pro Glu Gly Ser Arg Phe Asp Leu Asn Asp Val
            20                  25                  30

Tyr Val Tyr Trp Gln Thr Ser Glu Ser Lys Thr Val Val Thr Tyr His
        35                  40                  45

Ile Pro Gln Asn Ser Ser Leu Glu Asn Val Asp Ser Arg Tyr Arg Asn
    50                  55                  60

Arg Ala Leu Met Ser Pro Ala Gly Met Leu Arg Gly Asp Phe Ser Leu
65                  70                  75                  80

```
Arg Leu Phe Asn Val Thr Pro Gln Asp Glu Gln Lys Phe His Cys Leu
                85                  90                  95

Val Leu Ser Gln Ser Leu Gly Phe Gln Glu Val Leu Ser Val Glu
            100                 105                 110


<210> SEQ ID NO 197
<211> LENGTH: 111
<212> TYPE: PRT
<213> ORGANISM: Artificial Sequence
<220> FEATURE:
<223> OTHER INFORMATION: ICOSL v1 IgV

<400> SEQUENCE: 197

Asp Thr Gln Glu Lys Glu Val Arg Ala Met Val Gly Ser Asp Val Glu
1               5                   10                  15

Leu Ser Cys Ala Cys Pro Glu Gly Ser Arg Phe Asp Leu Asn Asp Val
            20                  25                  30

Tyr Val Tyr Trp Gln Thr Ser Glu Ser Lys Thr Val Val Thr Tyr His
        35                  40                  45

Ile Pro Gln Ser Ser Ser Leu Glu Asn Val Asp Ser Arg Tyr Arg Asn
    50                  55                  60

Arg Ala Leu Met Ser Pro Ala Gly Met Leu Arg Gly Asp Phe Ser Leu
65                  70                  75                  80

Arg Leu Phe Asn Val Thr Pro Gln Asp Glu Gln Lys Phe His Cys Leu
                85                  90                  95

Val Leu Ser Gln Ser Leu Gly Phe Gln Glu Val Leu Ser Val Glu
            100                 105                 110


<210> SEQ ID NO 198
<211> LENGTH: 111
<212> TYPE: PRT
<213> ORGANISM: Artificial Sequence
<220> FEATURE:
<223> OTHER INFORMATION: ICOSL v2 IgV

<400> SEQUENCE: 198

Asp Thr Gln Glu Lys Glu Val Arg Ala Met Val Gly Ser Asp Val Glu
1               5                   10                  15

Leu Ser Cys Ala Cys Pro Glu Gly Ser Arg Phe Asp Leu Asn Asp Val
            20                  25                  30

Tyr Val Tyr Trp Gln Thr Ser Glu Ser Lys Thr Val Val Thr Tyr His
        35                  40                  45

Ile Pro Gln His Ser Ser Leu Glu Asn Val Asp Ser Arg Tyr Arg Asn
    50                  55                  60

Arg Ala Leu Met Ser Pro Ala Gly Met Leu Arg Gly Asp Phe Ser Leu
65                  70                  75                  80

Arg Leu Phe Asn Val Thr Pro Gln Asp Glu Gln Lys Phe His Cys Leu
                85                  90                  95

Val Leu Ser Gln Ser Leu Gly Phe Gln Glu Val Leu Ser Val Glu
            100                 105                 110


<210> SEQ ID NO 199
<211> LENGTH: 111
<212> TYPE: PRT
<213> ORGANISM: Artificial Sequence
<220> FEATURE:
<223> OTHER INFORMATION: ICOSL v3 IgV

<400> SEQUENCE: 199

Asp Thr Gln Glu Lys Glu Val Arg Ala Met Val Gly Ser Asp Val Glu
```

```
1               5                   10                  15

Leu Ser Cys Ala Cys Pro Glu Gly Ser Arg Phe Asp Leu Asn Asp Val
            20                  25                  30

Tyr Val Tyr Trp Gln Thr Ser Glu Ser Lys Thr Val Val Thr Tyr His
        35                  40                  45

Ile Pro Gln Asp Ser Ser Leu Glu Asn Val Asp Ser Arg Tyr Arg Asn
    50                  55                  60

Arg Ala Leu Met Ser Pro Ala Gly Met Leu Arg Gly Asp Phe Ser Leu
65                  70                  75                  80

Arg Leu Phe Asn Val Thr Pro Gln Asp Glu Gln Lys Phe His Cys Leu
                85                  90                  95

Val Leu Ser Gln Ser Leu Gly Phe Gln Glu Val Leu Ser Val Glu
            100                 105                 110


<210> SEQ ID NO 200
<211> LENGTH: 111
<212> TYPE: PRT
<213> ORGANISM: Artificial Sequence
<220> FEATURE:
<223> OTHER INFORMATION: ICOSL v4 IgV

<400> SEQUENCE: 200

Asp Thr Gln Glu Lys Glu Val Arg Ala Met Val Gly Ser Asp Val Glu
1               5                   10                  15

Leu Ser Cys Ala Cys Pro Glu Gly Ser Arg Phe Asp Leu Asn Asp Val
            20                  25                  30

Tyr Val Tyr Trp Gln Thr Ser Glu Ser Lys Thr Val Val Thr Tyr His
        35                  40                  45

Ile Pro Gln Tyr Ser Ser Leu Glu Tyr Val Asp Ser Arg Tyr Arg Asn
    50                  55                  60

Arg Ala Leu Met Ser Pro Ala Gly Met Leu Arg Gly Asp Phe Ser Leu
65                  70                  75                  80

Arg Leu Phe Asn Val Thr Pro Gln Asp Glu Gln Lys Phe His Cys Leu
                85                  90                  95

Val Leu Ser Gln Ser Leu Gly Phe Gln Glu Val Leu Ser Val Glu
            100                 105                 110


<210> SEQ ID NO 201
<211> LENGTH: 111
<212> TYPE: PRT
<213> ORGANISM: Artificial Sequence
<220> FEATURE:
<223> OTHER INFORMATION: ICOSL v5 IgV

<400> SEQUENCE: 201

Asp Thr Gln Glu Lys Glu Val Arg Ala Met Val Gly Ser Asp Val Glu
1               5                   10                  15

Leu Ser Cys Ala Cys Pro Glu Gly Ser Arg Phe Asp Leu Asn Asp Val
            20                  25                  30

Tyr Val Tyr Trp Gln Thr Ser Glu Ser Lys Thr Val Val Thr Tyr His
        35                  40                  45

Ile Pro Gln His Ser Ser Leu Glu Tyr Val Asp Ser Arg Tyr Arg Asn
    50                  55                  60

Arg Ala Leu Met Ser Pro Ala Gly Met Leu Arg Gly Asp Phe Ser Leu
65                  70                  75                  80

Arg Leu Phe Asn Val Thr Pro Gln Asp Glu Gln Lys Phe His Cys Leu
                85                  90                  95
```

Val Leu Ser Pro Ser Leu Gly Phe Gln Glu Val Leu Ser Val Glu
100 105 110

<210> SEQ ID NO 202
<211> LENGTH: 111
<212> TYPE: PRT
<213> ORGANISM: Artificial Sequence
<220> FEATURE:
<223> OTHER INFORMATION: ICOSL v10 IgV

<400> SEQUENCE: 202

Asp Thr Gln Glu Lys Glu Val Arg Ala Met Val Gly Ser Asp Val Glu
1 5 10 15

Leu Ser Cys Ala Cys Pro Glu Gly Ser Arg Phe Asp Leu Asn Asp Val
20 25 30

Tyr Val Tyr Trp Gln Thr Ser Glu Ser Lys Thr Val Val Thr Tyr His
35 40 45

Ile Pro Gln His Ser Ser Leu Glu Asn Val Asp Ser Arg Tyr Arg Asn
50 55 60

Arg Ala Leu Met Ser Pro Ala Gly Met Leu Arg Gly Asp Phe Ser Leu
65 70 75 80

Arg Leu Phe Asn Val Thr Pro Gln Asp Glu Gln Arg Phe His Cys Leu
85 90 95

Val Leu Ser Gln Ser Leu Gly Phe Gln Glu Val Leu Ser Val Glu
100 105 110

<210> SEQ ID NO 203
<211> LENGTH: 111
<212> TYPE: PRT
<213> ORGANISM: Artificial Sequence
<220> FEATURE:
<223> OTHER INFORMATION: ICOSL v11 IgV

<400> SEQUENCE: 203

Asp Thr Gln Glu Lys Glu Val Arg Ala Met Val Gly Ser Asp Val Glu
1 5 10 15

Leu Ser Cys Ala Cys Pro Glu Gly Ser Arg Phe Asp Leu Asn Asp Val
20 25 30

Tyr Val Tyr Trp Gln Thr Ser Glu Ser Lys Thr Val Val Thr Tyr His
35 40 45

Ile Pro Gln His Ser Ser Leu Glu Asn Val Asp Ser Arg Tyr Arg Asn
50 55 60

Arg Ala Leu Met Ser Pro Ala Gly Met Leu Arg Gly Asp Phe Ser Leu
65 70 75 80

Arg Leu Phe Asn Val Thr Pro Gln Asp Glu Gln Lys Phe His Cys Leu
85 90 95

Val Leu Gly Gln Ser Leu Gly Phe Gln Glu Val Leu Ser Val Glu
100 105 110

<210> SEQ ID NO 204
<211> LENGTH: 111
<212> TYPE: PRT
<213> ORGANISM: Homo sapiens
<220> FEATURE:
<223> OTHER INFORMATION: ICOSL v12 IgV

<400> SEQUENCE: 204

Asp Thr Gln Glu Lys Glu Val Arg Ala Met Val Gly Ser Asp Val Glu
1 5 10 15

Leu Ser Cys Ala Cys Pro Glu Gly Ser Arg Phe Asp Leu Asn Asp Val

```
            20                  25                  30

Tyr Val Tyr Trp Gln Thr Ser Glu Ser Lys Thr Val Val Thr Tyr His
        35                  40                  45

Ile Pro Gln Tyr Ser Ser Leu Glu Asn Val Asp Ser Arg Tyr Arg Asn
    50                  55                  60

Arg Ala Leu Met Ser Pro Ala Gly Met Leu Arg Gly Asp Phe Ser Leu
65                  70                  75                  80

Arg Leu Phe Asn Val Thr Pro Gln Asp Glu Gln Lys Phe His Cys Leu
                85                  90                  95

Val Leu Ser Gln Ser Leu Gly Phe Gln Glu Val Leu Ser Val Glu
            100                 105                 110
```

<210> SEQ ID NO 205
<211> LENGTH: 111
<212> TYPE: PRT
<213> ORGANISM: Artificial Sequence
<220> FEATURE:
<223> OTHER INFORMATION: ICOSL v13 IgV

<400> SEQUENCE: 205

```
Asp Thr Gln Glu Lys Glu Val Arg Ala Met Val Gly Ser Asp Val Glu
1               5                   10                  15

Leu Ser Cys Ala Cys Pro Glu Gly Ser Arg Phe Asp Leu Asn Asp Val
            20                  25                  30

Tyr Val Tyr Trp Gln Thr Ser Glu Ser Lys Thr Val Val Thr Tyr His
        35                  40                  45

Ile Pro Gln Asn Ser Ser Leu Glu Tyr Val Asp Ser Arg Tyr Arg Asn
    50                  55                  60

Arg Ala Leu Met Ser Pro Ala Gly Met Leu Arg Gly Asp Phe Ser Leu
65                  70                  75                  80

Arg Leu Phe Asn Val Thr Pro Gln Asp Glu Gln Lys Phe His Cys Leu
                85                  90                  95

Val Leu Ser Gln Ser Leu Gly Phe Gln Glu Val Leu Ser Val Glu
            100                 105                 110
```

<210> SEQ ID NO 206
<211> LENGTH: 111
<212> TYPE: PRT
<213> ORGANISM: Artificial Sequence
<220> FEATURE:
<223> OTHER INFORMATION: ICOSL v14 IgV

<400> SEQUENCE: 206

```
Asp Thr Gln Glu Lys Glu Val Arg Ala Met Val Gly Ser Asp Val Glu
1               5                   10                  15

Leu Ser Cys Ala Cys Pro Glu Gly Ser Arg Phe Asp Leu Asn Asp Val
            20                  25                  30

Tyr Val Tyr Trp Gln Thr Ser Glu Ser Lys Thr Val Val Thr Tyr His
        35                  40                  45

Ile Pro Gln Asn Ser Ser Leu Glu Tyr Val Asp Ser Arg Tyr Arg Asn
    50                  55                  60

Arg Ala Leu Met Ser Pro Ala Gly Met Leu Arg Gly Asp Phe Ser Leu
65                  70                  75                  80

Arg Leu Phe Asn Val Thr Pro Gln Asp Glu Gln Lys Phe His Cys Leu
                85                  90                  95

Val Leu Ser Pro Ser Leu Gly Phe Gln Glu Val Leu Ser Val Glu
            100                 105                 110
```

<210> SEQ ID NO 207
<211> LENGTH: 111
<212> TYPE: PRT
<213> ORGANISM: Artificial Sequence
<220> FEATURE:
<223> OTHER INFORMATION: ICOSL v22 IgV

<400> SEQUENCE: 207

Asp Thr Gln Glu Lys Glu Val Arg Ala Met Val Gly Ser Asp Val Glu
1 5 10 15

Leu Ser Cys Ala Cys Pro Glu Gly Ser Arg Phe Asp Leu Asn Asp Val
20 25 30

Tyr Val Tyr Trp Gln Thr Ser Glu Ser Lys Thr Val Val Thr Tyr His
35 40 45

Ile Pro Gln Asn Ser Ala Leu Glu Asn Val Asp Ser Arg Tyr Arg Asn
50 55 60

Arg Ala Leu Met Ser Pro Ala Gly Met Leu Arg Gly Asp Phe Ser Leu
65 70 75 80

Arg Leu Phe Asn Val Thr Pro Gln Asp Glu Gln Lys Phe His Cys Leu
85 90 95

Val Leu Ser Gln Ser Leu Gly Phe Gln Glu Val Leu Ser Val Glu
100 105 110

<210> SEQ ID NO 208
<211> LENGTH: 111
<212> TYPE: PRT
<213> ORGANISM: Artificial Sequence
<220> FEATURE:
<223> OTHER INFORMATION: ICOSL v23 IgV

<400> SEQUENCE: 208

Asp Thr Gln Glu Lys Glu Val Arg Ala Met Val Gly Ser Asp Val Glu
1 5 10 15

Leu Ser Cys Ala Cys Pro Glu Gly Ser Arg Phe Asp Leu Asn Asp Val
20 25 30

Tyr Val Tyr Trp Gln Thr Ser Glu Ser Lys Thr Val Val Thr Tyr His
35 40 45

Ile Pro Gln Asp Ser Pro Leu Glu Asn Val Asp Ser Arg Tyr Arg Asn
50 55 60

Arg Ala Leu Met Ser Pro Ala Gly Met Leu Arg Gly Asp Phe Ser Leu
65 70 75 80

Arg Leu Phe Asn Val Thr Pro Gln Asp Glu Gln Lys Phe His Cys Leu
85 90 95

Val Leu Ser Gln Ser Leu Gly Phe Gln Glu Val Leu Ser Val Glu
100 105 110

<210> SEQ ID NO 209
<211> LENGTH: 111
<212> TYPE: PRT
<213> ORGANISM: Artificial Sequence
<220> FEATURE:
<223> OTHER INFORMATION: ICOSL v24 IgV

<400> SEQUENCE: 209

Asp Thr Gln Glu Lys Glu Val Arg Ala Met Val Gly Ser Asp Val Glu
1 5 10 15

Leu Ser Cys Ala Cys Pro Glu Gly Ser Arg Phe Asp Leu Asn Asp Val
20 25 30

Tyr Val Tyr Trp Gln Thr Ser Glu Ser Lys Thr Val Val Thr Tyr His

```
        35                  40                  45

Ile Pro Gln Lys Ser Ser Leu Glu Asn Val Asp Ser Arg Tyr Arg Asn
    50                  55                  60

Arg Ala Leu Met Ser Pro Ala Gly Met Leu Arg Gly Asp Phe Ser Leu
65                  70                  75                  80

Arg Leu Phe Asn Val Thr Pro Gln Asp Glu Gln Lys Phe His Cys Leu
                85                  90                  95

Val Leu Ser Gln Ser Leu Gly Phe Gln Glu Val Leu Ser Val Glu
            100                 105                 110


<210> SEQ ID NO 210
<211> LENGTH: 111
<212> TYPE: PRT
<213> ORGANISM: Homo sapiens
<220> FEATURE:
<223> OTHER INFORMATION: ICOSL v28 IgV

<400> SEQUENCE: 210

Asp Thr Gln Glu Lys Glu Val Arg Ala Met Val Gly Ser Asp Val Glu
1               5                   10                  15

Leu Ser Cys Ala Cys Pro Glu Gly Ser Arg Phe Asp Leu Asn Asp Val
            20                  25                  30

Tyr Val Tyr Trp Gln Thr Ser Glu Ser Lys Thr Val Val Thr Tyr His
        35                  40                  45

Ile Pro Gln Ser Ser Ser Leu Glu Asn Val Asp Ser Arg Tyr Arg Asn
    50                  55                  60

Arg Ala Leu Met Ser Pro Ala Gly Met Leu Arg Gly Asp Phe Ser Pro
65                  70                  75                  80

Arg Leu Phe Asn Val Thr Pro Gln Asp Glu Gln Lys Phe His Cys Leu
                85                  90                  95

Val Leu Ser Gln Ser Leu Gly Phe Gln Glu Val Leu Ser Val Glu
            100                 105                 110


<210> SEQ ID NO 211
<211> LENGTH: 111
<212> TYPE: PRT
<213> ORGANISM: Artificial Sequence
<220> FEATURE:
<223> OTHER INFORMATION: ICOSL v30 IgV

<400> SEQUENCE: 211

Asp Thr Gln Glu Lys Glu Val Arg Ala Met Val Gly Ser Asp Val Glu
1               5                   10                  15

Leu Ser Cys Ala Cys Pro Glu Gly Ser Arg Phe Asp Leu Asn Asp Val
            20                  25                  30

Tyr Val Tyr Trp Gln Thr Ser Glu Ser Lys Thr Val Val Thr Tyr His
        35                  40                  45

Ile Pro Gln Ser Ser Ser Leu Glu Asn Val Asp Ser Arg Tyr Arg Asn
    50                  55                  60

Arg Ala Leu Met Ser Pro Ala Gly Met Leu Gln Gly Asp Phe Ser Leu
65                  70                  75                  80

Arg Leu Phe Asn Val Thr Pro Gln Asp Glu Gln Lys Phe His Cys Leu
                85                  90                  95

Val Leu Ser Gln Ser Leu Gly Phe Gln Glu Val Leu Ser Val Glu
            100                 105                 110


<210> SEQ ID NO 212
<211> LENGTH: 111
```

<212> TYPE: PRT
<213> ORGANISM: Artificial Sequence
<220> FEATURE:
<223> OTHER INFORMATION: ICOSL v33 IgV

<400> SEQUENCE: 212

```
Asp Thr Gln Glu Lys Glu Val Arg Ala Met Val Gly Ser Asp Val Glu
1               5                   10                  15

Leu Ser Cys Ala Cys Pro Glu Gly Ser Arg Phe Asp Leu Asn Asp Val
            20                  25                  30

Tyr Val Tyr Trp Gln Thr Ser Glu Ser Lys Thr Val Val Thr Tyr His
        35                  40                  45

Ile Pro Gln Ser Ser Ser Leu Glu Tyr Val Asp Ser Arg Tyr Arg Asn
    50                  55                  60

Arg Ala Leu Met Ser Pro Ala Gly Met Leu Arg Gly Asp Phe Ser Leu
65                  70                  75                  80

Arg Leu Phe Asn Val Thr Pro Gln Asp Glu Gln Lys Phe Asp Cys Phe
                85                  90                  95

Val Phe Ser Arg Ser Leu Gly Phe Gln Glu Val Leu Ser Val Glu
            100                 105                 110
```

<210> SEQ ID NO 213
<211> LENGTH: 111
<212> TYPE: PRT
<213> ORGANISM: Artificial Sequence
<220> FEATURE:
<223> OTHER INFORMATION: ICOSL v34 IgV

<400> SEQUENCE: 213

```
Asp Thr Gln Glu Lys Glu Val Arg Ala Met Val Gly Ser Asp Val Glu
1               5                   10                  15

Leu Ser Cys Ala Cys Pro Glu Gly Ser Arg Phe Asp Leu Asn Asp Val
            20                  25                  30

Tyr Val Tyr Trp Gln Thr Ser Glu Ser Lys Thr Val Val Thr Tyr His
        35                  40                  45

Ile Pro Gln Ser Ser Ser Leu Glu Tyr Val Asp Ser Arg Tyr Arg Asn
    50                  55                  60

Arg Ala Leu Met Ser Pro Ala Gly Met Leu Arg Gly Asp Phe Ser Leu
65                  70                  75                  80

Arg Leu Phe Asn Val Thr Pro Gln Asp Glu Gln Lys Phe Asp Cys Phe
                85                  90                  95

Val Phe Ser Arg Ser Leu Glu Phe Gln Glu Val Leu Ser Val Glu
            100                 105                 110
```

<210> SEQ ID NO 214
<211> LENGTH: 108
<212> TYPE: PRT
<213> ORGANISM: Artificial Sequence
<220> FEATURE:
<223> OTHER INFORMATION: NKp30 WT IgC-like

<400> SEQUENCE: 214

```
Leu Trp Val Ser Gln Pro Pro Glu Ile Arg Thr Leu Glu Gly Ser Ser
1               5                   10                  15

Ala Phe Leu Pro Cys Ser Phe Asn Ala Ser Gln Gly Arg Leu Ala Ile
            20                  25                  30

Gly Ser Val Thr Trp Phe Arg Asp Glu Val Val Pro Gly Lys Glu Val
        35                  40                  45

Arg Asn Gly Thr Pro Glu Phe Arg Gly Arg Leu Ala Pro Leu Ala Ser
```

```
    50                  55                  60

Ser Arg Phe Leu His Asp His Gln Ala Glu Leu His Ile Arg Asp Val
65                  70                  75                  80

Arg Gly His Asp Ala Ser Ile Tyr Val Cys Arg Val Glu Val Leu Gly
                85                  90                  95

Leu Gly Val Gly Thr Gly Asn Gly Thr Arg Leu Val
            100                 105


<210> SEQ ID NO 215
<211> LENGTH: 108
<212> TYPE: PRT
<213> ORGANISM: Homo sapiens
<220> FEATURE:
<223> OTHER INFORMATION: NKp30 v1 IgC-like

<400> SEQUENCE: 215

Leu Trp Val Ser Gln Pro Pro Glu Ile Arg Thr Leu Glu Gly Ser Ser
1               5                   10                  15

Ala Phe Leu Pro Cys Ser Phe Asn Ala Ser Gln Gly Arg Val Ala Ile
            20                  25                  30

Gly Ser Val Thr Trp Phe Arg Asp Glu Val Val Pro Gly Lys Glu Val
        35                  40                  45

Arg Asn Gly Thr Pro Glu Phe Arg Gly Arg Leu Val Pro Leu Ala Pro
    50                  55                  60

Ser Arg Phe Leu His Asp His Gln Ala Glu Leu His Ile Arg Asp Val
65                  70                  75                  80

Arg Gly His Asp Ala Gly Ile Tyr Val Cys Arg Val Glu Val Leu Gly
                85                  90                  95

Leu Gly Val Gly Thr Gly Asn Gly Thr Arg Leu Val
            100                 105


<210> SEQ ID NO 216
<211> LENGTH: 108
<212> TYPE: PRT
<213> ORGANISM: Homo sapiens
<220> FEATURE:
<223> OTHER INFORMATION: NKp30 v2 IgC-like

<400> SEQUENCE: 216

Leu Trp Val Ser Gln Pro Pro Glu Ile Arg Thr Leu Glu Gly Ser Ser
1               5                   10                  15

Ala Phe Leu Pro Cys Ser Phe Asn Ala Ser Gln Gly Arg Val Ala Ile
            20                  25                  30

Gly Ser Val Thr Trp Phe Arg Asp Glu Val Val Pro Gly Lys Glu Val
        35                  40                  45

Arg Asn Gly Thr Pro Glu Phe Arg Gly Arg Leu Ala Pro Leu Ala Ser
    50                  55                  60

Ser Arg Phe Leu His Asp His Gln Ala Glu Leu His Ile Arg Asp Val
65                  70                  75                  80

Arg Gly His Asp Ala Ser Ile Tyr Val Cys Arg Val Glu Val Leu Gly
                85                  90                  95

Leu Gly Val Gly Thr Gly Asn Gly Thr Arg Leu Val
            100                 105


<210> SEQ ID NO 217
<211> LENGTH: 108
<212> TYPE: PRT
<213> ORGANISM: Homo sapiens
<220> FEATURE:
```

<223> OTHER INFORMATION: NKp30 v3 IgC-like

<400> SEQUENCE: 217

Leu Trp Val Ser Gln Pro Pro Glu Ile Arg Thr Leu Glu Gly Ser Ser
1               5                   10                  15

Ala Phe Leu Pro Cys Ser Phe Asn Ala Ser Gln Gly Arg Leu Ala Ile
            20                  25                  30

Gly Ser Val Thr Trp Phe Arg Asp Glu Val Val Pro Gly Lys Glu Val
        35                  40                  45

Arg Asn Gly Thr Pro Glu Phe Arg Gly Arg Leu Val Pro Leu Ala Ser
    50                  55                  60

Ser Arg Phe Leu His Asp His Gln Ala Glu Leu His Ile Arg Asp Val
65                  70                  75                  80

Arg Gly His Asp Ala Ser Ile Tyr Val Cys Arg Val Glu Val Leu Gly
                85                  90                  95

Leu Gly Val Gly Thr Gly Asn Gly Thr Arg Leu Val
            100                 105

<210> SEQ ID NO 218
<211> LENGTH: 108
<212> TYPE: PRT
<213> ORGANISM: Artificial Sequence
<220> FEATURE:
<223> OTHER INFORMATION: NKp30 v4 IgC-like

<400> SEQUENCE: 218

Leu Trp Val Ser Gln Pro Pro Glu Ile Arg Thr Leu Glu Gly Ser Ser
1               5                   10                  15

Ala Phe Leu Pro Cys Ser Phe Asn Ala Ser Gln Gly Arg Leu Ala Ile
            20                  25                  30

Gly Ser Val Thr Trp Phe Arg Asp Glu Val Val Pro Gly Lys Glu Val
        35                  40                  45

Arg Asn Gly Thr Pro Glu Phe Arg Gly Arg Leu Ala Pro Leu Ala Pro
    50                  55                  60

Ser Arg Phe Leu His Asp His Gln Ala Glu Leu His Ile Arg Asp Val
65                  70                  75                  80

Arg Gly His Asp Ala Ser Ile Tyr Val Cys Arg Val Glu Val Leu Gly
                85                  90                  95

Leu Gly Val Gly Thr Gly Asn Gly Thr Arg Leu Val
            100                 105

<210> SEQ ID NO 219
<211> LENGTH: 108
<212> TYPE: PRT
<213> ORGANISM: Artificial Sequence
<220> FEATURE:
<223> OTHER INFORMATION: NKp30 v5 IgC-like

<400> SEQUENCE: 219

Leu Trp Val Ser Gln Pro Pro Glu Ile Arg Thr Leu Glu Gly Ser Ser
1               5                   10                  15

Ala Phe Leu Pro Cys Ser Phe Asn Ala Ser Gln Gly Arg Leu Ala Ile
            20                  25                  30

Gly Ser Val Thr Trp Phe Arg Asp Glu Val Val Pro Gly Lys Glu Val
        35                  40                  45

Arg Asn Gly Thr Pro Glu Phe Arg Gly Arg Leu Ala Pro Leu Ala Ser
    50                  55                  60

Ser Arg Phe Leu His Asp His Gln Ala Glu Leu His Ile Arg Asp Val 65 70 75 80

Arg Gly His Asp Ala Gly Ile Tyr Val Cys Arg Val Glu Val Leu Gly
85 90 95

Leu Gly Val Gly Thr Gly Asn Gly Thr Arg Leu Val
100 105

<210> SEQ ID NO 220
<211> LENGTH: 99
<212> TYPE: PRT
<213> ORGANISM: Artificial Sequence
<220> FEATURE:
<223> OTHER INFORMATION: CD86 WT IgV

<400> SEQUENCE: 220

Asn Glu Thr Ala Asp Leu Pro Cys Gln Phe Ala Asn Ser Gln Asn Gln
1 5 10 15

Ser Leu Ser Glu Leu Val Val Phe Trp Gln Asp Gln Glu Asn Leu Val
20 25 30

Leu Asn Glu Val Tyr Leu Gly Lys Glu Lys Phe Asp Ser Val His Ser
35 40 45

Lys Tyr Met Gly Arg Thr Ser Phe Asp Ser Asp Ser Trp Thr Leu Arg
50 55 60

Leu His Asn Leu Gln Ile Lys Asp Lys Gly Leu Tyr Gln Cys Ile Ile
65 70 75 80

His His Lys Lys Pro Thr Gly Met Ile Arg Ile His Gln Met Asn Ser
85 90 95

Glu Leu Ser

<210> SEQ ID NO 221
<211> LENGTH: 99
<212> TYPE: PRT
<213> ORGANISM: Homo sapiens
<220> FEATURE:
<223> OTHER INFORMATION: CD86 v1 IgV

<400> SEQUENCE: 221

Asn Glu Thr Ala Asp Leu Pro Cys Gln Phe Ala Asn Ser Gln Asn Gln
1 5 10 15

Ser Leu Ser Glu Leu Val Val Phe Trp His Asp Gln Glu Asn Leu Val
20 25 30

Leu Asn Glu Val Tyr Leu Gly Lys Glu Lys Phe Asp Ser Val His Ser
35 40 45

Lys Tyr Met Gly Arg Thr Ser Phe Asp Ser Asp Ser Trp Thr Leu Arg
50 55 60

Leu His Asn Leu Gln Ile Lys Asp Lys Gly Leu Tyr Gln Cys Ile Ile
65 70 75 80

Leu His Lys Lys Pro Thr Gly Met Ile Arg Ile His His Met Asn Ser
85 90 95

Glu Leu Ser

<210> SEQ ID NO 222
<211> LENGTH: 99
<212> TYPE: PRT
<213> ORGANISM: Homo sapiens
<220> FEATURE:
<223> OTHER INFORMATION: CD86 v2 IgV

<400> SEQUENCE: 222

Asn Glu Thr Ala Asp Leu Pro Cys Gln Phe Ala Asn Ser Gln Asn Gln

```
1               5                   10                  15

Ser Leu Ser Glu Leu Val Val Phe Trp His Asp Gln Glu Asn Leu Val
            20                  25                  30

Leu Asn Glu Val Tyr Leu Gly Lys Glu Lys Phe Asp Ser Val His Ser
        35                  40                  45

Lys Tyr Met Gly Arg Thr Ser Phe Asp Ser Asp Ser Trp Thr Leu Arg
    50                  55                  60

Leu His Asn Leu Gln Ile Lys Asp Lys Gly Leu Tyr Gln Cys Ile Ile
65                  70                  75                  80

His His Lys Lys Pro Thr Gly Met Ile Arg Ile His Gln Met Asn Ser
                85                  90                  95

Glu Leu Ser


<210> SEQ ID NO 223
<211> LENGTH: 99
<212> TYPE: PRT
<213> ORGANISM: Homo sapiens
<220> FEATURE:
<223> OTHER INFORMATION: CD86 v3 IgV

<400> SEQUENCE: 223

Asn Glu Thr Ala Asp Leu Pro Cys Gln Phe Ala Asn Ser Gln Asn Gln
1               5                   10                  15

Ser Leu Ser Glu Leu Val Val Phe Trp Gln Asp Gln Glu Asn Leu Val
            20                  25                  30

Leu Asn Glu Val Tyr Leu Gly Lys Glu Lys Phe Asp Ser Val His Ser
        35                  40                  45

Lys Tyr Met Gly Arg Thr Ser Phe Asp Ser Asp Ser Trp Thr Leu Arg
    50                  55                  60

Leu His Asn Leu Gln Ile Lys Asp Lys Gly Leu Tyr Gln Cys Ile Ile
65                  70                  75                  80

Leu His Lys Lys Pro Thr Gly Met Ile Arg Ile His Gln Met Asn Ser
                85                  90                  95

Glu Leu Ser


<210> SEQ ID NO 224
<211> LENGTH: 99
<212> TYPE: PRT
<213> ORGANISM: Homo sapiens
<220> FEATURE:
<223> OTHER INFORMATION: CD86 v4 IgV

<400> SEQUENCE: 224

Asn Glu Thr Ala Asp Leu Pro Cys Gln Phe Ala Asn Ser Gln Asn Gln
1               5                   10                  15

Ser Leu Ser Glu Leu Val Val Phe Trp Gln Asp Gln Glu Asn Leu Val
            20                  25                  30

Leu Asn Glu Val Tyr Leu Gly Lys Glu Lys Phe Asp Ser Val His Ser
        35                  40                  45

Lys Tyr Met Gly Arg Thr Ser Phe Asp Ser Asp Ser Trp Thr Leu Arg
    50                  55                  60

Leu His Asn Leu Gln Ile Lys Asp Lys Gly Leu Tyr Gln Cys Ile Ile
65                  70                  75                  80

His His Lys Lys Pro Thr Gly Met Ile Arg Ile His His Met Asn Ser
                85                  90                  95

Glu Leu Ser
```

<210> SEQ ID NO 225
<211> LENGTH: 19
<212> TYPE: PRT
<213> ORGANISM: Homo sapiens
<220> FEATURE:
<223> OTHER INFORMATION: VH signal peptide

<400> SEQUENCE: 225

```
Met Gly Ser Thr Ala Ile Leu Ala Leu Leu Leu Ala Val Leu Gln Gly
1               5                   10                  15

Val Ser Ala
```

<210> SEQ ID NO 226
<211> LENGTH: 232
<212> TYPE: PRT
<213> ORGANISM: Homo sapiens
<220> FEATURE:
<223> OTHER INFORMATION: IgG1 Fc

<400> SEQUENCE: 226

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230
```

<210> SEQ ID NO 227
<211> LENGTH: 235
<212> TYPE: PRT
<213> ORGANISM: Homo sapiens
<220> FEATURE:
<223> OTHER INFORMATION: IgG2 Fc

<400> SEQUENCE: 227

Thr Lys Val Asp Lys Thr Val Glu Arg Lys Cys Cys Val Glu Cys Pro
1 5 10 15

Pro Cys Pro Ala Pro Pro Val Ala Gly Pro Ser Val Phe Leu Phe Pro
20 25 30

Pro Lys Pro Lys Asp Thr Leu Met Ile Ser Arg Thr Pro Glu Val Thr
35 40 45

Cys Val Val Val Asp Val Ser His Glu Asp Pro Glu Val Gln Phe Asn
50 55 60

Trp Tyr Val Asp Gly Val Glu Val His Asn Ala Lys Thr Lys Pro Arg
65 70 75 80

Glu Glu Gln Phe Asn Ser Thr Phe Arg Val Val Ser Val Leu Thr Val
85 90 95

Val His Gln Asp Trp Leu Asn Gly Lys Glu Tyr Lys Cys Lys Val Ser
100 105 110

Asn Lys Gly Leu Pro Ala Pro Ile Glu Lys Thr Ile Ser Lys Thr Lys
115 120 125

Gly Gln Pro Arg Glu Pro Gln Val Tyr Thr Leu Pro Pro Ser Arg Glu
130 135 140

Glu Met Thr Lys Asn Gln Val Ser Leu Thr Cys Leu Val Lys Gly Phe
145 150 155 160

Tyr Pro Ser Asp Ile Ala Val Glu Trp Glu Ser Asn Gly Gln Pro Glu
165 170 175

Asn Asn Tyr Lys Thr Thr Pro Pro Met Leu Asp Ser Asp Gly Ser Phe
180 185 190

Phe Leu Tyr Ser Lys Leu Thr Val Asp Lys Ser Arg Trp Gln Gln Gly
195 200 205

Asn Val Phe Ser Cys Ser Val Met His Glu Ala Leu His Asn His Tyr
210 215 220

Thr Gln Lys Ser Leu Ser Leu Ser Pro Gly Lys
225 230 235

<210> SEQ ID NO 228
<211> LENGTH: 15
<212> TYPE: PRT
<213> ORGANISM: Homo sapiens
<220> FEATURE:
<223> OTHER INFORMATION: IgV-IgV linker

<400> SEQUENCE: 228

Gly Gly Gly Gly Ser Gly Gly Gly Gly Ser Gly Gly Gly Gly Ser
1 5 10 15

<210> SEQ ID NO 229
<211> LENGTH: 10
<212> TYPE: PRT
<213> ORGANISM: Artificial Sequence
<220> FEATURE:
<223> OTHER INFORMATION: IgV-Fc linker 1

<400> SEQUENCE: 229

Gly Gly Gly Gly Ser Gly Gly Gly Gly Ser
1 5 10

<210> SEQ ID NO 230
<211> LENGTH: 13
<212> TYPE: PRT
<213> ORGANISM: Artificial Sequence
<220> FEATURE:
<223> OTHER INFORMATION: IgV-Fc linker 2

<400> SEQUENCE: 230

Gly Gly Gly Gly Ser Gly Gly Gly Gly Ser Ala Ala Ala
1               5                   10

<210> SEQ ID NO 231
<211> LENGTH: 15
<212> TYPE: PRT
<213> ORGANISM: Artificial Sequence
<220> FEATURE:
<223> OTHER INFORMATION: CD80 WT linker 1

<400> SEQUENCE: 231

Lys Ala Asp Phe Pro Thr Pro Ser Ile Ser Asp Phe Glu Ile Pro
1               5                   10                  15

<210> SEQ ID NO 232
<211> LENGTH: 10
<212> TYPE: PRT
<213> ORGANISM: Artificial Sequence
<220> FEATURE:
<223> OTHER INFORMATION: CD80 WT linker 2

<400> SEQUENCE: 232

Thr Thr Lys Gln Glu His Phe Pro Asp Asn
1               5                   10

<210> SEQ ID NO 233
<211> LENGTH: 11
<212> TYPE: PRT
<213> ORGANISM: Artificial Sequence
<220> FEATURE:
<223> OTHER INFORMATION: ICOSL WT linker 1

<400> SEQUENCE: 233

Val Thr Leu His Val Ala Ala Asn Phe Ser Val
1               5                   10

<210> SEQ ID NO 234
<211> LENGTH: 29
<212> TYPE: PRT
<213> ORGANISM: Artificial Sequence
<220> FEATURE:
<223> OTHER INFORMATION: ICOSL WT linker 2

<400> SEQUENCE: 234

Val Gly Ser Gln Thr Gly Asn Asp Ile Gly Glu Arg Asp Lys Ile Thr
1               5                   10                  15

Glu Asn Pro Val Ser Thr Gly Glu Lys Asn Ala Ala Thr
            20                  25

<210> SEQ ID NO 235
<211> LENGTH: 9
<212> TYPE: PRT
<213> ORGANISM: Artificial Sequence
<220> FEATURE:
<223> OTHER INFORMATION: NKp30 WT linker 1

<400> SEQUENCE: 235

Val Glu Lys Glu His Pro Gln Leu Gly
1               5

<210> SEQ ID NO 236
<211> LENGTH: 9
<212> TYPE: PRT
<213> ORGANISM: Artificial Sequence
<220> FEATURE:
<223> OTHER INFORMATION: CD86 WT linker 1

<400> SEQUENCE: 236

```
Ala Pro Leu Lys Ile Gln Ala Tyr Phe
1               5
```

```
<210> SEQ ID NO 237
<211> LENGTH: 18
<212> TYPE: PRT
<213> ORGANISM: Artificial Sequence
<220> FEATURE:
<223> OTHER INFORMATION: CD86 WT linker 2

<400> SEQUENCE: 237

Val Leu Ala Asn Phe Ser Gln Pro Glu Ile Val Pro Ile Ser Asn Ile
1               5                   10                  15

Thr Glu


<210> SEQ ID NO 238
<211> LENGTH: 22
<212> TYPE: PRT
<213> ORGANISM: Artificial Sequence
<220> FEATURE:
<223> OTHER INFORMATION: CD86 WT linker 3

<400> SEQUENCE: 238

Arg Leu Leu Ser Ser Pro Phe Ser Ile Glu Leu Glu Asp Pro Gln Pro
1               5                   10                  15

Pro Pro Asp His Ile Pro
            20


<210> SEQ ID NO 239
<211> LENGTH: 238
<212> TYPE: PRT
<213> ORGANISM: Artificial Sequence
<220> FEATURE:
<223> OTHER INFORMATION: ICOSL v35 ECD

<400> SEQUENCE: 239

Asp Thr Gln Glu Lys Glu Val Arg Ala Met Val Gly Ser Asp Val Glu
1               5                   10                  15

Leu Ser Cys Ala Cys Pro Glu Gly Ser Arg Phe Asp Leu Asn Asp Val
            20                  25                  30

Tyr Val Tyr Trp Gln Thr Ser Glu Ser Lys Thr Val Val Thr Tyr His
        35                  40                  45

Ile Pro Gln Ser Ser Ser Leu Glu Asn Val Asp Ser Arg Tyr Arg Asn
    50                  55                  60

Arg Ala Leu Met Ser Pro Ala Gly Met Leu Arg Gly Asp Phe Ser Leu
65                  70                  75                  80

Arg Leu Phe Asn Val Thr Pro Gln Asp Glu Gln Lys Phe His Cys Leu
                85                  90                  95

Val Leu Ser Gln Ser Leu Glu Phe Gln Glu Val Leu Ser Val Glu Val
            100                 105                 110

Thr Leu His Val Ala Ala Asn Phe Ser Val Pro Val Val Ser Ala Pro
        115                 120                 125

His Ser Pro Ser Gln Asp Glu Leu Thr Phe Thr Cys Thr Ser Ile Asn
    130                 135                 140

Gly Tyr Pro Arg Pro Asn Val Tyr Trp Ile Asn Lys Thr Asp Asn Ser
145                 150                 155                 160
```

```
Leu Leu Asp Gln Ala Leu Gln Asn Asp Thr Val Phe Leu Asn Met Arg
                165                 170                 175

Gly Leu Tyr Asp Val Val Ser Val Leu Arg Ile Ala Arg Thr Pro Ser
            180                 185                 190

Val Asn Ile Gly Cys Cys Ile Glu Asn Val Leu Leu Gln Gln Asn Leu
        195                 200                 205

Thr Val Gly Ser Gln Thr Gly Asn Asp Ile Gly Glu Arg Asp Lys Ile
    210                 215                 220

Thr Glu Asn Pro Val Ser Thr Gly Glu Lys Asn Ala Ala Thr
225                 230                 235


<210> SEQ ID NO 240
<211> LENGTH: 111
<212> TYPE: PRT
<213> ORGANISM: Artificial Sequence
<220> FEATURE:
<223> OTHER INFORMATION: ICOSL v35 IgV

<400> SEQUENCE: 240

Asp Thr Gln Glu Lys Glu Val Arg Ala Met Val Gly Ser Asp Val Glu
1               5                   10                  15

Leu Ser Cys Ala Cys Pro Glu Gly Ser Arg Phe Asp Leu Asn Asp Val
            20                  25                  30

Tyr Val Tyr Trp Gln Thr Ser Glu Ser Lys Thr Val Val Thr Tyr His
        35                  40                  45

Ile Pro Gln Ser Ser Ser Leu Glu Asn Val Asp Ser Arg Tyr Arg Asn
    50                  55                  60

Arg Ala Leu Met Ser Pro Ala Gly Met Leu Arg Gly Asp Phe Ser Leu
65                  70                  75                  80

Arg Leu Phe Asn Val Thr Pro Gln Asp Glu Gln Lys Phe His Cys Leu
                85                  90                  95

Val Leu Ser Gln Ser Leu Glu Phe Gln Glu Val Leu Ser Val Glu
            100                 105                 110
```

IMMUNOMODULATORY PROTEINS WITH TUNABLE AFFINITIES

CROSS-REFERENCE TO RELATED APPLICATIONS

This application is a divisional application of U.S. patent Application Ser. No. 15/567,068, which is a National Stage application under 35 U.S.C. § 371 of International Application No. PCT/US2016/027995, filed Apr. 15, 2016, which claims priority from U.S. provisional application No. 62/149,437 filed Apr. 17, 2015, entitled "Immunomodulatory Proteins with Tunable Affinities" and to U.S. provisional application No. 62/218,534 filed Sep. 14, 2015, entitled "Immunomodulatory Proteins with Tunable Affinities," the contents of each of which are incorporated by reference in their entirety.

INCORPORATION BY REFERENCE OF SEQUENCE LISTING

The present application is being filed along with a Sequence Listing in electronic format. The Sequence Listing is provided as a file entitled 761612000110SeqList. TXT, created Mar. 29, 2022, which is 386,148 bytes in size. The information in the electronic format of the Sequence Listing is incorporated by reference in its entirety.

FIELD

The present invention relates to therapeutic proteins for modulating immune response in the treatment of cancer and immunological diseases.

BACKGROUND

Modulation of the immune response by intervening in the processes that occur in the immunological synapse (IS) formed by and between antigen-presenting cells (APCs) or target cells and lymphocytes is of increasing medical interest. Currently, biologics used to enhance or suppress immune response have generally been limited to immunoglobulins (e.g., anti-PD-1 mAbs) or soluble receptors (e.g., Fc-CTLA4). Soluble receptors suffer from a number of deficiencies. While useful for antagonizing interactions between proteins, soluble receptors often lack the ability to agonize such interactions. Antibodies have proven less limited in this regard and examples of both agonistic and antagonistic antibodies are known in the art. Nevertheless, both soluble receptors and antibodies lack important attributes that are critical to function in the IS. Mechanistically, cell surface proteins in the IS can involve the coordinated and often simultaneous interaction of multiple protein targets with a single protein to which they bind. IS interactions occur in close association with the junction of two cells, and a single protein in this structure can interact with both a protein on the same cell (cis) as well as a protein on the associated cell (trans), likely at the same time. Thus, there is a need for improved molecules for modulation of immune responses. Provided are embodiments that meet such needs.

SUMMARY

Provided herein are immunomodulatory proteins that exhibit altered binding affinities to binding partners that are immune protein ligands involved in immunological responses. In some embodiments, the provided immunomodulatory proteins can modulate, such as potentiate or dampen, the activity of the immune protein ligand, thereby modulating immunological responses. In some embodiments, also provided are methods and uses for modulating immune responses by contacting cells expressing one or more of the immune proteins ligands with a provided immunomodulatory protein, for example, in the immunotherapeutic treatment of diseases or conditions that are treatable by modulating of the immune response.

In some embodiments, provided herein is an immunomodulatory protein, comprising at least one non-immunoglobulin affinity modified immunoglobulin superfamily (IgSF) domain comprising one or more amino acid substitution(s) in a wild-type IgSF domain, wherein: the at least one affinity modified IgSF domain has increased binding to at least two cognate binding partners compared to the wild-type IgSF domain; and the at least one affinity modified IgSF domain specifically binds non-competitively to the at least two cognate binding partners. In some embodiments, the at least two cognate binding partners are cell surface molecular species expressed on the surface of a mammalian cell. In some embodiments, the cell surface molecular species are expressed in cis configuration or trans configuration. In some embodiments, the mammalian cell is one of two mammalian cells forming an immunological synapse (IS) and each of the cell surface molecular species is expressed on at least one of the two mammalian cells forming the IS. In some embodiments, at least one of the mammalian cells is a lymphocyte. In some embodiments, the lymphocyte is an NK cell or a T cell. In some embodiments, binding of the affinity modified IgSF domain modulates immunological activity of the lymphocyte.

In some embodiments, the immunomodulatory protein is capable of effecting increased immunological activity compared the wild-type protein comprising the wild-type IgSF domain. In some embodiments, the immunomodulatory protein is capable of effecting decreased immunological activity compared to the wild-type protein comprising the wild-type IgSF domain. In some embodiments, at least one of the mammalian cells is a tumor cell. In some embodiments, the mammalian cells are human cells. In some embodiments, the affinity modified IgSF domain is capable of specifically binding to the two mammalian cells forming the IS.

In some embodiments according to any one of the immunomodulatory proteins described above, the wild-type IgSF domain is from an IgSF family member of a family selected from Signal-Regulatory Protein (SIRP) Family, Triggering Receptor Expressed On Myeloid Cells Like (TREML) Family, Carcinoembryonic Antigen-related Cell Adhesion Molecule (CEACAM) Family, Sialic Acid Binding Ig-Like Lectin (SIGLEC) Family, Butyrophilin Family, B7 family, CD28 family, V-set and Immunoglobulin Domain Containing (VSIG) family, V-set transmembrane Domain (VSTM) family, Major Histocompatibility Complex (MHC) family, Signaling lymphocytic activation molecule (SLAM) family, Leukocyte immunoglobulin-like receptor (LIR), Nectin (Nec) family, Nectin-like (NECL) family, Poliovirus receptor related (PVR) family, Natural cytotoxicity triggering receptor (NCR) family, T cell immunoglobulin and mucin (TIM) family or Killer-cell immunoglobulin-like receptors (KIR) family. In some embodiments, the wild-type IgSF domain is from an IgSF member selected from CD80, CD86, PD-L1, PD-L2, ICOS Ligand, B7-H3, B7-H4, CD28, CTLA4, PD-1, ICOS, BTLA, CD4, CD8-alpha, CD8-beta, LAG3, TIM-3, CEACAM1, TIGIT, PVR, PVRL2, CD226, CD2, CD160, CD200, CD200R or Nkp30. In some embodiments, the wild-type IgSF domain is a human IgSF member.

In some embodiments according to any one of the immunomodulatory proteins described above, the wild-type IgSF domain is an IgV domain, an IgC1 domain, an IgC2 domain or a specific binding fragment thereof. In some embodiments, the affinity-modified IgSF domain is an affinity modified IgV domain, affinity modified IgC1 domain or an affinity modified IgC2 domain or is a specific binding fragment thereof comprising the one or more amino acid substitutions.

In some embodiments according to any one of the immunomodulatory proteins described above, the immunomodulatory protein comprises at least two non-immunoglobulin affinity modified IgSF domains. In some embodiments each of the non-immunoglobulin affinity modified IgSF domains binds to a different cognate binding partner, wherein the two affinity modified IgSF domain specifically binds non-competitively to the at least two different cognate binding partners. In some embodiments, the at least two non-immunoglobulin affinity modified IgSF domains each comprise one or more different amino acid substitutions in the same wild-type IgSF domain. In some embodiments, the at least two non-immunoglobulin affinity modified IgSF domains each comprise one or more amino acid substitutions in different wild-type IgSF domains. In some embodiments, the different wild-type IgSF domains are from different IgSF family members.

In some embodiments according to any one of the immunomodulatory proteins described above, the immunomodulatory protein comprises only one non-immunoglobulin affinity modified IgSF domain.

In some embodiments according to any one of the immunomodulatory proteins described above, the affinity-modified IgSF comprises at least 85% sequence identity to a wild-type IgSF domain or a specific binding fragment thereof contained in the sequence of amino acids set forth in any of SEQ ID NOS: 1-27. In some embodiments, the immunomodulatory protein further comprises a second affinity-modified IgSF, wherein the second affinity-modified IgSF domain comprises at least 85% sequence identity to a wild-type IgSF domain or a specific binding fragment thereof contained in the sequence of amino acids set forth in any of SEQ ID NOS: 1-27.

In some embodiments according to any one of the immunomodulatory proteins described above, the wild-type IgSF domain is a member of the B7 family. In some embodiments, the wild-type IgSF domain is a domain of CD80, CD86 or ICOSLG. In some embodiments, the wild-type IgSF domain is a domain of CD80.

In some embodiments according to any one of the immunomodulatory proteins described above, provided herein is an immunomodulatory protein, comprising at least one affinity modified CD80 immunoglobulin superfamily (IgSF) domain comprising one or more amino acid substitution(s) in a wild-type CD80 IgSF domain, wherein the at least one affinity modified CD80 IgSF domain has increased binding to at least two cognate binding partners compared to the wild-type CD80 IgSF domain.

In some embodiments according to any one of the immunomodulatory proteins described above, the cognate binding partners are CD28 and PD-L1. In some embodiments, the wild-type IgSF domain is an IgV domain and/or the affinity modified CD80 domain is an affinity modified IgV domain. In some embodiments, the affinity-modified domain comprises at least 85% sequence identity to a wild-type CD80 domain or a specific binding fragment thereof contained in the sequence of amino acids set forth in SEQ ID NO:1.

In some embodiments according to any one of the immunomodulatory proteins described above, the at least one affinity modified IgSF domain comprises at least 1 and no more than twenty amino acid substitutions in the wild-type IgSF domain. In some embodiments, the at least one affinity modified IgSF domain comprises at least 1 and no more than ten amino acid substitutions in the wild-type IgSF domain. In some embodiments, the at least one affinity modified IgSF domain comprises at least 1 and no more than five amino acid substitutions in the wild-type IgSF domain.

In some embodiments according to any one of the immunomodulatory proteins described above, the affinity modified IgSF domain has at least 120% of the binding affinity as its wild-type IgSF domain to each of the at least two cognate binding partners.

In some embodiments according to any one of the immunomodulatory proteins described above, the immunomodulatory protein further comprises a non-affinity modified IgSF domain.

In some embodiments according to any one of the immunomodulatory proteins described above, the immunomodulatory protein is soluble. In some embodiments, the immunomodulatory protein lacks a transmembrane domain or a cytoplasmic domain. In some embodiments, the immunomodulatory protein comprises only the extracellular domain (ECD) or a specific binding fragment thereof comprising the affinity modified IgSF domain.

In some embodiments according to any one of the immunomodulatory proteins described above, the immunomodulatory protein is glycosylated or pegylated.

In some embodiments according to any one of the immunomodulatory proteins described above, the immunomodulatory protein is linked to a multimerization domain. In some embodiments, the immunomodulatory protein is linked to an Fc domain or a variant thereof with reduced effector function. In some embodiments, the Fc domain is an IgG1 domain, an IgG2 domain or is a variant thereof with reduced effector function. In some embodiments, the Fc domain is mammalian, optionally human; or the variant Fc domain comprises one or more amino acid modifications compared to an unmodified Fc domain that is mammalian, optionally human. In some embodiments, the Fc domain or variant thereof comprises the sequence of amino acids set forth in SEQ ID NO:226 or SEQ ID NO:227 or a sequence of amino acids that exhibits at least 85% sequence identity to SEQ ID NO:226 or SEQ ID NO:227.

In some embodiments according to any one of the immunomodulatory proteins described above, the immunomodulatory protein is linked indirectly via a linker.

In some embodiments according to any one of the immunomodulatory proteins described above, the immunomodulatory protein is a dimer.

In some embodiments according to any one of the immunomodulatory proteins described above, the immunomodulatory protein is attached to a liposomal membrane.

Also provided are immunomodulatory proteins comprising at least two non-immunoglobulin immunoglobulin superfamily (IgSF) domains, wherein: at least one is an affinity modified IgSF domain and the at least two non-immunoglobulin IgSF domains each independently bind to at least one different binding partner. In some embodiments, the at least two non-immunoglobulin IgSF domains bind non-competitively to the different binding partners. In some embodiments, the affinity modified IgSF domain contains one more amino acid substitutions in a first wild-type or unmodified IgSF domain. In some embodiments, the other of the IgSF domain is a wild-type or unmodified IgSF domain. In some embodiments, the other of the IgSF domain is also an affinity modified IgSF domain.

In some embodiments according to any of the above immunomodulatory proteins, the immunomodulatory protein contains at least two affinity modified non-immunoglobulin IgSF domains (a first affinity modified IgSF domain and a second affinity modified IgSF domain) in which the first non-immunoglobulin modified IgSF domain comprises one or more amino acid substitutions in a first wild-type-type IgSF domain and the second non-immunoglobulin modified IgSF domain comprises one or more amino acid substitutions in a second wild-type IgSF domain, and in which the first and second non-immunoglobulin modified IgSF domain each specifically bind to at least one different cognate binding partner. In some embodiments, the at least two non-immunoglobulin IgSF domains bind non-competitively to the different binding partners. In some embodiments, the first and second non-immunoglobulin modified IgSF domain is affinity-modified to exhibit altered binding to its cognate binding partner. Thus, in some embodiments, the first and second non-immunoglobulin modified IgSF domains are affinity-modified IgSF domains. In some embodiments, the first non-immunoglobulin modified IgSF domain exhibits altered binding to at least one of its cognate binding partner(s) compared to the first wild-type IgSF domain; and the second non-immunoglobulin modified IgSF domain exhibits altered binding to at least one of its cognate binding partner(s) compared to the second wild-type IgSF domain. In some embodiments, the altered binding is independently either increased or decreased.

In some embodiments, the different cognate binding partners are cell surface molecular species expressed on the surface of a mammalian cell. In some embodiments, the different cell surface molecular species are expressed in cis configuration or trans configuration. In some embodiments, the mammalian cell is one of two mammalian cells forming an immunological synapse (IS) and the different cell surface molecular species is expressed on at least one of the two mammalian cells forming the IS. In some embodiments, at least one of the mammalian cells is a lymphocyte. In some embodiments, the lymphocyte is an NK cell or a T cell. In some embodiments, binding of the immunomodulatory protein to the cell modulates the immunological activity of the lymphocyte. In some embodiments, the immunomodulatory protein is capable of effecting increased immunological activity compared to the wild-type protein comprising the wild-type IgSF domain. In some embodiments, the immunomodulatory protein is capable of effecting decreased immunological activity compared to the wild-type protein comprising the wild-type IgSF domain. In some embodiments, at least one of the mammalian cells is a tumor cell. In some embodiments, the mammalian cells are human cells. In some embodiments, the immunomodulatory protein is capable of specifically binding to the two mammalian cells forming the IS.

In some embodiments according to any one of the immunomodulatory proteins described above, the first and second modified IgSF domains each comprise one or more amino acid substitutions in different wild-type IgSF domains. In some embodiments, the different wild-type IgSF domains are from different IgSF family members. In some embodiments, the first and second modified IgSF domains are non-wild-type combinations. In some embodiments, the first wild-type IgSF domain and second wild-type IgSF domain each individually is from an IgSF family member of a family selected from Signal-Regulatory Protein (SIRP) Family, Triggering Receptor Expressed On Myeloid Cells Like (TREML) Family, Carcinoembryonic Antigen-related Cell Adhesion Molecule (CEACAM) Family, Sialic Acid Binding Ig-Like Lectin (SIGLEC) Family, Butyrophilin Family, B7 family, CD28 family, V-set and Immunoglobulin Domain Containing (VSIG) family, V-set transmembrane Domain (VSTM) family, Major Histocompatibility Complex (MHC) family, Signaling lymphocytic activation molecule (SLAM) family, Leukocyte immunoglobulin-like receptor (LIR), Nectin (Nec) family, Nectin-like (NECL) family, Poliovirus receptor related (PVR) family, Natural cytotoxicity triggering receptor (NCR) family, T cell immunoglobulin and mucin (TIM) family or Killer-cell immunoglobulin-like receptors (KIR) family. In some embodiments, the first wild-type IgSF domain and second wild-type IgSF domain each individually is from an IgSF member selected from CD80, CD86, PD-L1, PD-L2, ICOS Ligand, B7-H3, B7-H4, CD28, CTLA4, PD-1, ICOS, BTLA, CD4, CD8-alpha, CD8-beta, LAG3, TIM-3, CEACAM1, TIGIT, PVR, PVRL2, CD226, CD2, CD160, CD200, CD200R or Nkp30.

In some embodiments according to any one of the immunomodulatory proteins described above, the first modified IgSF domain and the second modified IgSF domain each individually comprises at least 85% sequence identity to a wild-type IgSF domain or a specific binding fragment thereof contained in the sequence of amino acids set forth in any of SEQ ID NOS: 1-27.

In some embodiments according to any one of the immunomodulatory proteins described above, the first and second wild-type IgSF domain each individually is a member of the B7 family. In some embodiments, the first and second wild-type IgSF domain each individually is from CD80, CD86 or ICOSLG. In some embodiments, the first or second wild-type IgSF domain is from a member of the B7 family and the other of the first or second wild-type IgSF domain is from another IgSF family.

In some embodiments according to any one of the immunomodulatory proteins described above, the first and second wild-type IgSF domain is from ICOSLG and NKp30.

In some embodiments according to any one of the immunomodulatory proteins described above, the first and second wild-type IgSF domain is from CD80 and NKp30.

In some embodiments according to any one of the immunomodulatory proteins described above, the first and second wild-type IgSF domain each individually is a human IgSF member.

In some embodiments according to any one of the immunomodulatory proteins described above, the first and second wild-type IgSF domain each individually is an IgV domain, and IgC1 domain, an IgC2 domain or a specific binding thereof. In some embodiments, the first non-immunoglobulin modified domain and the second non-immunoglobulin modified domain each individually is a modified IgV domain, modified IgC1 domain or a modified IgC2 domain or is a specific binding fragment thereof comprising the one or more amino acid substitutions. In some embodiments, at least one of the first non-immunoglobulin modified domain or the second non-immunoglobulin modified domain is a modified IgV domain. In some embodiments, the first non-immunoglobulin modified IgSF domain and the second non-immunoglobulin modified IgSF domain each individually comprise 1 and no more than twenty amino acid substitutions. In some embodiments, the first non-immunoglobulin modified IgSF domain and the second non-immunoglobulin modified IgSF domain each individually comprise 1 and no more than ten amino acid substitutions. In some embodiments, the first non-immunoglobulin modified IgSF domain and the second non-immunoglobulin modified IgSF domain each individually comprise 1 and no more than five amino acid substitutions.

In some embodiments according to any one of the immunomodulatory proteins described above, at least one of the first or second non-immunoglobulin modified IgSF domain has between 10% and 90% of the binding affinity of the wild-type IgSF domain to at least one of its cognate binding partner. In some embodiments, at least one of the first of second non-immunoglobulin modified IgSF domain has at least 120% of the binding affinity of the wild-type IgSF domain to at least one of its cognate binding partner.

In some embodiments according to any one of the immunomodulatory proteins described above, the first and second non-immunoglobulin modified IgSF domain each individually has at least 120% of the binding affinity of the wild-type IgSF domain to at least one of its cognate binding partner.

In some embodiments according to any one of the immunomodulatory proteins described above, the immunomodulatory protein is soluble.

In some embodiments according to any one of the immunomodulatory proteins described above, the immunomodulatory protein is glycosylated or pegylated.

In some embodiments according to any one of the immunomodulatory proteins described above, the immunomodulatory protein is linked to a multimerization domain. In some embodiments, the immunomodulatory protein is linked to an Fc domain or a variant thereof with reduced effector function. In some embodiments, the Fc domain is an IgG1 domain, an IgG2 domain or is a variant thereof with reduced effector function. In some embodiments, the Fc domain is mammalian, optionally human; or the variant Fc domain comprises one or more amino acid modifications compared to an unmodified Fc domain that is mammalian, optionally human. In some embodiments, the Fc domain or variant thereof comprises the sequence of amino acids set forth in SEQ ID NO:226 or SEQ ID NO:227 or a sequence of amino acids that exhibits at least 85% sequence identity to SEQ ID NO:226 or SEQ ID NO:227.

In some embodiments according to any one of the immunomodulatory proteins described above, the variant CD80 polypeptide is linked indirectly via a linker.

In some embodiments according to any one of the immunomodulatory proteins described above, the immunomodulatory protein is a dimer.

In some embodiments according to any one of the immunomodulatory proteins described above, the immunomodulatory protein further comprises one or more additional non-immunoglobulin IgSF domain that is the same of different from the first or second non-immunoglobulin modified IgSF domain. In some embodiments, the one or more additional non-immunoglobulin IgSF domain is an affinity modified IgSF domain.

In some embodiments according to any one of the immunomodulatory proteins described above, the immunomodulatory protein is attached to a liposomal membrane.

In some embodiments, provided herein is a nucleic acid molecule, encoding the immunomodulatory polypeptide according to any one of the embodiments described above. In some embodiments, the nucleic acid molecule is synthetic nucleic acid. In some embodiments, the nucleic acid molecule is cDNA.

In some embodiments, provided herein is a vector, comprising the nucleic acid molecule according to any one of the embodiments described above. In some embodiments, the vector is an expression vector.

In some embodiments, provided herein is a cell, comprising the vector of according to any one of the embodiments described above. In some embodiments, the cell is a eukaryotic cell or prokaryotic cell.

In some embodiments, provided herein is a method of producing an immunomodulatory protein, comprising introducing the nucleic acid molecule according to any one of the embodiments described above or vector according to any one of the embodiments described above into a host cell under conditions to express the protein in the cell. In some embodiments, the method further comprises isolating or purifying the immunomodulatory protein from the cell.

In some embodiments, provided herein is a pharmaceutical composition, comprising the immunomodulatory protein according to any one of the embodiments described above. In some embodiments, the pharmaceutical composition comprises a pharmaceutically acceptable excipient. In some embodiments, the pharmaceutical composition is sterile.

In some embodiments, provided herein is an article of manufacture comprising the pharmaceutical composition according to any one of the embodiments described above in a vial. In some embodiments, the vial is sealed.

In some embodiments, provided herein is a kit comprising the pharmaceutical composition according to any one of the embodiments described above, and instructions for use.

In some embodiments, provided herein is a kit comprising the article of manufacture according to any one of the embodiments described above, and instructions for use.

In some embodiments, provided herein is a method of modulating an immune response in a subject, comprising administering therapeutically effective amount of the immunomodulatory protein according to any one of the embodiments described above to the subject. In some embodiments, modulating the immune response treats a disease or condition in the subject. In some embodiments, the immune response is increased. In some embodiments, the disease or condition is a tumor or cancer. In some embodiments, the disease or condition is selected from melanoma, lung cancer, bladder cancer or a hematological malignancy. In some embodiments, the immune response is decreased. In some embodiments, the disease or condition is an inflammatory disease or condition. In some embodiments, the disease or condition is selected from Crohn's disease, ulcerative colitis, multiple sclerosis, asthma, rheumatoid arthritis, or psoriasis.

In some embodiments, provided herein is a method of identifying an affinity modified immunomodulatory protein, comprising: a) contacting a modified protein comprising at least one non-immunoglobulin modified immunoglobulin superfamily (IgSF) domain or specific binding fragment thereof with at least two cognate binding partners under conditions capable of effecting binding of the protein with the at least two cognate binding partners, wherein the at least one modified IgSF domain comprises one or more amino acid substitutions in a wild-type IgSF domain; b) identifying a modified protein comprising the modified IgSF domain that has increased binding to at least one of the two cognate binding partners compared to a protein comprising the wild-type IgSF domain; and c) selecting a modified protein comprising the modified IgSF domain that binds non-competitively to the at least two cognate binding partners, thereby identifying the affinity modified immunomodulatory protein. In some embodiments, step b) comprises identifying a modified protein comprising a modified IgSF domain that has increased binding to each of the at least two cognate binding partners compared to a protein comprising the wild-type domain. In some embodiments, prior to step a), introducing one or more amino acid substitutions into the wild-type IgSF domain, thereby generating a modified protein comprising the modified IgSF domain. In some embodiments, the modified protein comprises at least two modified IgSF domains or specific binding fragments thereof, wherein the first IgSF domain comprises one or more amino acid substitutions in a first wild-type-type IgSF domain and the second non-immunoglobulin affinity modified IgSF domain comprises one or more amino acid substitutions in a second wild-type IgSF domain. In some embodiments, the first and second non-immunoglobulin affinity modified IgSF domain each specifically bind to at least one different cognate binding partner.

In some embodiments, also provided are immunomodulatory protein comprising at least one non-immunoglobulin affinity modified immunoglobulin superfamily (IgSF) domain. In some embodiments, the affinity modified IgSF domain specifically binds non-competitively to at least two cell-surface molecular species. In some embodiments, each of the molecular species is expressed on at least one of two mammalian cells forming an immunological synapse (IS). In some embodiments, the molecular species are in cis configuration or trans configuration. In some embodiments, one of the mammalian cells is a lymphocyte and binding of the affinity modified IgSF domain modulates immunological activity of the lymphocyte. In some embodiments, the affinity modified IgSF domain specifically binds to the two mammalian cells forming the IS.

In some embodiments, the immunomodulatory protein comprises at least two non-immunoglobulin affinity modified IgSF domains and the immunomodulatory protein specifically binds to the two mammalian cells forming the IS. In some embodiments, the immunomodulatory protein comprises at least two affinity modified IgSF domains, wherein the affinity modified IgSF domains are not the same species of IgSF domain.

In some embodiments, one of the two mammalian cells is a tumor cell. In some embodiments, the lymphocyte is an NK cell or a T-cell. In some embodiments, the mammalian cells are a mouse, rat, cynomolgus monkey, or human cells.

In some embodiments, the IgSF cell surface molecular species are human IgSF members.

In some embodiments, the immunomodulatory protein comprises an affinity modified mammalian IgSF member. In some embodiments, the affinity modified IgSF domain is an affinity modified IgV, IgC1, or IgC2 domain. In some embodiments, the affinity modified IgSF domain differs by at least one and no more than ten amino acid substitutions from its wild-type IgSF domain. In some embodiments, the affinity modified IgSF domain differs by at least one and no more than five amino acid substitutions from its wild-type IgSF domain.

In some embodiments, the affinity modified human IgSF member is at least one of: CD80, PVR, ICOSLG, or HAVCR2. In some embodiments, the affinity modified IgSF domain comprises at least one affinity modified human CD80 domain. In some embodiments, the affinity modified IgSF domain is a human CD80 IgSF domain.

In some embodiments, the immunomodulatory protein has at least 85% sequence identity with an amino acid sequence selected from SEQ ID NOS: 1-27, or a fragment thereof. In some embodiments, the immunomodulatory protein has at least 90% sequence identity with an amino acid sequence selected from SEQ ID NOS: 1-27 or a fragment thereof. In some embodiments, the immunomodulatory protein has at least 95% sequence identity with an amino acid sequence selected from SEQ ID NOS: 1-27, or a fragment thereof. In some embodiments, the immunomodulatory protein has at least 99% sequence identity with an amino acid sequence selected from SEQ ID NOS: 1-27, or a fragment thereof. In some embodiments, the immunomodulatory protein having at least 85%, 90%, 95%, or 99% sequence identity with an amino acid sequence selected from SEQ ID NOS: 1-27 or a fragment thereof further comprises a second immunomodulatory protein, wherein the second immunomodulatory protein has at least 85%, 90%, 95%, or 99% sequence identity with an amino acid sequence selected from SEQ ID NOS: 1-27 or a fragment thereof.

In some embodiments, the immunological activity is enhanced. In others it's suppressed.

In some embodiments, the affinity modified IgSF domain has between 10% and 90% of the binding affinity of the wild-type IgSF domain to at least one of the two cell surface molecular species. In some embodiments, the affinity modified IgSF domain specifically binds non-competitively to exactly one IgSF member. In some embodiments, the affinity modified IgSF domain has at least 120% of the binding affinity as its wild-type IgSF domain to at least one of the two cell surface molecular species.

In some embodiments, the immunomodulatory protein is covalently bonded, directly or indirectly, to an antibody fragment crystallizable (Fc). In some embodiments, the immunomodulatory protein is glycosylated or pegylated. In some embodiments, the immunomodulatory protein is soluble. In some embodiments, the immunomodulatory protein is embedded in a liposomal membrane. In some embodiments, the immunomodulatory protein is dimerized by intermolecular disulfide bonds.

In some embodiments, the immunomodulatory protein is in a pharmaceutically acceptable carrier.

In another aspect, provided herein are immunomodulatory protein comprising at least two non-immunoglobulin affinity modified immunoglobulin superfamily (IgSF) domains. The affinity modified IgSF domains each specifically binds to its own cell surface molecular species. Each of the molecular species is expressed on at least one of the two mammalian cells forming an immunological synapse (IS) and one of the mammalian cells is a lymphocyte. The molecular species are, in some embodiments, in cis configuration or trans configuration. Binding of the affinity modified IgSF domain modulates immunological activity of the lymphocyte. In some embodiments, at least one of the affinity modified IgSF domains binds competitively. In some embodiments, the affinity modified IgSF domains are not the same species of IgSF domain. In some embodiments, the affinity modified IgSF domains are non-wild type combinations. In some embodiments, the cell surface molecular species are human IgSF members. In some embodiments, the at least two affinity modified IgSF domains are from at least one of: CD80, CD86, CD274, PDCD1LG2, ICOSLG, CD276, VTCN1, CD28, CTLA4, PDCD1, ICOS, BTLA, CD4, CD8A, CD8B, LAG3, HAVCR2, CEACAM1, TIGIT, PVR, PVRL2, CD226, CD2, CD160, CD200, NKp30, or CD200R1.

In some embodiments, the immunomodulatory protein comprises at least two affinity modified mammalian IgSF members. In some embodiments, the mammalian IgSF members are human IgSF members. In some embodiments, the mammalian IgSF members are at least two of: CD80, CD86, CD274, PDCD1LG2, ICOSLG, CD276, VTCN1, CD28, CTLA4, PDCD1, ICOS, BTLA, CD4, CD8A, CD8B, LAG3, HAVCR2, CEACAM1, TIGIT, PVR, PVRL2, CD226, CD2, CD160, CD200, NKp30, or CD200R1. In some embodiments, immunological activity is enhanced. In some embodiments, immunological activity is suppressed. In some embodiments, one of the two mammalian cells is a tumor cell. In some embodiments, the lymphocyte is an NK cell or a T-cell. In some embodiments, the mammalian cells are a mouse, rat, cynomolgus monkey, or human cells. In some embodiments, at least one of the two affinity modified IgSF domains has between 10% and 90% of the binding affinity of the wild-type IgSF domain to at least one of the cell surface molecular species. In some embodiments, at least one of the two affinity modified IgSF domains specifically binds to exactly one cell surface molecular species. In some embodiments, at least one of the two affinity modified IgSF domains has at least 120% of the binding affinity as its wild-type IgSF domain to at least one of the two cell surface molecular species. In some embodiments, the affinity modified IgSF domains are at least one of an IgV, IgC1, or IgC2 domain. In some embodiments, each of the at least two affinity modified IgSF domains differs by at least one and no more than ten amino acid substitutions from its wild-type IgSF domain. In some embodiments, each of the at least two affinity modified IgSF domains differs by at least one and no more than five amino acid substitutions from its wild-type IgSF domain. In some embodiments, the immunomodulatory protein is covalently bonded, directly or indirectly, to an antibody fragment crystallizable (Fc). In some embodiments, the immunomodulatory protein is in a pharmaceutically acceptable carrier. In some embodiments, the immunomodulatory protein is glycosylated or pegylated. In some embodiments, the immunomodulatory protein is soluble. In some embodiments, the immunomodulatory protein is embedded in a liposomal membrane. In some embodiments, the immunomodulatory protein is dimerized by intermolecular disulfide bonds.

In another aspect, the present invention relates to a recombinant nucleic acid encoding any of the immunomodulatory proteins summarized above.

In another aspect, the present invention relates to a recombinant expression vector comprising a nucleic acid encoding any of the immunomodulatory proteins summarized above.

In another aspect, the present invention relates to a recombinant host cell comprising an expression vector as summarized above.

In another aspect, the present invention relates to a method of making any of the immunomodulatory proteins summarized above. The method comprises culturing the recombinant host cell under immunomodulatory protein expressing conditions, expressing the immunomodulatory protein encoded by the recombinant expression vector therein, and purifying the recombinant immunomodulatory protein expressed thereby.

In another aspect, the present invention relates to a method of treating a mammalian patient in need of an enhanced or suppressed immunological response by administering a therapeutically effective amount of an immunomodulatory protein of any of the embodiments described above. In some embodiments, the enhanced immunological response treats melanoma, lung cancer, bladder cancer, or a hematological malignancy in the patient. In some embodiments, the suppressed immunological response treats Crohn's disease, ulcerative colitis, multiple sclerosis, asthma, rheumatoid arthritis, or psoriasis in the patient.

INCORPORATION BY REFERENCE

Figure 1A:
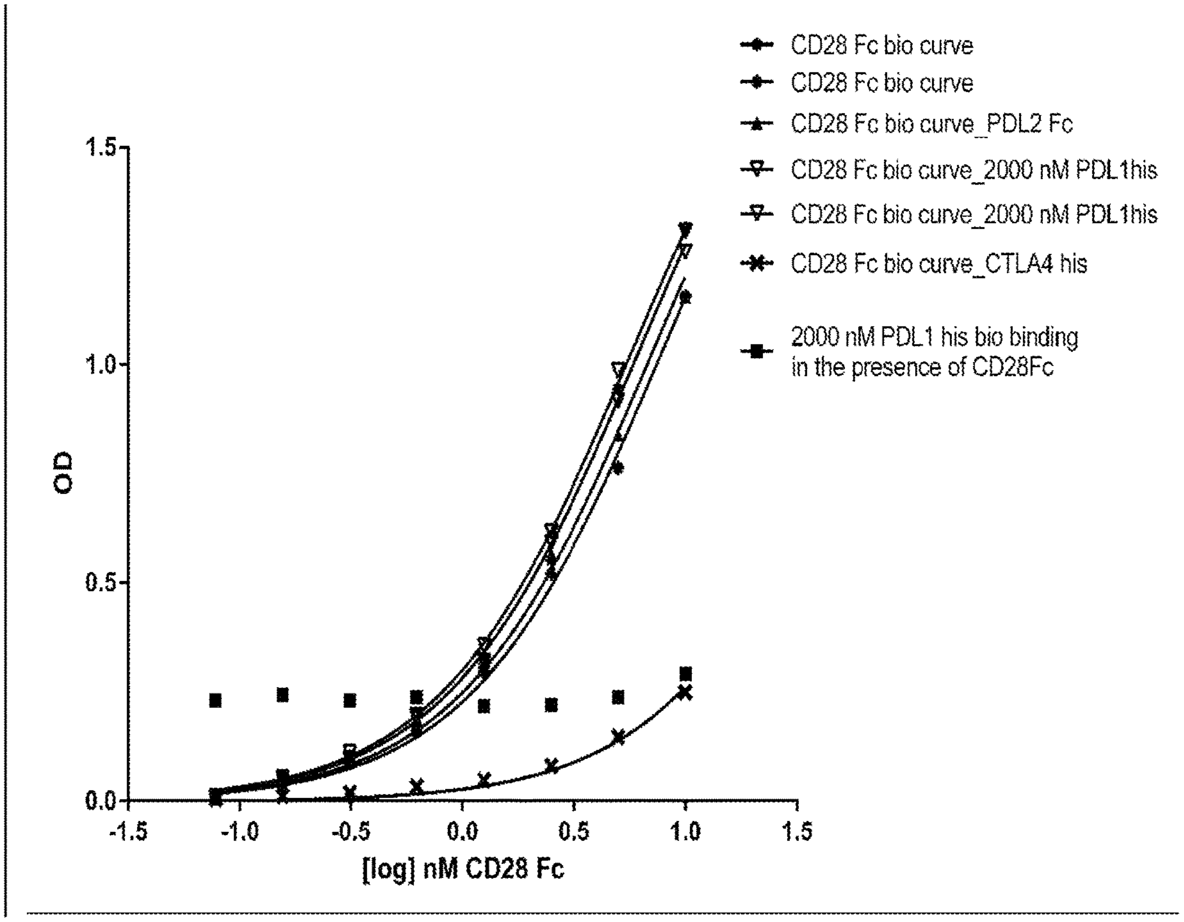
FIG. 1A depicts results of a competition binding assay for binding of biotinylated recombinant CD28 Fc fusion protein (rCD28.Fc) to immobilized CD80 variant A91G ECD-Fc fusion molecule in the presence of unlabeled recombinant human PD-L1-his, human CTLA-4-his or human-PD-L2-Fc fusion protein.

All publications, including patents, patent applications scientific articles and databases, mentioned in this specification are herein incorporated by reference in their entirety for all purposes to the same extent as if each individual publication, including patent, patent application, scientific article or database, were specifically and individually indicated to be incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

DETAILED DESCRIPTION

Provided herein are soluble immunomodulatory proteins that are capable of binding to one or more protein ligands, and generally two or more protein ligands, to modulate, e.g. induce, enhance or suppress, immunological immune responses. In some embodiments, the protein ligands are cell surface proteins expressed by immune cells that engage with one or more other immune receptor, e.g. on lymphocytes, to induce inhibitory or activating signals. For example, the interaction of certain receptors on lymphocytes with their cognate cell surface ligands to form an immunological synapse (IS) between antigen-presenting cells (APCs) or target cells and lymphocytes can provide costimulatory or inhibitory signals that can regulate the immune system. In some aspects, the immunomodulatory proteins provided herein can alter the interaction of cell surface protein ligands with their receptors to thereby modulate immune cells, such as T cell, activity.

In some embodiments, under normal physiological conditions, the T cell-mediated immune response is initiated by antigen recognition by the T cell receptor (TCR) and is regulated by a balance of co-stimulatory and inhibitory signals (i.e., immune checkpoint proteins). The immune system relies on immune checkpoints to prevent autoimmunity (i.e., self-tolerance) and to protect tissues from excessive damage during an immune response, for example during an attack against a pathogenic infection. In some cases, however, these immunomodulatory proteins can be dysregulated in diseases and conditions, including tumors, as a mechanism for evading the immune system.

Thus, in some aspects, immunotherapy that alters immune cell activity, such as T cell activity, can treat certain diseases and conditions in which the immune response is dysregulated. Therapeutic approaches that seek to modulate interactions in the IS would benefit from the ability to bind multiple IS targets simultaneously and in a manner that is sensitive to temporal sequence and spatial orientation. Current therapeutic approaches fall short of this goal. Instead, soluble receptors and antibodies typically bind no more than a single target protein at a time. This may be due to the absence of more than a single target species. Additionally, wild-type receptors and ligands possess low affinities for cognate binding partners, which preclude their use as soluble therapeutics.

Less trivially, however, soluble receptors and antibodies generally bind competitively (e.g., to no more than one target species at a time) and therefore lack the ability to simultaneously bind multiple targets. And while bispecific antibodies, as well as modalities comprising dual antigen binding regions, can bind to more than one target molecule simultaneously, the three-dimensional configuration typical of these modalities often precludes them intervening in key processes occurring in the IS in a manner consistent with their temporal and spatial requirements.

What is needed is an entirely new class of therapeutic molecules that have the specificity and affinity of antibodies or soluble receptors but, in addition, maintain the size, volume, and spatial orientation constraints required in the IS and possess increased affinity towards respective cognate binding partners. Further, such therapeutics would have the ability to bind to their targets non-competitively as well as competitively. A molecule with these properties would therefore have novel function in the ability to integrate into multi-protein complexes at IS and generate the desired binding configuration and resulting biological activity.

To this end, emerging immuno-oncology therapeutic regimes need to safely break tumor-induced T cell tolerance. Current state-of-the-art immuno-therapeutics block PD-1 or CTLA4, central inhibitory molecules of the B7/CD28 family that are known to limit T cell effector function. While antagonistic antibodies against such single targets function to disrupt immune synapse checkpoint signaling complexes, they fall short of simultaneously activating T cells. Conversely, bispecific antibody approaches activate T cells, but fall short of simultaneously blocking inhibitory ligands that regulate the induced signal.

To address these shortcomings, provided are therapeutic molecules that, in some embodiments, will both stimulate T-cell activation signaling and block inhibitory regulation simultaneously. In some embodiments, the provided immunomodulatory proteins relate to immunoglobulin superfamily (IgSF) components of the immune synapse that are known to have a dual role in both T-cell activation and blocking of inhibitory ligands. In particular aspects, the provided immunomodulatory proteins provide an immunotherapy platform using affinity modified native immune ligands to generate immunotherapy biologics that bind with tunable affinities to one or more of their cognate immune receptors in the treatment of a variety of oncological and immunological indications. In some aspects, IgSF based therapeutics engineered from immune system ligands, such as human immune system ligands, themselves are more likely to retain their ability to normally assemble into key pathways of the immune synapse and maintain normal interactions and regulatory functions in ways that antibodies or next-generation bi-specific reagents cannot. This is due to the relatively large size of antibodies as well as from the fact they are not natural components of the immune synapse. These unique features of human immune system ligands promise to provide a new level of immunotherapeutic efficacy and safety.

The section headings used herein are for organizational purposes only and are not to be construed as limiting the subject matter described.

I. DEFINITIONS

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

The terms used throughout this specification are defined as follows unless otherwise limited in specific instances. As used in the specification and the appended claims, the singular forms “a,” “an,” and “the” include plural referents unless the context clearly dictates otherwise. Unless defined otherwise, all technical and scientific terms, acronyms, and abbreviations used herein have the same meaning as commonly understood by one of ordinary skill in the art to which the invention pertains. Unless indicated otherwise, abbreviations and symbols for chemical and biochemical names is per IUPAC-IUB nomenclature. Unless indicated otherwise, all numerical ranges are inclusive of the values defining the range as well as all integer values in-between.

The term “affinity modified” as used in the context of an immunoglobulin superfamily domain, means a mammalian immunoglobulin superfamily (IgSF) domain having an altered amino acid sequence (relative to the wild-type control IgSF domain) such that it has an increased or decreased binding affinity or avidity to at least one of its cognate binding partners compared to the wild-type (i.e., non-affinity modified) IgSF control domain. In some embodiments, the IgSF domain can contain 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more amino acid differences, such as amino acid substitutions, in a wildtype or unmodified IgSF domain. An IgSF domain having an altered amino acid sequence (relative to the wild-type control IgSF domain) which does not have an increased or decreased binding affinity or avidity to at least one of its cognate binding partners compared to the wild-type IgSF control domain is a non-affinity modified IgSF domain. An increase or decrease in binding affinity or avidity can be determined using well known binding assays such as flow cytometry. Larsen et al., American Journal of Transplantation, Vol 5: 443-453 (2005). See also, Linsley et al., Immunity, 1: 7930801 (1994). An increase in a protein’s binding affinity or avidity to its cognate binding partner(s) is to a value at least 10% greater than that of the wild-type IgSF domain control and in some embodiments, at least 20%, 30%, 40%, 50%, 100%, 200%, 300%, 500%, 1000%, 5000%, or 10000% greater than that of the wild-type IgSF domain control value. A decrease in a protein’s binding affinity or avidity to at least one of its cognate binding partner is to a value no greater than 90% of the control but no less than 10% of the wild-type IgSF domain control value, and in some embodiments no greater than 80%, 70% 60%, 50%, 40%, 30%, or 20% but no less than 10% of the wild-type IgSF domain control value. An affinity modified protein is altered in primary amino acid sequence by substitution, addition, or deletion of amino acid residues. The term “affinity modified IgSF domain” is not be construed as imposing any condition for any particular starting composition or method by which the affinity modified IgSF domain was created. Thus, the affinity modified IgSF domains of the present invention are not limited to wild type IgSF domains that are then transformed to an affinity modified IgSF domain by any particular process of affinity modification. An affinity modified IgSF domain polypeptide can, for example, be generated starting from wild type mammalian IgSF domain sequence information, then modeled in silico for binding to its cognate binding partner, and finally recombinantly or chemically synthesized to yield the affinity modified IgSF domain composition of matter. In but one alternative example, an affinity modified IgSF domain can be created by site-directed mutagenesis of a wild-type IgSF domain. Thus, affinity modified IgSF domain denotes a product and not necessarily a product produced by any given process. A variety of techniques including recombinant methods, chemical synthesis, or combinations thereof, may be employed.

The terms "binding affinity," and "binding avidity" as used herein means the specific binding affinity and specific binding avidity, respectively, of a protein for its cognate binding partner under specific binding conditions. In biochemical kinetics avidity refers to the accumulated strength of multiple affinities of individual non-covalent binding interactions, such as between an IgSF domain and its cognate binding partner. As such, avidity is distinct from affinity, which describes the strength of a single interaction. Methods for determining binding affinity or avidity are known in art. See, for example, Larsen et al., American Journal of Transplantation, Vol 5: 443-453 (2005).

The term "biological half-life" refers to the amount of time it takes for a substance, such as an immunomodulatory polypeptide of the present invention, to lose half of its pharmacologic or physiologic activity or concentration. Biological half-life can be affected by elimination, excretion, degradation (e.g., enzymatic) of the substance, or absorption and concentration in certain organs or tissues of the body. In some embodiments, biological half-life can be assessed by determining the time it takes for the blood plasma concentration of the substance to reach half its steady state level ("plasma half-life"). Conjugates that can be used to derivatize and increase the biological half-life of polypeptides of the invention are known in the art and include, but are not limited to, polyethylene glycol (PEG), hydroxyethyl starch (HES), XTEN (extended recombinant peptides; see, WO2013130683), human serum albumin (HSA), bovine serum albumin (BSA), lipids (acylation), and poly-Pro-Ala-Ser (PAS), polyglutamic acid (glutamylation).

The term "cognate binding partner," in reference to a protein, such as an IgSF domain or an affinity modified IgSF domain, refers to at least one molecule (typically a native mammalian protein) to which the referenced protein specifically binds under specific binding conditions. A species of ligand recognized and specifically binding to its cognate receptor under specific binding conditions is an example of a cognate binding partner of that receptor. A "cognate cell surface binding partner" is a cognate binding partner expressed on a mammalian cell surface. In the present invention a "cell surface molecular species" is a cognate binding partner of the immunological synapse (IS), expressed on and by cells, such as mammalian cells, forming the immunological synapse.

The term "competitive binding" as used herein means that a protein is capable of specifically binding to at least two cognate binding partners but that specific binding of one cognate binding partner inhibits, such as prevents or precludes, simultaneous binding of the second cognate binding partner. Thus, in some cases, it is not possible for a protein to bind the two cognate binding partners at the same time. Generally, competitive binders contain the same or overlapping binding site for specific binding but this is not a requirement. In some embodiments, competitive binding causes a measurable inhibition (partial or complete) of specific binding of a protein to one of its cognate binding partner due to specific binding of a second cognate binding partner. A variety of methods are known to quantify competitive binding such as ELISA (enzyme linked immunosorbent assay) assays.

The term "conservative amino acid substitution" as used herein means an amino acid substitution in which an amino acid residue is substituted by another amino acid residue having a side chain R group with similar chemical properties (e.g., charge or hydrophobicity). Examples of groups of amino acids that have side chains with similar chemical properties include 1) aliphatic side chains: glycine, alanine, valine, leucine, and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartic acid and glutamic acid; and 7) sulfur-containing side chains: cysteine and methionine. Conservative amino acids substitution groups are: valine-leucine-isoleucine, phenylalanine-tyrosine, lysine-arginine, alanine-valine, glutamate-aspartate, and asparagine-glutamine.

The term, "corresponding to" with reference to positions of a protein, such as recitation that nucleotides or amino acid positions "correspond to" nucleotides or amino acid positions in a disclosed sequence, such as set forth in the Sequence listing, refers to nucleotides or amino acid positions identified upon alignment with the disclosed sequence based on structural sequence alignment or using a standard alignment algorithm, such as the GAP algorithm. By aligning the sequences, one skilled in the art can identify corresponding residues, for example, using conserved and identical amino acid residues as guides.

The term "cytokine" includes, e.g., but is not limited to, interleukins, interferons (IFN), chemokines, hematopoietic growth factors, tumor necrosis factors (TNF), and transforming growth factors. In general, these are small molecular weight proteins that regulate maturation, activation, proliferation, and differentiation of cells of the immune system.

The terms "decrease" or "attenuate" "or suppress" as used herein means to decrease by a statistically significant amount. A decrease can be at least 10%, 20%, 30%, 40%, 50%, 60%, 70%, 80%, 90%, or 100%.

The terms "derivatives" or "derivatized" refer to modification of an immunomodulatory protein by covalently linking it, directly or indirectly, so as to alter such characteristics as half-life, bioavailability, immunogenicity, solubility, toxicity, potency, or efficacy while retaining or enhancing its therapeutic benefit. Derivatives can be made by glycosylation, pegylation, lipidation, or Fc-fusion.

As used herein, domain (typically a sequence of three or more, generally 5 or 7 or more amino acids, such as 10 to 200 amino acid residues) refers to a portion of a molecule, such as a protein or encoding nucleic acid, that is structurally and/or functionally distinct from other portions of the molecule and is identifiable. For example, domains include those portions of a polypeptide chain that can form an independently folded structure within a protein made up of one or more structural motifs and/or that is recognized by virtue of a functional activity, such as binding activity. A protein can have one, or more than one, distinct domains. For example, a domain can be identified, defined or distinguished by homology of the primary sequence or structure to related family members, such as homology to motifs. In another example, a domain can be distinguished by its function, such as an ability to interact with a biomolecule, such as a cognate binding partner. A domain independently can exhibit a biological function or activity such that the domain independently or fused to another molecule can perform an activity, such as, for example binding. A domain can be a linear sequence of amino acids or a non-linear sequence of amino acids. Many polypeptides contain a plurality of domains. Such domains are known, and can be identified by those of skill in the art. For exemplification herein, definitions are provided, but it is understood that it is well within the skill in the art to recognize particular domains by name. If needed appropriate software can be employed to identify domains. It is understood that reference to amino acids, including to a specific sequence set forth as a SEQ ID NO used to describe domain organization of an IgSF domain are for illustrative purposes and are not meant to limit the scope of the embodiments provided. It is understood that polypeptides and the description of domains thereof are theoretically derived based on homology analysis and alignments with similar molecules. Thus, the exact locus can vary, and is not necessarily the same for each protein. Hence, the specific IgSF domain, such as specific IgV domain or IgC domain, can be several amino acids (one, two, three or four) longer or shorter.

The term "ectodomain" as used herein refers to the region of a membrane protein, such as a transmembrane protein, that lies outside the vesicular membrane. Ectodomains often comprise binding domains that specifically bind to ligands or cell surface receptors. The ectodomain of a cellular transmembrane protein is alternately referred to as an extracellular domain.

The terms "effective amount" or "therapeutically effective amount" refer to a quantity and/or concentration of a therapeutic composition of the invention, that when administered ex vivo (by contact with a cell from a patient) or in vivo (by administration into a patient) either alone (i.e., as a monotherapy) or in combination with additional therapeutic agents, yields a statistically significant inhibition of disease progression as, for example, by ameliorating or eliminating symptoms and/or the cause of the disease. An effective amount for treating an immune system disease or disorder may be an amount that relieves, lessens, or alleviates at least one symptom or biological response or effect associated with the disease or disorder, prevents progression of the disease or disorder, or improves physical functioning of the patient. In some embodiments the patient is a human patient.

The terms "enhanced" or "increased" as used herein in the context of increasing immunological activity of a mammalian lymphocyte means to increase interferon gamma (IFN-gamma) production, such as by a statistically significant amount. In some embodiments, the immunological activity can be assessed in a mixed lymphocyte reaction (MLR) assay. Methods of conducting MLR assays are known in the art. Wang et al., Cancer Immunol Res. 2014 September: 2(9):846-56. In some embodiments an enhancement can be an increase of at least 10%, 20%, 30%, 40%, 50%, 75%, 100%, 200%, 300%, 400%, or 500% greater than a non-zero control value.

The term "host cell" refers to a cell that can be used to express a protein encoded by a recombinant expression vector. A host cell can be a prokaryote, for example, *E. coli*, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Examples of host cells include Chinese hamster ovary (CHO) cells or their derivatives such as Veggie CHO and related cell lines which grow in serum-free media or CHO strain DX-B11, which is deficient in DHFR.

The term "immunological synapse" or "immune synapse" as used herein means the interface between a mammalian cell that expresses MHC I (major histocompatibility complex) or MHC II, such as an antigen-presenting cell or tumor cell, and a mammalian lymphocyte such as an effector T cell or Natural Killer (NK) cell.

The term "immunoglobulin" (abbreviated "Ig") as used herein is synonymous with the term "antibody" (abbreviated "Ab") and refers to a mammalian immunoglobulin protein including any of the five human classes: IgA (which includes subclasses IgA1 and IgA2), IgD, IgE, IgG (which includes subclasses IgG1, IgG2, IgG3, and IgG4), and IgM. The term is also inclusive of immunoglobulins that are less than full-length, whether wholly or partially synthetic (e.g., recombinant or chemical synthesis) or naturally produced, such as antigen binding fragment (Fab), variable fragment (Fv) containing $V_H$ and $V_L$, the single chain variable fragment (scFv) containing $V_H$ and $V_L$ linked together in one chain, as well as other antibody V region fragments, such as Fab', $F(ab)_2$, $F(ab')_2$, dsFv diabody, Fc, and Fd polypeptide fragments. Bispecific antibodies, homobispecific and heterobispecific, are included within the meaning of the term.

An Fc (fragment crystallizable) region or domain of an immunoglobulin molecule (also termed an Fc polypeptide) corresponds largely to the constant region of the immunoglobulin heavy chain, and is responsible for various functions, including the antibody's effector function(s). An immunoglobulin Fc fusion ("Fc-fusion") is a molecule comprising one or more polypeptides (or one or more small molecules) operably linked to an Fc region of an immunoglobulin. An Fc-fusion may comprise, for example, the Fc region of an antibody (which facilitates pharmacokinetics) and the IgSF domain of a wild-type or affinity modified immunoglobulin superfamily domain ("IgSF"), or other protein or fragment thereof. In some embodiments, the Fc additionally facilitates effector functions. In some embodiments, the Fc is a variant Fc that exhibits reduced (e.g. reduced greater than 30%, 40%, 50%, 60%, 70%, 80%, 90% or more) activity to facilitate an effector function. The IgSF domain mediates recognition of the cognate binding partner (comparable to that of antibody variable region of an antibody for an antigen). An immunoglobulin Fc region may be linked indirectly or directly to one or more polypeptides or small molecules (fusion partners). Various linkers are known in the art and can be used to link an Fc to a fusion partner to generate an Fc-fusion. An Fc-fusion protein of the invention typically comprises an immunoglobulin Fc region covalently linked, directly or indirectly, to at least one affinity modified IgSF domain. Fc-fusions of identical species can be dimerized to form Fc-fusion homodimers, or using non-identical species to form Fc-fusion heterodimers.

The term "immunoglobulin superfamily" or "IgSF" as used herein means the group of cell surface and soluble proteins that are involved in the recognition, binding, or adhesion processes of cells. Molecules are categorized as members of this superfamily based on shared structural features with immunoglobulins (i.e., antibodies); they all possess a domain known as an immunoglobulin domain or fold. Members of the IgSF include cell surface antigen receptors, co-receptors and co-stimulatory molecules of the immune system, molecules involved in antigen presentation to lymphocytes, cell adhesion molecules, certain cytokine receptors and intracellular muscle proteins. They are commonly associated with roles in the immune system. Proteins in the immunological synapse are often members of the IgSF. IgSF can also be classified into "subfamilies" based on shared properties such as function. Such subfamilies typically consist of from 4 to 30 IgSF members.

The terms "IgSF domain" or "immunoglobulin domain" or "Ig domain" as used herein refers a structural domain of IgSF proteins. Ig domains are named after the immunoglobulin molecules. They contain about 70-110 amino acids and are categorized according to their size and function. Ig-domains possess a characteristic Ig-fold, which has a sandwich-like structure formed by two sheets of antiparallel beta strands. Interactions between hydrophobic amino acids on the inner side of the sandwich and highly conserved disulfide bonds formed between cysteine residues in the B and F strands, stabilize the Ig-fold. One end of the Ig domain has a section called the complementarity determining region that is important for the specificity of antibodies for their ligands. The Ig like domains can be classified (into classes) as: IgV, IgC1, IgC2, or IgI. Most Ig domains are either variable (IgV) or constant (IgC). IgV domains with 9 beta strands are generally longer than IgC domains with 7 beta strands. Ig domains of some members of the IgSF resemble IgV domains in the amino acid sequence, yet are similar in size to IgC domains. These are called IgC2 domains, while standard IgC domains are called IgC1 domains. T-cell receptor (TCR) chains contain two Ig domains in the extracellular portion; one IgV domain at the N-terminus and one IgC1 domain adjacent to the cell membrane.

The term "IgSF species" as used herein means an ensemble of IgSF member proteins with identical or substantially identical primary amino acid sequence. Each mammalian immunoglobulin superfamily (IgSF) member defines a unique identity of all IgSF species that belong to that IgSF member. Thus, each IgSF family member is unique from other IgSF family members and, accordingly, each species of a particular IgSF family member is unique from the species of another IgSF family member. Nevertheless, variation between molecules that are of the same IgSF species may occur owing to differences in post-translational modification such as glycosylation, phosphorylation, ubiquitination, nitrosylation, methylation, acetylation, and lipidation. Additionally, minor sequence differences within a single IgSF species owing to gene polymorphisms constitute another form of variation within a single IgSF species as do wild type truncated forms of IgSF species owing to, for example, proteolytic cleavage. A "cell surface IgSF species" is an IgSF species expressed on the surface of a cell, generally a mammalian cell.

The term "immunological activity" as used herein in the context of mammalian lymphocytes means their expression of cytokines, such as chemokines or interleukins. Assays for determining enhancement or suppression of immunological activity include MLR assays for interferon-gamma (Wang et al., Cancer Immunol Res. 2014 September: 2(9):846-56), SEB (staphylococcal enterotoxin B) T cell stimulation assay (Wang et al., Cancer Immunol Res. 2014 September: 2(9): 846-56), and anti-CD3 T cell stimulation assays (Li and Kurlander, J Transl Med. 2010: 8: 104). Induction of an immune response results in an increase in immunological activity relative to quiescent lymphocytes. An immunomodulatory protein or affinity modified IgSF domain of the invention can in some embodiments increase or, in alternative embodiments, decrease IFN-gamma (interferon-gamma) expression in a primary T-cell assay relative to a wild-type IgSF member or IgSF domain control. Those of skill will recognize that the format of the primary T-cell assay used to determine an increase in IFN-gamma expression will differ from that employed to assay for a decrease in IFN-gamma expression. In assaying for the ability of an immunomodulatory protein or affinity modified IgSF domain of the invention to decrease IFN-gamma expression in a primary T-cell assay, a Mixed Lymphocyte Reaction (MLR) assay can be used as described in Example 6. Conveniently, a soluble form of an affinity modified IgSF domain of the invention can be employed to determine its ability to antagonize and thereby decrease the IFN-gamma expression in a MLR as likewise described in Example 6. Alternatively, in assaying for the ability of an immunomodulatory protein or affinity modified IgSF domain of the invention to increase IFN-gamma expression in a primary T-cell assay, a co-immobilization assay can be used. In a co-immobilization assay, a T-cell receptor signal, provided in some embodiments by anti-CD3 antibody, is used in conjunction with a co-immobilized affinity modified IgSF domain to determine the ability to increase IFN-gamma expression relative to a wild-type IgSF domain control.

An "immunomodulatory protein" is a protein that modulates immunological activity. By "modulation" or "modulating" an immune response is meant that immunological activity is either enhanced or suppressed. An immunomodulatory protein can be a single polypeptide chain or a multimer (dimers or higher order multimers) of at least two polypeptide chains covalently bonded to each other by, for example, interchain disulfide bonds. Thus, monomeric, dimeric, and higher order multimeric proteins are within the scope of the defined term. Multimeric proteins can be homomultimeric (of identical polypeptide chains) or heteromultimeric (of different polypeptide chains).

The term "increase" as used herein means to increase by a statistically significant amount. An increase can be at least 5%, 10%, 20%, 30%, 40%, 50%, 75%, 100%, or greater than a non-zero control value.

The term "lymphocyte" as used herein means any of three subtypes of white blood cell in a mammalian immune system. They include natural killer cells (NK cells) (which function in cell-mediated, cytotoxic innate immunity), T cells (for cell-mediated, cytotoxic adaptive immunity), and B cells (for humoral, antibody-driven adaptive immunity). T cells include: T helper cells, cytotoxic T-cells, natural killer T-cells, memory T-cells, regulatory T-cells, or gamma delta T-cells. Innate lymphoid cells (ILC) are also included within the definition of lymphocyte.

The terms "mammal," "subject," or "patient" specifically includes reference to at least one of a: human, chimpanzee, rhesus monkey, cynomolgus monkey, dog, cat, mouse, or rat.

The terms "modulating" or "modulate" as used herein in the contest of an immune response, such as a mammalian immune response, refer to any alteration, such as an increase or a decrease, of an existing or potential immune responses that occurs as a result of administration of an immunomodulatory protein of the present invention. Thus, it refers to an alteration, such as an increase or decrease, of an immune response as compared to the immune response that occurs or is present in the absence of the administration of the immunomodulatory protein. Such modulation includes any induction, or alteration in degree or extent, or suppression of immunological activity of an immune cell. Immune cells include B cells, T cells, NK (natural killer) cells, NK T cells, professional antigen-presenting cells (APCs), and non-professional antigen-presenting cells, and inflammatory cells (neutrophils, macrophages, monocytes, eosinophils, and basophils). Modulation includes any change imparted on an existing immune response, a developing immune response, a potential immune response, or the capacity to induce, regulate, influence, or respond to an immune response.

Modulation includes any alteration in the expression and/or function of genes, proteins and/or other molecules in immune cells as part of an immune response. Modulation of an immune response or modulation of immunological activity includes, for example, the following: elimination, deletion, or sequestration of immune cells; induction or generation of immune cells that can modulate the functional capacity of other cells such as autoreactive lymphocytes, antigen presenting cells, or inflammatory cells; induction of an unresponsive state in immune cells (i.e., anergy); enhancing or suppressing the activity or function of immune cells, including but not limited to altering the pattern of proteins expressed by these cells. Examples include altered production and/or secretion of certain classes of molecules such as cytokines, chemokines, growth factors, transcription factors, kinases, costimulatory molecules, or other cell surface receptors or any combination of these modulatory events. Modulation can be assessed, for example, by an alteration in IFN-gamma (interferon gamma) expression relative to or as compared to the wild-type or unmodified IgSF domain(s) control in a primary T cell assay (see, Zhao and Ji, Exp Cell Res. 2016 Jan. 1; 340(1) 132-138).

The term "molecular species" as used herein means an ensemble of proteins with identical or substantially identical primary amino acid sequence. Each mammalian immunoglobulin superfamily (IgSF) member defines a collection of identical or substantially identical molecular species. Thus, for example, human CD80 is an IgSF member and each human CD80 molecule is a species of CD80. Variation between molecules that are of the same molecular species may occur owing to differences in post-translational modification such as glycosylation, phosphorylation, ubiquitination, nitrosylation, methylation, acetylation, and lipidation. Additionally, minor sequence differences within a single molecular species owing to gene polymorphisms constitute another form of variation within a single molecular species as do wild type truncated forms of a single molecular species owing to, for example, proteolytic cleavage. A "cell surface molecular species" is a molecular species expressed on the surface of a mammalian cell. Two or more different species of protein, each of which is present exclusively on one or exclusively the other (but not both) of the two mammalian cells forming the IS, are said to be in "cis" or "cis configuration" with each other. Two different species of protein, the first of which is exclusively present on one of the two mammalian cells forming the IS and the second of which is present exclusively on the second of the two mammalian cells forming the IS, are said to be in "trans" or "trans configuration." Two different species of protein each of which is present on both of the two mammalian cells forming the IS are in both cis and trans configurations on these cells.

The term "non-competitive binding" as used herein means the ability of a protein to specifically bind simultaneously to at least two cognate binding partners. In some embodiments, the binding occurs under specific binding conditions. Thus, the protein is able to bind to at least two different cognate binding partners at the same time, although the binding interaction need not be for the same duration such that, in some cases, the protein is specifically bound to only one of the cognate binding partners. In some embodiments, the simultaneous binding is such that binding of one cognate binding partner does not substantially inhibit simultaneous binding to a second cognate binding partner. In some embodiments, non-competitive binding means that binding a second cognate binding partner to its binding site on the protein does not displace the binding of a first cognate binding partner to its binding site on the protein. Methods of assessing non-competitive binding are well known in the art such as the method described in Perez de La Lastra et al., Immunology, 1999 April: 96(4): 663-670. In some cases, in non-competitive interactions, the first cognate binding partner specifically binds at an interaction site that does not overlap with the interaction site of the second cognate binding partner such that binding of the second cognate binding partner does not directly interfere with the binding of the first cognate binding partner. Thus, any effect on binding of the cognate binding partner by the binding of the second cognate binding partner is through a mechanism other than direct interference with the binding of the first cognate binding partner. For example, in the context of enzyme-substrate interactions, a non-competitive inhibitor binds to a site other than the active site of the enzyme. Non-competitive binding encompasses uncompetitive binding interactions in which a second cognate binding partner specifically binds at an interaction site that does not overlap with the binding of the first cognate binding partner but binds to the second interaction site only when the first interaction site is occupied by the first cognate binding partner.

The terms "nucleic acid" and "polynucleotide" are used interchangeably to refer to a polymer of nucleic acid residues (e.g., deoxyribonucleotides or ribonucleotides) in either single- or double-stranded form. Unless specifically limited, the terms encompass nucleic acids containing known analogues of natural nucleotides and that have similar binding properties to it and are metabolized in a manner similar to naturally-occurring nucleotides. Unless otherwise indicated, a particular nucleic acid sequence also implicitly encompasses conservatively modified variants thereof (e.g., degenerate codon substitutions) and complementary nucleotide sequences as well as the sequence explicitly indicated. Specifically, degenerate codon substitutions may be achieved by generating sequences in which the third position of one or more selected (or all) codons is substituted with mixed-base and/or deoxyinosine residues. The term nucleic acid or polynucleotide encompasses cDNA or mRNA encoded by a gene.

The term "pharmaceutical composition" refers to a composition suitable for pharmaceutical use in a mammalian subject, often a human. A pharmaceutical composition typically comprises an effective amount of an active agent (e.g., an immunomodulatory protein of the invention) and a carrier, excipient, or diluent. The carrier, excipient, or diluent is typically a pharmaceutically acceptable carrier, excipient or diluent, respectively.

The terms "polypeptide" and "protein" are used interchangeably herein and refer to a molecular chain of two or more amino acids linked through peptide bonds. The terms do not refer to a specific length of the product. Thus, "peptides," and "oligopeptides," are included within the definition of polypeptide. The terms include post-translational modifications of the polypeptide, for example, glycosylations, acetylations, phosphorylations and the like. The terms also include molecules in which one or more amino acid analogs or non-canonical or unnatural amino acids are included as can be synthesized, or expressed recombinantly using known protein engineering techniques. In addition, proteins can be derivatized as described herein by well-known organic chemistry techniques.

The term "primary T-cell assay" as used herein refers to an in vitro assay to measure interferon-gamma ("IFN-gamma") expression. A variety of such primary T-cell assays are known in the art such as that described in Example 6. In a preferred embodiment, the assay used is anti-CD3 coimmobilization assay. In this assay, primary T cells are stimulated by anti-CD3 immobilized with or without additional recombinant proteins. Culture supernatants are harvested at timepoints, usually 24-72 hours. In another embodiment, the assay used is a mixed lymphocyte reaction (MLR). In this assay, primary T cells are simulated with allogenic APC. Culture supernatants are harvested at timepoints, usually 24-72 hours. Human IFN-gamma levels are measured in culture supernatants by standard ELISA techniques. Commercial kits are available from vendors and the assay is performed according to manufacturer's recommendation.

The term "purified" as applied to nucleic acids or immunomodulatory proteins of the invention generally denotes a nucleic acid or polypeptide that is substantially free from other components as determined by analytical techniques well known in the art (e.g., a purified polypeptide or polynucleotide forms a discrete band in an electrophoretic gel, chromatographic eluate, and/or a media subjected to density gradient centrifugation). For example, a nucleic acid or polypeptide that gives rise to essentially one band in an electrophoretic gel is "purified." A purified nucleic acid or immunomodulatory protein of the invention is at least about 50% pure, usually at least about 75%, 80%, 85%, 90%, 95%, 96%, 99% or more pure (e.g., percent by weight or on a molar basis).

The term "recombinant" indicates that the material (e.g., a nucleic acid or a polypeptide) has been artificially (i.e., non-naturally) altered by human intervention. The alteration can be performed on the material within, or removed from, its natural environment or state. For example, a "recombinant nucleic acid" is one that is made by recombining nucleic acids, e.g., during cloning, affinity modification, DNA shuffling or other well-known molecular biological procedures. A "recombinant DNA molecule," is comprised of segments of DNA joined together by means of such molecular biological techniques. The term "recombinant protein" or "recombinant polypeptide" as used herein refers to a protein molecule (e.g., an immunomodulatory protein) which is expressed using a recombinant DNA molecule. A "recombinant host cell" is a cell that contains and/or expresses a recombinant nucleic acid. Transcriptional control signals in eukaryotes comprise "promoter" and "enhancer" elements. Promoters and enhancers consist of short arrays of DNA sequences that interact specifically with cellular proteins involved in transcription. Promoter and enhancer elements have been isolated from a variety of eukaryotic sources including genes in yeast, insect and mammalian cells and viruses (analogous control elements, i.e., promoters, are also found in prokaryotes). The selection of a particular promoter and enhancer depends on what cell type is to be used to express the protein of interest. The terms "in operable combination," "in operable order" and "operably linked" as used herein refer to the linkage of nucleic acid sequences in such a manner or orientation that a nucleic acid molecule capable of directing the transcription of a given gene and/or the synthesis of a desired protein molecule is produced. The term also refers to the linkage of amino acid sequences in such a manner so that a functional protein is produced and/or transported.

The term "recombinant expression vector" as used herein refers to a DNA molecule containing a desired coding sequence (e.g., an immunomodulatory nucleic acid) and appropriate nucleic acid sequences necessary for the expression of the operably linked coding sequence in a particular host cell. Nucleic acid sequences necessary for expression in prokaryotes include a promoter, optionally an operator sequence, a ribosome binding site and possibly other sequences. Eukaryotic cells are known to utilize promoters, enhancers, and termination and polyadenylation signals. A secretory signal peptide sequence can also, optionally, be encoded by the recombinant expression vector, operably linked to the coding sequence for the inventive recombinant fusion protein, so that the expressed fusion protein can be secreted by the recombinant host cell, for more facile isolation of the fusion protein from the cell, if desired.

The term "sequence identity" as used herein refers to the sequence identity between genes or proteins at the nucleotide or amino acid level, respectively. "Sequence identity" is a measure of identity between proteins at the amino acid level and a measure of identity between nucleic acids at nucleotide level. The protein sequence identity may be determined by comparing the amino acid sequence in a given position in each sequence when the sequences are aligned. Similarly, the nucleic acid sequence identity may be determined by comparing the nucleotide sequence in a given position in each sequence when the sequences are aligned. Methods for the alignment of sequences for comparison are well known in the art, such methods include GAP, BESTFIT, BLAST, FASTA and TFASTA. The BLAST algorithm calculates percent sequence identity and performs a statistical analysis of the similarity between the two sequences. The software for performing BLAST analysis is publicly available through the National Center for Biotechnology Information (NCBI) website.

The term "soluble" as used herein in reference to proteins, means that the protein is not a membrane protein. In general, a soluble protein contains only the extracellular domain of an IgSF family member receptor, or a portion thereof containing an IgSF domain or domains or specific-binding fragments thereof.

The term "species" as used herein in the context of a nucleic acid sequence or a polypeptide sequence refers to an identical collection of such sequences. Slightly truncated sequences that differ (or encode a difference) from the full length species at the amino-terminus or carboxy-terminus by no more than 1, 2, or 3 amino acid residues are considered to be of a single species. Such microheterogeneities are a common feature of manufactured proteins.

The term "specifically binds" as used herein means the ability of a protein, under specific binding conditions, to bind to a target protein such that its affinity or avidity is at least 10 times as great, but optionally 50, 100, 250 or 500 times as great, or even at least 1000 times as great as the average affinity or avidity of the same protein to a collection of random peptides or polypeptides of sufficient statistical size. A specifically binding protein need not bind exclusively to a single target molecule (e.g., its cognate binding partner) but may specifically bind to a non-target molecule due to similarity in structural conformation between the target and non-target (e.g., paralogs or orthologs). Those of skill will recognize that specific binding to a molecule having the same function in a different species of animal (i.e., ortholog) or to a non-target molecule having a substantially similar epitope as the target molecule (e.g., paralog) is possible and does not detract from the specificity of binding which is determined relative to a statistically valid collection of unique non-targets (e.g., random polypeptides). Thus, an affinity modified polypeptide of the invention may specifically bind to more than one distinct species of target molecule due to cross-reactivity. Generally, such off-target specific binding is mitigated by reducing affinity or avidity for undesired targets. Solid-phase ELISA immunoassays or Biacore measurements can be used to determine specific binding between two proteins. Generally, interactions between two binding proteins have dissociation constants (Kd) less than $1\times10^{-5}$ M, and often as low as $1\times10^{-12}$ M. In certain aspects of the present disclosure, interactions between two binding proteins have dissociation constants of $1\times10^{-6}$ M, $1\times10^{-7}$ M, $1\times10^{-8}$ M, $1\times10^{-9}$ M, $1\times10^{-10}$ M or $1\times10^{-11}$ M.

The term "specific binding fragment" or "fragment" as used herein in reference to a mature (i.e., absent the signal peptide) wild-type IgSF domain, means a polypeptide that is shorter than the full-length mature IgSF domain and that specifically binds in vitro and/or in vivo to the mature wild-type IgSF domain's native cognate binding partner. In some embodiments, the specific binding fragment is at at least 20%, 30%, 40%, 50%, 60%, 70%, 75%, 80%, 85%, 90%, 95%, 96%, 97%, 98%, or 99% the sequence length of the full-length mature wild-type sequence. The specific binding fragment can be altered in sequence to form an affinity modified IgSF domain of the invention. In some embodiments, the specific binding fragment modulates immunological activity of a lymphocyte.

The terms "suppressed" or "decreased" as used herein means to decrease by a statistically significant amount. In some embodiments suppression can be a decrease of at least 10%, and up to 20%, 30%, 40%, 50%, 60%, 70%, 80%, or 90%.

The term "targeting moiety" as used herein refers to a composition that is covalently or non-covalently attached to, or physically encapsulates, a polypeptide comprising a wild-type and/or affinity modified IgSF domain of the present invention. The targeting moiety has specific binding affinity for a desired cognate binding partner such as a cell surface receptor or a tumor antigen such as tumor specific antigen (TSA) or a tumor associated antigen (TAA). Typically, the desired cognate binding partner is localized on a specific tissue or cell-type. Targeting moieties include: antibodies, antigen binding fragment (Fab), variable fragment (Fv) containing $V_H$ and $V_L$, the single chain variable fragment (scFv) containing $V_H$ and $V_L$ linked together in one chain, as well as other antibody V region fragments, such as Fab', $F(ab)_2$, $F(ab')_2$, dsFv diabody, nanobodies, soluble receptors, receptor ligands, affinity matured receptors or ligands, as well as small molecule (<500 dalton) compositions (e.g., specific binding receptor compositions). Targeting moieties can also be attached covalently or non-covalently to the lipid membrane of liposomes that encapsulate an immunomodulatory polypeptide of the present invention.

The terms "treating," "treatment," or "therapy" of a disease or disorder as used herein mean slowing, stopping or reversing the disease or disorders progression, as evidenced by decreasing, cessation or elimination of either clinical or diagnostic symptoms, by administration of an immunomodulatory protein of the present invention either alone or in combination with another compound as described herein. "Treating," "treatment," or "therapy" also means a decrease in the severity of symptoms in an acute or chronic disease or disorder or a decrease in the relapse rate as for example in the case of a relapsing or remitting autoimmune disease course or a decrease in inflammation in the case of an inflammatory aspect of an autoimmune disease. As used herein in the context of cancer, the terms "treatment" or, "inhibit," "inhibiting" or "inhibition" of cancer refers to at least one of: a statistically significant decrease in the rate of tumor growth, a cessation of tumor growth, or a reduction in the size, mass, metabolic activity, or volume of the tumor, as measured by standard criteria such as, but not limited to, the Response Evaluation Criteria for Solid Tumors (RECIST), or a statistically significant increase in progression free survival (PFS) or overall survival (OS). "Preventing," "prophylaxis," or "prevention" of a disease or disorder as used in the context of this invention refers to the administration of an immunomodulatory protein of the present invention, either alone or in combination with another compound, to prevent the occurrence or onset of a disease or disorder or some or all of the symptoms of a disease or disorder or to lessen the likelihood of the onset of a disease or disorder.

The term "tumor specific antigen" or "TSA" as used herein refers to an antigen that is present primarily on tumor cells of a mammalian subject but generally not found on normal cells of the mammalian subject. A tumor specific antigen need not be exclusive to tumor cells but the percentage of cells of a particular mammal that have the tumor specific antigen is sufficiently high or the levels of the tumor specific antigen on the surface of the tumor are sufficiently high such that it can be targeted by anti-tumor therapeutics, such as immunomodulatory polypeptides of the invention, and provide prevention or treatment of the mammal from the effects of the tumor. In some embodiments, in a random statistical sample of cells from a mammal with a tumor, at least 50% of the cells displaying a TSA are cancerous. In other embodiments, at least 60%, 70%, 80%, 85%, 90%, 95%, or 99% of the cells displaying a TSA are cancerous.

As used herein, "screening" refers to identification or selection of a molecule or portion thereof from a collection or library of molecules and/or portions thereof, based on determination of the activity or property of a molecule or portion thereof. Screening can be performed in any of a variety of ways, including, for example, by assays assessing direct binding (e.g. binding affinity) of the molecule to a target protein or by functional assays assessing modulation of an activity of a target protein.

The term "wild-type" or "natural" or "native" or "parental" as used herein is used in connection with biological materials such as nucleic acid molecules, proteins, IgSF members, host cells, and the like, refers to those which are found in nature and not modified by human intervention. A wild-type IgSF domain is a type of non-affinity modified IgSF domain. In some embodiments of immunomodulatory proteins of the invention, a non-affinity modified IgSF is a wild-type IgSF domain.

II. AFFINITY-MODIFIED IMMUNOMODULATORY PROTEINS

The present invention provides immunomodulatory proteins that have therapeutic utility by modulating immunological activity in a mammal with a disease or disorder in which modulation of the immune system response is beneficial.

The IgSF family members included within the scope of the immunomodulatory proteins of the present invention excludes antibodies (i.e., immunoglobulins) such as those that are mammalian or may be of mammalian origin. Thus, the present invention relates to non-immunoglobulin (i.e., non-antibody) IgSF domains. Wild-type mammalian IgSF family members that are not immunoglobulins (i.e. antibodies) are known in the art as are their nucleic and amino acid sequences. All non-immunoglobulin mammalian IgSF family members are included within the scope of the invention.

In some embodiments, the non-immunoglobulin IgSF family members, and the corresponding IgSF domains present therein, are of mouse, rat, cynomolgus monkey, or human origin. In some embodiments, the IgSF family members are members from at least or exactly one, two, three, four, five, or more IgSF subfamilies such as: Signal-Regulatory Protein (SIRP) Family, Triggering Receptor Expressed On Myeloid Cells Like (TREML) Family, Carcinoembryonic Antigen-related Cell Adhesion Molecule (CEACAM) Family, Sialic Acid Binding Ig-Like Lectin (SIGLEC) Family, Butyrophilin Family, B7 family, CD28 family, V-set and Immunoglobulin Domain Containing (VSIG) family, V-set transmembrane Domain (VSTM) family, Major Histocompatibility Complex (MHC) family, Signaling lymphocytic activation molecule (SLAM) family, Leukocyte immunoglobulin-like receptor (LIR), Nectin (Nec) family, Nectin-like (NECL) family, Poliovirus receptor related (PVR) family, Natural cytotoxicity triggering receptor (NCR) family, or Killer-cell immunoglobulin-like receptors (KIR) family.

In some embodiments, non-immunoglobulin IgSF family members, and the corresponding IgSF domains present therein, of an immunomodulatory protein of the invention, are affinity-modified compared to a mammalian IgSF member. In some embodiments, the mammalian IgSF member is one of the IgSF members or comprises an IgSF domain from one of the IgSF members as indicated in Table 1 including any mammalian orthologs thereof. Orthologs are genes in different species that evolved from a common ancestral gene by speciation. Normally, orthologs retain the same function in the course of evolution.

The first column of Table 1 provides the name and, optionally, the name of some possible synonyms for that particular IgSF member. The second column provides the protein identifier of the UniProtKB database, a publicly available database accessible via the internet at uniprot.org. The Universal Protein Resource (UniProt) is a comprehensive resource for protein sequence and annotation data. The UniProt databases include the UniProt Knowledgebase (UniProtKB). UniProt is a collaboration between the European Bioinformatics Institute (EMBL-EBI), the SIB Swiss Institute of Bioinformatics and the Protein Information Resource (PIR) and supported mainly by a grant from the U.S. National Institutes of Health (NIH). The third column provides the region where the indicated IgSF domain is located. The region is specified as a range where the domain is inclusive of the residues defining the range. Column 3 also indicates the IgSF domain class for the specified IgSF region. Colum 4 provides the region where the indicated additional domains are located (signal peptide, S; extracellular domain, E; transmembrane domain, T; cytoplasmic domain, C). Column 5 indicates for some of the listed IgSF members, some of its cognate cell surface binding partners.

Typically, the affinity modified IgSF domain of the provided embodiments is a human or murine affinity modified IgSF domain.

TABLE 1

IgSF members according to the present disclosure.

| IgSF Member (Synonyms) | UniProtKB Protein Identifier | IgSF Region & Domain Class | Other Domains | Cognate Cell Surface Binding Partners | IgSF Member Amino Acid Sequence (SEQ ID NO) Precursor (mature residues) | ECD |
|---|---|---|---|---|---|---|
| CD80 (B7-1) | NP_005182.1 P33681 | 35-138 or 37-138 IgV, 145-230 or 154-232 IgC | S: 1-34, E: 35-242, T: 243-263, C: 264-288 | CD28, CTLA4, PD-L1 | SEQ ID NO: 1 (35-288) | SEQ ID NO: 28 |
| CD86 (B7-2) | P42081.2 | 33-131 IgV, 150-225 IgC2 | S: 1-23, E: 24-247, T: 248-268, C: 269-329 | CD28, CTLA4 | SEQ ID NO: 2 (24-329) | SEQ ID NO: 29 |
| CD274 (PD-L1, B7-H1) | Q9NZQ7.1 | 24-130 IgV, 133-225 IgC2 | S: 1-18, E: 19-238, T: 239-259, C: 260-290 | PD-1, B7-1 | SEQ ID NO: 3 (19-290) | SEQ ID NO: 30 |
| PDCD1LG2 (PD-L2, CD273) | Q9BQ51.2 | 21-118 IgV, 122-203 IgC2 | S: 1-19, E: 20-220, T: 221-241, C: 242-273 | PD-1, RGMb | SEQ ID NO: 4 (20-273) | SEQ ID NO: 31 |
| ICOSLG (B7RP1, CD275, ICOSL, B7-H2) | O75144.2 | 19-129 IgV, 141-227 IgC2 | S: 1-18, E: 19-256, T: 257-277, C: 278-302 | ICOS, CD28, CTLA4 | SEQ ID NO: 5 (19-302) | SEQ ID NO: 32 |
| CD276 (B7-H3) | Q5ZPR3.1 | 29-139 IgV, 145-238 IgC2, 243-357 IgV, 367-453 IgC | S: 1-28, E: 29-466, T: 467-487, C: 488-534 | | SEQ ID NO: 6 (29-534) | SEQ ID NO: 33 |
| VTCN1 (B7-H4) | Q7Z7D3.1 | 35-146 IgV, 153-241 IgV | S: 1-24, E: 25-259, T: 260-280, C: 281-282 | | SEQ ID NO: 7 (25-282) | SEQ ID NO: 34 |
| CD28 | P10747.1 | 28-137 IgV | S: 1-18, E: 19-152, T: 153-179, C: 180-220 | B7-1, B7-2, B7RP1 | SEQ ID NO: 8 (19-220) | SEQ ID NO: 35 |
| CTLA4 | P16410.3 | 39-140 IgV | S: 1-35, E: 36-161, T: 162-182, C: 183-223 | B7-1, B7-2, B7RP1 | SEQ ID NO: 9 (36-223) | SEQ ID NO: 36 |

TABLE 1-continued

IgSF members according to the present disclosure.

| IgSF Member (Synonyms) | UniProtKB Protein Identifier | IgSF Region & Domain Class | Other Domains | Cognate Cell Surface Binding Partners | IgSF Member Amino Acid Sequence (SEQ ID NO) Precursor (mature residues) | ECD |
|---|---|---|---|---|---|---|
| PDCD1 (PD-1) | Q15116.3 | 35-145 IgV | S: 1-20, E: 21-170, T: 171-191, C: 192-288 | PD-L1, PD-L2 | SEQ ID NO: 10 (21-288) | SEQ ID NO: 37 |
| ICOS | Q9Y6W8.1 | 30-132 IgV | S: 1-20, E: 21-140, T: 141-161, C: 162-199 | B7RP1 | SEQ ID NO: 11 (21-199) | SEQ ID NO: 38 |
| BTLA (CD272) | Q7Z6A9.3 | 31-132 IgV | S: 1-30, E: 31-157, T: 158-178, C: 179-289 | HVEM | SEQ ID NO: 12 (31-289) | SEQ ID NO: 39 |
| CD4 | P01730.1 | 26-125 IgV, 126-203 IgC2, 204-317 IgC2, 317-389 IgC2 | S: 1-25, E: 26-396, T: 397-418, C: 419-458 | MHC class II | SEQ ID NO: 13 (26-458) | SEQ ID NO: 40 |
| CD8A (CD8-alpha) | P01732.1 | 22-135 IgV | S: 1-21, E: 22-182, T: 183-203, C: 204-235 | MHC class I | SEQ ID NO: 14 (22-235) | SEQ ID NO: 41 |
| CD8B (CD8-beta) | P10966.1 | 22-132 IgV | S: 1-21, E: 22-170, T: 171-191, C: 192-210 | MHC class I | SEQ ID NO: 15 (22-210) | SEQ ID NO: 42 |
| LAG3 | P18627.5 | 37-167 IgV, 168-252 IgC2, 265-343 IgC2, 349-419 IgC2 | S: 1-28, E: 29-450, T: 451-471, C: 472-525 | MHC class II | SEQ ID NO: 16 (29-525) | SEQ ID NO: 43 |
| HAVCR2 (TIM-3) | Q8TDQ0.3 | 22-124 IgV | S: 1-21, E: 22-202, T: 203-223, C: 224-301 | CEACAM-1, phosphatidylserine, Galectin-9, HMGB1 | SEQ ID NO: 17 (22-301) | SEQ ID NO: 44 |
| CEACAM1 | P13688.2 | 35-142 IgV, 145-232 IgC2, 237-317 IgC2, 323-413 IgC2 | S: 1-34, E: 35-428, T: 429-452, C: 453-526 | TIM-3 | SEQ ID NO: 18 (35-526) | SEQ ID NO: 45 |
| TIGIT | Q495A1.1 | 22-124 IgV | S: 1-21, E: 22-141, T: 142-162, C: 163-244 | CD155, CD112 | SEQ ID NO: 19 (22-244) | SEQ ID NO: 46 |
| PVR (CD155) | P15151.2 | 24-139 IgV, 145-237 IgC2, 244-328 IgC2 | S: 1-20, E: 21-343, T: 344-367, C: 368-417 | TIGIT, CD226, CD96, poliovirus | SEQ ID NO: 20 (21-417) | SEQ ID NO: 47 |
| PVRL2 (CD112) | Q92692.1 | 32-156 IgV, 162-256 IgC2, 261-345 IgC2 | S: 1-31, E: 32-360, T: 361-381, C: 382-538 | TIGIT, CD226, CD112R | SEQ ID NO: 21 (32-538) | SEQ ID NO: 48 |
| CD226 | Q15762.2 | 19-126 IgC2, 135-239 IgC2 | S: 1-18, E: 19-254, T: 255-275, C: 276-336 | CD155, CD112 | SEQ ID NO: 22 (19-336) | SEQ ID NO: 49 |
| CD2 | P06729.2 | 25-128 IgV, 129-209 IgC2 | S: 1-24, E: 25-209, T: 210-235, C: 236-351 | CD58 | SEQ ID NO: 23 (25-351) | SEQ ID NO: 50 |
| CD160 | O95971.1 | 27-122 IgV | N/A | HVEM, MHC family of proteins | SEQ ID NO: 24 (27-159) | SEQ ID NO: 51 |
| CD200 | P41217.4 | 31-141 IgV, 142-232 IgC2 | S: 1-30, E: 31-232, T: 233-259, C: 260-278 | CD200R | SEQ ID NO: 25 (31-278) | SEQ ID NO: 52 |

TABLE 1-continued

| IgSF members according to the present disclosure. | | | | | | |
|---|---|---|---|---|---|---|
| | | | | Cognate Cell | IgSF Member Amino Acid Sequence (SEQ ID NO) | |
| IgSF Member (Synonyms) | UniProtKB Protein Identifier | IgSF Region & Domain Class | Other Domains | Surface Binding Partners | Precursor (mature residues) | ECD |
| CD200R1 (CD200R) | Q8TD46.2 | 53-139 IgV, 140-228 IgC2 | S: 1-28, E: 29-243, T: 244-264, C: 265-325 | CD200 | SEQ ID NO: 26 (29-325) | SEQ ID NO: 53 |
| NCR3 (NKp30) | O14931.1 | 19-126 IgC-like | S: 1-18, E: 19-135, T: 136-156, C: 157-201 | B7-H6 | SEQ ID NO: 27 (19-201) | SEQ ID NO: 54 |

In some embodiments, the immunomodulatory proteins of the present invention comprise at least one affinity modified mammalian IgSF domain. The affinity modified IgSF domain can be affinity modified to specifically bind to a single or multiple (2, 3, 4, or more) cognate binding partners (also called a "counter structure ligand"). An IgSF domain can be affinity modified to independently increase or decrease specific binding affinity or avidity to each of the multiple cognate binding partners to which it binds. By this mechanism, specific binding to each of multiple cognate binding partners is independently tuned to a particular affinity or avidity.

In some embodiments, the cognate binding partner of an IgSF domain is at least one, and sometimes at least two or three of the cognate binding partners of the wild-type IgSF domain, such as those listed in Table 1. The sequence of the IgSF domain, such as a mammalian IgSF domain, is affinity modified by altering its sequence with at least one substitution, addition, or deletion. Alteration of the sequence can occur at the binding site for the cognate binding partner or at an allosteric site. In some embodiments, a nucleic acid encoding a IgSF domain, such as a mammalian IgSF domain, is affinity modified by substitution, addition, deletion, or combinations thereof, of specific and pre-determined nucleotide sites to yield a nucleic acid of the invention. In some contrasting embodiments, a nucleic acid encoding an IgSF domain, such as a mammalian IgSF domain, is affinity modified by substitution, addition, deletion, or combinations thereof, at random sites within the nucleic acid. In some embodiments, a combination of the two approaches (pre-determined and random) is utilized. In some embodiments, design of the affinity modified IgSF domains of the present invention is performed in silico.

In some embodiments, the affinity modified IgSF domain contains one or more amino acid substitutions (alternatively, "mutations" or "replacements") relative to a wild-type or unmodified polypeptide or a portion thereof containing an immunoglobulin superfamily (IgSF) domain, such as an IgV domain or an IgC domain or specific binding fragment of the IgV domain or the IgC domain. In some embodiments, the immunomodulatory protein comprises an affinity modified IgSF domain that contains an IgV domain or an IgC domain or specific binding fragments thereof in which the at least one of the amino acid substitutions is in the IgV domain or IgC domain or a specific binding fragment thereof. In some embodiments, by virtue of the altered binding activity or affinity, the IgV domain or IgC domain is an affinity-modified IgSF domain.

In some embodiments, the IgSF domain, such as a mammalian IgSF domain, is affinity modified in sequence with at least one but no more than a total of 2, 3, 4, 5, 6, 7, 8, 9, or 10 amino acid substitutions, additions, deletions, or combinations thereof. In some embodiments, the IgSF domain, such as a mammalian IgSF domain, is affinity modified in sequence with at least one but no more than 10, 9, 8, 7, 6, 5, 4, 3, or 2 amino acid substitutions. In some embodiments, the substitutions are conservative substitutions. In some embodiments, the substitutions are non-conservative. In some embodiments, the substitutions are a combination of conservative and non-conservative substitutions. In some embodiments, the modification in sequence is made at the binding site of the IgSF domain for its cognate binding partner.

In some embodiments, the wild-type or unmodified IgSF domain is a mammalian IgSF domain. In some embodiments, the wild-type or unmodified IgSF domain can be an IgSF domain that includes, but is not limited to, human, mouse, cynomolgus monkey, or rat. In some embodiments, the wild-type or unmodified IgSF domain is human.

In some embodiments, the wild-type or unmodified IgSF domain is an IgSF domain or specific binding fragment thereof contained in the sequence of amino acids set forth in any of SEQ ID NO:1-27 or a mature form thereof lacking the signal sequence, a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO:1-27 or a mature form thereof, or is a portion thereof containing an IgV domain or IgC domain or specific binding fragments thereof.

In some embodiments, the wild-type or unmodified IgSF domain is or comprises an extracellular domain of an IgSF family member or a portion thereof containing an IgSF domain (e.g. IgV domain or IgC domain). In some embodiments, the unmodified or wild-type IgSF domain comprises the amino acid sequence set forth in any of SEQ ID NOS:28-54, or an ortholog thereof. For example, the unmodified or wild-type IgSF domain can comprise (i) the sequence of amino acids set forth in any of SEQ ID NOS:28-54, (ii) a sequence of amino acids that has at least about 85%, 86%, 87%, 88%, 89%, 90%, 91%, 92%, 93%, 94%, 95%, 96%, 97%, 98%, 99% sequence identity to any of SEQ ID NOS: 28-54, or (iii) is a specific binding fragment of the sequence of amino acids set forth in any of SEQ ID NOS: 28-54 or a specific binding fragment of a sequence of amino acids that has at least at least about 85%, 86%, 87%, 88%, 89%, 90%, 91%, 92%, 93%, 94%, 95%, 96%, 97%, 98%, 99% sequence identity to any of SEQ ID NOS: 28-54 comprising an IgV domain or an IgC domain.

In some embodiments, the extracellular domain of an unmodified or wild-type IgSF domain can comprise more than one IgSF domain, for example, an IgV domain and an IgC domain. However, the affinity modified IgSF domain need not comprise both the IgV domain and the IgC domain. In some embodiments, the affinity modified IgSF domain comprises or consists essentially of the IgV domain or a specific binding fragment thereof. In some embodiments, the affinity modified IgSF domain comprises or consists essentially of the IgC domain or a specific binding fragment thereof. In some embodiments, the affinity modified IgSF domain comprises the IgV domain or a specific binding fragment thereof, and the IgC domain or a specific binding fragment thereof.

In some embodiments, the one or more amino acid substitutions of the affinity modified IgSF domain can be located in any one or more of the IgSF polypeptide domains. For example, in some embodiments, one or more amino acid substitutions are located in the extracellular domain of the IgSF polypeptide. In some embodiments, one or more amino acid substitutions are located in the IgV domain or specific binding fragment of the IgV domain. In some embodiments, one or more amino acid substitutions are located in the IgC domain or specific binding fragment of the IgC domain.

In some embodiments, at least one IgSF domain, such as a mammalian IgSF domain, of an immunomodulatory protein provided herein is independently affinity modified in sequence to have at least 99%, 98%, 97%, 96%, 95%, 94%, 93%, 92%, 91%, 90%, 89%, 88%, 87%, 86% 85%, or 80% sequence identity with a wild-type or unmodified IgSF domain or specific binding fragment thereof contained in a wild-type or unmodified IgSF protein, such as but not limited to, those disclosed in Table 1 as SEQ ID NOS: 1-27.

In some embodiments, the IgSF domain of an immunomodulatory protein provided herein is a specific binding fragment of a wild-type or unmodified IgSF domain contained in a wild-type or unmodified IgSF protein, such as but not limited to, those disclosed in Table 1 in SEQ ID NOS: 1-27. In some embodiments, the specific binding fragment can have an amino acid length of at least 50 amino acids, such as at least 60, 70, 80, 90, 100, or 110 amino acids. In some embodiments, the specific binding fragment of the IgV domain contains an amino acid sequence that is at least about 85%, 86%, 87%, 88%, 89%, 90%, 91%, 92%, 93%, 94%, 95%, 96%, 97%, 98%, 99% of the length of the wild-type or unmodified IgV domain. In some embodiments, the specific binding fragment of the IgC domain comprises an amino acid sequence that is at least about 85%, 86%, 87%, 88%, 89%, 90%, 91%, 92%, 93%, 94%, 95%, 96%, 97%, 98%, 99% of the length of the wild-type or unmodified IgC domain. In some embodiments, the specific binding fragment modulates immunological activity. In more specific embodiments, the specific binding fragment of an IgSF domain increases immunological activity. In alternative embodiments, the specific binding fragment decreases immunological activity.

To determine the percent identity of two nucleic acid sequences or of two amino acids, the sequences are aligned for optimal comparison purposes (e.g., gaps may be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment the two sequences are the same length. One may manually align the sequences and count the number of identical nucleic acids or amino acids. Alternatively, alignment of two sequences for the determination of percent identity may be accomplished using a mathematical algorithm. Such an algorithm is incorporated into the NBLAST and XBLAST programs. BLAST nucleotide searches may be performed with the NBLAST program, score=100, wordlength=12, to obtain nucleotide sequences homologous to a nucleic acid molecules of the invention. BLAST protein searches may be performed with the XBLAST program, score=50, wordlength=3 to obtain amino acid sequences homologous to a protein molecule of the invention. To obtain gapped alignments for comparison purposes, Gapped BLAST may be utilized. Alternatively, PSI-Blast may be used to perform an iterated search which detects distant relationships between molecules. When utilising the NBLAST, XBLAST, and Gapped BLAST programs, the default parameters of the respective programs may be used such as those available on the NCBI website. Alternatively, sequence identity may be calculated after the sequences have been aligned e.g. by the BLAST program in the NCBI database. Generally, the default settings with respect to e.g. "scoring matrix" and "gap penalty" may be used for alignment. In the context of the present invention, the BLASTN and PSI BLAST NCBI default settings may be employed.

In some embodiments, the immunomodulatory protein contains at least one affinity modified IgSF domain. In some embodiments, the immunomodulatory protein further contains at least one affinity modified domain and further contains at least one non-affinity modified IgSF domain (e.g. unmodified or wildtype IgSF domain). In some embodiments, the immunomodulatory protein contains at least two affinity modified domains. In some embodiments, the immunomodulatory protein can contain a plurality of non-affinity modified IgSF domains and/or affinity modified IgSF domains such as 1, 2, 3, 4, 5, or 6 non-affinity modified IgSF and/or affinity modified IgSF domains.

In some embodiments, at least one non-affinity modified IgSF domain and/or one affinity modified IgSF domain present in an immunomodulatory protein provided herein specifically binds to at least one cell surface molecular species expressed on mammalian cells forming the immunological synapse (IS). Of course, in some embodiments, an immunomodulatory protein provided herein comprises a plurality of non-affinity modified IgSF domains and/or affinity modified IgSF domains such as 1, 2, 3, 4, 5, or 6 non-affinity modified IgSF and/or affinity modified IgSF domains. One or more of these non-affinity modified IgSF domains and/or affinity modified IgSF domains can independently specifically bind to either one or both of the mammalian cells forming the IS.

Often, the cell surface molecular species to which the affinity modified IgSF domain specifically binds will be the cognate binding partner of the wild type IgSF family member or wild type IgSF domain that has been affinity modified. In some embodiments, the cell surface molecular species is a mammalian IgSF member. In some embodiments, the cell surface molecular species is a human IgSF member. In some embodiments, the cell surface molecular species will be the cell surface cognate binding partners as indicated in Table 1.

In some embodiments, the cell surface molecular species will be a viral protein, such as a poliovirus protein, on the cell surface of a mammalian cell such as a human cell.

In some embodiments, at least one non-affinity modified and/or affinity modified IgSF domain of an immunomodulatory protein provided herein binds to at least two or three cell surface molecular species present on mammalian cells forming the IS. The cell surface molecular species to which the non-affinity modified IgSF domains and/or the affinity modified IgSF domains of the invention specifically bind to can exclusively be on one or the other of the two mammalian cells (i.e. in cis configuration) forming the IS or, alternatively, the cell surface molecular species can be present on both.

In some embodiments, the affinity modified IgSF domain specifically binds to at least two cell surface molecular species wherein one of the molecular species is present on one of the two mammalian cells forming the IS and the other molecular species is present on the second of the two mammalian cells forming the IS. In such embodiments, the cell surface molecular species is not necessarily present solely on one or the other of the two mammalian cells forming the IS (i.e., in a trans configuration) although in some embodiments it is. Thus, embodiments provided herein include those wherein each cell surface molecular species is exclusively on one or the other of the mammalian cells forming the IS (cis configuration) as well as those where the cell surface molecular species to which each affinity modified IgSF binds is present on both of the mammalian cells forming the IS (i.e., cis and trans configuration).

Those of skill will recognize that antigen presenting cells (APCs) and tumor cells form an immunological synapse with lymphocytes. Thus, in some embodiments at least one non-affinity modified IgSF domain and/or at least one affinity modified IgSF domain of the immunomodulatory protein specifically binds to only cell surface molecular species present on a cancer cell, wherein the cancer cell in conjunction with a lymphocyte forms the IS. In other embodiments, at least one non-affinity modified IgSF domain and/or at least one affinity modified IgSF domain of the immunomodulatory protein specifically binds to only cell surface molecular species present on a lymphocyte, wherein the lymphocyte in conjunction with an APC or tumor cell forms the IS. In some embodiments, the non-affinity modified IgSF domain and/or affinity modified IgSF domain bind to cell surface molecular species present on both the target cell (or APC) and the lymphocyte forming the IS.

Embodiments of the invention include those in which an immunomodulatory protein provided herein comprises at least one affinity modified IgSF domain with an amino acid sequence that differs from a wild-type or unmodified IgSF domain (e.g. a mammalian IgSF domain) such that its binding affinity (or avidity if in a multimeric or other relevant structure), under specific binding conditions, to at least one of its cognate binding partners is either increased or decreased relative to the unaltered wild-type or unmodified IgSF domain control. In some embodiments, an affinity modified IgSF domain has a binding affinity for a cognate binding partner that differs from that of a wild-type or unmodified IgSF control sequence as determined by, for example, solid-phase ELISA immunoassays, flow cytometry or Biacore assays. In some embodiments, the IgSF domain has an increased binding affinity for one or more cognate binding partners. In some embodiments, the affinity modified IgSF domain has a decreased binding affinity for one or more cognate binding partners, relative to a wild-type or unmodified IgSF domain. In some embodiments, the cognate binding partner can be a mammalian protein, such as a human protein or a murine protein.

Binding affinities for each of the cognate binding partners are independent; that is, in some embodiments, an affinity modified IgSF domain has an increased binding affinity for one, two or three different cognate binding partners, and a decreased binding affinity for one, two or three of different cognate binding partners, relative to a wild-type or unmodified ICOSL polypeptide.

In some embodiments of an immunomodulatory protein provided herein, the binding affinity or avidity of the affinity modified IgSF domain is increased at least 10%, 20%, 30%, 40%, 50%, 100%, 200%, 300%, 400%, 500%, 1000%, 5000%, or 10,000% relative to the wild type or unmodified control IgSF domain. In some embodiments, the increase in binding affinity relative to the wild-type or unmodified IgSF domain is more than 1.2-fold, 1.5-fold, 2-fold, 3-fold, 4-fold, 5-fold, 6-fold, 7-fold, 8-fold, 9-fold, 10-fold, 20-fold, 30-fold 40-fold or 50-fold.

In some embodiments, the binding affinity or avidity is decreased at least 10%, and up to 20%, 30%, 40%, 50%, 60%, 70%, 80% or up to 90% relative to the wild type or unmodified control IgSF domain. In some embodiments, the decrease in binding affinity relative to the wild-type or unmodified IgSF domain is more than 1.2-fold, 1.5-fold, 2-fold, 3-fold, 4-fold, 5-fold, 6-fold, 7-fold, 8-fold, 9-fold, 10-fold, 20-fold, 30-fold 40-fold or 50-fold.

In some embodiments, the specific binding affinity of an affinity modified IgSF domain to a cognate binding partner can be at least $1\times10^{-5}$ M, $1\times10^{-6}$ M, $1\times10^{-7}$ M, $1\times10^{-8}$ M, $1\times10^{-9}$ M, $1\times10^{-10}$ M or $1\times10^{-11}$M, or $1\times10^{-12}$ M.

In some embodiments, an immunomodulatory protein provided comprises at least two IgSF domains in which at least one of the IgSF domain is affinity modified while in some embodiments both are affinity modified, and wherein at least one of the affinity modified IgSF domains has increased affinity (or avidity) to its cognate binding partner and at least one affinity modified IgSF domain has a decreased affinity (or avidity) to its cognate binding partner.

In some embodiments, an IgSF domain that otherwise binds to multiple cell surface molecular species is affinity modified such that it substantially no longer specifically binds to one of its cognate cell surface molecular species. Thus, in these embodiments the specific binding to one of its cognate cell surface molecular species is reduced to specific binding of no more than 10% of the wild type level and often no more than 7%, 5%, 3%, 1%, or no detectable or statistically significant specific binding.

In these embodiments, a specific binding site on a mammalian IgSF domain is inactivated or substantially inactivated with respect to at least one of the cell surface molecular species. Thus, for example, if a wild type IgSF domain specifically binds to exactly two cell surface molecular species then in some embodiments it is affinity modified to specifically bind to exactly one cell surface molecular species (whereby determination of the number of affinity modified IgSF domains disregards any substantially immunologically inactive fractional sequence thereof). And, if a wild type IgSF domain specifically binds to exactly three cell surface molecular species then in some embodiments it is affinity modified to specifically bind to exactly two cell surface molecular species. The IgSF domain that is affinity modified to substantially no longer specifically bind to one of its cognate cell surface molecular species can be an IgSF domain that otherwise specifically binds competitively or non-competitively to its cell surface molecular species.

Those of skill will appreciate that a wild type IgSF domain that competitively binds to two cognate binding partners can nonetheless be inactivated with respect to exactly one of them if, for example, their binding sites are not precisely coextensive but merely overlap such that specific binding of one inhibits binding of the other cognate binding partner and yet both competitive binding sites are distinct.

The non-affinity modified IgSF domains and/or affinity modified IgSF domains of the immunomodulatory proteins provided can in some embodiments specifically bind competitively to its cognate cell surface molecular species. In other embodiments the non-affinity modified IgSF domains and/or affinity modified IgSF domains of an immunomodulatory protein provided herein specifically bind non-competitively to its cognate cell surface molecular species. Any number of the non-affinity modified IgSF domains and/or affinity modified IgSF domains present in an immunomodulatory protein provided herein can specifically bind competitively or non-competitively.

In some embodiments, the immunomodulatory protein provided herein comprises at least two non-affinity modified IgSF domains, or at least one non-affinity modified IgSF domain and at least one affinity modified IgSF domain, or at least two affinity modified IgSF domains wherein one IgSF domain specifically binds competitively and a second IgSF domain binds non-competitively to its cognate cell surface molecular species. More generally, an immunomodulatory protein provided herein can comprise 1, 2, 3, 4, 5, or 6 competitive or 1, 2, 3, 4, 5, or 6 non-competitive binding non-affinity modified IgSF and/or affinity modified IgSF domains or any combination thereof. Thus, an immunomodulatory protein provided herein can have the number of non-competitive and competitive binding IgSF domains, respectively, of: 0 and 1, 0 and 2, 0 and 3, 0 and 4, 1 and 0, 1 and 1, 1 and 2, 1 and 3, 2 and 0, 2 and 1, 2 and 2, 2 and 3, 3 and 0, 3 and 1, 3 and 2, 3 and 3, 4 and 0, 4 and 1, and, 4 and 2.

A plurality of non-affinity modified and/or affinity modified IgSF domains immunomodulatory protein provided herein need not be covalently linked directly to one another. In some embodiments, an intervening span of one or more amino acid residues indirectly covalently bonds the non-affinity modified and/or affinity modified IgSF domains to each other. The linkage can be via the N-terminal to C-terminal residues.

In some embodiments, the linkage can be made via side chains of amino acid residues that are not located at the N-terminus or C-terminus of the non-affinity modified or affinity modified IgSF domain. Thus, linkages can be made via terminal or internal amino acid residues or combinations thereof.

The "peptide linkers" that link the non-affinity modified and/or affinity modified IgSF domains can be a single amino acid residue or greater in length. In some embodiments, the peptide linker has at least one amino acid residue but is no more than 20, 19, 18, 17, 16, 15, 14, 13, 12, 11, 10, 9, 8, 7, 6, 5, 4, 3, 2, or 1 amino acid residues in length. In some embodiments, the linker is (in one-letter amino acid code): GGGGS ("4GS") or multimers of the 4GS linker, such as repeats of 2, 3, 4, or 5 4GS linkers. In further optional embodiments, a series of alanine residues are interposed between 4GS linkers and to an Fc to which the immunomodulatory protein is covalently linked. In some embodiments, the number of alanine residues in each series is: 2, 3, 4, 5, or 6 alanines.

A. Exemplary Affinity Modified IgSF Domains

In some embodiments, the affinity modified IgSF domain has one or more amino acid substitutions in an IgSF domain of a wild-type or unmodified IgSF protein, such as set forth in Table 1 above. The one or more amino acid substitutions can be in the ectodomain of the wild-type or unmodified IgSF domain, such as the extracellular domain. In some embodiments, the one or more amino acid substitutions are in the IgV domain or specific binding fragment thereof. In some embodiments, the one or more amino acid substitutions are in the IgC domain or specific binding fragment thereof. In some embodiments of the affinity modified IgSF domain, some of the one or more amino acid substitutions are in the IgV domain or a specific binding fragment thereof, and some of the one or more amino acid substitutions are in the IgC domain or a specific binding fragment thereof.

In some embodiments, the affinity modified IgSF domain has up to 1, 2, 3, 4, 5, 6, 7, 8, 9, 10, 11, 12, 13, 14, 15, 16, 17, 18, 19, or 20 amino acid substitutions. The substitutions can be in the IgV domain or the IgC domain. In some embodiments, the affinity modified IgSF domain has up to 1, 2, 3, 4, 5, 6, 7, 8, 9, 10, 11, 12, 13, 14, 15, 16, 17, 18, 19, or 20 amino acid substitutions in the IgV domain or specific binding fragment thereof. In some embodiments, the affinity modified IgSF domain has up to 1, 2, 3, 4, 5, 6, 7, 8, 9, 10, 11, 12, 13, 14, 15, 16, 17, 18, 19, or 20 amino acid substitutions in the IgC domain or specific binding fragment thereof. In some embodiments, the affinity modified IgSF domain has at least about 85%, 86%, 86%, 88%, 89%, 90%, 91%, 92%, 93%, 94%, 95%, 96%, 97%, 98%, or 99% sequence identity with the wild-type or unmodified IgSF domain or specific binding fragment thereof, such as the IgSF domain contained in the IgSF protein set forth in any of SEQ ID NOS: 1-27.

In some embodiments, the affinity modified IgSF domain contains one or more amino acid substitutions in a wild-type or unmodified IgSF domain of a B7 IgSF family member. In some embodiments, the B7 IgSF family member is CD80, CD86 or ICOS Ligand (ICOSL). In some embodiments, the affinity modified IgSF domain has at least about 85%, 86%, 86%, 88%, 89%, 90%, 91%, 92%, 93%, 94%, 95%, 96%, 97%, 98%, or 99% sequence identity with the wild-type or unmodified IgSF domain or specific binding fragment thereof, such as the IgSF domain contained in the IgSF protein set forth in any of SEQ ID NOS: 1, 2 or 5. Exemplary affinity modified IgSF domains of CD80 are set forth in Table 2. Exemplary affinity modified IgSF domains of ICOSL are set forth in Table 3. Exemplary affinity modified IgSF domains of CD86 are set forth in Table 4.

TABLE 2

Exemplary variant CD80 polypeptides

| Mutation(s) | ECD SEQ ID NO | IgV SEQ ID NO |
|---|---|---|
| Wild-type | 28 | 152 |
| L70Q/A91G | 55 | 153 |
| L70Q/A91G/T130A | 56 | |
| L70Q/A91G/I118A/T120S/T130A | 57 | |
| V4M/L70Q/A91G/T120S/T130A | 58 | 154 |
| L70Q/A91G/T120S/T130A | 59 | |
| V20L/L70Q/A91S/T120S/T130A | 60 | 155 |
| S44P/L70Q/A91G/T130A | 61 | 156 |
| L70Q/A91G/E117G/T120S/T130A | 62 | |
| A91G/T120S/T130A | 63 | 157 |
| L70R/A91G/T120S/T130A | 64 | 158 |
| L70Q/E81A/A91G/T120S/I127T/T130A | 65 | 159 |
| L70Q/Y87N/A91G/T130A | 66 | 160 |

TABLE 2-continued

| Exemplary variant CD80 polypeptides | | |
|---|---|---|
| Mutation(s) | ECD SEQ ID NO | IgV SEQ ID NO |
| T28S/L70Q/A91G/E95K/T120S/T130A | 67 | 161 |
| N63S/L70Q/A91G/T120S/T130A | 68 | 162 |
| K36E/I67T/L70Q/A91G/T120S/T130A/N152T | 69 | 163 |
| E52G/L70Q/A91G/T120S/T130A | 70 | 164 |
| K37E/F59S/L70Q/A91G/T120S/T130A | 71 | 165 |
| A91G/S103P | 72 | |
| K89E/T130A | 73 | 166 |
| A91G | 74 | |
| D60V/A91G/T120S/T130A | 75 | 167 |
| K54M/A91G/T120S | 76 | 168 |
| M38T/L70Q/E77G/A91G/T120S/T130A/N152T | 77 | 169 |
| R29H/E52G/L70R/E88G/A91G/T130A | 78 | 170 |
| Y31H/T41G/L70Q/A91G/T120S/T130A | 79 | 171 |
| V68A/110A | 80 | 172 |
| S66H/D90G/T110A/F116L | 81 | 173 |
| R29H/E52G/T120S/T130A | 82 | 174 |
| A91G/L102S | 83 | |
| I67T/L70Q/A91G/T120S | 84 | 175 |
| L70Q/A91G/T110A/T120S/T130A | 85 | |
| M38V/T41D/M43I/W50G/D76G/V83A/K89E/T120S/T130A | 86 | 176 |
| V22A/L70Q/S121P | 87 | 177 |
| A12V/S15F/Y31H/T41G/T130A/P137L/N152T | 88 | 178 |
| I67F/L70R/E88G/A91G/T120S/T130A | 89 | 179 |
| E24G/L25P/L70Q/T120S | 90 | 180 |
| A91G/F92L/F108L/T120S | 91 | 181 |
| R29D/Y31L/Q33H/K36G/M38I/T41A/M43R/M47T/E81V/L85R/K89N/A91T/F92P/K93V/R94L/I118T/N149S | 92 | 182 |
| R29D/Y31L/Q33H/K36G/M38I/T41A/M43R/M47T/E81V/L85R/K89N/A91T/F92P/K93V/R94L/N144S/N149S | 93 | |
| R29D/Y31L/Q33H/K36G/M38I/T41A/M42T/M43R/M47T/E81V/L85R/K89N/A91T/F92P/K93V/R94L/L148S/N149S | 94 | 183 |
| E24G/R29D/Y31L/Q33H/K36G/M38I/T41A/M43R/M47T/F59L/E81V/L85R/K89N/A91T/F92P/K93V/R94L/H96R/N149S/C182S | 95 | 184 |
| R29D/Y31L/Q33H/K36G/M38I/T41A/M43R/M47T/E81V/L85R/K89N/A91T/F92P/K93V/R94L/N149S | 96 | |
| R29V/M43Q/E81R/L85I/K89R/D90L/A91E/F92N/K93Q/R94G | 97 | 185 |
| T41I/A91G | 98 | 186 |
| K89R/D90K/A91G/F92Y/K93R/N122S/N177S | 99 | 187 |
| K89R/D90K/A91G/F92Y/K93R | 100 | |
| K36G/K37Q/M38I/F59L/E81V/L85R/K89N/A91T/F92P/K93V/R94L/E99G/T130A/N149S | 101 | 188 |
| E88D/K89R/D90K/A91G/F92Y/K93R | 102 | 189 |
| K36G/K37Q/M38I/L40M | 103 | 190 |
| K36G | 104 | 191 |
| R29H/Y31H/T41G/Y87N/E88G/K89E/D90N/A91G/P109S | 105 | 192 |
| A12T/H18L/N43V/F59L/E77K/P109S/I118T | 106 | 193 |
| R29V/Y31F/K36G/M38L/N43Q/E81R/V83I/L85I/K89R/D90L/A91E/F92N/K93Q/R94G | 107 | 194 |
| V68M/L70P/L72P/K86E | 108 | 195 |

TABLE 3

| Exemplary variant ICOSL polypeptides | | |
|---|---|---|
| Mutation(s) | ECD SEQ ID NO | IgV SEQ ID NO |
| Wild-type | 32 | 196 |
| N52S | 109 | 197 |
| N52H | 110 | 198 |
| N52D | 111 | 199 |

TABLE 3-continued

| Exemplary variant ICOSL polypeptides | | |
|---|---|---|
| Mutation(s) | ECD SEQ ID NO | IgV SEQ ID NO |
| N52Y/N57Y/F138L/L203P | 112 | 200 |
| N52H/N57Y/Q100P | 113 | 201 |
| N52S/Y146C/Y152C | 114 | |
| N52H/C198R | 115 | |
| N52H/C140D/T225A | 116 | |
| N52H/C198R/T225A | 117 | |
| N52H/K92R | 118 | 202 |
| N52H/S99G | 119 | 203 |
| N52Y | 120 | 204 |
| N57Y | 121 | 205 |
| N57Y/Q100P | 122 | 206 |
| N52S/S130G/Y152C | 123 | |
| N52S/Y152C | 124 | |
| N52S/C198R | 125 | |
| N52Y/N57Y/Y152C | 126 | |
| N52Y/N57Y/129P/C198R | 127 | |
| N52H/L161P/C198R | 128 | |
| N52S/T113E | 129 | |
| S54A | 130 | 207 |
| N52D/S54P | 131 | 208 |
| N52K/L208P | 132 | 209 |
| N52S/Y152H | 133 | |
| N52D/V151A | 134 | |
| N52H/I143T | 135 | |
| N52S/L80P | 136 | 210 |
| F120S/Y152H/N201S | 137 | |
| N52S/R75Q/L203P | 138 | 211 |
| N52S/D158G | 139 | |
| N52D/Q133H | 140 | |
| N52S/N57Y/H94D/L96F/L98F/Q100R | 141 | 212 |
| N52S/N57Y/H94D/L96F/L98F/Q100R/G103E/F120S | 142 | 213 |
| N52S/G103E | 239 | 240 |

TABLE 4

| Exemplary variant CD86 polypeptides | | |
|---|---|---|
| Mutation(s) | ECD SEQ ID NO | IgC SEQ ID NO |
| Wild-type | 29 | 220 |
| Q35H/H90L/Q102H | 148 | 221 |
| Q35H | 149 | 222 |
| H90L | 150 | 223 |
| Q102H | 151 | 224 |

In some embodiments, the affinity modified IgSF domain contains one or more amino acid substitutions in a wild-type or unmodified IgSF domain of an NkP30 family member. In some embodiments, the affinity modified IgSF domain has at least about 85%, 86%, 86%, 88%, 89%, 90%, 91%, 92%, 93%, 94%, 95%, 96%, 97%, 98%, or 99% sequence identity with the wild-type or unmodified IgSF domain or specific binding fragment thereof, such as the IgSF domain contained in the IgSF protein set forth in SEQ ID NO: 27. Table 5 provides exemplary affinity modified NkP30 IgSF domains.

TABLE 5

| Exemplary variant NKp30 polypeptides | | |
|---|---|---|
| Mutation(s) | ECD SEQ ID NO | IgV SEQ ID NO |
| Wild-type | 54 | 214 |
| L30V/A60V/S64P/S86G | 143 | 215 |
| L30V | 144 | 216 |
| A60V | 145 | 217 |
| S64P | 146 | 218 |
| S86G | 147 | 219 |

B. Types of Affinity-Modified Immunomodulatory Protein

I. Dual Binding Affinity Modified Domain

In some embodiments, the immunomodulatory protein provided herein can comprise the sequence of at least one IgSF domain of a wild-type mammalian non-immunoglobulin (i.e., non-antibody) IgSF family member, wherein at least one IgSF domain therein is affinity modified ("Type I" immunomodulatory proteins). In some embodiments, the at least one modified IgSF domain specifically binds non-competitively to the at least two cognate binding partners.

In some embodiments, the immunomodulatory protein comprises at least one non-immunoglobulin affinity modified immunoglobulin superfamily (IgSF) domain that specifically binds non-competitively to at least two cognate binding partners. In some embodiments, the affinity modified domain exhibits increased binding to at least one of the cognate binding partners compared to the wild-type or unmodified IgSF domain. In some embodiments, the affinity modified domain exhibits increased binding to at least two different cognate binding partners.

In some embodiments of a Type I immunomodulatory protein of the invention, the unmodified or wild-type IgSF member, such as mammalian IgSF member, is one of the IgSF members or comprise an IgSF domain from one of the IgSF members as indicated in Table 1 including any mammalian orthologs thereof.

In some embodiments, additional IgSF domains present within the Type I immunomodulatory protein can be non-affinity modified and/or affinity modified, such as at least two, three, four, or five IgSF domains and, in some embodiments, exactly two, three, four, or five IgSF domains.

In some embodiments, a Type I immunomodulatory protein herein comprising at least one non-immunoglobulin affinity modified immunoglobulin superfamily (IgSF) domain comprising one or more amino acid substitution(s) in a wild-type or unmodified IgSF domain, in which the affinity modified IgSF domain has 1) altered, e.g. increased or decreased, binding to at least two cognate binding partners compared to the wild-type or unmodified IgSF domain; and 2) the at least one affinity modified IgSF domain specifically binds non-competitively to the at least two cognate binding partners. In some embodiments, the affinity modified IgSF domain of the Type I immunomodulatory protein has increased binding to at least two cognate binding partners. In some embodiments, the affinity modified IgSF domain of the Type I immunomodulatory protein has decreased binding to at least two cognate binding partners. In some embodiments, the affinity modified IgSF domain of the Type I immunomodulatory protein has increased binding to at least one cognate binding partner and decreased binding to at least one other different cognate binding partner.

In some embodiments, the two cognate binding partners are expressed on the surface of at least two different cells, such as two different mammalian cells. For example, in some embodiments, one cognate binding partner is expressed on a lymphocyte and another cognate binding partner is expressed on an antigen-presenting cells. In some embodiments, the two cognate binding partners are expressed on the same cell type, such as same immune cell. In some embodiment, the Type I immunomodulatory protein is capable of modulating the immunological activity of one or more of the immune cells, such as the immunological activity of a lymphocyte, for example, a T cell. In some embodiments, immunological activity is increased. In some embodiments, immunological activity is decreased.

In some embodiments, the immunomodulatory protein comprises or consists essentially of only one affinity modified IgSF domain, which binds non-competitively to the at least two cognate binding partners. In some embodiments, the affinity modified domain is an affinity modified IgV domain. In some embodiments, the affinity modified domain is an affinity modified IgC domain.

In some embodiments, a Type I immunomodulatory protein provided herein comprises an affinity modified CD80 IgSF domain that non-competitively specifically binds to CD28 and PDL1. In some embodiments, the affinity modified CD80 IgSF domain is an IgV domain. In some embodiments, the immunomodulatory protein further comprises a further non-affinity modified IgSF domain.

2 Stacked or Multi-Domain Immunomodulatory Proteins

In some embodiments of the present invention, an immunomodulatory protein comprises a combination (a "non-wild-type combination") and/or arrangement (a "non-wild type arrangement" or "non-wild-type permutation") of an affinity modified and/or non-affinity modified IgSF domain sequences that are not found in wild-type IgSF family members ("Type II" immunomodulatory proteins). The sequences of the IgSF domains which are non-affinity modified (e.g., wild-type) or have been affinity modified can be mammalian, such as from mouse, rat, cynomolgus monkey, or human origin, or combinations thereof. The number of such non-affinity modified or affinity modified IgSF domains present in these embodiments of a Type II immunomodulatory protein (whether non-wild type combinations or non-wild type arrangements) is at least 2, 3, 4, or 5 and in some embodiments exactly 2, 3, 4, or 5 IgSF domains (whereby determination of the number of affinity modified IgSF domains disregards any non-specific binding fractional sequences thereof and/or substantially immunologically inactive fractional sequences thereof).

In some embodiments, the Type II immunomodulatory proteins of the invention comprise a non-wild type combination of IgSF domains wherein the IgSF domains can be an IgSF domain of an IgSF family member from those listed in Table 1. Thus, in some embodiments, the immunodulatory protein can contain a first and second IgSF domain that can each be an affinity-modified IgSF domain containing one or more amino acid substitutions compared to an IgSF domain contained in an IgSF family member set forth in Table 1.

In some embodiments, IgSF domains are each independently an affinity or non-affinity modified IgSF domain contained in an IgSF family member of a family selected from Signal-Regulatory Protein (SIRP) Family, Triggering Receptor Expressed On Myeloid Cells Like (TREML) Family, Carcinoembryonic Antigen-related Cell Adhesion Molecule (CEACAM) Family, Sialic Acid Binding Ig-Like Lectin (SIGLEC) Family, Butyrophilin Family, B7 family, CD28 family, V-set and Immunoglobulin Domain Containing (VSIG) family, V-set transmembrane Domain (VSTM) family, Major Histocompatibility Complex (MHC) family, Signaling lymphocytic activation molecule (SLAM) family, Leukocyte immunoglobulin-like receptor (LIR), Nectin (Nec) family, Nectin-like (NECL) family, Poliovirus receptor related (PVR) family, Natural cytotoxicity triggering receptor (NCR) family, T cell immunoglobulin and mucin (TIM) family or Killer-cell immunoglobulin-like receptors (KIR) family. In some embodiments, the IgSF domains are each independently derived from an IgSF protein selected from the group consisting of CD80 (B7-1), CD86 (B7-2), CD274 (PD-L1, B7-H1), PDCD1LG2 (PD-L2, CD273), ICOSLG (B7RP1, CD275, ICOSL, B7-H2), CD276 (B7-H3), VTCN1 (B7-H4), CD28, CTLA4, PDCD1 (PD-1), ICOS, BTLA (CD272), CD4, CD8A (CD8-alpha), CD8B (CD8-beta), LAG3, HAVCR2 (TIM-3), CEACAM1, TIGIT, PVR (CD155), PVRL2 (CD112), CD226, CD2, CD160, CD200, CD200R1 (CD200R), and NC R3 (NKp30).

In some embodiments, the IgSF domains independently contain one or more amino acid substitutions compared to an IgSF domain in a wild-type or unmodified IgSF domain, such as an IgSF domain in an IgSF family member set forth in Table 1. In some embodiments, the affinity-modified IgSF domain comprises at least 85%, 86%, 87%, 88%, 89%, 90%, 91%, 92%, 93%, 94%, 95%, 96%, 97%, 98%, 99% or more sequence identity to a wild-type or unmodified IgSF domain or a specific binding fragment thereof contained in the sequence of amino acids set forth in any of SEQ ID NOS: 1-27. In some embodiments, the wild-type or unmodified IgSF domain is an IgV domain or an IgC domain, such as an IgC1 or IgC2 domain. In some embodiments, the affinity modified IgSF domain is an affinity-modified IgV domain or IgC domain.

In some embodiments of a Type II immunomodulatory protein of the invention, the number of IgSF domains is at least 2 wherein the number of affinity modified and the number of non-affinity modified IgSF domains is each independently at least: 0, 1, 2, 3, 4, 5, or 6. Thus, the number of affinity modified IgSF domains and the number of non-affinity modified IgSF domains, respectively, (affinity modified IgSF domain: non-affinity modified IgSF domain), can be exactly or at least: 2:0 (affinity modified:wild-type), 0:2, 2:1, 1:2, 2:2, 2:3, 3:2, 2:4, 4:2, 1:1, 1:3, 3:1, 1:4, 4:1, 1:5, or 5:1.

In some embodiments of a Type II immunomodulatory protein, at least two of the non-affinity modified and/or affinity modified IgSF domains are identical IgSF domains.

In some embodiments, a Type II immunomodulatory protein of the present invention comprises at least two affinity modified and/or non-affinity modified IgSF domains from a single IgSF member but in a non-wild-type arrangement (alternatively, "permutation"). One illustrative example of a non-wild type arrangement or permutation is an immunomodulatory protein of the present invention comprising a non-wild-type order of affinity modified and/or non-affinity modified IgSF domain sequences relative to those found in the wild-type mammalian IgSF family member whose IgSF domain sequences served as the source of the non-affinity modified and/or affinity modified IgSF domains. The mammalian wild-type IgSF members in the preceding embodiment specifically includes those listed in Table 1. Thus, in one example, if the wild-type family member comprises an IgC1 domain proximal to the transmembrane domain of a cell surface protein and an IgV domain distal to the transmembrane domain, then an immunomodulatory protein of the present invention can comprise an IgV proximal and an IgC1 distal to the transmembrane domain albeit in a non-affinity modified and/or affinity modified form. The presence, in an immunomodulatory protein of the present invention, of both non-wild-type combinations and non-wild-type arrangements of non-affinity modified and/or affinity modified IgSF domains is also within the scope of the present invention.

In some embodiments of a Type II immunomodulatory protein, the non-affinity modified and/or affinity modified IgSF domains are non-identical (i.e., different) IgSF domains. Non-identical affinity modified IgSF domains specifically bind, under specific binding conditions, different cognate binding partners and are "non-identical" irrespective of whether or not the wild-type IgSF domains from which they are engineered was the same. Thus, for example, a non-wild-type combination of at least two non-identical IgSF domains in an immunomodulatory protein of the present invention can comprise at least one IgSF domain sequence whose origin is from and unique to one IgSF family member, and at least one of a second IgSF domain sequence whose origin is from and unique to another IgSF family member, wherein the IgSF domains of the immunomodulatory protein are in non-affinity modified and/or affinity modified form. However, in alternative embodiments, the two non-identical IgSF domains originate from the same IgSF domain sequence but at least one is affinity modified such that they specifically bind to different cognate binding partners.

In some embodiments, the number of non-identical non-affinity modified and/or affinity modified IgSF domains present in an immunomodulatory protein of the invention is at least 2, 3, 4, or 5 and in some embodiments exactly 2, 3, 4, or 5 non-identical non-affinity modified and/or affinity modified IgSF domains. In some embodiments, the non-identical IgSF domains are combinations from at least two IgSF members indicated in Table 1, and in some embodiments at least 3 or 4 IgSF members of Table 1.

In some specific embodiments, a Type II immunomodulatory protein of the invention comprises an affinity modified NKp30 IgSF domain and an affinity modified ICOSLG IgSF domain, affinity modified CD80 IgSF domain or an affinity modified CD86 IgSF domain. In some embodiments, a Type II immunomodulatory protein comprises an affinity modified IgSF domain from at least two B7 family members. In some embodiments, the immunomodulatory proteins comprises at least two affinity modified domains from an affinity modified CD80 IgSF domain, an affinity modified ICOSL IgSF domain or an affinity modified CD86 IgSF domain or specific binding fragments thereof. In some embodiments, the affinity modified domains are linked via at least or exactly 1, 2, 3, 4 G4S domains.

A plurality of non-affinity modified and/or affinity modified IgSF domains in a stacked immunomodulatory protein polypeptide chain need not be covalently linked directly to one another. In some embodiments, an intervening span of one or more amino acid residues indirectly covalently bonds the non-affinity modified and/or affinity modified IgSF domains to each other. The linkage can be via the N-terminal to C-terminal residues.

In some embodiments, the linkage can be made via side chains of amino acid residues that are not located at the N-terminus or C-terminus of the non-affinity modified and/or affinity modified IgSF domain. Thus, linkages can be made via terminal or internal amino acid residues or combinations thereof.

In some embodiments, the "peptide linkers" that link the non-affinity modified and/or affinity modified IgSF domains can be a single amino acid residue or greater in length. In some embodiments, the peptide linker has at least one amino acid residue but is no more than 20, 19, 18, 17, 16, 15, 14, 13, 12, 11, 10, 9, 8, 7, 6, 5, 4, 3, 2, or 1 amino acid residues in length. In some embodiments, the linker is (in one-letter amino acid code): GGGGS ("4GS") or multimers of the 4GS linker, such as repeats of 2, 3, 4, or 5 4GS linkers. In further optional embodiments, a series of alanine residues are interposed between a peptide linker (such as a 4GS linker or multimer thereof) and an Fc to which the immunomodulatory protein is covalently linked. In some embodiments, the number of alanine residues in each series is: 2, 3, 4, 5, or 6 alanines.

In some embodiments, the non-affinity modified and/or affinity modified IgSF domains are linked by "wild-type peptide linkers" inserted at the N-terminus and/or C-terminus of the first and/or second non-affinity modified and/or affinity modified IgSF domains. In some embodiments, there is present a leading peptide linker inserted at the N-terminus of the first IgSF domain and/or a first trailing sequence inserted at the C-terminus of the first non-affinity modified and/or affinity modified IgSF domain. In some embodiments, there is present a second leading peptide linker inserted at the N-terminus of the second IgSF domain and/or a second trailing sequence inserted at the C-terminus of the second non-affinity modified and/or affinity modified IgSF domain. When the first and second non-affinity modified and/or affinity modified IgSF domains are derived from the same parental protein and are connected in the same orientation, wild-type peptide linkers between the first and second non-affinity modified and/or affinity modified IgSF domains are not duplicated. For example, when the first trailing wild-type peptide linker and the second leading wild-type peptide linker are the same, the Type II immunomodulatory protein does not comprise either the first trailing wild-type peptide linker or the second leading wild-type peptide linker.

In some embodiments, the Type II immunomodulatory protein comprises a first leading wild-type peptide linker inserted at the N-terminus of the first non-affinity modified and/or affinity modified IgSF domain, wherein the first leading wild-type peptide linker comprises at least 5 (such as at least about any of 6, 7, 8, 9, 10, 11, 12, 13, 14, 15, or more) consecutive amino acids from the intervening sequence in the wild-type protein from which the first non-affinity modified and/or affinity modified IgSF domain is derived between the parental IgSF domain and the immediately preceding domain (such as a signal peptide or an IgSF domain). In some embodiments, the first leading wild-type peptide linker comprises the entire intervening sequence in the wild-type protein from which the first non-affinity modified and/or affinity modified IgSF domain is derived between the parental IgSF domain and the immediately preceding domain (such as a signal peptide or an IgSF domain).

In some embodiments, the Type II immunomodulatory protein further comprises a first trailing wild-type peptide linker inserted at the C-terminus of the first non-affinity modified and/or affinity modified IgSF domain, wherein the first trailing wild-type peptide linker comprises at least 5 (such as at least about any of 6, 7, 8, 9, 10, 11, 12, 13, 14, 15, or more) consecutive amino acids from the intervening sequence in the wild-type protein from which the first non-affinity modified and/or affinity modified IgSF domain is derived between the parental IgSF domain and the immediately following domain (such as an IgSF domain or a transmembrane domain). In some embodiments, the first trailing wild-type peptide linker comprises the entire intervening sequence in the wild-type protein from which the first non-affinity modified and/or affinity modified IgSF domain is derived between the parental IgSF domain and the immediately following domain (such as an IgSF domain or a transmembrane domain).

In some embodiments, the Type II immunomodulatory protein further comprises a second leading wild-type peptide linker inserted at the N-terminus of the second non-affinity modified and/or affinity modified IgSF domain, wherein the second leading wild-type peptide linker comprises at least 5 (such as at least about any of 6, 7, 8, 9, 10, 11, 12, 13, 14, 15, or more) consecutive amino acids from the intervening sequence in the wild-type protein from which the second non-affinity modified and/or affinity modified IgSF domain is derived between the parental IgSF domain and the immediately preceding domain (such as a signal peptide or an IgSF domain). In some embodiments, the second leading wild-type peptide linker comprises the entire intervening sequence in the wild-type protein from which the second non-affinity modified and/or affinity modified IgSF domain is derived between the parental IgSF domain and the immediately preceding domain (such as a signal peptide or an IgSF domain).

In some embodiments, the Type II immunomodulatory protein further comprises a second trailing wild-type peptide linker inserted at the C-terminus of the second non-affinity modified and/or affinity modified IgSF domain, wherein the second trailing wild-type peptide linker comprises at least 5 (such as at least about any of 6, 7, 8, 9, 10, 11, 12, 13, 14, 15, or more) consecutive amino acids from the intervening sequence in the wild-type protein from which the second non-affinity modified and/or affinity modified IgSF domain is derived between the parental IgSF domain and the immediately following domain (such as an IgSF domain or a transmembrane domain). In some embodiments, the second trailing wild-type peptide linker comprises the entire intervening sequence in the wild-type protein from which the second non-affinity modified and/or affinity modified IgSF domain is derived between the parental IgSF domain and the immediately following domain (such as an IgSF domain or a transmembrane domain).

Exemplary of a leading sequence and trailing sequence for a Type II protein containing a CD80 IgSF domain is set forth in SEQ ID NO:231 and SEQ ID NO:232. Exemplary of a leading sequence and trailing sequence for a Type II protein containing an ICOSL IgSF domain is set forth in SEQ ID NO: 233 and 234. Exemplary of a leading sequence and a trailing sequence for a Type II protein containing an CD86 IgSF domain is set forth in any of SEQ ID NOS: 236-238. Exemplary of a wild-type linker sequence for a Type II protein containing an NKp30 IgSF domain is set forth in SEQ ID NO:235.

C. Format of Affinity-Modified Immunomodulatory Protein

In some embodiments an immunomodulatory protein provided herein is in soluble form. Those of skill will appreciate that cell surface proteins typically have an intracellular, transmembrane, and extracellular domain (ECD) and that a soluble form of such proteins can be made using the extracellular domain or an immunologically active subsequence thereof. Thus, in some embodiments, the immunomodulatory protein containing an affinity modified IgSF domain lacks a transmembrane domain or a portion of the transmembrane domain. In some embodiments, the immunomodulatory protein containing an affinity modified IgSF domain lacks the intracellular (cytoplasmic) domain or a portion of the intracellular domain. In some embodiments, the immunomodulatory protein contains an affinity modified IgSF domain that only contains the ECD domain or a portion thereof containing an IgV domain and/or IgC domain or specific binding fragments thereof.

In some embodiments, the soluble form of an immunomodulatory protein of the present invention is covalently bonded, directly or indirectly, to an immunoglobulin Fc. Generally, the Fc is covalently bonded to the amino terminus of the immunomodulatory protein. The immunoglobulin Fc is in some embodiments a mammalian IgG class immunoglobulin, such as IgG1 or IgG2. In particular embodiments, the Fc will be human IgG1 or IgG2 Fc. It will be appreciated by those of skill in the art that small changes, such as 1, 2, 3, or 4, amino acid substitutions, deletions, additions, or combinations thereof, can be made to an Fc without substantially changing its pharmacokinetic properties. Such changes made be made, for example, to aid in manufacturability or to enhance, suppress, or eliminate antibody-dependent cell-mediated cytotoxicity. The term "Fc" as used herein is meant to embrace such molecules.

In some embodiments, the Fc is murine or human Fc. In some embodiments, the Fc is derived from IgG1, such as human IgG1. In some embodiments, the Fc comprises the amino acid sequence set forth in SEQ ID NO: 226 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO:226. In some embodiments, the Fc is derived from IgG2, such as human IgG2. In some embodiments, the Fc comprises the amino acid sequence set forth in SEQ ID NO: 227 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO:227.

In some embodiments, one or more amino acid modifications may be introduced into the Fc region of an IgSF-Fc variant fusion provided herein, thereby generating an Fc region variant. In some embodiments, the Fc region variant has decreased effector function. There are many examples of changes or mutations to Fc sequences that can alter effector function. For example, WO 00/42072, WO2006019447 and Shields et al. J Biol. Chem. 9(2): 6591-6604 (2001) describe exemplary Fc variants with improved or diminished binding to FcRs. The contents of those publications are specifically incorporated herein by reference.

In some embodiments, the Fc region that possesses some but not all effector functions, which makes it a desirable candidate for applications in which the half-life of the Fc fusion in vivo is important yet certain effector functions (such as CDC and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the Fc-ICOSL variant fusion lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assay methods may be employed (see, for example, ACTI™ non-radioactive cytotoxicity assay for flow cytometry (CellTechnology, Inc. Mountain View, Calif.; and CytoTox 96™ non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad. Sci. USA* 95:652-656 (1998). C1q binding assays may also be carried out to confirm that the Fc-ICOSL variant fusion is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (see, e.g., Petkova, S. B. et al., *Int'l. Immunol.* 18(12):1759-1769 (2006)).

Fc fusions with reduced effector function include those with substitution of one or more of Fc region residues 238, 265, 269, 270, 297, 327 and 329 by EU numbering (U.S. Pat. No. 6,737,056). Such Fc mutants include Fc mutants with substitutions at two or more of amino acid positions 265, 269, 270, 297 and 327 by EU numbering, including the so-called "DANA" Fc mutant with substitution of residues 265 and 297 to alanine (U.S. Pat. No. 7,332,581).

Certain Fc variants with improved or diminished binding to FcRs are described. (See, e.g., U.S. Pat. No. 6,737,056; WO 2004/056312, WO2006019447 and Shields et al., *J. Biol. Chem.* 9(2): 6591-6604 (2001).)

In some embodiments, alterations are made in the Fc region that result in diminished C1q binding and/or Complement Dependent Cytotoxicity (CDC), e.g., as described in U.S. Pat. No. 6,194,551, WO 99/51642, and Idusogie et al., *J. Immunol.* 164: 4178-4184 (2000).

In some embodiments, there is provided an ICOSL-Fc variant fusion comprising a variant Fc region comprising one or more amino acid substitutions which increase half-life and/or improve binding to the neonatal Fc receptor (FcRn). Antibodies with increased half-lives and improved binding to FcRn are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434 by EU numbering, e.g., substitution of Fc region residue 434 (U.S. Pat. No. 7,371,826).

See also Duncan & Winter, *Nature* 322:738-40 (1988); U.S. Pat. Nos. 5,648,260; 5,624,821; and WO 94/29351 concerning other examples of Fc region variants.

In some embodiments, the Fc is an IgG1 variant that contains at least one amino acid substitution that is N82G by numbering of SEQ ID NO:226 (corresponding to N297G by EU numbering). In some embodiments, the variant Fc region further comprises a C5S amino acid modification. For example, in some embodiments, the variant Fc region comprises the following amino acid modifications: C5S and N82G.

In some embodiments, indirect covalent bonding of an Fc to an immunomodulatory protein of the present invention can be made via, for example, via a single amino acid or via a peptide (two or more amino acid residues in length) linker. Further, the single polypeptide chains of such Fc-fusion molecules can be dimerized through a variety of means including via inter-polypeptide chain disulfide bonds. Dimerized forms of the immunomodulatory proteins of the invention can comprise two identical or substantially identical species of polypeptides of the invention (homodimers), or separate species of polypeptide chains of the invention (heterodimers). It will be appreciated that microheterogeneities can exist even between the same species of polypeptide chain owing to minor differences in amino-terminus and carboxy-terminus residues from minor differences in expression or proteolysis, or to differences resulting from post-translational modification. Nonetheless, such substantially identical chains are deemed to be homodimeric. Derivatized immunomodulatory proteins are within the scope of the present invention and are often made to, for example, provide altered physico-chemical or pharmacokinetic properties.

In even more specific embodiments, the preceding specific embodiments are covalently linked to an Fc, such as a human IgG1 or IgG2 domain. In a further specific embodiment, the Fc is attached to an immunomodulatory protein via one or more G4S domains, often with at least or exactly one, two, three, four, or five successive alanine residues directly linked to the Fc and to the immunomodulatory protein.

In other embodiments, an immunomodulatory protein provided herein is bound to a liposomal membrane. A variety of methods to covalently or non-covalently attach proteins to a liposome surface are known in the art such as by amide conjugation or disulfide/thioether conjugation.

D. Functional Activity of Immunomodulatory Proteins

In some embodiments, the immunomodulatory proteins containing an affinity modified IgSF domain provided herein (full-length and/or specific binding fragments or stack constructs or fusion thereof) exhibit immunomodulatory activity to modulate T cell activation. Functionally, and irrespective of whether specific binding to its cognate binding partner is increased or decreased, the immunomodulatory proteins provided herein act to enhance or suppress immunological activity of lymphocytes relative to lymphocytes under the appropriate assay controls, such as in an MLR assay. In some embodiments, an immunomodulatory protein provided herein comprises at least two affinity modified IgSF domains wherein at least one of the affinity modified IgSF domains acts to enhance immunological activity and at least one affinity modified IgSF domain acts to suppress immunological activity.

In some embodiments, the provided immunomodulatory proteins modulate IFN-gamma expression in a primary T cell assay relative to a wild-type or unmodified IgSF domain control. In some cases, modulation of IFN-gamma expression can increase or decrease IFN-gamma expression relative to the control. Assays to determine specific binding and IFN-gamma expression are well-known in the art and include the MLR (mixed lymphocyte reaction) assays measuring interferon-gamma cytokine levels in culture supernatants (Wang et al., *Cancer Immunol* Res. 2014 September: 2(9):846-56), SEB (staphylococcal enterotoxin B) T cell stimulation assay (Wang et al., *Cancer Immunol* Res. 2014 September: 2(9):846-56), and anti-CD3 T cell stimulation assays (Li and Kurlander, *J Transl Med.* 2010: 8: 104).

In some embodiments, an immunomodulatory protein containing an affinity modified domain can in some embodiments increase or, in alternative embodiments, decrease IFN-gamma (interferon-gamma) expression in a primary T-cell assay relative to a wild-type IgSF domain control. In some embodiments of the provided polypeptides containing an affinity modified IgSF domain, the polypeptide can increase IFN-gamma expression and, in alternative embodiments, decrease IFN-gamma expression in a primary T-cell assay relative to a wild-type ICOSL control. In some embodiments of the provided polypeptides containing multiple affinity modified IgSF domains, the polypeptide can increase IFN-gamma expression and, in alternative embodiments, decrease IFN-gamma expression in a primary T-cell assay relative to a wild-type IgSF domain control.

Those of skill will recognize that the format of the primary T-cell assay used to determine an increase in IFN-gamma expression can differ from that employed to assay for a decrease in IFN-gamma expression. In assaying for the ability of an immunomodulatory protein to decrease IFN-gamma expression in a primary T-cell assay, a Mixed Lymphocyte Reaction (MLR) assay can be used as described in Example 6. In some cases, a soluble form of immunomodulatory protein can be employed to determine the ability of the affinity modified IgSF domain to antagonize and thereby decrease the IFN-gamma expression in a MLR as likewise described in Example 6.

Alternatively, in assaying for the ability of an immunomodulatory protein to increase IFN-gamma expression in a primary T-cell assay, a co-immobilization assay can be used as described in Example 6. In a co-immobilization assay, a TCR signal, provided in some embodiments by anti-CD3 antibody, is used in conjunction with a co-immobilized immunomodulatory protein containing an affinity modified IgSF domain to determine the ability to increase IFN-gamma expression relative to an IgSF domain control. In some cases, a soluble form of an immunomodulatory protein that is multimerized to a degree to provide multivalent binding can be employed to determine the ability of the immunomodulatory protein to agonize and thereby increase the IFN-gamma expression in a MLR as likewise described in Example 6.

Use of proper controls is known to those of skill in the art, however, in the aforementioned embodiments, the control typically involves use of the unmodified IgSF domain, such as a wild-type of native IgSF isoform from the same mammalian species from which the IgSF domain was derived or developed. Irrespective of whether the binding affinity to either one or both of cognate binding partners is increased or decreased, a particular immunomodulatory protein in some embodiments will increase IFN-gamma expression and, in alternative embodiments, decrease IFN-gamma expression in a primary T-cell assay relative to a wild-type IgSF domain control.

In some embodiments, an immunomodulatory protein, e.g. containing an affinity modified IgSF domain, increases IFN-gamma expression (i.e., protein expression) relative to a wild-type or unmodified IgSF domain control by at least: 5%, 10%, 20%, 30%, 40%, 50%, 60%, 70%, 80%, 90%, or higher. In other embodiments, an immunomodulatory protein, e.g. containing an affinity modified IgSF domain, decreases IFN-gamma expression (i.e. protein expression) relative to a wild-type or unmodified IgSF domain control by at least: 5%, 10%, 20%, 30%, 40%, 50%, 60%, 70%, 80%, 90%, or higher. In some embodiments, an enhancement of immunological activity can be an increase of at least 10%, 20%, 30%, 40%, 50%, 75%, 100%, 200%, 300%, 400%, or 500% greater than a non-zero control value such as in a MLR assay. Wang et al., Cancer Immunol Res. 2014 September: 2(9):846-56. In some embodiments, suppression of immunological activity can be a decrease of at least 10%, and up to 20%, 30%, 40%, 50%, 60%, 70%, 80%, or 90%.

III. NUCLEIC ACIDS AND METHODS OF MAKING PROTEINS

The present invention provides isolated or recombinant nucleic acids collectively referred to as "nucleic acids of the invention" which encode any of the various embodiments of the immunomodulatory proteins (Type I and Type II) of the invention. Nucleic acids of the invention, including all described below, are useful in recombinant production (e.g., expression) of polypeptides of the invention. The nucleic acids of the invention can be in the form of RNA or in the form of DNA, and include mRNA, cRNA, recombinant or synthetic RNA and DNA, and cDNA. The nucleic acids of the invention are typically DNA molecules, and usually double-stranded DNA molecules. However, single-stranded DNA, single-stranded RNA, double-stranded RNA, and hybrid DNA/RNA nucleic acids or combinations thereof comprising any of the nucleotide sequences of the invention also are provided.

The present invention also relates to expression vectors and host cells useful in producing the immunomodulatory proteins of the present invention. The immunomodulatory proteins of the invention can be made in transformed host cells using recombinant DNA techniques. To do so, a recombinant DNA molecule encoding an immunomodulatory protein is prepared. Methods of preparing such DNA molecules are well known in the art. For instance, sequences coding for the peptides could be excised from DNA using suitable restriction enzymes. Alternatively, the DNA molecule could be synthesized using chemical synthesis techniques, such as the phosphoramidite method. Also, a combination of these techniques could be used. In some instances, a recombinant or synthetic nucleic acid may be generated through polymerase chain reaction (PCR).

The invention also includes expression vectors capable of expressing the immunomodulatory proteins in an appropriate host cell under conditions suited to expression of the immunomodulatory protein. A recombinant expression vector comprises the DNA molecule that codes for the immunomodulatory protein operatively linked to appropriate expression control sequences. Methods of affecting this operative linking, either before or after the DNA molecule is inserted into the vector, are well known. Expression control sequences include promoters, activators, enhancers, operators, ribosomal binding sites, start signals, stop signals, cap signals, polyadenylation signals, and other signals involved with the control of transcription or translation. The resulting recombinant expression vector having the DNA molecule thereon is used to transform an appropriate host. This transformation can be performed using methods well known in the art. In some embodiments, a nucleic acid of the invention further comprises nucleotide sequence that encodes a secretory or signal peptide operably linked to the nucleic acid encoding an immunomodulatory protein of the invention such that the immunomodulatory protein is recovered from the culture medium, host cell, or host cell periplasm.

Any of a large number of available and well-known host cells can be used in the practice of this invention. The selection of a suitable host is dependent upon a number of factors recognized by the art. These include, for example, compatibility with the chosen expression vector, toxicity of the peptides encoded by the DNA molecule, rate of transformation, ease of recovery of the peptides, expression characteristics, bio-safety and costs. A balance of these factors must be struck with the understanding that not all hosts can be equally effective for the expression of a particular DNA sequence. Host cells can be a variety of eukaryotic cells, such as in yeast cells, or with mammalian cells such as Chinese hamster ovary (CHO) or HEK293 cells. Host cells can also be prokaryotic cells, such as with *E. coli*. The transformed host is cultured under immunomodulatory protein expressing conditions, and then purified. Recombinant host cells can be cultured under conventional fermentation conditions so that the desired immunomodulatory proteins are expressed. Such fermentation conditions are well known in the art. Finally, the immunomodulatory proteins are recovered and purified from recombinant cell cultures by any of a number of methods well known in the art, including ammonium sulfate or ethanol precipitation, acid extraction, anion or cation exchange chromatography, phosphocellulose chromatography, hydrophobic interaction chromatography, and affinity chromatography. Protein refolding steps can be used, as desired, in completing configuration of the mature protein. Finally, high performance liquid chromatography (HPLC) can be employed in the final purification steps. Immunomodulatory proteins of the present invention can also be made by synthetic methods. Solid phase synthesis is the preferred technique of making individual peptides since it is the most cost-effective method of making small peptides. For example, well known solid phase synthesis techniques include the use of protecting groups, linkers, and solid phase supports, as well as specific protection and deprotection reaction conditions, linker cleavage conditions, use of scavengers, and other aspects of solid phase peptide synthesis. Peptides can then be assembled into the immunomodulatory proteins of the present invention.

The means by which the affinity modified IgSF domains of the immunomodulatory invention are designed or created is not limited to any particular method. In some embodiments, however, wild-type IgSF domains are mutagenized (site specific, random, or combinations thereof) from wild-type IgSF genetic material and screened for altered binding according to the methods disclosed in the Examples. Methods or mutagenizing nucleic acids is known to those of skill in the art. In some embodiments, the affinity modified IgSF domains are synthesized de novo utilizing protein or nucleic acid sequences available at any number of publicly available databases and then subsequently screened. The National Center for Biotechnology Information provides such information and its website is publicly accessible via the internet as is the UniProtKB database as discussed previously.

IV. METHODS OF SCREENING OR IDENTIFYING AFFINITY MODIFIED IGSF DOMAINS

Provided herein is a method of identifying an affinity modified immunomodulatory protein that is capable of binding to two or more cognate binding partners at the same time or in a non-competitive manner. In some embodiments, the method comprises: a) contacting a modified protein comprising at least one non-immunoglobulin modified immunoglobulin superfamily (IgSF) domain or specific binding fragment thereof with at least two cognate binding partners under conditions capable of effecting binding of the protein with the at least two cognate binding partners, wherein the at least one modified IgSF domain comprises one or more amino acid substitutions in a wild-type IgSF domain; b) identifying a modified protein comprising the modified IgSF domain that has increased binding to at least one of the two cognate binding partners compared to a protein comprising the wild-type IgSF domain; and c) selecting a modified protein comprising the modified IgSF domain that binds non-competitively to the at least two cognate binding partners, thereby identifying the affinity modified immunomodulatory protein. In some embodiments, the affinity modified protein that is selected is capable or binding the two cognate binding partners simultaneously at the same time. It is within the level of a skilled artisan to assess or determine the presence of non-competitive binding interactions of a protein for two more different ligands. Exemplary of such methods are described in Example 7.

In some embodiments, the IgSF domain is a non-immunoglobulin IgSF domain. In some embodiments, the modified or variant protein is one in which one or more amino acid substitutions, deletions or insertions have been made in the IgSF domain of any of a non-immunoglobulin IgSF family member, such as any set forth in Table 1. In some embodiments, the modified or variant IgSF domain or the modified protein containing the modified or variant IgSF domain contains at least 1, 2, 3, 4, 5, 6, 7, 8, 9, 10, 11, 12, 13, 14, 15, 16, 17, 18, 19 or 20 amino acid changes, such as amino acid substitutions.

In some embodiments, libraries of modified or variant proteins are generated by mutating any one or more amino acid residues of a protein known to contain a non-immunoglobulin IgSF domain using any method commonly known in the art. Any of the methods employed in the art for generating, engineering or diversifying a binding molecule can be used in generating a modified IgSF domain herein. Exemplary of such methods for generating, engineering or diversifying a binding molecule include, but are not limited to, methods described in U.S. Pat. Nos. 5,223,409; 5,571,698, 5,750,373, 5,821,047; 5,837,500; 5,733,743; 5,871,907; 5,969,108; 6,040,136; 6,172,197; 6,291,159; 6,955,877; 6,979,538; 6,831,161; 7,063,943; 7,118,879; 7,208,293; 7,332,571; 7,385,028; 7,696,312; 7,638,299; 7,888,533; 7,642,044; U.S. Patent Application No. US20080300163; US20090208454; US20090155843; US20080113412; US20100035812; US20100093608; US20110015345; For example, an IgSF-contain can be used in methods in place of other binding molecules in methods of diversification or engineering of biomolecules.

Methods for generating libraries of binding molecules and for creating diversity in the library are well known in the art and can be employed to generate libraries of protein variants. Approaches for generating diversity include targeted and non-targeted approaches well known in the art. For example, known approaches for generating diverse nucleic acid and polypeptide libraries include, but are not limited to error-prone PCR, cassette mutagenesis; mutual primer extension; template-assisted ligation and extension; codon cassette mutagenesis; oligonucleotide-directed mutagenesis; amplification using degenerate oligonucleotide primers, including overlap and two-step PCR; and combined approaches, such as combinatorial multiple cassette mutagenesis (CMCM) and related techniques. A skilled artisan is familiar with these techniques.

Examples of methods to mutate a protein to generate libraries of candidate modified protein molecules include methods that result in random mutagenesis across the entire protein sequence or methods that result in mutagenesis of a select region or domain of the protein. Mutations can be introduced randomly, using methods that result in random mutagenesis of the protein, or more systematically, using methods that specifically create single or multiple amino acid change at a targeted position. Both random mutagenesis and systematic site-directed mutagenesis can be used to introduce one or more mutations in the protein. The variant protein can harbor one or more amino acid substitutions, insertions or deletions compared to the wildtype or unmodified protein used as the scaffold to generate the library. The substitutions or insertions can be with any naturally occurring amino acids or non-naturally occurring amino acids.

In methods for identifying or generating a variant or modified protein containing a non-immunoglobulin IgSF domain in accord with the provided methods, one or more regions of the protein, such as an IgSF domain or domains of the protein, can be modified using random mutagenesis of a region to generate one or a plurality of modified protein molecules. For example, a library of variants can be generated containing a plurality of modified molecules that each differ by at least one amino acid replacement (i.e. substitution) deletion or insertion in an IgSF domain compared to a corresponding unmodified or wild-type protein containing the IgSF domain. The amino acid substitution(s) can be substitutions(s) of naturally occurring amino acids or non-naturally occurring amino acids compared to the unmodified or wild-type protein. Generally, the libraries provided herein include libraries containing at least 2, 3, 4, 5, 6, 7, 8, 9, 10, 20, 30, 40, 50, $10^2$, $10^3$, $10^4$, $2\times10^4$, $3\times10^4$, $4\times10^4$, $5\times10^4$, $6\times10^4$, $7\times10^4$, $8\times10^4$, $9\times10^4$, $10^5$, $10^6$, $10^7$, $10^8$, $10^9$ or more different members. The generated library containing a plurality of modified proteins can be generated as a display library, including a combinatorial library where display of the variant is by, for example, phage display, cell-surface display, bead display, ribosome display, or others. The libraries can be used to screen for modified or variant proteins containing non-immunoglobulin IgSF domains that specifically bind non-competitively to the at least two cognate binding partners.

In some embodiments, prior to selecting a modified protein comprising the modified IgSF domain that binds non-competitively to the at least two cognate binding partners, the method includes combining two or more modified IgSF domain or specific binding fragments thereof identified in step (b) to generate a stacked molecule construct containing a plurality of different modified IgSF domains.

Thus, in some embodiments, provided herein is a method of identifying an affinity modified immunomodulatory protein, comprising: a) contacting a modified protein comprising at least one non-immunoglobulin modified immunoglobulin superfamily (IgSF) domain or specific binding fragment thereof with at least two cognate binding partners under conditions capable of effecting binding of the protein with the at least two cognate binding partners, wherein the at least one modified IgSF domain comprises one or more amino acid substitutions in a wild-type IgSF domain; b) identifying a modified protein comprising the modified IgSF domain that has increased binding to at least one of the two cognate binding partners compared to a protein comprising the wild-type IgSF domain; c) combining two or more modified IgSF domains present in two or more identified proteins to generate a fusion (stacked) protein comprising a first modified IgSF domain linked to a second IgSF domain; and d) selecting a modified protein comprising the modified IgSF domains that binds non-competitively to the at least two cognate binding partners, thereby identifying the affinity modified immunomodulatory protein.

In some embodiments, the at least two cognate binding partners are cell surface molecular species expressed on the surface of a mammalian cell. In some embodiments, the cell surface molecular species are expressed in cis configuration or trans configuration. In some embodiments, the mammalian cell is one of two mammalian cells forming an immunological synapse (IS) and each of the cell surface molecular species is expressed on at least one of the two mammalian cells forming the IS. In some embodiments, at least one of the mammalian cells is a lymphocyte, which can be an NK cell or a T cell. In some embodiments, at least one of the mammalian cells is a tumor cell. In some embodiments, at least one of the mammalian cells is an antigen-presenting cell.

In some embodiments, the two or more cognate binding partners are independently a ligand of an IgSF member selected from CD80, CD86, PD-L1, PD-L2, ICOS Ligand, B7-H3, B7-H4, CD28, CTLA4, PD-1, ICOS, BTLA, CD4, CD8-alpha, CD8-beta, LAG3, TIM-3, CEACAM1, TIGIT, PVR, PVRL2, CD226, CD2, CD160, CD200, CD200R or Nkp30. In some embodiments, the two or more cognate binding partners are independently a ligand of a B7 family member. In some embodiments, the two or more cognate binding partners are selected from two or more of CD28, CTLA-4, ICOS or PD-L1.

V. PHARMACEUTICAL COMPOSITIONS AND FORMULATIONS

A pharmaceutical composition comprising a therapeutic composition of the invention may contain formulation materials for modifying, maintaining or preserving, for example, the pH, osmolarity, viscosity, clarity, color, isotonicity, odor, sterility, stability, rate of dissolution or release, adsorption, or penetration of the composition. The primary vehicle or carrier in a pharmaceutical composition may be either aqueous or non-aqueous in nature. For example, a suitable vehicle or carrier may be water for injection or physiological saline, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0-8.5, or acetate buffer of about pH 4.0-5.5, which may further include sorbitol or a suitable substitute therefore. In one embodiment of the present invention, binding agent compositions may be prepared for storage by mixing the selected composition having the desired degree of purity with optional formulation agents in the form of a lyophilized cake or an aqueous solution. Further, the binding agent product may be formulated as a lyophilizate using appropriate excipients such as sucrose.

The formulation components are present in concentrations that are acceptable to the site of administration. For example, buffers are used to maintain the composition at physiological pH or at slightly lower pH, typically within a pH range of from about 5 to about 8. A particularly suitable vehicle for parenteral administration is sterile distilled water in which a binding agent is formulated as a sterile, isotonic solution, properly preserved. Yet another preparation can involve the formulation of the desired molecule with an agent, such as injectable microspheres, bio-erodible particles, polymeric compounds (polylactic acid, polyglycolic acid), beads, or liposomes, that provide for the controlled or sustained release of the product which may then be delivered via a depot injection.

In another aspect, pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances that increase the viscosity of the suspension, such as sodium carboxymethyl cellulose, sorbitol, or dextran. Additional pharmaceutical compositions will be evident to those skilled in the art, including formulations involving binding agent molecules in sustained- or controlled-delivery formulations. Techniques for formulating a variety of other sustained- or controlled-delivery means, such as liposome carriers, bio-erodible microparticles or porous beads and depot injections, are also known to those skilled in the art. The pharmaceutical composition to be used for in vivo administration typically must be sterile. This may be accomplished by filtration through sterile filtration membranes. Where the composition is lyophilized, sterilization using this method may be conducted either prior to or following lyophilization and reconstitution. The composition for parenteral administration may be stored in lyophilized form or in solution. In addition, parenteral compositions generally are placed into a container having a sterile access port, for example, an intravenous solution bag or vial having a stopper pierceable by a hypodermic injection needle.

In some embodiments, the pharmaceutical composition is sterile. Sterilization may be accomplished by filtration through sterile filtration membranes or radiation. Where the composition is lyophilized, sterilization using this method may be conducted either prior to or following lyophilization and reconstitution. The composition for parenteral administration may be stored in lyophilized form or in solution. In addition, parenteral compositions generally are placed into a container having a sterile access port, for example, an intravenous solution bag or vial having a stopper pierceable by a hypodermic injection needle.

Once the pharmaceutical composition has been formulated, it may be stored in sterile vials as a solution, suspension, gel, emulsion, solid, or a dehydrated or lyophilized powder. Such formulations may be stored either in a ready-to-use form or in a form (e.g., lyophilized) requiring reconstitution prior to administration. An effective amount of a pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the binding agent molecule is being used, the route of administration, and the size (body weight, body surface or organ size) and condition (the age and general health) of the patient. Accordingly, the clinician may titer the dosage and modify the route of administration to obtain the optimal therapeutic effect. The therapeutic composition of the invention can be administered parentally, subcutaneously, or intravenously, or as described elsewhere herein. The therapeutic composition of the invention may be administered in a therapeutically effective amount one, two, three or four times per month, two times per week, biweekly (every two weeks), or bimonthly (every two months). Administration may last for a period of 1, 2, 3, 4, 5, 6, 7, 8, 9, 10, 11, or 12 months or longer (e.g., one, two, three, four or more years, including for the life of the subject).

Generally, dosages and routes of administration of the pharmaceutical composition are determined according to the size and condition of the subject, according to standard pharmaceutical practice. For example, the therapeutically effective dose can be estimated initially either in cell culture assays or in animal models such as mice, rats, rabbits, dogs, pigs, or monkeys. An animal model may also be used to determine the appropriate concentration range and route of administration. Such information can then be used to determine useful doses and routes for administration in humans. The exact dosage will be determined in light of factors related to the subject requiring treatment. Dosage and administration are adjusted to provide sufficient levels of the active compound or to maintain the desired effect. Factors that may be taken into account include the severity of the disease state, the general health of the subject, the age, weight, and gender of the subject, time and frequency of administration, drug combination(s), reaction sensitivities, and response to therapy.

In some embodiments, the pharmaceutical composition is administered to a subject through any route, including orally, transdermally, by inhalation, intravenously, intra-arterially, intramuscularly, direct application to a wound site, application to a surgical site, intraperitoneally, by suppository, subcutaneously, intradermally, transcutaneously, by nebulization, intrapleurally, intraventricularly, intra-articularly, intraocularly, or intraspinally.

In some embodiments, the dosage of the pharmaceutical composition is a single dose or a repeated dose. In some embodiments, the doses are given to a subject once per day, twice per day, three times per day, or four or more times per day. In some embodiments, about 1 or more (such as about 2 or more, about 3 or more, about 4 or more, about 5 or more, about 6 or more, or about 7 or more) doses are given in a week. In some embodiments, multiple doses are given over the course of days, weeks, months, or years. In some embodiments, a course of treatment is about 1 or more doses (such as about 2 or more does, about 3 or more doses, about 4 or more doses, about 5 or more doses, about 7 or more doses, about 10 or more doses, about 15 or more doses, about 25 or more doses, about 40 or more doses, about 50 or more doses, or about 100 or more doses).

In some embodiments, an administered dose of the pharmaceutical composition is about 1 μg of protein per kg subject body mass or more (such as about 2 μg of protein per kg subject body mass or more, about 5 μg of protein per kg subject body mass or more, about 10 μg of protein per kg subject body mass or more, about 25 μg of protein per kg subject body mass or more, about 50 μg of protein per kg subject body mass or more, about 100 μg of protein per kg subject body mass or more, about 250 μg of protein per kg subject body mass or more, about 500 μg of protein per kg subject body mass or more, about 1 mg of protein per kg subject body mass or more, about 2 mg of protein per kg subject body mass or more, or about 5 mg of protein per kg subject body mass or more).

For any compound, the therapeutically effective dose can be estimated initially either in cell culture assays or in animal models such as mice, rats, rabbits, dogs, pigs, or monkeys. An animal model may also be used to determine the appropriate concentration range and route of administration. Such information can then be used to determine useful doses and routes for administration in humans. The exact dosage will be determined in light of factors related to the subject requiring treatment. Dosage and administration are adjusted to provide sufficient levels of the active compound or to maintain the desired effect. Factors that may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation. The frequency of dosing will depend upon the pharmacokinetic parameters of the molecule in the formulation used. Typically, a composition is administered until a dosage is reached that achieves the desired effect. The composition may therefore be administered as a single dose, or as multiple doses (at the same or different concentrations/dosages) over time, or as a continuous infusion. Further refinement of the appropriate dosage is routinely made. Appropriate dosages may be ascertained through use of appropriate dose-response data.

In some embodiments, one or more biomarkers or physiological markers for therapeutic effect can be monitored including T cell activation or proliferation, cytokine synthesis or production (e.g., production of TNF-α, IFN-γ, IL-2), induction of various activation markers (e.g., CD25, IL-2 receptor), inflammation, joint swelling or tenderness, serum level of C-reactive protein, anti-collagen antibody production, and/or T cell-dependent antibody response(s).

An injectable pharmaceutical composition comprising a suitable pharmaceutically acceptable excipient or carrier (e.g., PBS) and an effective amount of a therapeutic composition of the invention can be administered parenterally, intramuscularly, intraperitoneally, intravenously, subdermally, transdermally, subcutaneously, or intradermally to a mammalian patient. Administration can be facilitated via liposomes. The skin and muscle are generally preferred targets for administration of the therapeutic composition of the invention, by any suitable technique. Thus, the delivery of the therapeutic composition of the invention into or through the skin of a mammalian subject (e.g., human), is a feature of the invention. Such molecules of the invention can be administered in a pharmaceutically acceptable injectable solution into or through the skin, e.g., intramuscularly, or intraperitoneally. Administration can also be accomplished by transdermal devices, or, more typically, biolistic delivery of the therapeutic composition of the invention into, or through the skin of the subject or into exposed muscle of the mammalian subject.

A variety of means are known for determining if administration of a therapeutic composition of the invention sufficiently modulates immunological activity by eliminating, sequestering, or inactivating immune cells mediating or capable of mediating an undesired immune response; inducing, generating, or turning on immune cells that mediate or are capable of mediating a protective immune response; changing the physical or functional properties of immune cells; or a combination of these effects. Examples of measurements of the modulation of immunological activity include, but are not limited to, examination of the presence or absence of immune cell populations (using flow cytometry, immunohistochemistry, histology, electron microscopy, polymerase chain reaction (PCR)); measurement of the functional capacity of immune cells including ability or resistance to proliferate or divide in response to a signal (such as using T cell proliferation assays and pepscan analysis based on 3H-thymidine incorporation following stimulation with anti-CD3 antibody, anti-T cell receptor antibody, anti-CD28 antibody, calcium ionophores, PMA, antigen presenting cells loaded with a peptide or protein antigen; B cell proliferation assays); measurement of the ability to kill or lyse other cells (such as cytotoxic T cell assays); measurements of the cytokines, chemokines, cell surface molecules, antibodies and other products of the cells (e.g., by flow cytometry, enzyme-linked immunosorbent assays, Western blot analysis, protein microarray analysis, immunoprecipitation analysis); measurement of biochemical markers of activation of immune cells or signaling pathways within immune cells (e.g., Western blot and immunoprecipitation analysis of tyrosine, serine or threonine phosphorylation, polypeptide cleavage, and formation or dissociation of protein complexes; protein array analysis; DNA transcriptional, profiling using DNA arrays or subtractive hybridization); measurements of cell death by apoptosis, necrosis, or other mechanisms (e.g., annexin V staining, TUNEL assays, gel electrophoresis to measure DNA laddering, histology; fluorogenic caspase assays, Western blot analysis of caspase substrates); measurement of the genes, proteins, and other molecules produced by immune cells (e.g., Northern blot analysis, polymerase chain reaction, DNA microarrays, protein microarrays, 2-dimensional gel electrophoresis, Western blot analysis, enzyme linked immunosorbent assays, flow cytometry); and measurement of clinical symptoms or outcomes such as improvement of autoimmune, neurodegenerative, and other diseases involving self proteins or self polypeptides (clinical scores, requirements for use of additional therapies, functional status, imaging studies) for example, by measuring relapse rate or disease severity (using clinical scores known to the ordinarily skilled artisan) in the case of multiple sclerosis, measuring blood glucose in the case of type I diabetes, or joint inflammation in the case of rheumatoid arthritis.

Also provided herein are articles of manufacture comprising the pharmaceutical compositions described herein in suitable packaging. Suitable packaging for compositions (such as ophthalmic compositions) described herein are known in the art, and include, for example, vials (such as sealed vials), vessels, ampules, bottles, jars, flexible packaging (e.g., sealed Mylar or plastic bags), and the like. These articles of manufacture may further be sterilized and/or sealed.

Further provided are kits comprising the pharmaceutical compositions (or articles of manufacture) described herein, which may further comprise instruction(s) on methods of using the composition, such as uses described herein. The kits described herein may also include other materials desirable from a commercial and user standpoint, including other buffers, diluents, filters, needles, syringes, and package inserts with instructions for performing any methods described herein.

VI. THERAPEUTIC APPLICATIONS

Immunomodulatory proteins of the invention are believed to have utility in a variety of applications, including, but not limited to, e.g., in prophylactic or therapeutic methods (collectively, a "therapeutic composition of the invention") for treating a variety of immune system diseases or conditions in a mammal in which modulation or regulation of the immune system and immune system responses is beneficial. For example, suppressing an immune response can be beneficial in prophylactic and/or therapeutic methods for inhibiting rejection of a tissue, cell, or organ transplant from a donor by a recipient. In a therapeutic context, the mammalian subject is typically one with an immune system disease or condition, and administration is conducted to prevent further progression of the disease or condition. For example, administration of a therapeutic composition of the invention to a subject suffering from an immune system disease (e.g., autoimmune disease) can result in suppression or inhibition of such immune system attack or biological responses associated therewith. By suppressing this immune system attack on healthy body tissues, the resulting physical symptoms (e.g., pain, joint inflammation, joint swelling or tenderness) resulting from or associated with such attack on healthy tissues can be decreased or alleviated, and the biological and physical damage resulting from or associated with the immune system attack can be decreased, retarded, or stopped. In a prophylactic context, the subject may be one with, susceptible to, or believed to present an immune system disease, disorder or condition, and administration is typically conducted to prevent progression of the disease, disorder or condition, inhibit or alleviate symptoms, signs, or biological responses associated therewith, prevent bodily damage potentially resulting therefrom, and/or maintain or improve the subject's physical functioning.

The immune system disease or disorder of the patient may be or involve, e.g., but is not limited to, Addison's Disease, Allergy, Alopecia Areata, Alzheimer's, Antineutrophil cytoplasmic antibodies (ANCA)-associated vasculitis, Ankylosing Spondylitis, Antiphospholipid Syndrome (Hughes Syndrome), arthritis, Asthma, Atherosclerosis, Atherosclerotic plaque, autoimmune disease (e.g., lupus, RA, MS, Graves' disease, etc.), Autoimmune Hemolytic Anemia, Autoimmune Hepatitis, Autoimmune inner ear disease, Autoimmune Lymphoproliferative syndrome, Autoimmune Myocarditis, Autoimmune Oophoritis, Autoimmune Orchitis, Azoospermia, Behcet's Disease, Berger's Disease, Bullous Pemphigoid, Cardiomyopathy, Cardiovascular disease, Celiac Sprue/Coeliac disease, Chronic Fatigue Immune Dysfunction Syndrome (CFIDS), Chronic idiopathic polyneuritis, Chronic Inflammatory Demyelinating, Polyradicalneuropathy (CIPD), Chronic relapsing polyneuropathy (Guillain-Barré syndrome), Churg-Strauss Syndrome (CSS), Cicatricial Pemphigoid, Cold Agglutinin Disease (CAD), COPD, CREST syndrome, Crohn's disease, Dermatitis, Herpetiformus, Dermatomyositis, diabetes, Discoid Lupus, Eczema, Epidermolysis bullosa acquisita, Essential Mixed Cryoglobulinemia, Evan's Syndrome, Exopthalmos, Fibromyalgia, Goodpasture's Syndrome, graft-related disease or disorder, Graves' Disease, GVHD, Hashimoto's Thyroiditis, Idiopathic Pulmonary Fibrosis, Idiopathic Thrombocytopenia Purpura (ITP), IgA Nephropathy, immunoproliferative disease or disorder (e.g., psoriasis), Inflammatory bowel disease (IBD), Insulin Dependent Diabetes Mellitus (IDDM), Interstitial lung disease, juvenile diabetes, Juvenile Arthritis, juvenile idiopathic arthritis (JIA), Kawasaki's Disease, Lambert-Eaton Myasthenic Syndrome, Lichen Planus, lupus, Lupus Nephritis, Lymphoscytic Lypophisitis, Ménière's Disease, Miller Fish Syndrome/acute disseminated encephalomyeloradiculopathy, Mixed Connective Tissue Disease, Multiple Sclerosis (MS), muscular rheumatism, Myalgic encephalomyelitis (ME), Myasthenia Gravis, Ocular Inflammation, Pemphigus Foliaceus, Pemphigus Vulgaris, Pernicious Anaemia, Polyarteritis Nodosa, Polychondritis, Polyglandular Syndromes (Whitaker's syndrome), Polymyalgia Rheumatica, Polymyositis, Primary Agammaglobulinemia, Primary Biliary Cirrhosis/Autoimmune cholangiopathy, Psoriasis, Psoriatic arthritis, Raynaud's Phenomenon, Reiter's Syndrome/Reactive arthritis, Restenosis, Rheumatic Fever, rheumatic disease, Rheumatoid Arthritis, Sarcoidosis, Schmidt's syndrome, Scleroderma, Sjörgen's Syndrome, Solid-organ transplant rejection (kidney, heart, liver, lung, etc.), Stiff-Man Syndrome, Systemic Lupus Erythematosus (SLE), systemic scleroderma, Takayasu Arteritis, Temporal Arteritis/Giant Cell Arteritis, Thyroiditis, Type 1 diabetes, Type 2 diabetes, Ulcerative colitis, Uveitis, Vasculitis, Vitiligo, Wegener's Granulomatosis, and preventing or suppressing an immune response associated with rejection of a donor tissue, cell, graft, or organ transplant by a recipient subject. Graft-related diseases or disorders include graft versus host disease (GVDH), such as associated with bone marrow transplantation, and immune disorders resulting from or associated with rejection of organ, tissue, or cell graft transplantation (e.g., tissue or cell allografts or xenografts), including, e.g., grafts of skin, muscle, neurons, islets, organs, parenchymal cells of the liver, etc. With regard to a donor tissue, cell, graft or solid organ transplant in a recipient subject, it is believed that a therapeutic composition of the invention disclosed herein may be effective in preventing acute rejection of such transplant in the recipient and/or for long-term maintenance therapy to prevent rejection of such transplant in the recipient (e.g., inhibiting rejection of insulin-producing islet cell transplant from a donor in the subject recipient suffering from diabetes).

A therapeutic composition of the invention can also be used to inhibit growth of mammalian, particularly human, cancer cells as a monotherapy (i.e., as a single agent), in combination with at least one chemotherapeutic agent (i.e., a combination therapy), in combination with a cancer vaccine, in combination with an immune checkpoint inhibitor and/or in combination with radiation therapy. In some aspects of the present disclosure, the immune checkpoint inhibitor is nivolumab, tremelimumab, pembrolizumab, ipilimumab, or the like. An effective amount of a therapeutic composition is administered to inhibit, halt, or reverse progression of cancers that are sensitive to modulation of immunological activity by immunomodulatory proteins of the present invention. Human cancer cells can be treated in vivo, or ex vivo. In ex vivo treatment of a human patient, tissue or fluids containing cancer cells are treated outside the body and then the tissue or fluids are reintroduced back into the patient. In some embodiments, the cancer is treated in a human patient in vivo by administration of the therapeutic composition into the patient. Thus, the present invention provides ex vivo and in vivo methods to inhibit, halt, or reverse progression of the tumor, or otherwise result in a statistically significant increase in progression-free survival (i.e., the length of time during and after treatment in which a patient is living with cancer that does not get worse), or overall survival (also called "survival rate;" i.e., the percentage of people in a study or treatment group who are alive for a certain period of time after they were diagnosed with or treated for cancer) relative to treatment with a control. The cancers which can be treated by the methods of the invention include, but are not limited to, melanoma, bladder cancer, hematological malignancies (leukemia, lymphoma, myeloma), liver cancer, brain cancer, renal cancer, breast cancer, pancreatic cancer (adenocarcinoma), colorectal cancer, lung cancer (small cell lung cancer and non-small-cell lung cancer), spleen cancer, cancer of the thymus or blood cells (i.e., leukemia), prostate cancer, testicular cancer, ovarian cancer, uterine cancer, gastric carcinoma, or Ewing's sarcoma.

VII. EXEMPLARY EMBODIMENTS

Among the provided embodiments are:

Embodiment 1. In some embodiments, there is provided an immunomodulatory protein, comprising at least one non-immunoglobulin affinity modified immunoglobulin superfamily (IgSF) domain comprising one or more amino acid substitution(s) in a wild-type IgSF domain, wherein: the at least one affinity modified IgSF domain has increased binding to at least two cognate binding partners compared to the wild-type IgSF domain; and the at least one affinity modified IgSF domain specifically binds non-competitively to the at least two cognate binding partners.

Embodiment 2. In some further embodiments of embodiment 1, the at least two cognate binding partners are cell surface molecular species expressed on the surface of a mammalian cell.

Embodiment 3. In some further embodiments of embodiment 2, the cell surface molecular species are expressed in cis configuration or trans configuration.

Embodiment 4. In some further embodiments of embodiment 2 or embodiment 3, the mammalian cell is one of two mammalian cells forming an immunological synapse (IS) and each of the cell surface molecular species is expressed on at least one of the two mammalian cells forming the IS.

Embodiment 5. In some further embodiments of any one of embodiments 2-4, at least one of the mammalian cells is a lymphocyte.

Embodiment 6. In some further embodiments of embodiment 5, the lymphocyte is an NK cell or a T cell.

Embodiment 7. In some further embodiments of any one of embodiments 5-6, binding of the affinity modified IgSF domain modulates immunological activity of the lymphocyte.

Embodiment 8. In some further embodiments of embodiment 7, the immunomodulatory protein is capable of effecting increased immunological activity compared the wild-type protein comprising the wild-type IgSF domain.

Embodiment 9. In some further embodiments of embodiment 7, the immunomodulatory protein is capable of effecting decreased immunological activity compared to the wild-type protein comprising the wild-type IgSF domain.

Embodiment 10. In some further embodiments of any one of embodiments 2-9, at least one of the mammalian cells is a tumor cell.

Embodiment 11. In some further embodiments of any one of embodiments 2-10, the mammalian cells are human cells.

Embodiment 12. In some further embodiments of any one of embodiments 4-11, the affinity modified IgSF domain is capable of specifically binding to the two mammalian cells forming the IS.

Embodiment 13. In some further embodiments of any one of embodiments 1-12, the wild-type IgSF domain is from an IgSF family member of a family selected from Signal-Regulatory Protein (SIRP) Family, Triggering Receptor Expressed On Myeloid Cells Like (TREML) Family, Carcinoembryonic Antigen-related Cell Adhesion Molecule (CEACAM) Family, Sialic Acid Binding Ig-Like Lectin (SIGLEC) Family, Butyrophilin Family, B7 family, CD28 family, V-set and Immunoglobulin Domain Containing (VSIG) family, V-set transmembrane Domain (VSTM) family, Major Histocompatibility Complex (MHC) family, Signaling lymphocytic activation molecule (SLAM) family, Leukocyte immunoglobulin-like receptor (LIR), Nectin (Nec) family, Nectin-like (NECL) family, Poliovirus receptor related (PVR) family, Natural cytotoxicity triggering receptor (NCR) family, T cell immunoglobulin and mucin (TIM) family or Killer-cell immunoglobulin-like receptors (KIR) family.

Embodiment 14. In some further embodiments of any one of embodiments 1-13, the wild-type IgSF domain is from an IgSF member selected from CD80, CD86, PD-L1, PD-L2, ICOS Ligand, B7-H3, B7-H4, CD28, CTLA4, PD-1, ICOS, BTLA, CD4, CD8-alpha, CD8-beta, LAG3, TIM-3, CEACAM1, TIGIT, PVR, PVRL2, CD226, CD2, CD160, CD200, CD200R or Nkp30.

Embodiment 15. In some further embodiments of any one of embodiments 1-14, the wild-type IgSF domain is a human IgSF member.

Embodiment 16. In some further embodiments of any one of embodiments 1-15, the wild-type IgSF domain is an IgV domain, an IgC1 domain, an IgC2 domain or a specific binding fragment thereof.

Embodiment 17. In some further embodiments of any one of embodiments 1-16, the affinity-modified IgSF domain is an affinity modified IgV domain, affinity modified IgC1 domain or an affinity modified IgC2 domain or is a specific binding fragment thereof comprising the one or more amino acid substitutions.

Embodiment 18. In some further embodiments of any one of embodiments 1-17, the immunomodulatory protein comprises at least two non-immunoglobulin affinity modified IgSF domains.

Embodiment 19. In some further embodiments of embodiment 18, the at least two non-immunoglobulin affinity modified IgSF domains each comprise one or more different amino acid substitutions in the same wild-type IgSF domain.

Embodiment 20. In some further embodiments of embodiment 19, the at least two non-immunoglobulin affinity modified IgSF domains each comprise one or more amino acid substitutions in different wild-type IgSF domains.

Embodiment 21. In some further embodiments of embodiment 20, the different wild-type IgSF domains are from different IgSF family members.

Embodiment 22. In some further embodiments of any one of embodiments 1-17, the immunomodulatory protein comprises only one non-immunoglobulin affinity modified IgSF domain.

Embodiment 23. In some further embodiments of any one of embodiments 1-22, the affinity-modified IgSF comprises at least 85% sequence identity to a wild-type IgSF domain or a specific binding fragment thereof contained in the sequence of amino acids set forth in any of SEQ ID NOS: 1-27.

Embodiment 24. In some further embodiments of embodiment 23, the immunomodulatory protein further comprises a second affinity-modified IgSF, wherein the second affinity-modified IgSF domain comprises at least 85% sequence identity to a wild-type IgSF domain or a specific binding fragment thereof contained in the sequence of amino acids set forth in any of SEQ ID NOS: 1-27.

Embodiment 25. In some further embodiments of any one of embodiments 1-24, the wild-type IgSF domain is a member of the B7 family.

Embodiment 26. In some further embodiments of any one of embodiments 1-25, the wild-type IgSF domain is a domain of CD80, CD86 or ICOSLG.

Embodiment 27. In some further embodiments of any one of embodiments 1-26, the wild-type IgSF domain is a domain of CD80.

Embodiment 28. In some embodiments, there is provided an immunomodulatory protein, comprising at least one affinity modified CD80 immunoglobulin superfamily (IgSF) domain comprising one or more amino acid substitution(s) in a wild-type CD80 IgSF domain, wherein the at least one affinity modified CD80 IgSF domain has increased binding to at least two cognate binding partners compared to the wild-type CD80 IgSF domain.

Embodiment 29. In some further embodiments of embodiment 27 or embodiment 28, the cognate binding partners are CD28 and PD-L1.

Embodiment 30. In some further embodiments of any one of embodiments 27-29, the wild-type IgSF domain is an IgV domain and/or the affinity modified CD80 domain is an affinity modified IgV domain.

Embodiment 31. In some further embodiments of any one of embodiments 27-30, the affinity-modified domain comprises at least 85% sequence identity to a wild-type CD80 domain or a specific binding fragment thereof contained in the sequence of amino acids set forth in SEQ ID NO:1.

Embodiment 32. In some further embodiments of any one of embodiments 1-31, the at least one affinity modified IgSF domain comprises at least 1 and no more than twenty amino acid substitutions in the wild-type IgSF domain.

Embodiment 33. In some further embodiments of any one of embodiments 1-32, the at least one affinity modified IgSF domain comprises at least 1 and no more than ten amino acid substitutions in the wild-type IgSF domain.

Embodiment 34. In some further embodiments of any one of embodiments 1-33, the at least one affinity modified IgSF domain comprises at least 1 and no more than five amino acid substitutions in the wild-type IgSF domain.

Embodiment 35. In some further embodiments of any one of embodiments 1-34, the affinity modified IgSF domain has at least 120% of the binding affinity as its wild-type IgSF domain to each of the at least two cognate binding partners.

Embodiment 36. In some further embodiments of any one of embodiments 1-35, the immunomodulatory protein further comprises a non-affinity modified IgSF domain.

Embodiment 37. In some further embodiments of any one of embodiments 1-36, the immunomodulatory protein is soluble.

Embodiment 38. In some further embodiments of any one of embodiments 1-37, the immunomodulatory protein lacks a transmembrane domain or a cytoplasmic domain.

Embodiment 39. In some further embodiments of any one of embodiments 1-38, the immunomodulatory protein comprises only the extracellular domain (ECD) or a specific binding fragment thereof comprising the affinity modified IgSF domain.

Embodiment 40. In some further embodiments of any one of embodiments 1-39, the immunomodulatory protein is glycosylated or pegylated.

Embodiment 41. In some further embodiments of any one of embodiments 1-40, the immunomodulatory protein is linked to a multimerization domain.

Embodiment 42. In some further embodiments of any one of embodiments 1-41, the immunomodulatory protein is linked to an Fc domain or a variant thereof with reduced effector function.

Embodiment 43. In some further embodiments of embodiment 42, the Fc domain is an IgG1 domain, an IgG2 domain or is a variant thereof with reduced effector function.

Embodiment 44. In some further embodiments of any one of embodiments 39-41, the Fc domain is mammalian, optionally human; or the variant Fc domain comprises one or more amino acid modifications compared to an unmodified Fc domain that is mammalian, optionally human.

Embodiment 45. In some further embodiments of any one of embodiments 42-44, the Fe domain or variant thereof comprises the sequence of amino acids set forth in SEQ ID NO:226 or SEQ ID NO:227 or a sequence of amino acids that exhibits at least 85% sequence identity to SEQ ID NO:226 or SEQ ID NO:227.

Embodiment 46. In some further embodiments of any one of embodiments 38-41, the immunomodulatory protein is linked indirectly via a linker.

Embodiment 47. In some further embodiments of any one of embodiments 41-46, the immunomodulatory protein is a dimer.

Embodiment 48. In some further embodiments of any one of embodiments 1-47, the immunomodulatory protein is attached to a liposomal membrane.

Embodiment 49. In some embodiments, there is provided an immunomodulatory protein, comprising at least two non-immunoglobulin immunoglobulin superfamily (IgSF) domains, wherein: at least one of the non-immunoglobulin modified IgSF domain is affinity-modified to exhibit altered binding to its cognate binding partner; and the at least two non-immunoglobulin modified IgSF domain each independently specifically bind to at least one different cognate binding partner.

Embodiment 50. In some further embodiments of embodiment 49, the each of the at least two non-immunoglobulin IgSF domains are affinity-modified IgSF domains, wherein the first non-immunoglobulin modified IgSF domain comprises one or more amino acid substitutions in a first wild-type-type IgSF domain and the second non-immunoglobulin modified IgSF domain comprises one or more amino acid substitutions in a second wild-type IgSF domain.

Embodiment 51. In some further embodiments of embodiment 50, the first non-immunoglobulin modified IgSF domain exhibits altered binding to at least one of its cognate binding partner(s) compared to the first wild-type IgSF domain; and the second non-immunoglobulin modified IgSF domain exhibits altered binding to at least one of its cognate binding partner(s) compared to the second wild-type IgSF domain.

Embodiment 52. In some further embodiments of any one of embodiments 49-51, the different cognate binding partners are cell surface molecular species expressed on the surface of a mammalian cell.

Embodiment 53. In some further embodiments of embodiment 52, the different cell surface molecular species are expressed in cis configuration or trans configuration.

Embodiment 54. In some further embodiments of embodiment 52 or embodiment 53, the mammalian cell is one of two mammalian cells forming an immunological synapse (IS) and the different cell surface molecular species is expressed on at least one of the two mammalian cells forming the IS.

Embodiment 55. In some further embodiments of any one of embodiments 52-54, at least one of the mammalian cells is a lymphocyte.

Embodiment 56. In some further embodiments of embodiment 55, the lymphocyte is an NK cell or a T cell.

Embodiment 57. In some further embodiments of embodiment 55 or embodiment 56, binding of the immunomodulatory protein to the cell modulates the immunological activity of the lymphocyte.

Embodiment 58. In some further embodiments of embodiment 57, the immunomodulatory protein is capable of effecting increased immunological activity compared to the wild-type protein comprising the wild-type IgSF domain.

Embodiment 59. In some further embodiments of embodiment 57, the immunomodulatory protein is capable of effecting decreased immunological activity compared to the wild-type protein comprising the wild-type IgSF domain.

Embodiment 60. In some further embodiments of any one of embodiments 52-59, at least one of the mammalian cells is a tumor cell.

Embodiment 61. In some further embodiments of any one of embodiments 52-60, the mammalian cells are human cells.

Embodiment 62. In some further embodiments of any one of embodiments 54-61, the immunomodulatory protein is capable of specifically binding to the two mammalian cells forming the IS.

Embodiment 63. In some further embodiments of any one of embodiments 49-62, the first and second modified IgSF domains each comprise one or more amino acid substitutions in different wild-type IgSF domains.

Embodiment 64. In some further embodiments of embodiment 63, the different wild-type IgSF domains are from different IgSF family members.

Embodiment 65. In some further embodiments of any one of embodiments 49-64, the first and second modified IgSF domains are non-wild-type combinations.

Embodiment 66. In some further embodiments of any one of embodiments 49-65, the first wild-type IgSF domain and second wild-type IgSF domain each individually is from an IgSF family member of a family selected from Signal-Regulatory Protein (SIRP) Family, Triggering Receptor Expressed On Myeloid Cells Like (TREML) Family, Carcinoembryonic Antigen-related Cell Adhesion Molecule (CEACAM) Family, Sialic Acid Binding Ig-Like Lectin (SIGLEC) Family, Butyrophilin Family, B7 family, CD28 family, V-set and Immunoglobulin Domain Containing (VSIG) family, V-set transmembrane Domain (VSTM) family, Major Histocompatibility Complex (MHC) family, Signaling lymphocytic activation molecule (SLAM) family, Leukocyte immunoglobulin-like receptor (LIR), Nectin (Nec) family, Nectin-like (NECL) family, Poliovirus receptor related (PVR) family, Natural cytotoxicity triggering receptor (NCR) family, T cell immunoglobulin and mucin (TIM) family or Killer-cell immunoglobulin-like receptors (KIR) family.

Embodiment 67. In some further embodiments of any one of embodiments 49-66, the first wild-type IgSF domain and second wild-type IgSF domain each individually is from an IgSF member selected from CD80, CD86, PD-L1, PD-L2, ICOS Ligand, B7-H3, B7-H4, CD28, CTLA4, PD-1, ICOS, BTLA, CD4, CD8-alpha, CD8-beta, LAG3, TIM-3, CEACAM1, TIGIT, PVR, PVRL2, CD226, CD2, CD160, CD200, CD200R or Nkp30.

Embodiment 68. In some further embodiments of any one of embodiments 49-67, the first modified IgSF domain and the second modified IgSF domain each individually comprises at least 85% sequence identity to a wild-type IgSF domain or a specific binding fragment thereof contained in the sequence of amino acids set forth in any of SEQ ID NOS: 1-27.

Embodiment 69. In some further embodiments of any one of embodiments 49-68, the first and second wild-type IgSF domain each individually is a member of the B7 family.

Embodiment 70. In some further embodiments of embodiment 69, the first and second wild-type IgSF domain each individually is from CD80, CD86 or ICOSLG.

Embodiment 71. In some further embodiments of any one of embodiments 49-68, the first or second wild-type IgSF domain is from a member of the B7 family and the other of the first or second wild-type IgSF domain is from another IgSF family.

Embodiment 72. In some further embodiments of any one of embodiments 49-68 and 71, the first and second wild-type IgSF domain is from ICOSLG and NKp30.

Embodiment 73. In some further embodiments of any one of embodiments 49-68 and 71, the first and second wild-type IgSF domain is from CD80 and NKp30.

Embodiment 74. In some further embodiments of any one of embodiments 49-73, the first and second wild-type IgSF domain each individually is a human IgSF member.

Embodiment 75. In some further embodiments of any one of embodiments 49-74, the first and second wild-type IgSF domain each individually is an IgV domain, and IgC1 domain, an IgC2 domain or a specific binding thereof.

Embodiment 76. In some further embodiments of any one of embodiments 49-75, the first non-immunoglobulin modified domain and the second non-immunoglobulin modified domain each individually is a modified IgV domain, modified IgC1 domain or a modified IgC2 domain or is a specific binding fragment thereof comprising the one or more amino acid substitutions.

Embodiment 77. In some further embodiments of any one of embodiments 49-76, at least one of the first non-immunoglobulin modified domain or the second non-immunoglobulin modified domain is a modified IgV domain.

Embodiment 78. In some further embodiments of any one of embodiments 49-77, the first non-immunoglobulin modified IgSF domain and the second non-immunoglobulin modified IgSF domain each individually comprise 1 and no more than twenty amino acid substitutions.

Embodiment 79. In some further embodiments of any one of embodiments 49-78, the first non-immunoglobulin modified IgSF domain and the second non-immunoglobulin modified IgSF domain each individually comprise 1 and no more than ten amino acid substitutions.

Embodiment 80. In some further embodiments of any one of embodiments 49-79, the first non-immunoglobulin modified IgSF domain and the second non-immunoglobulin modified IgSF domain each individually comprise 1 and no more than five amino acid substitutions.

Embodiment 81. In some further embodiments of any one of embodiments 49-80, at least one of the first or second non-immunoglobulin modified IgSF domain has between 10% and 90% of the binding affinity of the wild-type IgSF domain to at least one of its cognate binding partner.

Embodiment 82. In some further embodiments of any one of embodiments 49-81, at least one of the first of second non-immunoglobulin modified IgSF domain has at least 120% of the binding affinity of the wild-type IgSF domain to at least one of its cognate binding partner.

Embodiment 83. In some further embodiments of any one of embodiments 49-80 and 82, the first and second non-immunoglobulin modified IgSF domain each individually has at least 120% of the binding affinity of the wild-type IgSF domain to at least one of its cognate binding partner.

Embodiment 84. In some further embodiments of any one of embodiments 49-83, the immunomodulatory protein is soluble.

Embodiment 85. In some further embodiments of any one of embodiments 49-84, the immunomodulatory protein is glycosylated or pegylated.

Embodiment 86. In some further embodiments of any one of embodiments 49-85, the immunomodulatory protein is linked to a multimerization domain.

Embodiment 87. In some further embodiments of any one of embodiments 49-86, the immunomodulatory protein is linked to an Fc domain or a variant thereof with reduced effector function.

Embodiment 88. In some further embodiments of embodiment 87, the Fc domain is an IgG1 domain, an IgG2 domain or is a variant thereof with reduced effector function.

Embodiment 89. In some further embodiments of embodiment 87 or embodiment 88, the Fc domain is mammalian, optionally human; or the variant Fc domain comprises one or more amino acid modifications compared to an unmodified Fc domain that is mammalian, optionally human.

Embodiment 90. In some further embodiments of any one of embodiments 87-89, the Fc domain or variant thereof comprises the sequence of amino acids set forth in SEQ ID NO:226 or SEQ ID NO:227 or a sequence of amino acids that exhibits at least 85% sequence identity to SEQ ID NO:226 or SEQ ID NO:227.

Embodiment 91. In some further embodiments of any one of embodiments 86-90, the variant CD80 polypeptide is linked indirectly via a linker.

Embodiment 92. In some further embodiments of any one of embodiments 86-91, the immunomodulatory protein is a dimer.

Embodiment 93. In some further embodiments of any one of embodiments 49-92, the immunomodulatory protein further comprises one or more additional non-immunoglobulin IgSF domain that is the same of different from the first or second non-immunoglobulin modified IgSF domain.

Embodiment 94. In some further embodiments of embodiment 93, the one or more additional non-immunoglobulin IgSF domain is an affinity modified IgSF domain.

Embodiment 95. In some further embodiments of any one of embodiment 49-94, the immunomodulatory protein is attached to a liposomal membrane.

Embodiment 96. In some embodiments, there is provided a nucleic acid molecule, encoding the immunomodulatory polypeptide of any of embodiments 1-95.

Embodiment 97. In some further embodiments of embodiment 96, the nucleic acid is synthetic nucleic acid.

Embodiment 98. In some further embodiments of embodiment 96 or embodiment 97, the nucleic acid is cDNA.

Embodiment 99. In some embodiments, there is provided a vector, comprising the nucleic acid molecule of any of embodiments 96-98.

Embodiment 100. In some further embodiments of embodiment 99, the vector is an expression vector.

Embodiment 101. In some embodiments, there is provided a cell, comprising the vector of embodiment 99 or embodiment 100.

Embodiment 102. In some further embodiments of embodiment 101, the cell is a eukaryotic cell or prokaryotic cell.

Embodiment 103. In some embodiments, there is provided a method of producing an immunomodulatory protein, comprising introducing the nucleic acid molecule of any of embodiments 96-98 or vector of embodiment 99 or embodiment 100 into a host cell under conditions to express the protein in the cell.

Embodiment 104. In some further embodiments of embodiment 103, the method further comprises isolating or purifying the immunomodulatory protein from the cell.

Embodiment 105. In some embodiments, there is provided a pharmaceutical composition, comprising the immunomodulatory protein of any of embodiments 1-95.

Embodiment 106. In some further embodiments of embodiment 105, the pharmaceutical composition comprises a pharmaceutically acceptable excipient.

Embodiment 107. In some further embodiments of embodiment 105 or embodiment 106, the pharmaceutical composition is sterile.

Embodiment 108. In some embodiments, there is provided an article of manufacture comprising the pharmaceutical composition of any of embodiments 105-107 in a vial.

Embodiment 109. In some further embodiments of embodiment 108, the vial is sealed.

Embodiment 110. In some embodiments, there is provided a kit comprising the pharmaceutical composition of any of embodiments 105-107, and instructions for use.

Embodiment 111. In some embodiments, there is provided a kit comprising the article of manufacture according to embodiment 108 or embodiment 109, and instructions for use.

Embodiment 112. In some embodiments, there is provided a method of modulating an immune response in a subject, comprising administering therapeutically effective amount of the immunomodulatory protein of any of embodiments 1-95 to the subject.

Embodiment 113. In some further embodiments of embodiment 112, modulating the immune response treats a disease or condition in the subject.

Embodiment 114. In some further embodiments of embodiment 112 or embodiment 113, the immune response is increased.

Embodiment 115. In some further embodiments of embodiment 114, the disease or condition is a tumor or cancer.

Embodiment 116. In some further embodiments of embodiment 114 or embodiment 115, the disease or condition is selected from melanoma, lung cancer, bladder cancer or a hematological malignancy.

Embodiment 117. In some further embodiments of embodiment 112 or embodiment 113, the immune response is decreased.

Embodiment 118. In some further embodiments of embodiment 117, the disease or condition is an inflammatory disease or condition.

Embodiment 119. In some further embodiments of embodiment 117 or embodiment 118, the disease or condition is selected from Crohn's disease, ulcerative colitis, multiple sclerosis, asthma, rheumatoid arthritis, or psoriasis.

Embodiment 120. In some embodiments, there is provided a method of identifying an affinity modified immunomodulatory protein, comprising: a) contacting a modified protein comprising at least one non-immunoglobulin modified immunoglobulin superfamily (IgSF) domain or specific binding fragment thereof with at least two cognate binding partners under conditions capable of effecting binding of the protein with the at least two cognate binding partners, wherein the at least one modified IgSF domain comprises one or more amino acid substitutions in a wild-type IgSF domain; b) identifying a modified protein comprising the modified IgSF domain that has increased binding to at least one of the two cognate binding partners compared to a protein comprising the wild-type IgSF domain; and c) selecting a modified protein comprising the modified IgSF domain that binds non-competitively to the at least two cognate binding partners, thereby identifying the affinity modified immunomodulatory protein.

Embodiment 121. In some further embodiments of embodiment 120, step b) comprises identifying a modified protein comprising a modified IgSF domain that has increased binding to each of the at least two cognate binding partners compared to a protein comprising the wild-type domain.

Embodiment 122. In some further embodiments of embodiment 120 or embodiment 121, prior to step a), introducing one or more amino acid substitutions into the wild-type IgSF domain, thereby generating a modified protein comprising the modified IgSF domain.

Embodiment 123. In some further embodiments of any one of embodiments 120-122, the modified protein comprises at least two modified IgSF domains or specific binding fragments thereof, wherein the first IgSF domain comprises one or more amino acid substitutions in a first wild-type-type IgSF domain and the second non-immunoglobulin affinity modified IgSF domain comprises one or more amino acid substitutions in a second wild-type IgSF domain.

Embodiment 124. In some further embodiments of embodiment 123, the first and second non-immunoglobulin affinity modified IgSF domain each specifically bind to at least one different cognate binding partner.

Embodiment 125. In some embodiments, there is provided an immunomodulatory protein comprising at least one non-immunoglobulin affinity-modified immunoglobulin superfamily (IgSF) domain, wherein the affinity-modified IgSF domain specifically binds non-competitively to at least two cell-surface molecular species, wherein each of the molecular species is expressed on at least one of the two mammalian cells forming an immunological synapse (IS), wherein one of the mammalian cells is a lymphocyte and wherein binding of the affinity-modified IgSF domain modulates immunological activity of the lymphocyte.

Embodiment 126. In some further embodiments of embodiment 125, the affinity modified IgSF domain specifically binds to the two mammalian cells forming the IS.

Embodiment 127. In some further embodiments of embodiment 125 or embodiment 126, the immunomodulatory protein comprises at least two non-immunoglobulin affinity modified IgSF domains and the immunomodulatory protein specifically binds to the two mammalian cells forming the IS.

Embodiment 128. In some further embodiments of any one of embodiments 125-127, the IgSF cell surface molecular species are human IgSF members.

Embodiment 129. In some further embodiments of any one of embodiments 125-128, the affinity modified IgSF domain comprises at least one affinity modified human CD80 domain.

Embodiment 130. In some further embodiments of any one of embodiments 125-129, the immunomodulatory protein comprises an affinity modified mammalian IgSF member.

Embodiment 131. In some further embodiments of any one of embodiments 125-130, the affinity modified mammalian IgSF member is at least one of: CD80, PVR, ICOSLG, or HAVCR2.

Embodiment 132. In some further embodiments of any one of embodiments 125-131, immunological activity is enhanced.

Embodiment 133. In some further embodiments of any one of embodiments 125-132, immunological activity is suppressed.

Embodiment 134. In some further embodiments of any one of embodiments 125-133, one of the two mammalian cells is a tumor cell.

Embodiment 135. In some further embodiments of any one of embodiments 125-134, the lymphocyte is an NK cell or a T-cell.

Embodiment 136. In some further embodiments of any one of embodiments 125-135, the mammalian cells are a mouse, rat, cynomolgous monkey, or human cells.

Embodiment 137. In some further embodiments of any one of embodiments 125-136, the affinity modified IgSF domain has between 10% and 90% of the binding affinity of the wild-type IgSF domain to at least one of the two cell surface molecular species.

Embodiment 138. In some further embodiments of any one of embodiments 125-137, the affinity modified IgSF domain specifically binds non-competitively to exactly one IgSF member.

Embodiment 139. In some further embodiments of any one of embodiments 125-138, the affinity modified IgSF domain has at least 120% of the binding affinity as its wild-type IgSF domain to at least one of the two cell surface molecular species.

Embodiment 140. In some further embodiments of any one of embodiments 125-139, the affinity modified IgSF domain is an affinity modified IgV, IgC1, or IgC2 domain.

Embodiment 141. In some further embodiments of any one of embodiments 125-140, the affinity modified IgSF domain differs by at least one and no more than ten amino acid substitutions from its wild-type IgSF domain.

Embodiment 142. In some further embodiments of any one of embodiments 125-141, the affinity modified IgSF domain differs by at least one and no more than five amino acid substitutions from its wild-type IgSF domain.

Embodiment 143. In some further embodiments of any one of embodiments 125-142, the affinity modified IgSF domain is a human CD80 IgSF domain.

Embodiment 144. In some further embodiments of any one of embodiments 125-143, the immunomodulatory protein comprises at least two affinity-modified IgSF domains, wherein the affinity modified IgSF domains are not the same species of IgSF domain.

Embodiment 145. In some further embodiments of any one of embodiments 125-144, the immunomodulatory protein is covalently bonded, directly or indirectly, to an antibody fragment crystallizable (Fc).

Embodiment 146. In some further embodiments of any one of embodiments 125-145, the immunomodulator protein is in a pharmaceutically acceptable carrier.

Embodiment 147. In some further embodiments of any one of embodiments 125-146, the immunomodulatory protein is glycosylated or pegylated.

Embodiment 148. In some further embodiments of any one of embodiments 125-147, the immunomodulatory protein is soluble.

Embodiment 149. In some further embodiments of any one of embodiments 125-148, the immunomodulatory protein is attached to a liposomal membrane.

Embodiment 150. In some further embodiments of any one of embodiments 125-149, the immunomodulatory protein is dimerized by intermolecular disulfide bonds.

Embodiment 151. In some further embodiments of any one of embodiments 125-150, the cell surface molecular species are expressed in cis configuration or trans configuration.

Embodiment 152. In some embodiments, there is provided an immunomodulatory protein comprising at least two non-immunoglobulin affinity-modified immunoglobulin superfamily (IgSF) domains, wherein the affinity-modified IgSF domains each specifically binds to a different cell surface molecular species, wherein each of the molecular species is expressed on at least one of the two mammalian cells forming an immunological synapse (IS), wherein one of the mammalian cells is a lymphocyte, and wherein binding of the affinity-modified IgSF domain modulates immunological activity of the lymphocyte.

Embodiment 153. In some further embodiments of any one of embodiments 125-152, at least one of the affinity modified IgSF domains binds competitively.

Embodiment 154. In some further embodiments of any one of embodiments 125-153, the affinity modified IgSF domains are not the same species of IgSF domain.

Embodiment 155. In some further embodiments of any one of embodiments 125-154, the affinity modified IgSF domains are non-wild type combinations.

Embodiment 156. In some further embodiments of any one of embodiments 125-155, the cell surface molecular species are human IgSF members.

Embodiment 157. In some further embodiments of any one of embodiments 125-156, the at least two affinity modified IgSF domains are from at least one of: CD80, CD86, CD274, PDCD1LG2, ICOSLG, CD276, VTCN1, CD28, CTLA4, PDCD1, ICOS, BTLA, CD4, CD8A, CD8B, LAG3, HAVCR2, CEACAM1, TIGIT, PVR, PVRL2, CD226, CD2, CD160, CD200, or CD200R1.

Embodiment 158. In some further embodiments of any one of embodiments 125-157, the immunomodulatory protein comprises at least two affinity modified mammalian IgSF members.

Embodiment 159. In some further embodiments of any one of embodiments 125-158, the mammalian IgSF members are human IgSF members.

Embodiment 160. In some further embodiments of any one of embodiments 125-159, the mammalian IgSF members are at least two of: CD80, CD86, CD274, PDCD1LG2, ICOSLG, CD276, VTCN1, CD28, CTLA4, PDCD1, ICOS, BTLA, CD4, CD8A, CD8B, LAG3, HAVCR2, CEACAM1, TIGIT, PVR, PVRL2, CD226, CD2, CD160, CD200, or CD200R1.

Embodiment 161. In some further embodiments of any one of embodiments 125-160, immunological activity is enhanced.

Embodiment 38. In some further embodiments of any one of embodiments 125-1, immunological activity is suppressed.

Embodiment 162. In some further embodiments of any one of embodiments 125-161, one of the two mammalian cells is a tumor cell.

Embodiment 163. In some further embodiments of any one of embodiments 125-162, the lymphocyte is an NK cell or a T-cell.

Embodiment 164. In some further embodiments of any one of embodiments 125-163, the mammalian cells are a mouse, rat, cynomolgous monkey, or human cells.

Embodiment 165. In some further embodiments of any one of embodiments 125-164, at least one of the two affinity modified IgSF domains has between 10% and 90% of the binding affinity of the wild-type IgSF domain to at least one of the cell surface molecular species.

Embodiment 166. In some further embodiments of any one of embodiments 125-165, at least one of the two affinity modified IgSF domains specifically binds to exactly one cell surface molecular species.

Embodiment 167. In some further embodiments of any one of embodiments 125-166, at least one of the two affinity modified IgSF domains has at least 120% of the binding affinity as its wild-type IgSF domain to at least one of the two cell surface molecular species.

Embodiment 168. In some further embodiments of any one of embodiments 125-167, the affinity modified IgSF domains are at least one of an IgV, IgC1, or IgC2 domain.

Embodiment 169. In some further embodiments of any one of embodiments 125-168, each of the at least two affinity modified IgSF domains differs by at least one and no more than ten amino acid substitutions from its wild-type IgSF domain.

Embodiment 170. In some further embodiments of any one of embodiments 125-169, each of the at least two affinity modified IgSF domains differs by at least one and no more than five amino acid substitutions from its wild-type IgSF domain.

Embodiment 171. In some further embodiments of any one of embodiments 125-170, the immunomodulatory protein is covalently bonded, directly or indirectly, to an antibody fragment crystallizable (Fc).

Embodiment 172. In some further embodiments of any one of embodiments 125-171, the immunomodulatory protein is in a pharmaceutically acceptable carrier.

Embodiment 173. In some further embodiments of any one of embodiments 125-172, the protein is glycosylated or pegylated.

Embodiment 174. In some further embodiments of any one of embodiments 125-173, the protein is soluble.

Embodiment 175. In some further embodiments of any one of embodiments 125-174, the protein is bonded to a liposomal membrane.

Embodiment 176. In some further embodiments of any one of embodiments 125-175, the protein is dimerized by intermolecular disulfide bonds.

Embodiment 177. In some further embodiments of any one of embodiments 125-176, the cell surface molecular species are expressed in cis configuration or trans configuration.

Embodiment 178. In some further embodiments of any one of embodiments 125-177, the immunomodulatory protein has at least 85% sequence identity with an amino acid sequence selected from SEQ ID NOS: 1-26, a combination, or a fragment thereof.

Embodiment 179. In some further embodiments of any one of embodiments 125-178, the immunomodulatory protein has at least 90% sequence identity with an amino acid sequence selected from SEQ ID NOS: 1-26, a combination, or a fragment thereof.

Embodiment 180. In some further embodiments of any one of embodiments 125-179, the immunomodulatory protein has at least 95% sequence identity with an amino acid sequence selected from SEQ ID NOS: 1-26, a combination, or a fragment thereof.

Embodiment 181. In some further embodiments of any one of embodiments 125-180, the immunomodulatory protein has at least 99% sequence identity with an amino acid sequence selected from SEQ ID NOS: 1-26, a combination, or a fragment thereof.

Embodiment 182. In some further embodiments of any one of embodiments 125-181, the immunomodulatory protein further comprises a second immunomodulatory protein, wherein the second immunomodulatory protein has at least 85% sequence identity with an amino acid sequence selected from SEQ ID NOS: 1-26 or a fragment thereof.

Embodiment 183. In some further embodiments of any one of embodiments 125-182, the immunomodulatory protein further comprises a second immunomodulatory protein, wherein the second immunomodulatory protein has at least 90% sequence identity with an amino acid sequence selected from SEQ ID NOS: 1-26 or a fragment thereof.

Embodiment 184. In some further embodiments of any one of embodiments 125-183, the immunomodulatory protein further comprises a second immunomodulatory protein, wherein the second immunomodulatory protein has at least 95% sequence identity with an amino acid sequence selected from SEQ ID NOS: 1-26 or a fragment thereof.

Embodiment 185. In some further embodiments of any one of embodiments 125-184, the immunomodulatory protein further comprises a second immunomodulatory protein, wherein the second immunomodulatory protein has at least 99% sequence identity with an amino acid sequence selected from SEQ ID NOS: 1-26 or a fragment thereof.

Embodiment 186. In some embodiments, there is provided a recombinant nucleic acid encoding any one of the immunomodulatory proteins of embodiments 125-185.

Embodiment 187. In some embodiments, there is provided a recombinant expression vector comprising a nucleic acid of embodiment 186.

Embodiment 188. In some embodiments, there is provided a recombinant host cell comprising the expression vector of embodiment 187.

Embodiment 189. In some embodiments, there is provided a method of making an immunomodulatory protein of any one of embodiments 125-185, comprising culturing the recombinant host cell under immunomodulatory protein expressing conditions, expressing the immunomodulatory protein encoded by the recombinant expression vector therein, and purifying the recombinant immunomodulatory protein expressed thereby.

Embodiment 190. In some embodiments, there is provided a method of treating a mammalian patient in need of an enhanced or suppressed immunological response by administering a therapeutically effective amount of immunomodulatory protein of any one of embodiments 125-185.

Embodiment 191. In some further embodiments of embodiment 190, the enhanced immunological response treats melanoma, lung cancer, bladder cancer, or a hematological malignancy in the patient.

Embodiment 192. In some further embodiments of embodiment 190, the suppressed immunological response treats Crohn's disease, ulcerative colitis, multiple sclerosis, asthma, rheumatoid arthritis, or psoriasis in the patient.

VIII. EXAMPLES

The following examples are included for illustrative purposes only and are not intended to limit the scope of the invention.

Examples 1-8 describe the design, creation, and screening of affinity modified CD80 (B7-1), CD86 (B7-2), ICOSL, and NKp30 immunomodulatory proteins, which are components of the immune synapse (IS) that have a demonstrated dual role in both immune activation and inhibition. These examples demonstrate that affinity modification of IgSF domains yields proteins that can act to both increase and decrease immunological activity. This work also describes the various combinations of those domains fused in pairs (i.e., stacked) to form a Type II immunomodulatory protein to achieve immunomodulatory activity.

Example 1

Generation of Mutant DNA Constructs of IgSF Domains

Example 1 describes the generation of mutant DNA constructs of human CD80, CD86, ICOSL, and NKp30 IgSF domains for translation and expression on the surface of yeast as yeast display libraries.

A. Degenerate Libraries

For libraries that target specific residues of target protein for complete or partial randomization with degenerate codons, the coding DNA's for the extracellular domains (ECD) of human CD80 (SEQ ID NO:28), ICOSL (SEQ ID NO:32), and NKp30 (SEQ ID NO:54) were ordered from Integrated DNA Technologies (Coralville, IA) as a set of overlapping oligonucleotides of up to 80 base pairs (bp) in length. To generate a library of diverse variants of each ECD, the oligonucleotides contained desired degenerate codons at desired amino acid positions. Degenerate codons were generated using an algorithm at the URL: rosetta-design.med.unc.edu/SwiftLib/.

In general, positions to mutate and degenerate codons were chosen as follows: crystal structures (CD80, NKp30) or homology models (ICOSL) of the target-ligand pairs of interest were used to identify ligand contact residues as well as residues that are at the protein interaction interface. This analysis was performed using a structure viewer available at the URL: spdbv.vital-it.ch). For example, a crystal structure for CD80 bound to CTLA4 is publicly available at the URL: www.rcsb.org/pdb/explore/explore.do?structureId=1I8L) and a targeted library was designed based on the CD80::CTLA4 interface for selection of improved binders to CTLA4. However, there are no CD80 structures available with ligands CD28 and PDL1, so the same library was also used to select for binders of CD28 (binds the same region on CD80 as CTLA4) and PDL1 (not known if PDL1 binds the same site as CTLA4).

The next step in library design was the alignment of human, mouse, rat and monkey CD80, ICOSL or NKp30 sequences to identify conserved residues. Based on this analysis, conserved target residues were mutated with degenerate codons that only specified conservative amino acid changes plus the wild-type residue. Residues that were not conserved, were mutated more aggressively, but also including the wild-type residue. Degenerate codons that also encoded the wild-type residue were deployed to avoid excessive mutagenesis of target protein. For the same reason, only up to 20 positions were targeted for mutagenesis at a time. These residues were a combination of contact residues and non-contact interface residues.

The oligonucleotides were dissolved in sterile water, mixed in equimolar ratios, heated to 95° C. for five minutes and slowly cooled to room temperature for annealing. ECD-specific oligonucleotide primers that anneal to the start and end of the ECDs, respectively, were then used to generate PCR product. ECD-specific oligonucleotides which overlap by 40-50 bp with a modified version of pBYDS03 cloning vector (Life Technologies USA), beyond and including the BamH1 and Kpn1 cloning sites, were then used to amplify 100 ng of PCR product from the prior step to generate a total of 5 μg of DNA. Both PCR's were by polymerase chain reaction (PCR) using OneTaq 2×PCR master mix (New England Biolabs, USA). The second PCR products were purified using a PCR purification kit (Qiagen, Germany) and resuspended in sterile deionized water.

To prepare for library insertion, a modified yeast display version of vector pBYDS03 was digested with BamH1 and Kpn1 restriction enzymes (New England Biolabs, USA) and the large vector fragment was gel-purified and dissolved in sterile, deionized water. Electroporation-ready DNA for the next step was generated by mixing 12 μg of library DNA with 4 μg of linearized vector in a total volume of 50 μl deionized and sterile water. An alternative way to generate targeted libraries, was to carry out site-directed mutagenesis (Multisite kit, Agilent, USA) of target ECD's with oligonucleotides containing degenerate codons. This approach was used to generate sublibraries that only target specific stretches of target protein for mutagenesis. In these cases, sublibraries were mixed before proceeding to the selection steps. In general, library sizes were in the range of 10E7 to 10E8 clones, except that sublibraries were only in the range of 10E4 to 10E5. Large libraries were generated for CD80, ICOSL, CD86 and NKp30. Sublibraries were generated for CD80, ICOSL and NKp30.

B. Random Libraries

Random libraries were also constructed to identify variants of the ECD of CD80 (SEQ ID NO:28), CD86 (SEQ ID NO: 29), ICOSL (SEQ ID NO:32) and NKp30 (SEQ ID NO:54. DNA encoding wild-type ECDs was cloned between the BamH1 and Kpn1 sites of modified yeast display vector pBYDS03 and then released using the same restriction enzymes. The released DNA was then mutagenized with the Genemorph II kit (Agilent, USA) so as to generate an average of three to five amino acid changes per library variant. Mutagenized DNA was then amplified by the two-step PCR and further processed as described above for targeted libraries.

Example 2

Introduction of DNA Libraries into Yeast

Example 2 describes the introduction of CD80, CD86, ICOSL, and NKp30 DNA libraries into yeast.

To introduce degenerate and random library DNA into yeast, electroporation-competent cells of yeast strain BJ5464 (ATCC.org; ATCC number 208288) were prepared and electroporated on a Gene Pulser II (Biorad, USA) with the electroporation-ready DNA from the step above essentially as described (Colby, D. W. et al. 2004 Methods Enzymology 388, 348-358). The only exception is that transformed cells were grown in non-inducing minimal selective SCD-Leu medium to accommodate the LEU2 selective marker carried by modified plasmid pBYDS03.

Library size was determined by plating dilutions of freshly recovered cells on SCD-Leu agar plates and then extrapolating library size from the number of single colonies from plating that generated at least 50 colonies per plate. The remainder of the electroporated culture was grown to saturation and cells from this culture were subcultured into the same medium once more to minimize the fraction of untransformed cells. To maintain library diversity, this subculturing step was carried out using an inoculum that contained at least 10× more cells than the calculated library size. Cells from the second saturated culture were resuspended in fresh medium containing sterile 25% (weight/volume) glycerol to a density of 10E10/ml and frozen and stored at −80° C. (frozen library stock).

One liter of SCD-Leu media consists of 14.7 grams of sodium citrate, 4.29 grams of citric acid monohydrate, 20 grams of dextrose, 6.7 grams of Difco brand yeast nitrogen base, and 1.6 grams yeast synthetic drop-out media supplement without leucine. Media was filtered sterilized before use using a 0.2 μM vacuum filter device.

Library size was determined by plating dilutions of freshly recovered cells on SCD-Leu agar plates and then extrapolating library size from the number of single colonies from a plating that generate at least 50 colonies per plate.

To segregate plasmid from cells that contain two or more different library clones, a number of cells corresponding to 10 times the library size, were taken from the overnight SCD-Leu culture and subcultured 1/100 into fresh SCD-Leu medium and grown overnight. Cells from this overnight culture were resuspended in sterile 25% (weight/volume) glycerol to a density of 10E10/ml and frozen and stored at −80° C. (frozen library stock).

Example 3

Yeast Selection

Example 3 describes the selection of yeast expressing affinity modified variants of CD80, CD86, ICOSL, and NKp30.

A number of cells equal to at least 10 times the library size were thawed from individual library stocks, suspended to 0.1×10E6 cells/ml in non-inducing SCD-Leu medium, and grown overnight. The next day, a number of cells equal to 10 times the library size were centrifuged at 2000 RPM for two minutes and resuspended to 0.5×10E6 cells/ml in inducing SCDG-Leu media. One liter of the SCDG-Leu induction media consists of 5.4 grams $Na_2HPO_4$, 8.56 grams of $NaH_2PO_4*H_2O$, 20 grams galactose, 2.0 grams dextrose, 6.7 grams Difco yeast nitrogen base, and 1.6 grams of yeast synthetic drop out media supplement without leucine dissolved in water and sterilized through a 0.22 μm membrane filter device. The culture was grown for two days at 20° C. to induce expression of library proteins on the yeast cell surface.

Cells were processed with magnetic beads to reduce non-binders and enrich for all CD80, CD86, ICOSL or NKp30 variants with the ability to bind their exogenous recombinant counter-structure proteins. For example, yeast displayed targeted or random CD80 libraries were selected against each of CD28, CTL-4, PD-L1, ICOS, and B7-H6 separately. This was then followed by two to three rounds of flow cytometry sorting using exogenous counter-structure protein staining to enrich the fraction of yeast cells that displays improved binders. Magnetic bead enrichment and selections by flow cytometry are essentially as described in Keith D. Miller, 1 Noah B. Pefaur, 2 and Cheryl L. Baird 1 Current Protocols in Cytometry 4.7.1-4.7.30, July 2008.

With CD80, CD86, ICOSL, and NKp30 libraries, target ligand proteins were sourced from R&D Systems (USA) as follows: human rCD28.Fc (i.e., recombinant CD28-Fc fusion protein), rPDL1.Fc, rCTLA4.Fc, rICOS.Fc, and rB7H6.Fc. Magnetic streptavidin beads were obtained from New England Biolabs, USA. For biotinylation of counter-structure protein, biotinylation kit cat #21955, Life Technologies, USA, was used. For two-color, flow cytometric sorting, a Becton Dickinson FACS Aria II sorter was used. CD80, CD86, ICOSL, or NKp30 display levels were monitored with an anti-hemagglutinin antibody labeled with Alexafluor 488 (Life Technologies, USA). Ligand binding Fc fusion proteins rCD28.Fc, rCTLA4.Fc, rPDL1.Fc, rICOS.Fc, or rB7-H6.Fc were detected with PE conjugated human Ig specific goat Fab (Jackson ImmunoResearch, USA). Doublet yeast were gated out using forward scatter (FSC)/side scatter (SSC) parameters, and sort gates were based upon higher ligand binding detected in FL4 that possessed more limited tag expression binding in FL1.

Yeast outputs from the flow cytometric sorts were assayed for higher specific binding affinity. Sort output yeast were expanded and re-induced to express the particular IgSF affinity modified domain variants they encode. This population then can be compared to the parental, wild-type yeast strain, or any other selected outputs, such as the bead output yeast population, by flow cytometry.

For ICOSL, the second sort outputs (F2) were compared to parental ICOSL yeast for binding of each rICOS.Fc, rCD28.Fc, and rCTLA4.Fc by double staining each population with anti-HA (hemagglutinin) tag expression and the anti-human Fc secondary to detect ligand binding.

In the case of ICOSL yeast variants selected for binding to ICOS, the F2 sort outputs gave Mean Fluorescence Intensity (MFI) values of 997, when stained with 5.6 nM rICOS.Fc, whereas the parental ICOSL strain MFI was measured at 397 when stained with the same concentration of rICOS.Fc. This represents a roughly three-fold improvement of the average binding in this F2 selected pool of clones, and it is predicted that individual clones from that pool will have much better improved MFI/affinity when individually tested.

In the case of ICOSL yeast variants selected for binding to CD28, the F2 sort outputs gave MFI values of 640 when stained with 100 nM rCD28.Fc, whereas the parental ICOSL strain MFI was measured at 29 when stained with the same concentration of rCD28.Fc (22-fold improvement). In the case of ICOSL yeast variants selected for binding to CTLA4, the F2 sort outputs gave MFI values of 949 when stained with 100 nM rCTLA4.Fc, whereas the parental ICOSL strain MFI was measured at 29 when stained with the same concentration of rCTLA4.Fc (32-fold improvement).

In the case of NKp30 yeast variants selected for binding to B7-H6, the F2 sort outputs gave MFI values of 533 when stained with 16.6 nM rB7H6.Fc, whereas the parental NKp30 strain MFI was measured at 90 when stained with the same concentration of rB7H6.Fc (6-fold improvement).

Importantly, the MFIs of all F2 outputs described above when measured with the anti-HA tag antibody on FL1 did not increase and sometimes went down compared to wild-type strains, indicating that increased binding was not a function of increased expression of the selected variants on the surface of yeast, and validated gating strategies of only selecting mid to low expressors with high ligand binding.

Example 4

Reformatting Selection Outputs as Fc-Fusions and in Various Immunomodulatory Protein Types Example 4 describes reformatting of selection outputs as immunomodulatory proteins containing an affinity modified (variant) extracellular domain (ECD) of CD80 or ICOSL, fused to an Fc molecule (variant ECD-Fc fusion molecules).

Output cells from final flow cytometric CD80 and ICOSL sorts were grown to terminal density in SCD-Leu medium. Plasmid DNA's from each output were isolated using a yeast plasmid DNA isolation kit (Zymoresearch, USA). For Fc fusions, PCR primers with added restriction sites suitable for cloning into the Fc fusion vector of choice were used to batch-amplify from the plasmid DNA preps the coding DNA's for the mutant target ECD's. After restriction digestion, the PCR products were ligated into an appropriate Fc fusion vector followed by chemical transformation into strain XL1 Blue *E. coli* (Agilent, USA) or NEB5alpha (New England Biolabs) as directed by supplier. Exemplary of an Fc fusion vector is pFUSE-hIgG1-Fc2 (Invivogen, USA).

Dilutions of transformation reactions were plated on LB-agar containing 100 μg/ml carbenicillin (Teknova, USA) to generate single colonies. Up to 96 colonies from each transformation were then grown in 96 well plates to saturation overnight at 37C in LB-broth (Teknova cat #L8112) and a small aliquot from each well was submitted for DNA sequencing of the ECD insert in order to identify the mutation(s) in all clones. Sample preparation for DNA sequencing was carried out using protocols provided by the service provider (Genewiz; South Plainfield, NJ). After removal of sample for DNA sequencing, glycerol was then added to the remaining cultures for a final glycerol content of 25% and plates were stored at −20° C. for future use as master plates (see below). Alternatively, samples for DNA sequencing were generated by replica plating from grown liquid cultures to solid agar plates using a disposable 96 well replicator (VWR, USA). These plates were incubated overnight to generate growth patches and the plates were submitted to Genewiz as specified by Genewiz.

After identification of clones of interest from analysis of Genewiz-generated DNA sequencing data, clones of interest were recovered from master plates and individually grown to density in 5 ml liquid LB-broth containing 100 μg/ml carbenicillin (Teknova, USA) and 2 ml of each culture were then used for preparation of approximately 10 μg of mini-prep plasmid DNA of each clone using a standard kit such as the Pureyield kit (Promega). Identification of clones of interest generally involved the following steps. First, DNA sequence data files were downloaded from the Genewiz website. All sequences were then manually curated so that they start at the beginning of the ECD coding region. The curated sequences were then batch-translated using a suitable program available at the URL: www.ebi.ac.uk/Tools/st/emboss_transeq/. The translated sequences were then aligned using a suitable program available at the URL: multalin.toulouse.inra.fr/multalin/multalin.html.

Clones of interest were then identified using the following criteria: 1) identical clone occurs at least two times in the alignment and 2) a mutation occurs at least two times in the alignment and preferably in distinct clones. Clones that meet at least one of these criteria were clones that have been enriched by our sorting process due to improved binding.

To generate immunomodulatory proteins containing an ECD of CD80 or ICOSL with at least one affinity-modified domain, the encoding nucleic acid molecule was generated to encode a protein designed as follows: signal peptide followed by variant (mutant) ECD followed by a linker of three alanines (AAA) followed by a human IgG1 Fc containing the mutation N82G with reference to wild-type human IgG1 Fc set forth in SEQ ID NO: 226. Since the construct does not include any antibody light chains that can form a covalent bond with a cysteine, the human IgG1 Fc also contains replacement of the cysteine residues to a serine residue at position 5 (C5S) compared to the wild-type or unmodified Fc set forth in SEQ ID NO: 226.

In addition, Example 8 below describes further immunomodulatory proteins that were generated as stack constructs containing at least two different affinity modified domains from identified variant CD80, CD86, ICOSL, and NKp30 molecules linked together and fused to an Fc.

Example 5

Expression and Purification of Fc-Fusions

Example 5 describes the high throughput expression and purification of Fc-fusion proteins containing variant ECD CD80, CD86, ICOSL, and Nkp30.

Recombinant variant Fc fusion proteins were produced with Expi293 expression system (Invitrogen, USA). 4 μg of each plasmid DNA from the previous step was added to 200 μl Opti-MEM (Invitrogen, USA) at the same time as 10.8 μl ExpiFectamine was separately added to another 200 μl Opti-MEM. After 5 minutes, the 200 μl of plasmid DNA was mixed with the 200 μl of ExpiFectamine and was further incubated for an additional 20 minutes before adding this mixture to cells. Ten million Expi293 cells were dispensed into separate wells of a sterile 10 ml, conical bottom, deep 24 well growth plate (Thomson Instrument Company, USA) in a volume 3.4 ml Expi293 media (Invitrogen, USA). Plates were shaken for 5 days at 120 RPM in a mammalian cell culture incubator set to 95% humidity and 8% $CO_2$. Following a 5 day incubation, cells were pelleted and culture supernatants were removed.

Protein was purified from supernatants using a high throughput 96 well Protein A purification kit using the manufacturer's protocol (Catalog number 45202, Life Technologies, USA). Resulting elution fractions were buffer exchanged into PBS using Zeba 96 well spin desalting plate (Catalog number 89807, Life Technologies, USA) using the manufacturer's protocol. Purified protein was quantitated using 280 nm absorbance measured by Nanodrop instrument (Thermo Fisher Scientific, USA), and protein purity was assessed by loading 5 μg of protein on NUPAGE pre-cast, polyacrylamide gels (Life Technologies, USA) under denaturing and reducing conditions and subsequent gel electrophoresis. Proteins were visualized in gel using standard Coomassie staining.

Example 6

Assessment of Binding and Activity of Affinity-Matured IgSF Domain-Containing Molecules A. Binding to Cell-Expressed Counter Structures This Example describes Fc-fusion binding studies to show specificity and affinity of CD80 and ICOSL domain variant immunomodulatory proteins for cognate binding partners.

To produce cells expressing cognate binding partners, full-length mammalian surface expression constructs for each of human CD28, CTLA4, PD-L1, ICOS, and B7-H6 were designed in pcDNA3.1 expression vector (Life Technologies) and sourced from Genscript, USA. Binding studies were carried out using the Expi293F transient transfection system (Life Technologies, USA) described above. The number of cells needed for the experiment was determined, and the appropriate 30 ml scale of transfection was performed using the manufacturer's suggested protocol. For each CD28, CTLA-4, PD-L1, ICOS, B7-H6 or mock 30 ml transfection, 75 million Expi293F cells were incubated with 30 μg expression construct DNA and 1.5 ml diluted ExpiFectamine 293 reagent for 48 hours, at which point cells were harvested for staining.

For staining by flow cytometry, 200,000 cells of appropriate transient transfection or negative control were plated in 96 well round bottom plates. Cells were spun down and resuspended in staining buffer (PBS (phosphate buffered saline), 1% BSA (bovine serum albumin), and 0.1% sodium azide) for 20 minutes to block non-specific binding. Afterwards, cells were centrifuged again and resuspended in staining buffer containing 100 nM to 1 nM variant immunomodulatory protein, depending on the experiment of each candidate CD80 variant Fc, ICOSL variant Fc, or stacked IgSF variant Fc fusion protein in 50 μl. Primary staining was performed on ice for 45 minutes, before washing cells in staining buffer twice. PE-conjugated anti-human Fc (Jackson ImmunoResearch, USA) was diluted 1:150 in 50 μl staining buffer and added to cells and incubated another 30 minutes on ice. Secondary antibody was washed out twice, cells were fixed in 4% formaldehyde/PBS, and samples were analyzed on FACScan flow cytometer (Becton Dickinson, USA).

Mean Fluorescence Intensity (MFI) was calculated for each transfectant and negative parental line with Cell Quest Pro software (Becton Dickinson, USA).

B. Bioactivity Characterization

This Example further describes Fc-fusion variant protein bioactivity characterization in human primary T cell in vitro assays.

1. Mixed Lymphocyte Reaction (MLR)

Soluble rICOSL.Fc or rCD80.Fc bioactivity was tested in a human Mixed Lymphocyte Reaction (MLR). Human primary dendritic cells (DC) were generated by culturing monocytes isolated from PBMC (BenTech Bio, USA) in vitro for 7 days with 500 U/ml rIL-4 (R&D Systems, USA) and 250 U/ml rGM-CSF (R&D Systems, USA) in Ex-Vivo 15 media (Lonza, Switzerland). 10,000 matured DC and 100,000 purified allogeneic CD4+ T cells (BenTech Bio, USA) were co-cultured with ICOSL or CD80 variant Fc fusion proteins and controls in 96 well round bottom plates in 200 μl final volume of Ex-Vivo 15 media. On day 5, IFN-gamma secretion in culture supernatants was analyzed using the Human IFN-gamma Duoset ELISA kit (R&D Systems, USA). Optical density was measured by VMax ELISA Microplate Reader (Molecular Devices, USA) and quantitated against titrated rIFN-gamma standard included in the IFN-gamma Duo-set kit (R&D Systems, USA).

2. Anti-CD03 Coimmobilization Assay

Costimulatory bioactivity of ICOSL and CD80 Fc fusion variants was determined in anti-CD3 coimmobilization assays. 1 nM or 4 nM mouse anti-human CD3 (OKT3, Biolegends, USA) was diluted in PBS with 1 nM to 80 nM rICOSL.Fc or rCD80.Fc variant proteins. This mixture was added to tissue culture treated flat bottom 96 well plates (Corning, USA) overnight to facilitate adherence of the stimulatory proteins to the wells of the plate. The next day, unbound protein was washed off the plates and 100,000 purified human pan T cells (BenTech Bio, US) or human T cell clone BC3 (Astarte Biologics, USA) were added to each well in a final volume of 200 μl of Ex-Vivo 15 media (Lonza, Switzerland). Cells were cultured 3 days before harvesting culture supernatants and measuring human IFN-gamma levels with Duoset ELISA kit (R&D Systems, USA) as mentioned above.

C. Results

Results for the binding and activity studies for exemplary tested variants are shown in Tables 6-8. In particular, Table 6 indicates exemplary IgSF domain amino acid substitutions (replacements) in the ECD of CD80 selected in the screen for affinity-maturation against the respective cognate structure CD28. Table 7 indicates exemplary IgSF domain amino acid substitutions (replacements) in the ECD of CD80 selected in the screen for affinity-maturation against the respective cognate structure PD-L1. Table 8 indicates exemplary IgSF domain amino acid substitutions (replacements) in the ECD of ICOSL selected in the screen for affinity-maturation against the respective cognate structures ICOS and CD28. For each Table, the exemplary amino acid substitutions are designated by amino acid position number corresponding to the respective reference unmodified ECD sequence as follows. For example, the reference unmodified ECD sequence in Tables 6 and 7 is the unmodified CD80 ECD sequence set forth in SEQ ID NO:28 and the reference unmodified ECD sequence in Table 8 is the unmodified ICOSL ECD sequence (SEQ ID NO:32). The amino acid position is indicated in the middle, with the corresponding unmodified (e.g. wild-type) amino acid listed before the number and the identified variant amino acid substitution listed after the number. Column 2 sets forth the SEQ ID NO identifier for the variant ECD for each variant ECD-Fc fusion molecule.

Also shown is the binding activity as measured by the Mean Fluorescence Intensity (MFI) value for binding of each variant Fc-fusion molecule to cells engineered to express the cognate counter structure ligand and the ratio of the MFI compared to the binding of the corresponding unmodified ECD-Fc fusion molecule not containing the amino acid substitution(s) to the same cell-expressed counter structure ligand. The functional activity of the variant Fc-fusion molecules to modulate the activity of T cells also is shown based on the calculated levels of IFN-gamma in culture supernatants (pg/ml) generated either i) with the indicated variant ECD-Fc fusion molecule coimmobilized with anti-CD3 or ii) with the indicated variant ECD-Fc fusion molecule in an MLR assay. The Tables also depict the ratio of IFN-gamma produced by each variant ECD-Fc compared to the corresponding unmodified ECD-Fc in both functional assays.

As shown, the selections resulted in the identification of a number of CD80 or ICOSL IgSF domain variants that were affinity-modified to exhibit increased binding for at least one, and in some cases more than one, cognate counter structure ligand. In addition, the results showed that affinity modification of the variant molecules also exhibited improved activities to both increase and decrease immunological activity depending on the format of the molecule. For example, coimmobilization of the ligand likely provides a multivalent interaction with the cell to cluster or increase the avidity to favor agonist activity and increase T cell activation compared to the unmodified (e.g. wildtype) ECD-Fc molecule not containing the amino acid replacement(s). However, when the molecule is provided as a bivalent Fc molecule in solution, the same IgSF domain variants exhibited an antagonist activity to decrease T cell activation compared to the unmodified (e.g. wildtype) ECD-Fv molecule not containing the amino acid replacement(s).

TABLE 6

CD80 variants selected against CD28. Molecule sequences, binding data, and costimulatory bioactivity data.

| | | Binding | | | Coimmobilization with anti-CD3 | MLR IFN-gamma |
|---|---|---|---|---|---|---|
| CD80 mutation(s) | SEQ ID NO (ECD) | CD28 MFI (parental ratio) | CTLA-4 MFI (parental ratio) | PD-L1 MFI (parental ratio) | IFN-gamma pg/mL (parental ratio) | levels pg/mL (parental ratio) |
| L70Q/A91G | 55 | 125 (1.31) | 283 (1.36) | 6 (0.08) | 93 (1.12) | 716 (0.83) |
| L70Q/A91G/T130A | 56 | 96 (1.01) | 234 (1.13) | 7 (0.10) | 99 (1.19) | 752 (0.87) |
| L70Q/A91G/I118A/T120S/T130A | 57 | 123 (1.29) | 226 (1.09) | 7 (0.10) | 86 (1.03) | 741 (0.86) |

TABLE 6-continued

CD80 variants selected against CD28. Molecule sequences, binding data, and costimulatory bioactivity data.

| | | Binding | | | Coimmobilization with anti-CD3 | MLR IFN-gamma |
|---|---|---|---|---|---|---|
| CD80 mutation(s) | SEQ ID NO (ECD) | CD28 MFI (parental ratio) | CTLA-4 MFI (parental ratio) | PD-L1 MFI (parental ratio) | IFN-gamma pg/mL (parental ratio) | levels pg/mL (parental ratio) |
| V4M/L70Q/A91G/T120S/T130A | 58 | 89 (0.94) | 263 (1.26) | 6 (0.09) | 139 (1.67) | 991 (1.14) |
| L70Q/A91G/T120S/T130A | 59 | 106 (1.12) | 263 (1.26) | 6 (0.09) | 104 (1.25) | 741 (0.86) |
| V20L/L70Q/A91S/T120S/T130A | 60 | 105 (1.11) | 200 (0.96) | 9 (0.13) | 195 (2.34) | 710 (0.82) |
| S44P/L70Q/A91G/T130A | 61 | 88 (0.92) | 134 (0.64) | 5 (0.07) | 142 (1.71) | 854 (0.99) |
| L70Q/A91G/E117G/T120S/T130A | 62 | 120 (1.27) | 193 (0.93) | 6 (0.08) | 98 (1.05) | 736 (0.85) |
| A91G/T120S/T130A | 63 | 84 (0.89) | 231 (1.11) | 44 (0.62) | 276 (3.33) | 714 (0.82) |
| L70R/A91G/T120S/T130A | 64 | 125 (1.32) | 227 (1.09) | 6 (0.09) | 105 (1.26) | 702 (0.81) |
| L70Q/E81A/A91G/T120S/I127T/T130A | 65 | 140 (1.48) | 185 (0.89) | 18 (0.25) | 98 (1.18) | 772 (0.89) |
| L70Q/Y87N/A91G/T130A | 66 | 108 (1.13) | 181 (0.87) | 6 (0.08) | 136 (1.63) | 769 (0.89) |
| T28S/L70Q/A91G/E95K/T120S/T130A | 67 | 32 (0.34) | 65 (0.31) | 6 (0.08) | 120 (1.44) | 834 (0.96) |
| N63S/L70Q/A91G/T120S/T130A | 68 | 124 (1.30) | 165 (0.79) | 6 (0.08) | 116 (1.39) | 705 (0.81) |
| K36E/I67T/L70Q/A91G/T120S/ | 69 | 8 (0.09) | 21 (0.10) | 5 (0.08) | 53 (0.63) | 852 (0.98) |
| T130A/N152T E52G/L70Q/A91G/T120S/T130A | 70 | 113 (1.19) | 245 (1.18) | 6 (0.08) | 94 (1.13) | 874 (1.01) |
| K37E/F59S/L70Q/A91G/T120S/T130A | 71 | 20 (0.21) | 74 (0.36) | 6 (0.08) | 109 (1.31) | 863 (1.00) |
| A91G/S103P | 72 | 39 (0.41) | 56 (0.27) | 9 (0.13) | 124 (1.49) | 670 (0.77) |
| K89E/T130A | 73 | 90 (0.95) | 148 (0.71) | 75 (1.07) | 204 (2.45) | 761 (0.88) |
| A91G | 74 | 96 (1.01) | 200 (0.96) | 85 (1.21) | 220 (2.65) | 877 (1.01) |
| D60V/A91G/T120S/T130A | 75 | 111 (1.17) | 222 (1.07) | 12 (0.18) | 120 (1.44) | 744 (0.86) |
| K54M/A91G/T120S | 76 | 68 (0.71) | 131 (0.63) | 5 (0.08) | 152 (1.83) | 685 (0.79) |
| M38T/L70Q/E77G/A91G/T120S/T130A/N152T | 77 | 61 (0.64) | 102 (0.49) | 5 (0.07) | 119 (1.43) | 796 (0.92) |
| R29H/E52G/L70R/E88G/A91G/T130A | 78 | 100 (1.05) | 119 (0.57) | 5 (0.08) | 200 (2.41) | 740 (0.85) |
| Y31H/T41G/L70Q/A91G/T120S/T130A | 79 | 85 (0.89) | 85 (0.41) | 6 (0.08) | 288 (3.47) | 782 (0.90) |
| V68A/T110A | 80 | 103 (1.08) | 233 (1.12) | 48 (0.68) | 163 (1.96) | 861 (0.99) |
| S66H/D90G/T110A/F116L | 81 | 33 (0.35) | 121 (0.58) | 11 (0.15) | 129 (1.55) | 758 (0.88) |
| R29H/E52G/T120S/T130A | 82 | 66 (0.69) | 141 (0.68) | 11 (0.15) | 124 (1.49) | 800 (0.92) |
| A91G/L102S | 83 | 6 (0.06) | 6 (0.03) | 5 (0.08) | 75 (0.90) | 698 (0.81) |
| I67T/L70Q/A91G/T120S | 84 | 98 (1.03) | 160 (0.77) | 5 (0.08) | 1751 (21.1) | 794 (0.92) |
| L70Q/A91G/T110A/T120S/T130A | 85 | 8 (0.09) | 14 (0.07) | 5 (0.07) | 77 (0.93) | 656 (0.76) |
| M38V/T41D/M43I/W50G/D76G/V83A/K89E/T120S/T130A | 86 | 5 (0.06) | 8 (0.04) | 8 (0.11) | 82 (0.99) | 671 (0.78) |
| V22A/L70Q/S121P | 87 | 5 (0.06) | 7 (0.04) | 5 (0.07) | 105 (1.27) | 976 (1.13) |
| A12V/S15F/Y31H/T41G/T130A/P137L/N152T | 88 | 6 (0.06) | 6 (0.03) | 5 (0.08) | 104 (1.25) | 711 (0.82) |
| I67F/L70R/E88G/A91G/T120S/T130A | 89 | 5 (0.05) | 6 (0.03) | 6 (0.08) | 62 (0.74) | 1003 (1.16) |

TABLE 6-continued

CD80 variants selected against CD28. Molecule sequences, binding data, and costimulatory bioactivity data.

| CD80 mutation(s) | SEQ ID NO (ECD) | Binding: CD28 MFI (parental ratio) | Binding: CTLA-4 MFI (parental ratio) | Binding: PD-L1 MFI (parental ratio) | Coimmobilization with anti-CD3: IFN-gamma pg/mL (parental ratio) | MLR IFN-gamma: levels pg/mL (parental ratio) |
|---|---|---|---|---|---|---|
| E24G/L25P/L70Q/T120S | 90 | 26 (0.27) | 38 (0.18) | 8 (0.11) | 101 (1.21) | 969 (1.12) |
| A91G/F92L/F108L/T120S | 91 | 50 (0.53) | 128 (0.61) | 16 (0.11) | 59 (0.71) | 665 (0.77) |
| WT CD80 | 28 | 95 (1.00) | 208 (1.00) | 70 (1.00) | 83 (1.00) | 866 (1.00) |

TABLE 7

CD80 variants selected against PD-L1. Molecule sequences, binding data, and costimulatory bioactivity data.

| CD80 mutation(s) | SEQ ID NO (ECD) | Binding: CD28 MFI (parental ratio) | Binding: CTLA-4 MFI (parental ratio) | Binding: PD-L1 MFI (parental ratio) | Coimmobilization with anti-CD3: IFN-gamma pg/mL (parental ratio) | MLR IFN-gamma: levels pg/mL (parental ratio) |
|---|---|---|---|---|---|---|
| R29D/Y31L/Q33H/K36G/M38I/T41A/M43R/M47T/E81V/L85R/K89N/A91T/F92P/K93V/R94L/I118T/N149S | 92 | 1071 (0.08) | 1089 (0.02) | 37245 (2.09) | 387 (0.76) | 5028 (0.26) |
| R29D/Y31L/Q33H/K36G/M381/T41A/M43R/M47T/E81V/L85R/K89N/A91T/F92P/K93V/R94L/N144S/N149S | 93 | 1065 (0.08) | 956 (0.02) | 30713 (1.72) | 400 (0.79) | 7943 (0.41) |
| R29D/Y31L/Q33H/K36G/M38I/T41A/M42T/M43R/M47T/E81V/L85R/K89N/A91T/F92P/K93V/R94L/L148S/N149S | 94 | 926 (0.07) | 954 (0.02) | 47072 (2.64) | 464 (0.91) | 17387 (0.91) |
| E24G/R29D/Y31L/Q33H/K36G/M38I/T41A/M43R/M47T/F59L/E81V/L85R/K89N/A91T/F92P/K93V/R94L/H96R | 95 | 1074 (0.08) | 1022 (0.02) | 1121 (0.06) | 406 (0.80) | 13146 (0.69) |
| R29D/Y31L/Q33H/K36G/M38I/T41A/M43R/M47T/E81V/L85R/K89N/A91T/F92P/K93V/R94L/N149S | 96 | 1018 (0.08) | 974 (0.02) | 25434 (1.43) | 405 (0.80) | 24029 (1.25) |
| R29V/M43Q/E81R/L85I/K89R/D90L/A91E/F92N/K93Q/R94G | 97 | 1029 (0.08) | 996 (0.02) | 1575 (0.09) | 342 (0.67) | 11695 (0.61) |
| T41I/A91G | 98 | 17890 (1.35) | 50624 (1.01) | 12562 (0.70) | 433 (0.85) | 26052 (1.36) |
| K89R/D90K/A91G/F92Y/K93R/N122S/N178S | 99 | 41687 (3.15) | 49429 (0.99) | 20140 (1.13) | 773 (1.52) | 6345 (0.33) |
| K89R/D90K/A91G/F92Y/K93R | 100 | 51663 (3.91) | 72214 (1.44) | 26405 (1.48) | 1125 (2.21) | 9356 (0.49) |
| K36G/K37Q/M38I/F59L/E81V/L85R/K89N/A91T/F92P/K93V/R94L/E99G/T130A/N149S | 101 | 1298 (0.10) | 1271 (0.03) | 3126 (0.18) | 507 (1.00) | 3095 (0.16) |

TABLE 7-continued

CD80 variants selected against PD-L1. Molecule sequences, binding data, and costimulatory bioactivity data.

| | | Binding | | | Coimmobilization with anti-CD3 | MLR IFN-gamma |
|---|---|---|---|---|---|---|
| CD80 mutation(s) | SEQ ID NO (ECD) | CD28 MFI (parental ratio) | CTLA-4 MFI (parental ratio) | PD-L1 MFI (parental ratio) | IFN-gamma pg/mL (parental ratio) | levels pg/mL (parental ratio) |
| AE88D/K89R/D90K/ A91G/F92Y/K93R | 102 | 31535 (2.38) | 50868 (1.02) | 29077 (1.63) | 944 (1.85) | 5922 (0.31) |
| K36G/K37Q/M38I/ L40M | 103 | 1170 (0.09) | 1405 (0.03) | 959 (0.05) | 427 (0.84) | 811 (0.04) |
| K36G | 104 | 29766 (2.25) | 58889 (1.18) | 20143 (1.13) | 699 (1.37) | 30558 (1.59) |
| WTCD80 | 28 | 13224 (1.00) | 50101 (1.00) | 17846 (1.00) | 509 (1.00) | 19211 (1.00) |

TABLE 8

ICOSL variants selected against CD28 or ICOS. Molecule sequences, binding data, and costimulatory bioactivity data.

| | | Binding | | Coimmobilization with anti-CD3 IFN-gamma | MLR IFN-gamma |
|---|---|---|---|---|---|
| ICOSL mutation(s) | SEQ ID NO (ECD) | ICOS OD (parental ratio) | CD28 MFI (parental ratio) | pg/ml (parental ratio) | levels pg/ml (parental ratio) |
| N52S | 109 | 1.33 (1.55) | 162 (9.00) | 1334 (1.93) | 300 (0.44) |
| N52H | 110 | 1.30 (1.51) | 368 (20.44) | 1268 (1.83) | 39 (0.06) |
| N52D | 111 | 1.59 (1.85) | 130 (7.22) | 1943 (2.80) | 190 (0.28) |
| N52Y/N57Y/ F138L/L203P | 112 | 1.02 (1.19) | 398 (22.11) | 510* (1.47*) | 18 (0.03) |
| N52H/N57Y/Q100P | 113 | 1.57 (1.83) | 447 (24.83) | 2199 (3.18) | 25 (0.04) |
| N52S/Y146C/ Y152C | 114 | 1.26 (1.47) | 39 (2.17) | 1647 (2.38) | 152 (0.22) |
| N52H/C198R | 115 | 1.16 (1.35) | 363 (20.17) | 744* (2.15*) | ND (ND) |
| N52H/C140D/T225A | 116 | ND (ND) | 154 (8.56) | 522* (1.51*) | ND (ND) |
| N52H/C198R/T225A | 117 | 1.41 (1.64) | 344 (19.11) | 778* (2.25*) | 0 (0) |
| N52H/K92R | 118 | 1.48 (1.72) | 347 (19.28) | 288* (0.83*) | 89 (0.13) |
| N52H/S99G | 119 | 0.09 (0.10) | 29 (1.61) | 184* (0.53*) | 421 (0.61) |
| N52Y | 120 | 0.08 (0.09) | 18 (1.00) | 184* (0.53*) | 568 (0.83) |
| N57Y | 121 | 1.40 (1.63) | 101 (5.61) | 580* (1.68*) | 176 (0.26) |
| N57Y/Q100P | 122 | 0.62 (0.72) | 285 (15.83) | 301* (0.87*) | 177 (0.26) |
| N52S/S130G/ Y152C | 123 | 0.16 (0.19) | 24 (1.33) | 266* (0.77*) | 1617 (2.35) |
| N52S/Y152C | 124 | 0.18 (0.21) | 29 (1.61) | 238* (0.69*) | 363 (0.53) |
| N52S/C198R | 125 | 1.80 (2.09) | 82 (4.56) | 1427 (2.06) | 201 (0.29) |
| N52Y/N57Y/Y152C | 126 | 0.08 (0.09) | 56 (3.11) | 377* (1.09*) | 439 (0.64) |
| N52Y/N57Y/ H129P/C198R | 127 | ND (ND) | 449 (24.94) | 1192 (1.72) | ND (ND) |
| N52H/L161P/ C198R | 128 | 0.18 (0.21) | 343 (19.05) | 643* (1.86*) | 447 (0.65) |
| N52S/T113E | 129 | 1.51 (1.76) | 54 (3.00) | 451* (1.30*) | 345 (0.50) |
| S54A | 130 | 1.62 (1.88) | 48 (2.67) | 386* (1.12*) | 771 (1.12) |

TABLE 8-continued

ICOSL variants selected against CD28 or ICOS. Molecule sequences, binding data, and costimulatory bioactivity data.

| | | Binding | | Coimmobilization with anti-CD3 IFN-gamma | MLR IFN-gamma |
|---|---|---|---|---|---|
| ICOSL mutation(s) | SEQ ID NO (ECD) | ICOS OD (parental ratio) | CD28 MFI (parental ratio) | pg/ml (parental ratio) | levels pg/ml (parental ratio) |
| N52D/S54P | 131 | 1.50 (1.74) | 38 (2.11) | 476* (1.38*) | 227 (0.33) |
| N52K/L208P | 132 | 1.91 (2.22) | 291 (16.17) | 1509 (2.18) | 137 (0.20) |
| N52S/Y152H | 133 | 0.85 (0.99) | 68 (3.78) | 2158 (3.12) | 221 (0.32) |
| N52D/V151A | 134 | 0.90 (1.05) | 19 (1.06) | 341* (0.99*) | 450 (0.66) |
| N52H/I143T | 135 | 1.83 (2.13) | 350 (19.44) | 2216 (3.20) | 112 (0.16) |
| N52S/L80P | 136 | 0.09 (0.10) | 22 (1.22) | 192* (0.55*) | 340 (0.49) |
| F120S/Y152H/N201S | 137 | 0.63 (0.73) | 16 (0.89) | 351* (1.01*) | 712 (1.04) |
| N52S/R75Q/L203P | 138 | 1.71 (1.99) | 12 (0.67) | 1996 (2.88) | 136 (0.20) |
| N52S/D158G | 139 | 1.33 (1.55) | 39 (2.17) | 325* (0.94*) | 277 (0.40) |
| N52D/Q133H | 140 | 1.53 (1.78) | 104 (5.78) | 365* (1.05*) | 178 (0.26) |
| WT ICOSL | 32 | 0.86 (1.00) | 18 (1.00) | 692/346* (1.00) | 687 (1.00) |

*Parental ratio calculated using 346 pg/ml IFN-gamma for WT ICOSL

Example 7

Ligand Binding Competition Assay

As shown in Example 6, several CD80 variant molecules exhibited improved binding to one or both of CD28 and PD-L1. To further assess the binding activity of CD80 to ligands CD28 and PD-L1, this Example describes a ligand competition assay assessing the non-competitive nature of exemplary CD80 variants to bind both CD28 and PD-L1.

An ELISA based binding assay was set up incorporating plate-bound CD80 variant A91G ECD-Fc to assess the ability of CD80 to simultaneously bind CD28 and PD-L1. Maxisorp 96 well ELISA plates (Nunc, USA) were coated overnight with 100 nM human recombinant CD80 variant A91G ECD-Fc fusion protein in PBS. The following day unbound protein was washed out, and the plate was blocked with 1% bovine serum albumin (Millipore, USA)/PBS for 1 hour at room temperature. This blocking reagent was washed out three times with PBS/0.05% Tween, which included a two minute incubation on a platform shaker for each wash.

In one arm of the competition assay, CD80 was incubated with CD28, and then CD28-bound CD80 was then assessed for competitive binding in the presence of either the other known CD80 ligand counter structures PD-L1 or CTLA-4 or negative control ligand PD-L2. Specifically, biotinylated recombinant human CD28 Fc fusion protein (rCD28.Fc; R&D Systems) was titrated into the wells starting at 10 nM, diluting out for eight points with 1:2 dilutions in 25 μl volume. Immediately after adding the biotinylated rCD28.Fc, unlabeled competitive binders, recombinant human PD-L1 monomeric his-tagged protein, recombinant human CTLA-4 monomeric his-tagged protein, or a negative control human recombinant PD-L2 Fc fusion protein (R&D Systems) were added to wells at 2000/1000/500 nM respectively in 25 μl volume for a final volume of 50 μl. These proteins were incubated together for one hour before repeating the three wash steps as described above.

After washing, 2.5 ng per well of HRP-conjugated streptavidin (Jackson Immunoresearch, USA) was diluted in 1% BSA/PBS and added to wells to detect bound biotinylated rCD28.Fc. After one hour incubation, wells were washed again three times as described above. To detect signal, 50 μl of TMB substrate (Pierce, USA) was added to wells following wash and incubated for 7 minutes, before adding 50 ul 2M sulfuric acid stop solution. Optical density was determined on an Emax Plus microplate reader (Molecular Devices, USA). Optical density values were graphed in Prism (Graphpad, USA).

The results are set forth in FIG. 1A. The results showed decreased binding of biotinylated rCD28.Fc to the CD80 variant A91G ECD-Fc fusion protein with titration of the rCD28.Fc. When rCD28.Fc binding was performed in the presence of non-competitive control protein, rPDL2, there was no decrease in CD28 binding for CD80 (solid triangle). In contrast, a competitive control protein, rCTLA-4, when incubated with the CD28.Fc, did result in decreased CD28 binding for CD80 as expected (x line). When recombinant PD-L1 was incubated with CD28.Fc, no decrease in CD28 binding to CD80 was observed, which demonstrated that the epitopes of CD28 and PD-L1 for CD80 are non-competitive. Binding of the recombinant PD-L1 protein used in the CD28 competition assay to CD80 was confirmed by incubating the biotinylated PD-L1 in the presence of non-biotinylated rCD28.Fc (square).

The reverse competition also was set up in which CD80 was incubated with PD-L1, and then PD-L1-bound CD80 was then assessed for competitive binding in the presence of either the other known CD80 ligand counter structures CD28 or CTLA-4 or negative control ligand PD-L2. Specifically, the assay was performed by titrating biotinylated recombinant human PD-L1-his monomeric protein into wells containing the recombinant CD80 variant. Because binding is weaker with this ligand, titrations started at 5000 nM with similar 1:2 dilutions over eight points in 25 μL. When the rPD-L1-his was used to detect binding, the competitive ligands human rCD28.Fc, human rCTLA-4.Fc, or human rPD-L2.Fc control were added at 2.5 nM final concentration in 25 μl for a total volume of 50 μl. The subsequent washes, detection, and OD measurements were the same as described above.

Figure 1B:
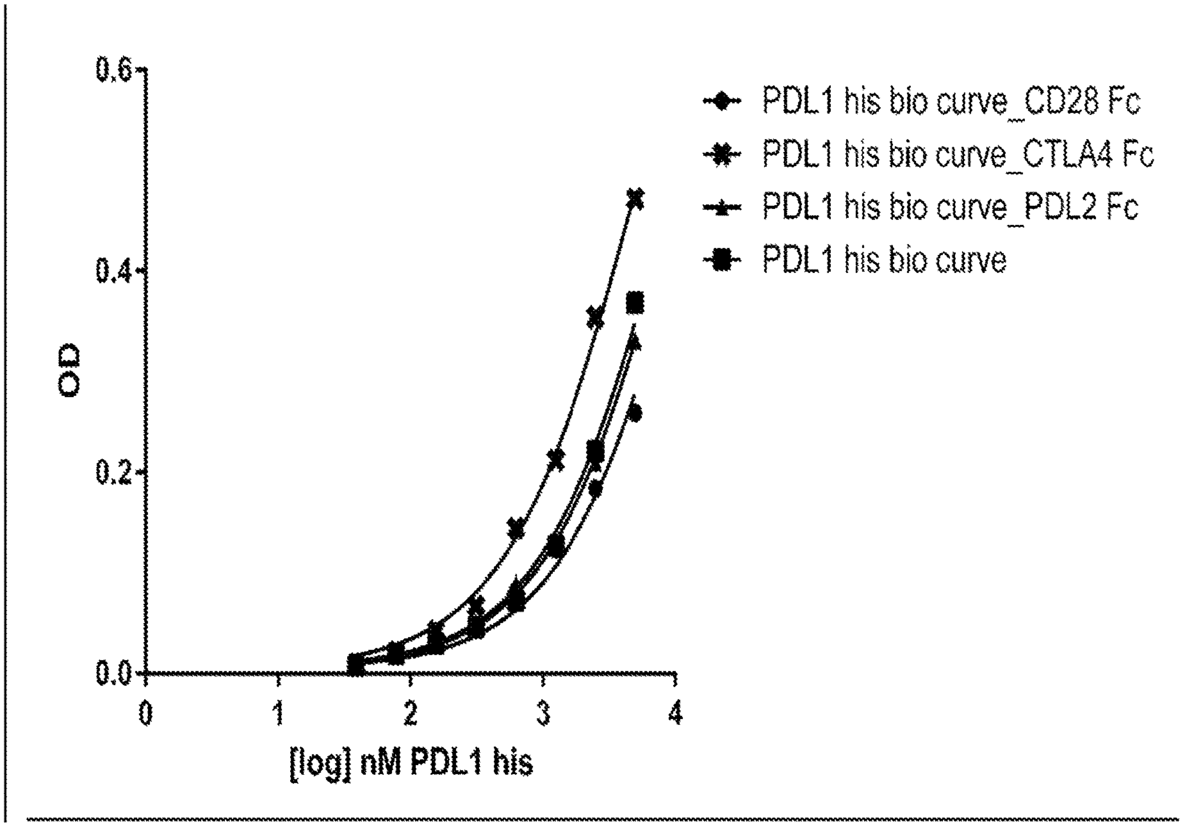
FIG. 1B depicts results of a competition binding assay for binding of biotinulated recombinant human PD-L1-his monomeric protein to immobilized CD80 variant A91G ECD-Fc fusion molecule in the presence of unlabeled recombinant human rCD28.Fc, human CTLA-4.Fc or human PD-L2.Fc

The results are set forth in FIG. 1B. Titrated PD-L1-his binding alone confirmed that PD-L1 bound to the CD80 variant A91G ECD-Fc fusion molecule immobilized on the plate (square). When PD-L1-his binding was performed in the presence of non-competitive control protein, rPDL2, there was no decrease in PD-L1 binding for CD80 (triangle). The CD28-competitive control protein, rCTLA-4, when incubated with the PD-L1-his, did not result in decreased PD-L1 binding for CD80 (x line), even though CTLA-4 is competitive for CD28. This result further demonstrated that lack of competition between CD28 and PD-L1 for CD80 binding. Finally, when PD-L1-his was incubated with CD28.Fc, no decrease in PD-L1 binding to CD80 was observed, which demonstrated that the epitopes of CD28 and PD-L1 for CD80 are non-competitive.

Thus, the results showed that CTLA-4, but not PD-L1 or the negative control PD-L2, competed for binding of CD28 to CD80 (FIG. 1A) and that CD28, CTLA-4, and PD-L2 did not compete for binding of PD-L1 to CD80 (FIG. 1B). Thus, these results demonstrated that CD28 and PD-L1 are non-competitive binders of CD80, and that this non-competitive binding can be demonstrated independently of which ligand is being detected in the ELISA.

Example 8

Generation and Assessment of Stacked Molecules Containing Different Affinity-Modified Domains Selected variant molecules described above that were affinity-modified for one or more counter structure ligand were used to generate "stack" molecule (i.e., Type II immunomodulatory protein) containing two or more affinity-modified IgSF domains. Stack constructs were obtained as geneblocks (Integrated DNA Technologies, Coralville, IA) that encode the stack in a format that enables its fusion to Fc by standard Gibson assembly using a Gibson assembly kit (New England Biolabs).

The encoding nucleic acid molecule of all stacks was generated to encode a protein designed as follows: Signal peptide, followed by the first variant IgV of interest, followed by a 15 amino acid linker which is composed of three GGGGS (G4S) motifs (SEQ ID NO:228), followed by the second IgV of interest, followed by two GGGGS linkers (SEQ ID NO: 229) followed by three alanines (AAA), followed by a human IgG1 Fc as described above. To maximize the chance for correct folding of the IgV domains in each stack, the first IgV was preceded by all residues that normally occur in the wild-type protein between this IgV and the signal peptide (leading sequence). Similarly, the first IgV was followed by all residues that normally connect it in the wild-type protein to either the next Ig domain (typically an IgC domain) or if such a second IgV domain is absent, the residues that connect it to the transmembrane domain (trailing sequence). The same design principle was applied to the second IgV domain except that when both IgV domains were derived from same parental protein (e.g. a CD80 IgV stacked with another CD80 IgV), the linker between both was not duplicated.

Table 9 sets forth the design for exemplary stacked constructs. The exemplary stack molecules shown in Table 9 contain the IgV domains as indicated and additionally leading or trailing sequences as described above. In the Table, the following components are present in order: signal peptide (SP; SEQ ID NO:225), IgV domain 1 (IgV1), trailing sequence 1 (TS1), linker 1 (LR1; SEQ ID NO:228), IgV domain 2 (IgV2), trailing sequence 2 (TS2), linker 2 (LR2; SEQ ID NO:230) and Fc domain (SEQ ID NO:226 containing C5S/N82G amino acid substitution). In some cases, a leading sequence 1 (LS1) is present between the signal peptide and IgV1 and in some cases a leading sequence 2 (LS2) is present between the linker and IgV2.

TABLE 9

Amino acid sequence (SEQ ID NO) of components of exemplary stacked constructs

| | | First domain | | | | Second domain | | | | |
|---|---|---|---|---|---|---|---|---|---|---|
| | SP | LS1 | IgV1 | TS1 | LR1 | LS2 | IgV2 | TS2 | LR2 | Fc |
| NKp30 WT ICOSL WT | + | − | SEQ ID NO: 214 | SEQ ID NO: 235 | + | − | SEQ ID NO: 196 | SEQ ID NO: 233 | + | + |
| NKp30 L30V/A60V/S64P/S86G ICOSL N525/N57Y/H94D/L96F/L98F/Q100R | + | − | SEQ ID NO: 215 | SEQ ID NO: 235 | + | − | SEQ ID NO: 212 | SEQ ID NO: 233 | + | + |
| NKp30 L30V/A60V/S64P/S86G) ICOSL N52D | + | − | SEQ ID NO: 215 | SEQ ID NO: 235 | + | − | SEQ ID NO: 199 | SEQ ID NO: 233 | + | + |
| NKp30 L30V/A60V/S64P/S86G ICOSL N52H/N57Y/Q100P | + | − | SEQ ID NO: 215 | SEQ ID NO: 235 | + | − | SEQ ID NO: 201 | SEQ ID NO: 233 | + | + |
| ICOSL WT Nkp30 WT | + | − | SEQ ID NO: 196 | SEQ ID NO: 233 | + | − | SEQ ID NO: 214 | SEQ ID NO: 235 | + | + |

TABLE 9-continued

| Amino acid sequence (SEQ ID NO) of components of exemplary stacked constructs | | | | | | | | | | |
|---|---|---|---|---|---|---|---|---|---|---|
| | | First domain | | | | Second domain | | | | |
| | SP | LS1 | IgV1 | TS1 | LR1 | LS2 | IgV2 | TS2 | LR2 | Fc |
| ICOSL N52D NKp30 L30V/A60V/S64P/S86G | + | − | SEQ ID NO: 199 | SEQ ID NO: 233 | + | − | SEQ ID NO: 215 | SEQ ID NO: 235 | + | + |
| ICOSL N52H/N57Y/Q100P NKp30 L30V/A60V/S64P/S86G | + | − | SEQ ID NO: 201 | SEQ ID NO: 233 | + | − | SEQ ID NO: 215 | SEQ ID NO: 235 | + | + |
| Domain 1: NKp30 WT Domain 2: CD80 WT | + | − | SEQ ID NO: 214 | SEQ ID NO: 235 | + | − | SEQ ID NO: 152 | SEQ ID NO: 231 | + | + |
| Domain 1: NKp30 WT Domain 2: CD86 WT | + | − | SEQ ID NO: 214 | SEQ ID NO: 235 | + | SEQ ID NO: 236 | SEQ ID NO: 220 | SEQ ID NO: 237 | + | + |
| Domain 1: NKp30 L30V/A60V/S64P/S86G Domain 2: CD80 R29H/Y31H/T41G/Y87N/E88G/K89E/D90N/A91G/P109S | + | − | SEQ ID NO: 215 | SEQ ID NO: 235 | + | − | SEQ ID NO: 192 | SEQ ID NO: 231 | + | + |
| Domain 1: NKp30 L30V/A60V/S64P/S86G Domain 2: CD80 I67T/L70Q/A91G/T120S | + | − | SEQ ID NO: 215 | SEQ ID NO: 235 | + | − | SEQ ID NO: 175 | SEQ ID NO: 231 | + | + |
| Domain 1: NKp30 L30V/A60V/S64P/S86G Domain 2: CD86 Q35H/H90L/Q102H | + | − | SEQ ID NO: 215 | SEQ ID NO: 235 | + | SEQ ID NO: 236 | SEQ ID NO: 221 | SEQ ID NO: 237 | + | + |
| Domain 1: CD80 WT Domain 2: Nkp30 WT | + | − | SEQ ID NO: 152 | SEQ ID NO: 231 | + | − | SEQ ID NO: 214 | SEQ ID NO: 235 | + | + |
| Domain 1: CD86 WT Domain 2: Nkp30 WT | + | SEQ ID NO: 236 | SEQ ID NO: 220 | SEQ ID NO: 237 | + | − | SEQ ID NO: 214 | SEQ ID NO: 235 | + | + |
| Domain 1: CD80 R29H/Y31H/T41G/Y87N/E88G/K89E/D90N/A91G/P109S Domain 2: NKp30 L30V/A60V/S64P/S86G | + | − | SEQ ID NO: 192 | SEQ ID NO: 231 | + | − | SEQ ID NO: 215 | SEQ ID NO: 235 | + | + |
| Domain 1: CD80 I67T/L70Q/A91G/T120S Domain 2: NKp30 L30V/A60V/S64P/S86G | + | − | SEQ ID NO: 175 | SEQ ID NO: 231 | + | − | SEQ ID NO: 215 | SEQ ID NO: 235 | + | + |
| Domain 1: CD86 Q35H/H9OL/Q102H Domain 2: NKp30 L30V/A60V/S64P/S86G | + | SEQ ID NO: 236 | SEQ ID NO: 221 | SEQ ID NO: 237 | + | − | SEQ ID NO: 215 | SEQ ID NO: 235 | + | + |
| Domain 1: CD80 WT Domain 2: ICOSL WT | + | − | SEQ ID NO: 152 | SEQ ID NO: 231 | + | − | SEQ ID NO: 196 | SEQ ID NO: 233 | + | + |
| Domain 1: CD80 WT Domain 2: CD86 WT | + | − | SEQ ID NO: 152 | SEQ ID NO: 231 | + | SEQ ID NO: 236 | SEQ ID NO: 220 | SEQ ID NO: 237 | + | + |
| Domain 1: CD80 WT Domain 2: CD80 WT | + | − | SEQ ID NO: 152 | SEQ ID NO: 231 | + | − | SEQ ID NO: 152 | SEQ ID NO: 231 | + | + |

TABLE 9-continued

Amino acid sequence (SEQ ID NO) of components of exemplary stacked constructs

| | SP | First domain LS1 | IgV1 | TS1 | LR1 | Second domain LS2 | IgV2 | TS2 | LR2 | Fc |
|---|---|---|---|---|---|---|---|---|---|---|
| Domain 1: CD80 E88D/K89R/D90K/A91G/F92Y/K93R Domain 2: CD80 R29H/Y31H/T41G/Y87N/E88G/K89E/D90N/A91G/P109S | + | − | SEQ ID NO: 189 | SEQ ID NO: 231 | + | − | SEQ ID NO: 192 | SEQ ID NO: 231 | + | + |
| Domain 1: CD80 A12T/H18L/M43V/F59L/E77K/P109S/I118T Domain 2: CD80 R29H/Y31H/T41G/Y87N/E88G/K89E/D90N/A91G/P109S | + | − | SEQ ID NO: 193 | SEQ ID NO: 231 | + | − | SEQ ID NO: 192 | SEQ ID NO: 231 | + | + |
| Domain 1: CD80 A12T/H18L/M43V/F59L/E77K/P109S/I118T Domain 2: CD80 I67T/L70Q/A91G/T120S | + | − | SEQ ID NO: 193 | SEQ ID NO: 231 | + | − | SEQ ID NO: 175 | SEQ ID NO: 231 | + | + |
| Domain 1: CD80 E88D/K89R/D90K/A91G/F92Y/K93R Domain 2: CD86 Q35H/H90L/Q102H | + | − | SEQ ID NO: 189 | SEQ ID NO: 231 | + | SEQ ID NO: 236 | SEQ ID NO: 221 | SEQ ID NO: 237 | + | + |
| Domain 1: CD80 A12T/H18L/M43V/F59L/E77K/P109S/I118T Domain 2: CD86 Q35H/H90L/Q102H | + | − | SEQ ID NO: 193 | SEQ ID NO: 231 | + | SEQ ID NO: 236 | SEQ ID NO: 221 | SEQ ID NO: 237 | + | + |
| Domain 1: CD80 E88D/K89R/D90K/A91G/F92Y/K93R Domain 2: ICOSL N525/N57Y/H94D/L96F/L98F/Q100R/G103E/F120S | + | − | SEQ ID NO: 189 | SEQ ID NO: 231 | + | − | SEQ ID NO: 213 | SEQ ID NO: 233 | + | + |
| Domain 1: CD80 A12T/H18L/M43V/F59L/E77K/P109S/I118T Domain 2: ICOSL N525/N57Y/H94D/L96F/L98F/Q100R/G103E/F120S | + | − | SEQ ID NO: 193 | SEQ ID NO: 231 | + | − | SEQ ID NO: 213 | SEQ ID NO: 233 | + | + |
| Domain 1: CD80 A12T/H18L/M43V/F59L/E77K/P109S/I118T Domain 2: ICOSL N52D | + | − | SEQ ID NO: 193 | SEQ ID NO: 231 | + | − | SEQ ID NO: 199 | SEQ ID NO: 233 | + | + |
| Domain 1: CD80 E88D/K89R/D90K/A91G/F92Y/K93R Domain 2: ICOSL N52H/N57Y/Q100P | + | − | SEQ ID NO: 189 | SEQ ID NO: 231 | + | − | SEQ ID NO: 201 | SEQ ID NO: 233 | + | + |
| Domain 1: CD80 A12T/H18L/M43V/F59L/E77K/P109S/I118T Domain 2: ICOSL N52H/N57Y/Q100P | + | − | SEQ ID NO: 193 | SEQ ID NO: 231 | + | − | SEQ ID NO: 201 | SEQ ID NO: 233 | + | + |
| Domain 1: ICOSL WT Domain 2: CD80 WT | + | − | SEQ ID NO: 196 | SEQ ID NO: 233 | + | − | SEQ ID NO: 152 | SEQ ID NO: 231 | + | + |
| Domain 1: CD86 WT Domain 2: CD80 WT | + | SEQ ID NO: 236 | SEQ ID NO: 220 | SEQ ID NO: 237 | + | − | SEQ ID NO: 152 | SEQ ID NO: 231 | + | + |

TABLE 9-continued

Amino acid sequence (SEQ ID NO) of components of exemplary stacked constructs

| | | First domain | | | | Second domain | | | | |
|---|---|---|---|---|---|---|---|---|---|---|
| | SP | LS1 | IgV1 | TS1 | LR1 | LS2 | IgV2 | TS2 | LR2 | Fc |
| Domain 1: CD80 R29H/Y31H/T41G/Y87N/E88G/K89E/D90N/A91G/P109S Domain 2: CD80 E88D/K89R/D90K/A91G/F92Y/K93R | + | − | SEQ ID NO: 192 | SEQ ID NO: 231 | + | − | SEQ ID NO: 189 | SEQ ID NO: 231 | + | + |
| Domain 1: CD80 R29H/Y31H/T41G/Y87N/E88G/K89E/D90N/A91G/P109S Domain 2: CD80 A12T/H18L/M43V/F59L/E77K/P109S/I118T | + | − | SEQ ID NO: 192 | SEQ ID NO: 231 | + | − | SEQ ID NO: 193 | SEQ ID NO: 231 | + | + |
| Domain 1: CD80 I67T/L70Q/A91G/T120S Domain 2: CD80 E88D/K89R/D90K/A91G/F92Y/K93R | + | − | SEQ ID NO: 175 | SEQ ID NO: 231 | + | − | SEQ ID NO: 189 | SEQ ID NO: 231 | + | + |
| Domain 1: CD80 I67T/L70Q/A91G/T120S Domain 2: CD80 A12T/H18L/M43V/F59L/E77K/P109S/I118T | + | − | SEQ ID NO: 175 | SEQ ID NO: 231 | + | − | SEQ ID NO: 193 | SEQ ID NO: 231 | + | + |
| Domain 1: CD86 Q35H/H90L/Q102H Domain 2: CD80 E88D/K89R/D90K/A91G/F92Y/K93R | + | SEQ ID NO: 236 | SEQ ID NO: 221 | SEQ ID NO: 237 | + | − | SEQ ID NO: 189 | SEQ ID NO: 231 | + | + |
| Domain 1: CD86 Q35H/H90L/Q102H Domain 2: CD80 A12T/H18L/M43V/F59L/E77K/P109S/I118T | + | SEQ ID NO: 236 | SEQ ID NO: 221 | SEQ ID NO: 237 | + | − | SEQ ID NO: 193 | SEQ ID NO: 231 | + | + |
| Domain 1: ICOSL N52S/N57Y/H94D/L96F/L98F/Q100R/G103E/F120S Domain 2: CD80 E88D/K89R/D90K/A91G/F92Y/K93R | + | − | SEQ ID NO: 213 | SEQ ID NO: 233 | + | − | SEQ ID NO: 189 | SEQ ID NO: 231 | + | + |
| Domain 1: ICOSL N52S/N57Y/H94D/L96F/L98F/Q100R/G103E/F120S Domain 2: CD80 A12T/H18L/M43V/F59L/E77K/P109S/I118T | + | − | SEQ ID NO: 213 | SEQ ID NO: 233 | + | − | SEQ ID NO: 193 | SEQ ID NO: 231 | + | + |
| Domain 1: ICOSL N52D Domain 2: CD80 E88D/K89R/D90K/A91G/F92Y/K93R | + | − | SEQ ID NO: 199 | SEQ ID NO: 233 | + | − | SEQ ID NO: 189 | SEQ ID NO: 231 | + | + |
| Domain 1: ICOSL N52D Domain: 2 CD80 A12T/H18L/M43V/F59L/E77K/P109S/I118T | + | − | SEQ ID NO: 199 | SEQ ID NO: 233 | + | − | SEQ ID NO: 193 | SEQ ID NO: 231 | + | + |
| Domain 1: ICOSL N52H/N57Y/Q100P Domain 2: CD80 E88D/K89R/D90K/A91G/F92Y/K93R | + | − | SEQ ID NO: 201 | SEQ ID NO: 233 | + | − | SEQ ID NO: 189 | SEQ ID NO: 231 | + | + |

TABLE 9-continued

Amino acid sequence (SEQ ID NO) of components of exemplary stacked constructs

| | SP | LS1 | IgV1 | TS1 | LR1 | LS2 | IgV2 | TS2 | LR2 | Fc |
|---|---|---|---|---|---|---|---|---|---|---|
| | | First domain | | | | Second domain | | | | |
| Domain 1: ICOSL N52H/N57Y/Q100P Domain 2: CD80 A12T/H18L/M43V/ F59L/E77K/P109S/ I118T | + | − | SEQ ID NO: 201 | SEQ ID NO: 233 | + | − | SEQ ID NO: 193 | SEQ ID NO: 231 | + | + |
| Domain 1: CD80 V68M/L70P/L72P/ K86E Domain 2: CD80 E88D/K89R/D90K/ A91G/F92Y/K93R | + | − | SEQ ID NO: 195 | SEQ ID NO: 231 | + | − | SEQ ID NO: 189 | SEQ ID NO: 231 | + | + |
| Domain 1: CD80 R29V/Y31F/K36G/ M38L/M43Q/E81R N83I/L85I/K89R/ D90L/A91E/F92N/ K93Q/R94G Domain 2: CD80 E88D/K89R/D90K/ A91G/F92Y/K93R | + | − | SEQ ID NO: 194 | SEQ ID NO: 231 | + | − | SEQ ID NO: 189 | SEQ ID NO: 231 | + | + |
| Domain 1: CD80 V68M/L70P/L72P/ K86E Domain 2: CD80 A12T/H18L/M43V/ F59L/E77K/P109S/ I118T | + | − | SEQ ID NO: 195 | SEQ ID NO: 231 | + | − | SEQ ID NO: 193 | SEQ ID NO: 231 | + | + |
| Domain 1: CD80 R29V/Y31F/K36G/ M38L/M43Q/E81R N83I/L85I/K89R/ D90L/A91E/F92N/ K93Q/R94G Domain 2: CD80 A12T/H18L/M43V/ F59L/E77K/P109S/ I118T | + | − | SEQ ID NO: 194 | SEQ ID NO: 231 | + | − | SEQ ID NO: 193 | SEQ ID NO: 231 | + | + |
| Domain 1: CD80 E88D/K89R/D90K/ A91G/F92Y/K93R Domain 2: CD80 V68M/L70P/L72P/ K86E | + | − | SEQ ID NO: 189 | SEQ ID NO: 231 | + | − | SEQ ID NO: 195 | SEQ ID NO: 231 | + | + |
| Domain 1: CD80 E88D/K89R/D90K/ A91G/F92Y/K93R Domain 2: CD80 R29V/Y31F/K36G/ M38L/M43Q/E81R N83I/L85I/K89R/ D90L/A91E/F92N/ K93Q/R94G | + | − | SEQ ID NO: 189 | SEQ ID NO: 231 | + | − | SEQ ID NO: 194 | SEQ ID NO: 231 | + | + |
| Domain 1: CD80 A12T/H18L/M43V/ F59L/E77K/P109S/ I118T Domain 2: CD80 V68M/L70P/L72P/ K86E | + | − | SEQ ID NO: 193 | SEQ ID NO: 231 | + | − | SEQ ID NO: 195 | SEQ ID NO: 231 | + | + |
| Domain 1: CD80 A12T/H18L/M43V/ F59L/E77K/P109S/ I118T Domain 2: CD80 R29V/Y31F/K36G/ M38L/M43Q/E81R/ V83I/L85I/K89R/ D90L/A91E/F92N/ K93Q/R94G | + | − | SEQ ID NO: 193 | SEQ ID NO: 231 | + | − | SEQ ID NO: 194 | SEQ ID NO: 231 | + | + |
| Domain 1: CD86 WT Domain 2: ICOSL WT | + | SEQ ID NO: 236 | SEQ ID NO: 220 | SEQ ID NO: 237 | + | − | SEQ ID NO: 196 | SEQ ID NO: 233 | + | + |

TABLE 9-continued

| Amino acid sequence (SEQ ID NO) of components of exemplary stacked constructs | | | | | | | | | | |
|---|---|---|---|---|---|---|---|---|---|---|
| | | First domain | | | | Second domain | | | | |
| | SP | LS1 | IgV1 | TS1 | LR1 | LS2 | IgV2 | TS2 | LR2 | Fc |
| Domain 1: CD80 R29H/Y31H/T41G/Y87N/E88G/K89E/D90N/A91G/P109S Domain 2: ICOSL N525/N57Y/H94D/L96F/L98F/Q100R/G103E/F120S | + | − | SEQ ID NO: 192 | SEQ ID NO: 231 | + | − | SEQ ID NO: 213 | SEQ ID NO: 233 | + | + |
| Domain 1: CD80 I67T/L70Q/A91G/T120S Domain 2: ICOSL N52S/N57Y/H94D/L96F/L98F/Q100R/G103E/F120S | + | − | SEQ ID NO: 175 | SEQ ID NO: 231 | + | − | SEQ ID NO: 213 | SEQ ID NO: 233 | + | + |
| Domain 1: CD80 R29H/Y31H/T41G/Y87N/E88G/K89E/D90N/A91G/P109S Domain 2: ICOSL N52D | + | − | SEQ ID NO: 192 | SEQ ID NO: 231 | + | − | SEQ ID NO: 199 | SEQ ID NO: 233 | + | + |
| Domain 1: CD80 I67T/L70Q/A91G/T120S Domain 2: ICOSL N52D | + | − | SEQ ID NO: 175 | SEQ ID NO: 231 | + | − | SEQ ID NO: 199 | SEQ ID NO: 233 | + | + |
| Domain 1: CD80 R29H/Y31H/T41G/Y87N/E88G/K89E/D90N/A91G/P109S Domain 2: ICOSL N52H/N57Y/Q100P | + | − | SEQ ID NO: 192 | SEQ ID NO: 231 | + | − | SEQ ID NO: 201 | SEQ ID NO: 233 | + | + |
| Domain 1: CD80 I67T/L70Q/A91G/T120S Domain 2: ICOSL N52H/N57Y/Q100P | + | − | SEQ ID NO: 175 | SEQ ID NO: 231 | + | − | SEQ ID NO: 201 | SEQ ID NO: 233 | + | + |
| Domain 1: CD86 Q35H/H90L/Q102H Domain 2: ICOSL N52S/N57Y/H94D/L96F/L98F/Q100R/G103E/F120S | + | SEQ ID NO: 236 | SEQ ID NO: 221 | SEQ ID NO: 237 | + | − | SEQ ID NO: 213 | SEQ ID NO: 233 | + | + |
| Domain 1: CD86 Q35H/H90L/Q102H Domain 2: ICOSL N52D | + | SEQ ID NO: 236 | SEQ ID NO: 221 | SEQ ID NO: 237 | + | − | SEQ ID NO: 199 | SEQ ID NO: 233 | + | + |
| Domain 1: CD86 Q35H/H90L/Q102H Domain 2: ICOSL N52H/N57Y/Q100P | + | SEQ ID NO: 236 | SEQ ID NO: 221 | SEQ ID NO: 237 | + | − | SEQ ID NO: 201 | SEQ ID NO: 233 | + | + |
| Domain 1: ICOSL WT Domain 2: CD86 WT | + | − | SEQ ID NO: 196 | SEQ ID NO: 233 | + | SEQ ID NO: 236 | SEQ ID NO: 220 | SEQ ID NO: 237 | + | + |
| Domain 1: ICOSL N52S/N57Y/H94D/L96F/L98F/Q100R/G103E/F120S Domain 2: CD80 R29H/Y31H/T41G/Y87N/E88G/K89E/D90N/A91G/P109S | + | − | SEQ ID NO: 213 | SEQ ID NO: 233 | + | − | SEQ ID NO: 192 | SEQ ID NO: 231 | + | + |
| Domain 1: ICOSL N52S/N57Y/H94D/L96F/L98F/Q100R/G103E/F120S Domain 2: CD80 I67T/L70Q/A91G/T120S | + | − | SEQ ID NO: 213 | SEQ ID NO: 233 | + | − | SEQ ID NO: 175 | SEQ ID NO: 231 | + | + |

TABLE 9-continued

Amino acid sequence (SEQ ID NO) of components of exemplary stacked constructs

| | SP | LS1 | IgV1 (First domain) | TS1 (First domain) | LR1 (First domain) | LS2 (Second domain) | IgV2 (Second domain) | TS2 (Second domain) | LR2 (Second domain) | Fc |
|---|---|---|---|---|---|---|---|---|---|---|
| Domain 1: ICOSL N52D Domain 2: CD80 R29H/Y31H/T41G/Y87N/E88G/K89E/D90N/A91G/P109S | + | − | SEQ ID NO: 199 | SEQ ID NO: 233 | + | − | SEQ ID NO: 192 | SEQ ID NO: 231 | + | + |
| Domain 1: ICOSL N52D Domain 2: CD80 I67T/L70Q/A91G/T120S | + | − | SEQ ID NO: 199 | SEQ ID NO: 233 | + | − | SEQ ID NO: 175 | SEQ ID NO: 231 | + | + |
| Domain 1: ICOSL N52H/N57Y/Q100P Domain 2: CD80 R29H/Y31H/T41G/Y87N/E88G/K89E/D90N/A91G/P109S | + | − | SEQ ID NO: 201 | SEQ ID NO: 233 | + | − | SEQ ID NO: 192 | SEQ ID NO: 231 | + | + |
| Domain 1: ICOSL N52S/N57Y/H94D/L96F/L98F/Q100R/G103E/F120S Domain 2: CD86 Q35H/H90L/Q102H | + | − | SEQ ID NO: 213 | SEQ ID NO: 233 | + | SEQ ID NO: 236 | SEQ ID NO: 221 | SEQ ID NO: 237 | + | + |
| Domain 1: ICOSL N52D Domain 2: CD86 Q35H/H90L/Q102H | + | − | SEQ ID NO: 199 | SEQ ID NO: 233 | + | SEQ ID NO: 236 | SEQ ID NO: 221 | SEQ ID NO: 237 | + | + |
| Domain 1: ICOSL N52H/N57Y/Q100P Domain 2: CD86 Q35H/H90L/Q102H | + | − | SEQ ID NO: 201 | SEQ ID NO: 233 | + | SEQ ID NO: 236 | SEQ ID NO: 221 | SEQ ID NO: 237 | + | + |

High throughput expression and purification of the variant IgV-stacked-Fc fusion molecules containing various combinations of variant IgV domains from CD80, CD86, ICOSL or Nkp30 containing at least one affinity-modified IgV domain were generated as described in Example 5. Binding of the variant IgV-stacked-Fc fusion molecules to respective counter structures and functional activity by anti-CD3 coimmobilization assay also were assessed as described in Example 6. For example, costimulatory bioactivy of the stacked IgSF Fc fusion proteins was determined in a similar immobilized anti-CD3 assay as above. In this case, 4 nM of anti-CD3 (OKT3, Biolegend, USA) was coimmobilized with 4 nM to 120 nM of human rB7-H6.Fc (R&D Systems, USA) or human rPD-L1.Fc (R&D Systems, USA) overnight on tissue-culture treated 96 well plates (Corning, USA). The following day unbound protein was washed off with PBS and 100,000 purified pan T cells were added to each well in 100 ul Ex-Vivo 15 media (Lonza, Switzerland). The stacked IgSF domains were subsequently added at concentrations ranging from 8 nM to 40 nM in a volume of 100 ul for 200 ul volume total. Cells were cultured 3 days before harvesting culture supernatants and measuring human IFN-gamma levels with Duoset ELISA kit (R&D Systems, USA) as mentioned above.

The results are set forth in Tables 10-14. Specifically, Table 10 sets forth binding and functional activity results for variant IgV-stacked-Fc fusion molecules containing an NKp30 IgV domain and an ICOSL IgV domain. Table 11 sets forth binding and functional activity results for variant IgV-stacked-Fv fusion molecules containing an Nkp30 IgV domain and a CD80 or CD86 IgV domain. Table 12 sets forth binding and functional activity results for variant IgV-stacked-Fc fusion molecules containing a variant CD80 IgV domain and a CD80, CD86 or ICOSL IgV domain. Table 13 sets forth binding and functional activity results for variant IgV-stacked-Fc fusion molecules containing two variant CD80 IgV domains. Table 14 sets forth results for variant IgV-stacked Fc fusion molecules containing a variant CD80 or CD86 IgV domain and a variant ICOSL IgV domain.

For each of Tables 10-14, Column 1 indicates the structural organization and orientation of the stacked, affinity modified or wild-type (WT) domains beginning with the amino terminal (N terminal) domain, followed by the middle WT or affinity modified domain located before the C terminal human IgG1 Fc domains. Column 2 sets forth the SEQ ID NO identifier for the sequence of each IgV domain contained in a respective "stack" molecule. Column 3 shows the binding partners which the indicated affinity modified stacked domains from column 1 were selected against.

Also shown is the binding activity as measured by the Mean Fluorescence Intensity (MFI) value for binding of each stack molecule to cells engineered to express various counter structure ligands and the ratio of the MFI compared to the binding of the corresponding stack molecule containing unmodified IgV domains not containing the amino acid substitution(s) to the same cell-expressed counter structure ligand. The functional activity of the variant stack molecules to modulate the activity of T cells also is shown based on the calculated levels of IFN-gamma in culture supernatants (pg/ml) generated with the indicated variant stack molecule in solution and the appropriate ligand coimmobilized with anti-CD3 as described in Example 6. The Tables also depict the ratio of IFN-gamma produced by each variant stack molecule compared to the corresponding unmodified stack molecule in the coimmobilization assay.

As shown, the results showed that it was possible to generate stack molecules containing at least one variant IgSF domains that exhibited affinity-modified activity of increased binding for at least one cognate counter structure ligand compared to a corresponding stack molecule containing the respective unmodified (e.g. wild-type) IgV domain. In some cases, the stack molecule, either from one or a combination of both variant IgSF domains in the molecule, exhibited increased binding for more than one cognate counter structure ligand. The results also showed that the order of the IgV domains in the stacked molecules could, in some cases, alter the degree of improved binding activity. In some cases, functional T cell activity also was altered when assessed in the targeted coimmobilization assay.

TABLE 10

Stacked variant IgV Fc fusion proteins containing an NKp30 IgV domain and an ICOSL IgV domain

| Domain Structure N terminal to C terminal: domain 1/domain 2/Fc | SEQ ID NO (IgV) | Counter structure selected against | Binding Activity B7H6 MFI (WT parental MFI ratio) | Binding Activity ICOS MFI (WT parental MFI ratio) | Binding Activity CD28 MFI (WT parental MFI ratio) | Anti-CD3 coimmobilization assay pg/mL IFN-gamma (WT parental IFN-gamma ratio) |
|---|---|---|---|---|---|---|
| Domain 1: NKp30 WT | 214 | — | 64538 | 26235 | 6337 | 235 |
| Domain 2: ICOSL WT | 196 | | (1.00) | (1.00) | (1.00) | (1.00) |
| Domain 1: NKp30 (L30V A60V S64P S86G) | 215 | B7-H6 | 59684 (0.92) | 12762 (0.49) | 9775 (1.54) | 214 (0.91) |
| Domain 2: ICOSL (N52S N57Y H94D L96F L98F Q100R) | 212 | ICOS-CD28 | | | | |
| Domain 1: NKp30 (L30V A60V S64P S86G) | 215 | B7-H6 | 65470 (1.01) | 30272 (1.15) | 9505 (1.50) | 219 (0.93) |
| Domain 2: ICOSL (N52D) | 199 | ICOS-CD28 | | | | |
| Domain 1: NKp30 (L30V A60V S64P S86G)/ | 215 | B7-H6 | 38153 (0.59) | 27903 (1.06) | 11300 (1.78) | 189 (0.80) |
| Domain 2: ICOSL (N52H N57Y Q100P) | 201 | ICOS-CD28 | | | | |
| Domain 1: ICOSL WT | 196 | — | 117853 | 70320 | 7916 | 231 |
| Domain 2: Nkp30 WT | 214 | | (1.0) | (1.0) | (1.0) | (1.0) |
| Domain 1: ICOSL (N52D) | 199 | ICOS-CD28 | 100396 (0.85) | 83912 (1.19) | 20778 (2.62) | 228 (0.98) |
| Domain 2: NKp30 (L30V A60V S64P S86G) | 215 | B7-H6 | | | | |
| Domain 1: ICOSL (N52H N57Y Q100P) | 201 | ICOS-CD28 | 82792 (0.70) | 68874 (0.98) | 72269 (9.12) | 561 (2.43) |
| Domain 2: NKp30 (L30V A60V S64P S86G) | 215 | B7-H6 | | | | |

TABLE 11

Stacked variant IgV Fc fusion proteins containing an NKp30 IgV domain and a CD80 or CD86 IgV domain

| Domain Structure N terminal to C terminal: domain 1/domain 2/Fc | SEQ ID NO (IgV) | Counter structure selected against | Binding Activity B7H6 MFI (WT parental MFI ratio) | Binding Activity CD28 MFI (WT parental MFI ratio) | Anti-CD3 coimmobilization assay pg/ml IFN-gamma (WT parental IFN-gamma ratio) |
|---|---|---|---|---|---|
| Domain 1: NKp30 WT | 214 | — | 88823 | 7022 | 68 |
| Domain 2: CD80 WT | 152 | | (1.00) | (1.00) | (1.00) |
| Domain 1: NKp30 WT | 214 | — | 14052 | 1690 | 92 |
| Domain 2: CD86 WT | 220 | | (1.00) | (1.00) | (1.00) |
| Domain 1: NKp30 (L30V A60V S64P S86G) | 215 | B7-H6 | 53279 (0.60) | 9027 (1.29) | 94 (1.38) |
| Domain 2: CD80 R29H/Y31H/T41G/Y87N/E88G/K89E/D90N/A91G/P109S | 192 | CD28 | | | |
| Domain 1: NKp30 (L30V A60V S64P S86G) | 215 | B7-H6 | 41370 (0.47) | 11240 (1.60) | 60 (0.88) |
| Domain 2: CD80 I67T/L70Q/A91G/T120S | 175 | CD28 | | | |
| Domain 1: NKp30 (L30V A60V S64P S86G)/ | 215 | B7-H6 | 68480 (4.87) | 9115 (5.39) | 110 (1.19) |
| Domain 2: CD86 Q35H/H90L/Q102H | 221 | CD28 | | | |

TABLE 11-continued

Stacked variant IgV Fc fusion proteins containing an NKp30 IgV domain and a CD80 or CD86 IgV domain

| Domain Structure N terminal to C terminal: domain 1/domain 2/Fc | SEQ ID NO (IgV) | Counter structure selected against | Binding Activity B7H6 MFI (WT parental MFI ratio) | Binding Activity CD28 MFI (WT parental MFI ratio) | Anti-CD3 coimmobilization assay pg/ml IFN-gamma (WT parental IFN-gamma ratio) |
|---|---|---|---|---|---|
| Domain 1: CD80 WT | 152 | — | 110461 | 13654 | 288 |
| Domain 2: Nkp30 WT | 214 | | (1.00) | (1.00) | (1.00) |
| Domain 1: CD86 WT | 220 | CD28 | 128899 | 26467 | 213 |
| Domain 2: Nkp30 WT | 214 | B7-H6 | (1.00) | (1.00) | (1.00) |
| Domain 1: CD80 R29H/Y31H/T41G/Y87N/E88G/K89E/D90N/A91G/P109S | 192 | CD28 | 55727 (0.50) | 4342 (0.32) | 100 (0.35) |
| Domain 2: NKp30 (L30V A60V S64P S86G) | 215 | B7-H6 | | | |
| Domain 1: CD80 I67T/L70Q/A91G/T120S | 175 | CD28 | 40412 (0.37) | 7094 (0.52) | 84 (0.29) |
| Domain 2: NKp30 (L30V A60V S64P S86G) | 215 | B7-H6 | | | |
| Domain 1: CD86 Q35H/H90L/Q102H | 221 | CD28 | 220836 (1.71) | 11590 (0.44) | 113 (0.53) |
| Domain 2: NKp30 (L30V A60V S64P S86G) | 215 | B7-H6 | | | |

TABLE 12

Stacked variant IgV Fc fusion proteins containing a CD80 IgV domain and a CD80, CD86, or ICOSL IgV domain

| Domain Structure N terminal to C terminal: domain 1/domain 2/Fc | SEQ ID NO (IgV) | Counter structure selected against | Binding Activity CD28 MFI (WT parental MFI ratio) | Binding Activity PD-L1 MFI (WT parental MFI ratio) | Binding Activity ICOS MFI (WT parental MFI ratio) | Anti-CD3 coimmobilization assay pg/mL IFN-gamma (WT parental IFN-gamma ratio) |
|---|---|---|---|---|---|---|
| Domain 1: CD80 WT | 152 | | 1230 | 2657 | 11122 | 69 |
| Domain 2: ICOSL WT | 196 | | (1.00) | (1.00) | (1.00) | (1.00) |
| Domain 1: CD80 WT | 152 | | 60278 | 2085 | | 59 |
| Domain 2: CD86 WT | 220 | | (1.00) | (1.00) | | (1.00) |
| Domain 1: CD80 WT | 152 | | 1634 | 6297 | | 98 |
| Domain 2: CD80 WT | 152 | | (1.00) | (1.00) | | (1.00) |
| Domain 1: CD80 E88D/K89R/D90K/A91G/F92Y/K93R | 189 | PD-L1 | 4308 (2.64) | 4234 (0.67) | | 214 (2.18) |
| Domain 2: CD80 R29H/Y31H/T41G/Y87N/E88G/K89E/D90N/A91G/P109S | 192 | CD28 | | | | |
| Domain 1: CD80 A12T/H18L/M43V/F59L/E77K/P109S/I118T | 193 | PD-L1 | 7613 (4.66) | 2030 (0.32) | | 137 (1.40) |
| Domain 2: CD80 R29H/Y31H/T41G/Y87N/E88G/K89E/D90N/A91G/P109S | 192 | CD28 | | | | |
| Domain 1: CD80 A12T/H18L/M43V/F59L/E77K/P109S/I118T | 193 | PD-L1 | 3851 (2.36) | 3657 (0.58) | | 81 (0.83) |
| Domain 2: CD80 I67T/L70Q/A91G/T120S | 175 | CD28 | | | | |
| Domain 1: CD80 E88D/K89R/D90K/A91G/F92Y/K93R | 189 | PD-L1 | 4117 (0.07) | 2914 (1.40) | | 96 (1.63) |
| Domain 2: CD86 Q35H/H90L/Q102H | 221 | CD28 | | | | |
| Domain 1: CD80 A12T/H18L/M43V/F59L/E77K/P109S/I118T | 193 | PD-L1 | 2868 (0.05) | 3611 (1.73) | | 94 (1.60) |

TABLE 12-continued

Stacked variant IgV Fc fusion proteins containing a CD80 IgV domain and a CD80, CD86, or ICOSL IgV domain

| Domain Structure N terminal to C terminal: domain 1/domain 2/Fc | SEQ ID NO (IgV) | Counter structure selected against | Binding Activity CD28 MFI (WT parental MFI ratio) | Binding Activity PD-L1 MFI (WT parental MFI ratio) | Binding Activity ICOS MFI (WT parental MFI ratio) | Anti-CD3 coimmobilization assay pg/mL IFN-gamma (WT parental IFN-gamma ratio) |
|---|---|---|---|---|---|---|
| Domain 2: CD86<br>Q35H/H90L/Q102H | 221 | CD28 | | | | |
| Domain 1: CD80<br>E88D/K89R/D90K/A91G/<br>F92Y/K93R | 189 | PD-L1 | 3383<br>(2.75) | 4515<br>(1.70) | 5158<br>(0.46) | 90<br>(1.30) |
| Domain 2: ICOSL<br>N52S/N57Y/H94D/L96F/<br>L98F/Q100R/G103E/<br>F120S | 213 | ICOS/<br>CD28 | | | | |
| Domain 1: CD80<br>A12T/H18L/M43V/F59L/<br>E77K/P109S/I118T | 193 | PD-L1 | 2,230<br>(1.81) | 2,148<br>(0.81) | 3,860<br>(0.35) | 112<br>(1.62) |
| Domain 2: ICOSL<br>N52S/N57Y/H94D/L96F/<br>L98F/Q100R/G103E/<br>F120S | 213 | ICOS/<br>CD28 | | | | |
| Domain 1: CD80<br>A12T/H18L/M43V/F59L/<br>E77K/P109S/I118T | 193 | PD-L1<br>ICOS/<br>CD28 | 5665<br>(4.61) | 6446<br>(2.43) | 15730<br>(1.41) | 126<br>(1.83) |
| Domain 2: ICOSL<br>N52D | 199 | | | | | |
| Domain 1: CD80<br>E88D/K89R/D90K/A91G/<br>F92Y/K93R | 189 | PD-L1 | 6260<br>(5.09) | 4543<br>(1.71) | 11995<br>(1.08) | 269<br>(3.90) |
| Domain 2: ICOSL<br>N52H/N57Y/Q100P | 201 | ICOS/<br>CD28 | | | | |
| Domain 1: CD80<br>A12T/H18L/M43V/F59L/<br>E77K/P109S/I118T | 193 | PD-L1 | 3359<br>(2.73) | 3874<br>(1.46) | 8541<br>(0.77) | 97<br>(1.41) |
| Domain 2: ICOSL<br>N52H/N57Y/Q100P | 201 | ICOS/<br>CD28 | | | | |
| Domain 1: ICOSL WT | 196 | | 3000 | 2966 | 14366 | 101 |
| Domain 2: CD80 WT | 152 | | (1.00) | (1.00) | (1.00) | (1.00) |
| Domain 1: CD86 WT | 220 | | 4946 | 1517 | | 125 |
| Domain 2: CD80 WT | 152 | | (1.00) | (1.00) | | (1.00) |
| Domain 1: CD80<br>R29H/Y31H/T41G/Y87N/<br>E88G/K89E/D90N/A91G/<br>P109S | 192 | CD28 | 2832<br>(1.73) | 3672<br>(0.58) | | 114<br>(1.16) |
| Domain 2: CD80<br>E88D/K89R/D90K/A91G/<br>F92Y/K93R | 189 | PD-L1 | | | | |
| Domain 1: CD80<br>R29H/Y31H/T41G/Y87N/<br>E88G/K89E/D90N/A91G/<br>P109S | 192 | CD28 | 4542<br>(2.78) | 2878<br>(0.45) | | 142<br>(1.45) |
| Domain 2: CD80<br>A12T/H18L/M43V/F59L/<br>E77K/P109S/I118T | 193 | PD-L1 | | | | |
| Domain 1: CD80<br>I67T/L70Q/A91G/T120S | 175 | CD28 | 938<br>(0.57) | 995<br>(0.16) | | 102<br>(1.04) |
| Domain 2: CD80<br>E88D/K89R/D90K/A91G/<br>F92Y/K93R | 189 | PD-L1 | | | | |
| Domain 1: CD80<br>I67T/L70Q/A91G/T120S | 175 | CD28 | 4153<br>(2.54) | 2827<br>(0.45) | | 108<br>(1.10) |
| Domain 2: CD80<br>A12T/H18L/M43V/F59L/<br>E77K/P109S/I118T | 193 | PD-L1 | | | | |
| Domain 1: CD86<br>Q35H/H90L/Q102H | 221 | CD28 | 14608<br>(2.95) | 2535<br>(1.67) | | 257<br>(2.06) |
| Domain 2: CD80<br>E88D/K89R/D90K/A91G/<br>F92Y/K93R | 189 | PD-L1 | | | | |
| Domain 1: CD86<br>Q35H/H90L/Q102H | 221 | CD28 | 2088<br>(0.42) | 2110<br>(1.39) | | 101<br>(0.81) |

TABLE 12-continued

Stacked variant IgV Fc fusion proteins containing a CD80 IgV domain and a CD80, CD86, or ICOSL IgV domain

| Domain Structure N terminal to C terminal: domain 1/domain 2/Fc | SEQ ID NO (IgV) | Counter structure selected against | Binding Activity CD28 MFI (WT parental MFI ratio) | PD-L1 MFI (WT parental MFI ratio) | ICOS MFI (WT parental MFI ratio) | Anti-CD3 coimmobilization assay pg/mL IFN-gamma (WT parental IFN-gamma ratio) |
|---|---|---|---|---|---|---|
| Domain 2: CD80 A12T/H18L/M43V/F59L/E77K/P109S/I118T | 193 | PD-L1 | | | | |
| Domain 1: ICOSL N52S/N57Y/H94D/L96F/L98F/Q100R/G103E/F120S | 213 | ICOS/CD28 | 3634 (1.21) | 4893 (1.65) | 6403 (0.45) | 123 (1.22) |
| Domain 2: CD80 E88D/K89R/D90K/A91G/F92Y/K93R | 189 | PD-L1 | 1095 (0.37) | 5929 (2.0) | 7923 (0.55) | 127 (1.26) |
| Domain 1: ICOSL N52S/N57Y/H94D/L96F/L98F/Q100R/G103E/F120S | 213 | ICOS/CD28 | | | | |
| Domain 2: CD80 A12T/H18L/M43V/F59L/E77K/P109S/I118T | 193 | PD-L1 | | | | |
| Domain 1: ICOSL N52D | 199 | ICOSL/CD28 | 2023 (0.67) | 5093 (1.72) | 16987 (1.18) | 125 (1.24) |
| Domain 2: CD80 E88D/K89R/D90K/A91G/F92Y/K93R | 189 | PD-L1 | | | | |
| Domain 1: ICOSL N52D | 199 | ICOS/CD28 | 3441 (1.15) | 3414 (1.15) | 20889 (1.45) | 165 (1.63) |
| Domain 2: CD80 A12T/H18L/M43V/F59L/E77K/P109S/I118T | 193 | PD-L1 | | | | |
| Domain 1: ICOSL N52H/N57Y/Q100P | 201 | ICOS/CD28 | 7835 (2.61) | 6634 (2.24) | 20779 (1.45) | 95 (0.94) |
| Domain 2: CD80 E88D/K89R/D90K/A91G/F92Y/K93R | 189 | PD-L1 | | | | |
| Domain 1: ICOSL N52H/N57Y/Q100P | 201 | ICOS/CD28 | 8472 (2.82) | 3789 (1.28) | 13974 (0.97) | 106 (1.05) |
| Domain 2: CD80 A12T/H18L/M43V/F59L/E77K/P109S/I118T | 193 | PD-L1 | | | | |

TABLE 13

Stacked variant IgV Fc fusion proteins containing two CD80 IgV domains

| Domain Structure N terminal to C terminal: domain 1/domain 2/Fc | SEQ ID NO (IgV) | Counter structure selected against | Binding Activity PD-L1 MFI (WT parental MFI ratio) | CTLA-4 MFI (WT parental MFI ratio) | Functional Activity MLR IFN-gamma pg/ml |
|---|---|---|---|---|---|
| Domain 1: CD80 WT | 152 | | 6297 | 4698 | 35166 |
| Domain 2: CD80 WT | 152 | | (1.00) | (1.00) | (1.00) |
| Domain 1: CD80 V68M/L70P/L72P/K86E | 195 | CTLA-4 | 2464 (0.39) | 4955 (1.05) | 5705 (0.16) |
| Domain 2: CD80 E88D/K89R/D90K/A91G/F92Y/K93R | 189 | PD-L1 | | | |
| Domain 1: CD80 R29V/Y31F/K36G/M38L/N43Q/E81R/V83I/L85I/K89R/D90L/A91E/F92N/K93Q/R94G | 194 | CTLA-4 | 1928 (0.31) | 1992 (0.42) | 1560 (0.04) |
| Domain 2: CD80 E88D/K89R/D90K/A91G/F92Y/K93R | 189 | PD-L1 | | | |
| Domain 1: CD80 V68M/L70P/L72P/K86E | 195 | CTLA-4 | 1215 (0.19) | 1382 (0.29) | 2171 (0.06) |

TABLE 13-continued

Stacked variant IgV Fc fusion proteins containing two CD80 IgV domains

| Domain Structure N terminal to C terminal: domain 1/domain 2/Fc | SEQ ID NO (IgV) | Counter structure selected against | Binding Activity PD-L1 MFI (WT parental MFI ratio) | Binding Activity CTLA-4 MFI (WT parental MFI ratio) | Functional Activity MLR IFN-gamma pg/ml |
|---|---|---|---|---|---|
| Domain 2: CD80 A12T/H18L/N43V/F59L/E77K/P109S/I118T | 193 | PD-L1 | | | |
| Domain 1: CD80 R29V/Y31F/K36G/M38L/N43Q/E81R/V83I/L85I/K89R/D90L/A91E/F92N/K93Q/R94G | 194 | CTLA-4 | 1592 (0.25) | 1962 (0.42) | 1512 (0.04) |
| Domain 2: CD80 A12T/H18L/N43V/F59L/E77K/P109S/I118T | 193 | PD-L1 | | | |
| Domain 1: CD80 E88D/K89R/D90K/A91G/F92Y/K93R | 189 | PD-L1 | 1747 (0.28) | 2057 (0.44) | 9739 (0.28) |
| Domain 2: CD80 V68M/L70P/L72P/K86E | 195 | CTLA-4 | | | |
| Domain 1: CD80 E88D/K89R/D90K/A91G/F92Y/K93R | 189 | PD-L1 | 1752 (0.28) | 1772 (0.38) | 5412 (0.15) |
| Domain 2: CD80 R29V/Y31F/K36G/M38L/N43Q/E81R/V83I/L85I/K89R/D90L/A91E/F92N/K93Q/R94G | 194 | CTLA-4 | | | |
| Domain 1: CD80 A12T/H18L/N43V/F59L/E77K/P109S/I118T | 193 | PD-L1 | 1636 (0.26) | 1887 (0.40) | 7608 (0.22) |
| Domain 2: CD80 V68M/L70P/L72P/K86E | 195 | CTLA-4 | | | |
| Domain 1: CD80 A12T/H18L/N43V/F59L/E77K/P109S/I118T | 193 | PD-L1 | 2037 (0.32) | 4822 (1.03) | 11158 (0.32) |
| Domain 2: CD80 R29V/Y31F/K36G/M38L/N43Q/E81R/V83I/L85I/K89R/D90L/A91E/F92N/K93Q/R94G | 194 | CTLA-4 | | | |

TABLE 14

Stacked variant IgV Fc fusion proteins containing a CD80 or CD86 IgV domain and an ICOSL IgV domain

| Domain Structure N terminal to C terminal: domain 1/domain 2/Fc | SEQ ID NO (IgV) | Counter structure selected against | Binding Activity PD-L1 MFI (WT parental MFI ratio) | Binding Activity CTLA-4 MFI (WT parental MFI ratio) | Functional Activity MLR IFN-gamma pg/ml |
|---|---|---|---|---|---|
| Domain 1: CD80 WT | 152 | | 1230 | 11122 | 1756 |
| Domain 2: ICOSL WT | 196 | | (1.00) | (1.00) | (1.00) |
| Domain 1: CD86 WT | 220 | | 29343 | 55193 | 6305 |
| Domain 2: ICOSL WT | 196 | | (1.00) | (1.00) | (1.00) |
| Domain 1: CD80 R29H/Y31H/T41G/Y87N/E88G/K89E/D90N/A91G/P109S | 192 | CD28 | 2280 (1.85) | 3181 (0.29) | 2281 (1.30) |
| Domain 2: ICOSL N52S/N57Y/H94D/L96F/L98F/Q100R/G103E/F120S | 213 | ICOS/CD28 | | | |
| Domain 1: CD80 I67T/L70Q/A91G/T120S | 175 | CD28 | 2309 (1.88) | 26982 (2.43) | 1561 (0.89) |
| Domain 2: ICOSL N52S/N57Y/H94D/L96F/L98F/Q100R/G103E/F120S | 213 | ICOS/CD28 | | | |
| Domain 1: CD80 R29H/Y31H/T41G/Y87N/E88G/K89E/D90N/A91G/P109S | 192 | CD28 | 4285 (3.48) | 22744 (2.04) | 1612 (0.92) |
| Domain 2: ICOSL N52D | 199 | ICOS/CD28 | | | |
| Domain 1: CD80 I67T/L70Q/A91G/T120S | 175 | CD28 | 3024 (2.46) | 16916 (1.52) | 3857 (2.20) |

TABLE 14-continued

Stacked variant IgV Fc fusion proteins containing a CD80 or CD86 IgV domain and an ICOSL IgV domain

| Domain Structure N terminal to C terminal: domain 1/domain 2/Fc | SEQ ID NO (IgV) | Counter structure selected against | Binding Activity PD-L1 MFI (WT parental MFI ratio) | Binding Activity CTLA-4 MFI (WT parental MFI ratio) | Functional Activity MLR IFN-gamma pg/ml |
|---|---|---|---|---|---|
| Domain 2: ICOSL N52D | 199 | ICOS/CD28 | | | |
| Domain 1: CD80 R29H/Y31H/T41G/Y87N/E88G/K89E/D90N/A91G/P109S | 192 | CD28 | 6503 (5.29) | 7240 (0.65) | 6886 (3.92) |
| Domain 2: ICOSL N52H/N57Y/Q100P | 201 | ICOS/CD28 | | | |
| Domain 1: CD80 I67T/L70Q/A91G/T120S | 175 | CD28 | 3110 (2.53) | 4848 (0.44) | 3393 (1.93) |
| Domain 2: ICOSL N52H/N57Y/Q100P | 201 | ICOS/CD28 | | | |
| Domain 1: CD86 Q35H/H90L/Q102H | 221 | CD28 | | | |
| Domain 2: ICOSL N52S/N57Y/H94D/L96F/L98F/Q100R/G103E/F120S | 213 | ICOS/CD28 | 11662 (0.40) | 21165 (0.38) | 880 (0.14) |
| Domain 1: CD86 Q35H/H90L/Q102H | 221 | CD28 | 24230 (0.83) | 73287 (1.33) | 1110 (0.18) |
| Domain 2: ICOSL N52D | 199 | ICOS/CD28 | | | |
| Domain 1: CD86 Q35H/H90L/Q102H | 221 | CD28 ICOS/CD28 | 1962 (0.07) | 1630 (0.03) | 587 (0.09) |
| Domain 2: ICOSL N52H/N57Y/Q100P | 201 | | | | |
| Domain 1: ICOSL WT | 196 | | 3000 | 14366 | 4113 |
| Domain 2: CD80 WT | 152 | | (1.00) | (1.00) | (1.00) |
| Domain 1: ICOSL WT | 196 | | 18005 | 53602 | 18393 |
| Domain 2: CD86 WT | 220 | | (1.00) | (1.00) | (1.00) |
| Domain 1: ICOSL N52S/N57Y/H94D/L96F/L98F/Q100R/G103E/F120S | 213 | ICOSL/CD28 | 10426 (3.48) | 51286 (3.57) | 18680 (4.54) |
| Domain 2: CD80 R29H/Y31H/T41G/Y87N/E88G/K89E/D90N/A91G/P109S | 192 | CD28 | | | |
| Domain 1: ICOSL N52S/N57Y/H94D/L96F/L98F/Q100R/G103E/F120S | 213 | ICOS/CD28 | 17751 (5.92) | 29790 (2.07) | 10637 (2.59) |
| Domain 2: CD80 I67T/L70Q/A91G/T120S | 175 | CD28 | | | |
| Domain 1: ICOSL N52D | 199 | ICOS/CD28 | 2788 (0.93) | 25870 (1.80) | 6205 (1.51) |
| Domain 2: CD80 R29H/Y31H/T41G/Y87N/E88G/K89E/D90N/A91G/P109S | 192 | CD28 | | | |
| Domain 1: ICOSL N52D | 199 | ICOS/CD28 | 2522 (0.84) | 13569 (0.94) | 5447 (1.32) |
| Domain 2: CD80 I67T/L70Q/A91G/T120S | 175 | CD28 | | | |
| Domain 1: ICOSL N52H/N57Y/Q100P | 201 | ICOS/CD28 | | | |
| Domain 2: CD80 R29H/Y31H/T41G/Y87N/E88G/K89E/D90N/A91G/P109S | 192 | CD28 | 9701 (3.23) | 9187 (0.64) | 5690 (1.38) |
| Domain 1: ICOSL N52S/N57Y/H94D/L96F/L98F/Q100R/G103E/F120S | 213 | ICOS/CD28 | 27050 (1.50) | 21257 (0.40) | 8131 (0.44) |
| Domain 2: CD86 Q35H/H90L/Q102H | 221 | CD28 | | | |
| Domain 1: ICOSL N52D | 199 | ICOS/CD28 | 34803 (1.93) | 80210 (1.50) | 6747 (0.37) |
| Domain 2: CD86 Q35H/H90L/Q102H | 221 | CD28 | | | |
| Domain 1: ICOSL N52H/N57Y/Q100P | 201 | ICOS/CD28 | 5948 (0.33) | 4268 (0.08) | 26219 (1.43) |
| Domain 2: CD86 Q35H/H90L/Q102H | 221 | CD28 | | | |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An immunomodulatory protein, comprising a CD86 immunoglobulin superfamily (IgSF) domain and an NKp30 IgSF domain, wherein the CD86 IGSF domain comprises a CD86 IgV domain and the NKp30 IgSF domain comprises an NKp30 IgV domain, and wherein:

the CD86 IgSF domain is an affinity-modified CD86 IgSF domain comprising one or more amino acid substitutions in a wild type CD86 IgSF domain, the amino acid substitutions in the wild-type CD86 IgSF domain comprise one or more of Q35H, H90L, and Q102H, and the affinity modified CD86 IgSF domain comprises a sequence of amino acids that has at least 95% sequence identity to a wild-type CD86 IgSF domain set forth in SEQ ID NO:29 or a portion thereof comprising the IgV domain set forth in SEQ ID NO:220; and/or the NKp30 IgSF domain is an affinity-modified NKp30 IgSF domain comprising one or more amino acid substitutions in a wild type NKp30 IgSF domain, the amino acid substitutions in the wild type NKp30 IgSF domain comprise one or more of L30V, A60V, S64P, and S86G, and the affinity-modified NKp30 IgSF domain comprises a sequence of amino acids that has at least 95% sequence identity to a wild-type NKp30 IgSF domain set forth in SEQ ID NO:54 or a portion thereof comprising the IgV domain set forth in SEQ ID NO:214.

2. The immunomodulatory protein of claim 1, wherein the CD86 IgSF domain is an affinity modified CD86 IgSF domain that has increased binding to CD28 compared to the wild-type CD86 IgSF domain.

3. The immunomodulatory protein of claim 1, wherein the NKp30 IgSF domain is an affinity modified NKp30 IgSF domain that has increased binding to B7-H6 compared to the wild-type NKp30 IgSF domain.

4. The immunomodulatory protein of claim 1, wherein the CD86 IgSF domain is an affinity modified CD86 IgSF domain that has increased binding to CD28 compared to the wild-type CD86 IgSF domain; and the NKp30 IgSF domain is an affinity modified NKp30 IgSF domain that has increased binding to B7-H6 compared to the wild-type NKp30 IgSF domain.

5. The immunomodulatory protein of claim 2, wherein the CD86 IgSF domain comprises the sequence of amino acids set forth in any of SEQ ID NOs: 148-151 and 221-224.

6. The immunomodulatory protein of claim 3, wherein the NKp30 IgSF domain comprises the sequence of amino acids set forth in any of SEQ ID NOs: 143-147 and 215-219.

7. The immunomodulatory protein of claim 4, wherein:

(a) the CD86 IgSF domain comprises the sequence of amino acids set forth in any of SEQ ID NOs: 148-151, and 221-224; and (b) the NKp30 IgSF domain comprises the sequence of amino set forth in any of SEQ ID NOs: 143-147 and 215-219.

8. The immunomodulatory protein of claim 4, wherein at least one of the CD86 and NKp30 IgSF domains is linked to an Fc domain that is a wild-type Fc domain or a variant thereof with reduced effector function.

9. The immunomodulatory protein of claim 8 that is a heterodimer.

10. The immunomodulatory protein of claim 8, wherein the Fc domain is an IgG1 domain, an IgG2 domain, or is a variant thereof with reduced effector function.

11. The immunomodulatory protein of claim 10, wherein the Fc domain or variant thereof comprises the sequence of amino acids set forth in SEQ ID NO:226 or SEQ ID NO:227.

12. The immunomodulatory protein of claim 10, wherein the CD86 IgSF domain is linked to the NKp30 IgSF domain indirectly via a linker.

13. The immunomodulatory protein of claim 1, wherein the immunomodulatory protein is purified.

14. The immunomodulatory protein of claim 7, wherein at least one of the CD86 and NKp30 IgSF domains is linked to an Fc domain that is a wild-type Fc domain or a variant thereof with reduced effector function.

15. The immunomodulatory protein of claim 14 that is a heterodimer.

16. The immunomodulatory protein of claim 14, wherein the Fc domain is an IgG1 domain, an IgG2 domain, or is a variant thereof with reduced effector function.

17. The immunomodulatory protein of claim 16, wherein the Fc domain of variant thereof comprises the sequence of amino acids set forth in SEQ ID NO:226 or SEQ ID NO: 227.

18. The immunomodulatory protein of claim 16, wherein the CD86 IgSF domain is linked to the NKp30 IgSF domain indirectly via a linker.

19. A pharmaceutical composition, comprising the immunomodulatory protein of claim 1.

20. The pharmaceutical composition of claim 19, comprising a pharmaceutically acceptable excipient.

21. The pharmaceutical composition of claim 19 that is sterile.

22. An article of manufacture comprising the pharmaceutical composition of claim 19 in a vial.

23. The article of manufacture of claim 22, wherein the vial is sealed.

24. A kit comprising the pharmaceutical composition of claim 19, and instructions for use.

25. A kit comprising the article of manufacture according to claim 23, and instructions for use.

* * * * *